United States Patent
Nudelman et al.

(10) Patent No.: US 9,499,484 B2
(45) Date of Patent: Nov. 22, 2016

(54) INDOLE, INDOLINE DERIVATIVES, COMPOSITIONS COMPRISING THEM AND USES THEREOF

(71) Applicant: YISSUM RESEARCH DEVELOPMENT COMPANY OF THE HEBREW UNIVERSITY OF JERUSALEM LTD, Jerusalem (IL)

(72) Inventors: Abraham Nudelman, Rehovot (IL); Marta Weinstock-Rosin, Jerusalem (IL)

(73) Assignee: YISSUM RESEARCH DEVELOPMENT COMPANY OF THE HEBREW UNIVERSITY OF JERUSALEM LTD, Jerusalem (IL)

( * ) Notice: Subject to any disclaimer, the term of this patent is extended or adjusted under 35 U.S.C. 154(b) by 0 days.

(21) Appl. No.: 14/390,171

(22) PCT Filed: Apr. 2, 2013

(86) PCT No.: PCT/IL2013/050301
§ 371 (c)(1),
(2) Date: Oct. 2, 2014

(87) PCT Pub. No.: WO2013/150529
PCT Pub. Date: Oct. 10, 2013

(65) Prior Publication Data
US 2015/0087617 A1    Mar. 26, 2015

Related U.S. Application Data

(60) Provisional application No. 61/619,150, filed on Apr. 2, 2012.

(51) Int. Cl.
| | | |
|---|---|---|
| A61K 31/40 | (2006.01) |
| C07D 209/18 | (2006.01) |
| C07D 235/06 | (2006.01) |
| C07D 403/06 | (2006.01) |
| C07D 209/08 | (2006.01) |
| C07D 209/12 | (2006.01) |
| C07D 209/14 | (2006.01) |
| C07F 7/18 | (2006.01) |
| C07D 235/04 | (2006.01) |
| C07F 7/02 | (2006.01) |

(52) U.S. Cl.
CPC ........... *C07D 209/18* (2013.01); *C07D 209/08* (2013.01); *C07D 209/12* (2013.01); *C07D 209/14* (2013.01); *C07D 235/04* (2013.01); *C07D 235/06* (2013.01); *C07D 403/06* (2013.01); *C07F 7/025* (2013.01); *C07F 7/1856* (2013.01)

(58) Field of Classification Search
USPC .......... 514/419, 394; 548/406, 491
See application file for complete search history.

(56) References Cited

U.S. PATENT DOCUMENTS

| 2,755,287 | A | 7/1956 | Schlittler et al. |
| 4,900,686 | A | 2/1990 | Arnost et al. |
| 6,002,018 | A | 12/1999 | Terranova et al. |
| 6,080,852 | A | 6/2000 | Lee et al. |
| 7,381,739 | B2 * | 6/2008 | Madera et al. ............... 514/415 |
| 7,799,782 | B2 * | 9/2010 | Munson ............... C07D 231/56 514/234.5 |
| 2011/0294850 | A1 * | 12/2011 | Sugimoto ............ C07D 209/08 514/314 |

FOREIGN PATENT DOCUMENTS

| WO | 2004089915 A1 | 10/2004 |
| WO | 2012163898 A1 | 12/2012 |

OTHER PUBLICATIONS

Masige's CAS: 126: 168565, 1997.*
Sugimoto et al. CAS: 153:286843, 2010.*
Furman et al., "Synthesis and in vitro evaluation of anti-inflammatory activity of ester and amine derivatives of indoline in RAW 264.7 and peritoneal macrophages" Bioorganic & Medicinal Chemistry Letters 24(10): 2283-2287 (2014).
Chyan et al., "Potent Neuroprotective Propertied against the Alzheimer B-Amyloid by an Endogenous Melatonin-related Indole Structure, Indole-3-propionic Acid" J. Biol. Chem. 274: 21937-21942 (1999).
Berge et al., "Pharmaceutical Salts" J. Pharm. Sci. 66 (1):1-19 (Jan. 1977).
Khorana et al, "Prospective Acetylcholinesterase Inhibitory Activity of Indole and Its Analogs", Bioorganic & Medicinal Chemistry Letters 22 (8):2885-2888 (Feb. 2012).
Safdy et al, "Tryptophan Analogues, 1. Synthesis and Antihypertensive Activity of Positional Isomers", Journal of Medicinal Chemistry, 25 (6) 723-730 (1982).
Petrova et al, Isomers of 5-hydroxyindoles possessing properties of quinonimines, Khimiya Geterotsiklicheskikh soedinenii, 7 : 1004-1005 (1972).
Svensson et al, "Brominatin of 4-dimethylamino-3-methylhenol and related indoline and tetrahyroquinoline derivatives", Acta Pharmaceutica Suecica, 10 (2) : 147-152 (1973).
Yanovsky et al, "Carbamate Derivatives of Indolines as Cholinesterase Inhibitors and Antioxidants for the Treatment of Alzheimer's Disease" Journal of Medicinal Chemistry, vol. 55, (23) : 10700-10715 (Nov. 2012).
Julia et al, "Recherches en serie indolique. XVII." Bulletin De La Societe Chimique De France, No. 4, 1966, pp. 1335-1342.
Juby et al "Preparation and Antiinflammatroy Properties of Some 1-Substituted 3-(5-Tetrazolylmethyl)indoles and Homologs", J Med Chem., 12(3):396-401 (1969).

\* cited by examiner

*Primary Examiner* — Rei-Tsang Shiao
(74) *Attorney, Agent, or Firm* — Browdy and Neimark, PLLC

(57) ABSTRACT

The invention provides indole and indoline derivatives and slats thereof, compositions comprising them and uses thereof for the treatment of diseases and disorders.

9 Claims, 8 Drawing Sheets

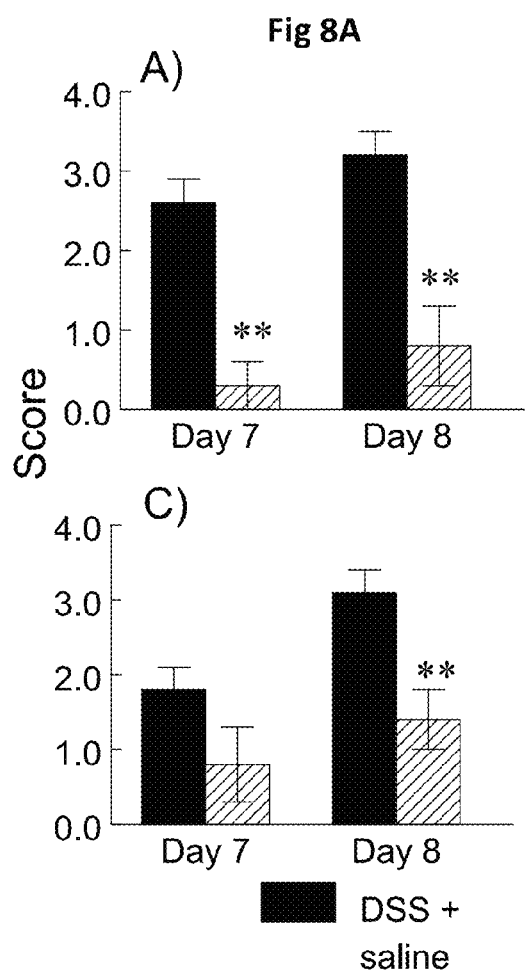
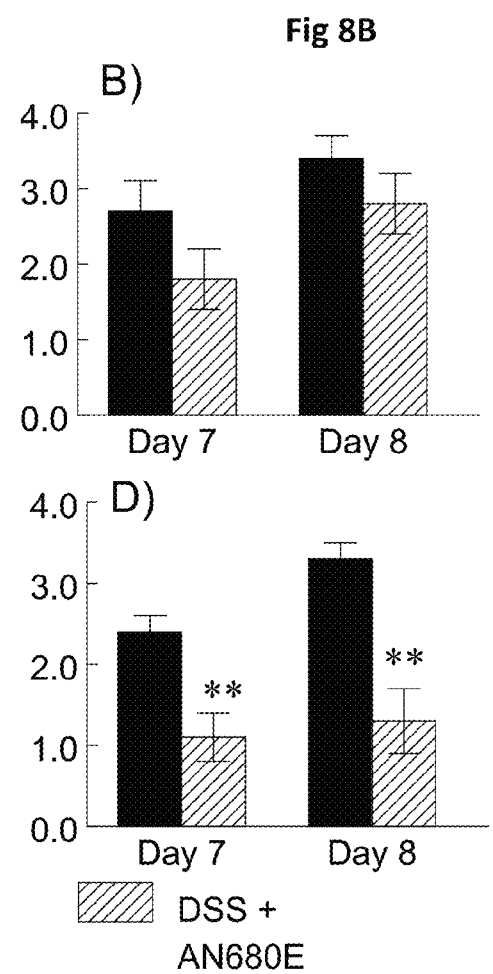
Fig 8A
Fig 8B
Fig 8C
Fig 8D

INDOLE, INDOLINE DERIVATIVES, COMPOSITIONS COMPRISING THEM AND USES THEREOF

FIELD

This invention relates to indole and indoline derivatives and slats thereof, compositions comprising them and uses thereof for the treatment of diseases and disorders.

BACKGROUND

Impaired mitochondrial function resulting in the production of reactive oxygen species and oxidative stress plays a key role in the aetiology of Alzheimer's disease (AD). Oxidative stress is accompanied by microglial activation and an increase in the release of nitric oxide (NO) and pro-inflammatory cytokines, which further compromises mitochondrial activity. These pathological changes may also contribute to neurodegeneration in other disorders, like Parkinson's disease, ischemic stroke and amyotropic lateral sclerosis. They are also seen in Mild Cognitive Impairment (MCI) a prodromal form of AD to which it progresses in a significant proportion of subjects.

The drugs most frequently employed for the treatment of AD are acetylcholine-esterase (AChE) inhibitors. Of these, donepezil has been shown to reduce the cytotoxic effects of oxidative stress and the release of NO and cytokines from activated microglia, but both of these actions occur at concentrations 10-100-fold higher than those inhibiting AChE. The occurrence of a potential protective effect against neurodegenerative processes at much higher than relevant therapeutic doses may explain why chronic treatment with donepezil of patients with MCI did not reduce the proportion converting to AD.

Oxidative stress and the release of pro-inflammatory cytokines also occurs in pathological conditions, such inflammatory bowel diseases (IBDs) ulcerative colitis and Crohn's disease, rheumatoid arthritis, type II diabetes and cardiac failure. The IBDs are characterized by strong leukocyte activation and infiltration into the intestinal tissues, the release of pro-inflammatory cytokines and enzymes and the formation of reactive oxygen species. The mucosa in patients with ulcerative colitis appears to be dominated by CD4+ lymphocytes with an atypical type 2 helper T cell (Th2) phenotype. Recruitment of inflammatory cells from the circulation is an important process to augment the inflammatory response. Activated macrophages produce pro-inflammatory cytokines TNF-α, IL-6 and IL-8 among others. TNF-α and IL-6 induce the expression of adhesion molecules like selectin, intercellular adhesion molecule-1 (ICAM-1) and adhesion molecule-1 in the vascular endothelium. This phenomenon causes the invasion of inflammatory cells into the mucosal layer. Leukocytes produce the superoxide radical and pro-inflammatory substances. These include arachidonic acid metabolites (leukotriene B4, prostaglandin E2), and nitric oxide (NO). NO interacts with superoxide radicals to produce peroxynitrite, which exerts a cytotoxic effect on gastrointestinal mucosa. Reactive oxygen metabolites play an important role in the direct injury of the intestinal mucosa. Therefore, in order to prevent this sequence of events and the resulting intestinal damage it is very important to reduce the release of pro-inflammatory cytokines and the perpetrators of oxidative-nitrative stress.

Current anti-inflammatory treatment for colitis employs 5-amino salicylate or its precursors, corticosteroids such as beclometasone or budesonide, immunosuppressive agents like azathioprine and immuno-regulatory agents like infliximab and adalimumab. However, while effective, some of the treatments may increase the risk of infections and produce other serious adverse effects in a significant proportion of patients.

Chyan et al., (J. Biol. Chem. 1999; 274: 21937-21942) reported that 3-indole-propionic acid (IPA) protects primary neurones in culture against oxidative damage induced by beta amyloid.

SUMMARY

There is therefore a need for therapeutic agents that can reduce the production of oxidative stress, and excessive release of NO and pro-inflammatory cytokines, but do not block their receptors, thereby preventing potentially beneficial effects of cytokines in other tissues. In order to achieve an effective treatment of neurological diseases such as for example AD, it is desirable that the therapeutic concentrations exhibiting inhibition of AChE would not be lower than those exhibiting anti-oxidant and anti-inflammatory activity as well.

The inventors of the present application have surprisingly found that derivatives of indoline were more potent and effective than IPA both as radical scavengers and in protecting cardiomyocytes from $H_2O_2$-induced cell death. Without being bound by theory this increased efficacy may result from the fact that the indolines have an anilinic type of amino group that should enable them to undergo a facile oxidation to the corresponding quinoidal type of compounds, whereas the indole which is aromatic may be more resistant to oxidation. Thus, as the indolines are oxidized they can act as reducing agents more readily than the corresponding indoles. Introduction of an electron rich group (such as for example hydroxyl group) into positions, such as for example 4 and 6 of the bicyclic ring, further increased the protective activity of the indolines against oxidative stress in cardiomyocytes. Carbamylation of the hydroxyl groups further provides acetylcholinesterase (AChE) and butyrylcholinesterase (BuChE) inhibitory activity.

The present invention provides a compound of general formula (I), including any stereoisomer and salt thereof:

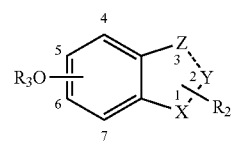

(I)

wherein

----- is a single or double bond;

X, Y, Z are each independently selected from C, CH, $CH_2$, N, NH, $NR_1$, O, S; provided that at least one of X, Y or Z is $NR_1$;

$R_1$ is selected from H, straight or branched $C_1$-$C_5$ alkyl, straight or branched $C_2$-$C_6$ alkenyl; straight or branched $C_2$-$C_6$ alkynyl; wherein said alkyl, alkenyl and alkynyl are each optionally substituted by at least one group selected from —C(=O)O($C_1$-$C_5$alkyl), $NR_7R_8$ and amino;

$R_2$ is selected from H, —COH, straight or branched $C_1$-$C_{10}$ alkyl, straight or branched $C_2$-$C_{10}$ alkenyl; wherein said alkyl and alkenyl are each substituted by at least one substituent selected from —$NO_2$, amino, amido, tetrazolyl, pentazolyl, —CONHSO$_2$H, —CONHSO$_2$phenyl and —COR$_4$; provided that when R$_1$ is H, R$_2$ is different than H;

R$_4$ is selected from —OH, —NH$_2$, —O(C$_1$-C$_{10}$alkyl), wherein said alkyl is optionally interrupted by at least one heteroatom selected from O or S; said alkyl is optionally substituted by at least one group selected from amino, morpholino, —O(C$_1$-C$_5$alkyl), and —OCO(C$_1$-C$_5$alkyl);

R$_3$ is selected from H, —OCOR$_5$ and CONR$_5$R$_6$; provided that when R$_3$ is H at least one of R$_1$ and R$_2$ are different than H;

R$_5$, R$_6$, R$_7$ and R$_8$ are each independently and differently selected from straight or branched C$_1$-C$_{10}$ alkyl and aryl; each optionally substituted by at least one substituent selected from —OH, C$_1$-C$_5$ alkoxy.

In some embodiments a compound of the invention has the general formula (II), including any stereoisomer and salt thereof:

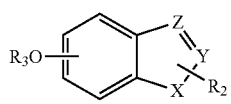

(II)

wherein R$_2$ and R$_3$ are as defined herein above. In further embodiments, X is NR$_1$, Y and Z are CH. In yet other embodiments, X is NR$_1$, Y is CH and Z is N. In some other embodiments, X is NR$_1$, Y is N and Z is CH. In further embodiments, X is NR$_3$, Y and Z are independently CH or CR$_2$.

In other embodiments a compound of the invention has the general formula (III), including any stereoisomer and salt thereof:

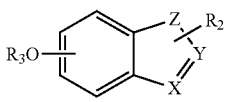

(III)

wherein R$_2$ and R$_3$ are as defined herein above. In some embodiments, Z is NR$_1$, X and Y are CH. In further embodiments, Z is NR$_1$, X is CH and Y is N. In other embodiments, Z is NR$_1$, X is N and Y is CH. In further embodiments, Z is NR$_1$, X and Y are independently CH or CR$_2$.

In other embodiments a compound of the invention has the general formula (IV), including any stereoisomer and salt thereof:

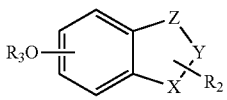

(IV)

wherein R$_2$ and R$_3$ are as defined herein above. In some embodiments, at least two of X, Y and Z are independently CH$_2$ or CHR$_2$.

In some embodiments a compound of the invention is defined as having R$_3$—CONR$_5$R$_6$; wherein R$_5$ and R$_6$ are as defined herein above.

In further embodiments, a compound of the invention has substituent —OR$_3$ substituted at positions 4, 6 or 7 of the bicyclic ring.

In another one of its aspects the invention provides a compound having the general formula (IV), including any stereoisomer and salt thereof:

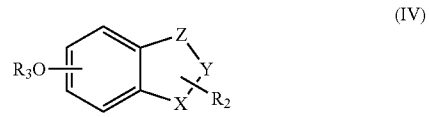

(IV)

wherein

X, Y, Z are each independently selected from CH, CH$_2$, NR$_1$, O and S; provided that at least one of X, Y or Z is NR$_1$;

R$_1$ is selected from H, straight or branched C$_1$-C$_5$ alkyl, straight or branched C$_2$-C$_6$ alkenyl; straight or branched C$_2$-C$_6$ alkynyl; wherein said alkyl, alkenyl and alkynyl are each optionally substituted by at least one group selected from —C(=O)O(C$_1$-C$_5$alkyl), NR$_7$R$_8$ and amino;

R$_2$ is selected from H, —COH, straight or branched C$_1$-C$_{10}$ alkyl, straight or branched C$_2$-C$_{10}$ alkenyl; wherein said alkyl and alkenyl are each substituted by at least one substituent selected from NO$_2$, amino, amido, tetrazolyl, pentazolyl, —CONHSO$_2$H, —CONHSO$_2$phenyl and —COR$_4$; provided that when R$_1$ is H, R$_2$ is different than H;

R$_4$ is selected from —OH, —NH$_2$, —O(C$_1$-C$_{10}$alkyl), wherein said alkyl is optionally interrupted by at least one heteroatom selected from O or S; said alkyl is optionally substituted by at least one group selected from amine, amino, morpholino, —O(C$_1$-C$_5$alkyl), and —OCO(C$_1$-C$_5$alkyl);

R$_3$ is selected from H, —OCOR$_5$ and —CONR$_5$R$_6$; provided that when R$_3$ is H at least one of R$_1$ and R$_2$ are different than H;

R$_5$, R$_6$, R$_7$ and R$_8$ are each independently and differently selected from straight or branched C$_1$-C$_{10}$ alkyl and aryl; each optionally substituted by at least one substituent selected from —OH, C$_1$-C$_5$ alkoxy.

In a further aspect the invention provides a compound having the general formula (V), including any stereoisomer and salt thereof:

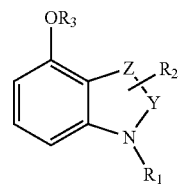

(V)

wherein

Y and Z are each independently selected from CH, CH$_2$, O and S;

R$_1$ is selected from H, straight or branched C$_1$-C$_5$ alkyl, straight or branched C$_2$-C$_6$ alkenyl; straight or branched C$_2$-C$_6$ alkynyl; wherein said alkyl, alkenyl and alkynyl are each optionally substituted by at least one group selected from —C(=O)O(C$_1$-C$_5$alkyl), NR$_7$R$_8$ and amino;

R$_2$ is selected from H, —COH, straight or branched C$_1$-C$_{10}$ alkyl, straight or branched C$_2$-C$_{10}$ alkenyl; wherein said alkyl and alkenyl are each substituted by at least one substituent selected from NO$_2$, amino, amido, tetrazolyl, pentazolyl, —CONHSO$_2$H, —CONHSO$_2$phenyl and —COR$_4$; provided that when R$_1$ is H, R$_2$ is different than H;

$R_4$ is selected from —OH, —NH$_2$, —O(C$_1$-C$_{10}$alkyl), wherein said alkyl is optionally interrupted by at least one heteroatom selected from O or S; said alkyl is optionally substituted by at least one group selected from amine, amino, morpholino, —O(C$_1$-C$_5$alkyl), and —OCO(C$_1$-C$_5$alkyl);

$R_3$ is selected from H, —OCOR$_5$ and CONR$_5$R$_6$; provided that when $R_3$ is H at least one of $R_1$ and $R_2$ are different than H;

$R_5$, $R_6$, $R_7$ and $R_8$ are each independently and differently selected from straight or branched C$_1$-C$_{10}$ alkyl and aryl; each optionally substituted by at least one substituent selected from —OH, C$_1$-C$_5$ alkoxy.

In yet another one of its aspects the invention provides a compound having the general formula (VI), including any stereoisomer and salt thereof:

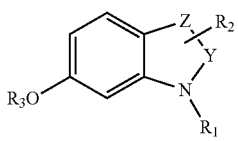

(VI)

wherein

Y and Z are each independently selected from CH, CH$_2$, O and S;

$R_1$ is selected from H, straight or branched C$_1$-C$_5$ alkyl, straight or branched C$_2$-C$_6$ alkenyl; straight or branched C$_2$-C$_6$ alkynyl; wherein said alkyl, alkenyl and alkynyl are each optionally substituted by at least one group selected from —C(=O)O(C$_1$-C$_5$alkyl), NR$_7$R$_8$ and amino;

$R_2$ is selected from H, —COH, straight or branched C$_1$-C$_{10}$ alkyl, straight or branched C$_2$-C$_{10}$ alkenyl; wherein said alkyl and alkenyl are each substituted by at least one substituent selected from —NO$_2$, amino, amido, tetrazolyl, pentazolyl, —CONHSO$_2$H, —CONHSO$_2$phenyl and —COR$_4$; provided that when $R_1$ is H, $R_2$ is different than H;

$R_4$ is selected from —OH, —NH$_2$, —O(C$_1$-C$_{10}$alkyl), wherein said alkyl is optionally interrupted by at least one heteroatom selected from O or S; said alkyl is optionally substituted by at least one group selected from amine, amino, morpholino, —O(C$_1$-C$_5$alkyl), and —OCO(C$_1$-C$_5$alkyl);

$R_3$ is selected from H, —OCOR$_5$ and CONR$_5$R$_6$; provided that when $R_3$ is H at least one of $R_1$ and $R_2$ are different than H;

$R_5$, $R_6$, $R_7$ and $R_8$ are each independently and differently selected from straight or branched C$_1$-C$_{10}$ alkyl and aryl; each optionally substituted by at least one substituent selected from —OH, C$_1$-C$_5$ alkoxy.

In another one of its aspects the invention provides a compound having the general formula (VII), including any stereoisomer and salt thereof:

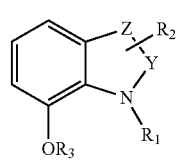

(VII)

wherein

Y and Z are each independently selected from CH, CH$_2$, O and S;

$R_1$ is selected from H, straight or branched C$_1$-C$_5$ alkyl, straight or branched C$_2$-C$_6$ alkenyl; straight or branched C$_2$-C$_6$ alkynyl; wherein said alkyl, alkenyl and alkynyl are each optionally substituted by at least one group selected from —C(=O)O(C$_1$-C$_5$alkyl), NR$_7$R$_8$ and amino;

$R_2$ is selected from H, —COH, straight or branched C$_1$-C$_{10}$ alkyl, straight or branched C$_2$-C$_{10}$ alkenyl; wherein said alkyl and alkenyl are each substituted by at least one substituent selected from NO$_2$, amino, amido, tetrazolyl, pentazolyl, —CONHSO$_2$H, —CONHSO$_2$phenyl and —COR$_4$; provided that when $R_1$ is H, $R_2$ is different than H;

$R_4$ is selected from —OH, —NH$_2$, —O(C$_1$-C$_{10}$alkyl), wherein said alkyl is optionally interrupted by at least one heteroatom selected from O or S; said alkyl is optionally substituted by at least one group selected from amine, amino, morpholino, —O(C$_1$-C$_5$alkyl), and —OCO(C$_1$-C$_5$alkyl);

$R_3$ is selected from H, —OCOR$_5$ and CONR$_5$R$_6$; provided that when $R_3$ is H at least one of $R_1$ and $R_2$ are different than H;

$R_5$, $R_6$, $R_7$ and $R_8$ are each independently and differently selected from straight or branched C$_1$-C$_{10}$ alkyl and aryl; each optionally substituted by at least one substituent selected from —OH, C$_1$-C$_5$ alkoxy.

The invention further encompasses a compound as defined hereinabove, being a pharmaceutically acceptable salt thereof.

The invention further provides a compound as defined hereinabove, for use as a medicament.

In a further one of its aspects the invention provides a compound as defined hereinabove, for use in the reduction of at least one condition selected from oxidative stress, release of NO and release of pro-inflammatory cytokine.

The term "reduction of oxidative stress" is meant to encompass any qualitative or quantitative reduction in the production and manifestation of reactive oxygen species in any biological system. Disturbances in the normal redox state of tissues can cause toxic effects through the production of peroxides and free radicals that damage all components of the cell, including proteins, lipids, and DNA. Some reactive oxidative species can even act as messengers in redox signaling. In humans, oxidative stress is involved in many conditions, diseases or disorders. Non-limiting examples include: Sickle Cell Disease; atherosclerosis, Parkinson's disease, Alzheimer's disease; heart failure; myocardial infarction; Schizophrenia; Bipolar disorder; fragile X syndrome and; chronic fatigue syndrome, colitis and diabetes. Short-term oxidative stress may also be important in prevention of aging by induction of a process named mitohormesis.

The term "reduction of release of NO" is meant to encompass any qualitative or quantitative reduction in the release of nitric oxide (NO) in any biological system. It is noted that NO has been demonstrated to activate NF-κB in peripheral blood mononuclear cells, an important transcription factor in iNOS gene expression in response to inflammation. Furthermore, chronic expression of NO is associated with various carcinomas and inflammatory conditions including Type-1 diabetes, multiple sclerosis, arthritis and ulcerative colitis.

The term "reduction of release of pro-inflammatory cytokine" is meant to encompass any qualitative or quantitative reduction in the release of at least one cytokine which promotes systemic inflammation in any biological system. Non-limiting examples include IL-1, and TNF alpha.

In another one of its aspects the invention provides a compound as defined herein above, for use in the inhibition of at least one of oxidative stress, inflammation and cholinesterase.

The term "inhibition" is meant to encompass any decrease (qualitative or quantitative) or prevention of oxidative stress, inflammation and/or cholinesterase in any biological system.

The term "inhibition of cholinesterase" is meant to encompass any quantitative or qualitative inhibition of any type of cholinesterase enzyme, including acetylcholinesterase (AChE) and butyrylcholinesterase (BuChE). Said inhibition is capable or decreasing or preventing the activity of any type of cholinesterase enzyme from breaking down acetylcholine, increasing both the level and duration of action of the neurotransmitter.

In another one of its aspects the invention provides a compound as defined herein above, for use in the prevention, treatment or slowing the progression of a neurodegenerative disease, disorder or condition including any symptoms thereof.

In some embodiments said conditions are associated with a neurodegenerative disease, disorder or symptom. In other embodiments said neurodegenerative disease, disorder or symptom is selected from Alzheimer's disease, Parkinson's disease, dementia, multiple sclerosis, meningitis, infective brain disease, ischemic stroke, amyotropic lateral sclerosis, mild cognitive impairment, and any combination thereof.

In a further aspect the invention provides a compound as defined herein above, for use in the prevention, treatment or slowing the progression of an inflammatory disease, disorder or condition including any symptoms thereof.

In some other embodiments said conditions are associated with an inflammatory disease, disorder or symptom. In further embodiments, said inflammatory disease, disorder or symptom is selected from ulcerative colitis, Crohn's disease, rheumatoid arthritis, diabetes, cardiac failure, chronic liver disease, chronic lung disease, meningitis, brain infections, complex regional pain syndrome (CRPS) and any combinations thereof.

The invention further encompasses a composition comprising at least one compound as defined herein above.

The invention further provides a use of a compound as defined herein above, for the preparation of a medicament.

The invention provides a use of a compound as defined herein above, for the preparation of a medicament for the treatment of a disease, disorder, condition or symptom associated with the inhibition of at least one of oxidative stress, inflammation and cholinesterase.

The invention further provides a use of a compound as defined herein above, for the preparation of a medicament for the reduction of at least one condition selected from oxidative stress, release of NO and release of pro-inflammatory cytokine.

In some embodiments said disease, disorder, condition or symptom associated with the inhibition of at least one of oxidative stress, inflammation and cholinesterase is selected from at least one of Alzheimer's disease, Parkinson's disease, ischemic stroke, amyotropic lateral sclerosis, multiple sclerosis, mild cognitive impairment, ulcerative colitis, Crohn's disease, rheumatoid arthritis, diabetes, cardiac failure, chronic liver disease, chronic lung disease, meningitis, infective brain disease, complex regional pain syndrome (CRPS) and any combinations thereof.

The invention further encompasses a compound of general formula (IV), including any stereoisomer and salt thereof for use in the reduction of at least one condition selected from oxidative stress, release of NO and release of at least one pro-inflammatory cytokine:

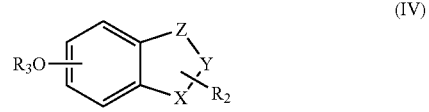

(IV)

wherein

X, Y, Z are each independently selected from C, CH, $CH_2$, $NR_1$, O, S, and N; provided that at least one of X, Y or Z is $NR_1$;

$R_1$ is selected from H, straight or branched $C_1$-$C_5$ alkyl, straight or branched $C_2$-$C_6$ alkenyl; straight or branched $C_2$-$C_6$ alkynyl; wherein said alkyl, alkenyl and alkynyl are each optionally substituted by at least one group selected from —C(═O)O($C_1$-$C_5$alkyl), $NR_7R_8$ and amino;

$R_2$ is selected from H, —COH, straight or branched $C_1$-$C_{10}$ alkyl, straight or branched $C_2$-$C_{10}$ alkenyl; wherein said alkyl and alkenyl are each optionally substituted by at least one substituent selected from $NO_2$, amino, amido, tetrazolyl, pentazolyl, —$CONHSO_2H$, —$CONHSO_2phenyl$ and —$COR_4$;

$R_4$ is selected from —OH, —$NH_2$, —O($C_1$-$C_{10}$alkyl), wherein said alkyl is optionally interrupted by at least one heteroatom selected from O or S; said alkyl is optionally substituted by at least one group selected from amine, amino, morpholino, —O($C_1$-$C_5$alkyl), and —OCO($C_1$-$C_5$alkyl);

$R_3$ is selected from H, —$OCOR_5$ and $CONR_5R_6$; provided that when $R_3$ is H at least one of $R_1$ and $R_2$ are different than H;

$R_5$, $R_6$, $R_7$ and $R_8$ are each independently and differently selected from straight or branched $C_1$-$C_{10}$ alkyl and aryl; each optionally substituted by at least one substituent selected from —OH, $C_1$-$C_5$ alkoxy.

In yet a further aspect the invention provides a compound of general formula (IV), including any stereoisomer and salt thereof; for use in the inhibition of at least one of oxidative stress, inflammation and cholinesterase:

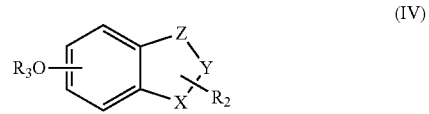

(IV)

wherein

X, Y, Z are each independently selected from C, CH, $CH_2$, $NR_1$, O, S, and N; provided that at least one of X, Y or Z is $NR_1$;

$R_1$ is selected from H, straight or branched $C_1$-$C_5$ alkyl, straight or branched $C_2$-$C_6$ alkenyl; straight or branched $C_2$-$C_6$ alkynyl; wherein said alkyl, alkenyl and alkynyl are each optionally substituted by at least one group selected from —C(═O)O($C_1$-$C_5$alkyl), $NR_7R_8$ and amino;

$R_2$ is selected from H, —COH, straight or branched $C_1$-$C_{10}$ alkyl, straight or branched $C_2$-$C_{10}$ alkenyl; wherein said alkyl and alkenyl are each optionally substituted by at least one substituent selected from $NO_2$, amino, amido, tetrazolyl, pentazolyl, —$CONHSO_2H$, —$CONHSO_2phenyl$ and —$COR_4$;

$R_4$ is selected from —OH, —$NH_2$, —O($C_1$-$C_{10}$alkyl), wherein said alkyl is optionally interrupted by at least one hetero atom selected from O or S; said alkyl is optionally substituted by at least one group selected from amine, amino, morpholino, —O(C$_1$-C$_5$alkyl), and —OCO(C$_1$-C$_5$alkyl);

R$_3$ is selected from H, —OCOR$_5$ and CONR$_5$R$_6$; provided that when R$_3$ is H at least one of R$_1$ and R$_2$ are different than H;

R$_5$, R$_6$, R$_7$ and R$_8$ are each independently and differently selected from straight or branched C$_1$-C$_{10}$ alkyl and aryl; each optionally substituted by at least one substituent selected from —OH, C$_1$-C$_5$ alkoxy.

In a further aspect the invention provide a compound of general formula (X)

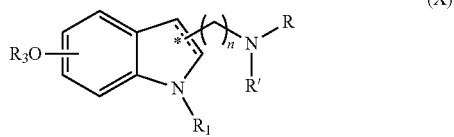

(X)

wherein n is an integer between 0 and 10 (0, 1, 2, 3, 4, 5, 6, 7, 8, 9 and 10); R and R' are each selected from H, straight or branched C$_{1-6}$ actyl, straight or branched C$_{1-6}$ alkyl, straight or branched C$_{2-6}$ alkenyl, straight or branched C$_{2-6}$ alkynyl, or form together with the N atom a heterocyclic ring selected from pyrrolidine, piperidine, morpholino and piperazino; and R$_1$ and R$_3$ are as defined herein above (provided that at least one of R$_1$ and R$_3$ are different than H when n=0). In some embodiments R$_1$ is selected from straight or branched C$_{1-6}$ alkyl, straight or branched C$_{2-6}$ alkenyl, straight or branched C$_{2-6}$ alkynyl optionally substituted by an amido group.

In some embodiments a compound of the invention is selected from:

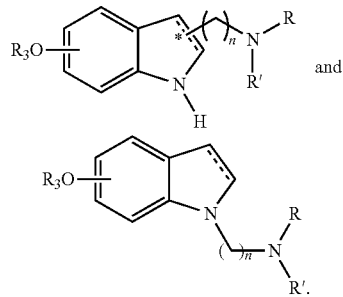

In another one of its aspects the invention provides a method of treating a disease, disorder, condition or symptom in a subject associated with the inhibition of at least one of oxidative stress, inflammation and cholinesterase; said method comprising administering to said subject an effective amount of at least one compound of general formula (IV), including any stereoisomer and salt thereof:

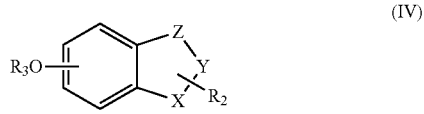

(IV)

wherein

X, Y, Z are each independently selected from C, CH, CH$_2$, NR$_1$, O, S, and N; provided that at least one of X, Y or Z is NR$_1$;

R$_1$ is selected from H, straight or branched C$_1$-C$_5$ alkyl, straight or branched C$_2$-C$_6$ alkenyl; straight or branched C$_2$-C$_6$ alkynyl; wherein said alkyl, alkenyl and alkynyl are each optionally substituted by at least one group selected from —C(=O)O(C$_1$-C$_5$alkyl), NR$_7$R$_8$ and amino;

R$_2$ is selected from H, —COH, straight or branched C$_1$-C$_{10}$ alkyl, straight or branched C$_2$-C$_{10}$ alkenyl; wherein said alkyl and alkenyl are each optionally substituted by at least one substituent selected from NO$_2$, amino, amido, tetrazolyl, pentazolyl, —CONHSO$_2$H, —CONHSO$_2$phenyl and —COR$_4$;

R$_4$ is selected from —OH, —NH$_2$, —O(C$_1$-C$_{10}$alkyl), wherein said alkyl is optionally interrupted by at least one hetero atom selected from O or S; said alkyl is optionally substituted by at least one group selected from amine, amino, morpholino, —O(C$_1$-C$_5$alkyl), and —OCO(C$_1$-C$_5$alkyl);

R$_3$ is selected from H, —OCOR$_5$ and —CONR$_5$R$_6$; provided that when R$_3$ is H at least one of R$_1$ and R$_2$ are different than H;

R$_5$, R$_6$, R$_7$ and R$_8$ are each independently and differently selected from straight or branched C$_1$-C$_{10}$ alkyl and aryl; each optionally substituted by at least one substituent selected from —OH, C$_1$-C$_5$ alkoxy.

In the structural formulae given herein and throughout the present specification, the following terms have the indicated meaning:

The term "C$_{1-6}$-alkyl" as used herein represents a saturated, branched or straight hydrocarbon group having from 1 to 6 carbon atoms. Typical C 1-6-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "C$_{2-6}$-alkenyl" as used herein represents a branched or straight hydrocarbon group having from 2 to 6 carbon atoms and at least one double bond. Examples of such groups include, but are not limited to, ethenyl, 1-propenyl, 2-propenyl, isopropenyl, 1,3-butadienyl, 1-butenyl, 2-butenyl, 1-pentenyl, 2-pentenyl, 1-hexenyl, 2-hexenyl and the like.

The term "C$_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 1-pentynyl, 2-pentynyl, 1-hexynyl, 2-hexynyl and the like.

The term "C$_{3-6}$-alkylene" as used herein represent a saturated, divalent, branched or straight hydrocarbon group having from 3 to 6 carbon atoms. Typical C 3-6-alkylene groups include, but are not limited to, 1,2-propylene, 1,3-propylene, butylene, isobutylidene, pentylene, hexylene and the like.

The term "C$_{3-6}$-alkenylene" as used herein represent a divalent, branched or straight hydrocarbon group having from 3 to 6 carbon atoms and at least one double bond. Typical C 3-6-alkenylene groups include, but are not limited to, n-propenylene, butenylene, pentenylene, hexenylene and the like.

The term "C$_{1-6}$-alkoxy" as used herein refers to the radical —O—C1-6-alkyl, wherein C 1-6-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "C$_{1-6}$-alkylthio" as used herein refers to the radical —S—C 1-6-alkyl, wherein C 1-6-alkyl is as defined above. Representative examples are methylthio, ethylthio, isopropylthio, n-propylthio, butylthio, pentylthio and the like.

The term "C$_{1-6}$-alkylsulfinyl" as used herein refers to the radical —S(═O)—C 1-6-alkyl, wherein C$_{1-6}$-alkyl is as defined above. Representative examples are methylsulfinyl, ethylsulfinyl, isopropylsulfinyl, n-propylsulfinyl, butylsulfinyl, pentylsulfinyl and the like.

The term "C$_{1-6}$-alkylsulfonyl" as used herein refers to the radical —S(═O) 2-C 1-6-alkyl, wherein C$_{1-6}$-alkyl is as defined above. Representative examples are methylsulfonyl, ethylsulfonyl, isopropylsulfonyl, n-propylsulfonyl, butylsulfonyl, pentylsulfonyl and the like.

The term "C$_{1-7}$-alkanoyl" as used herein refers to the radical —C(═O)H or —C(═O)C1-6-alkyl, wherein C 1-6-alkyl is as defined above. Representative examples are formyl, acetyl, propionyl, butanoyl, pentanoyl, hexanoyl, heptanoyl and the like.

The term "C$_{1-6}$-alkylcarbamoyl" as used herein refers to the radical —C(═O)NH—C$_{1-6}$-alkyl, wherein C$_{1-6}$-alkyl is as defined above. Representative examples are methylcarbamoyl, ethylcarbamoyl, isopropylcarbamoyl, n-propylcarbamoyl, butylcarbamoyl, pentylcarbamoyl, hexylcarbamoyl and the like.

The term "di-C$_{1-6}$-alkylcarbamoyl" as used herein refers to the radical —C(═O)N(C$_{1-6}$-alkyl)$_2$, wherein C$_{1-6}$-alkyl is as defined above. It should be understood that the C$_{1-6}$-alkyl groups may be the same or different. Representative examples are dimethylcarbamoyl, methylethylcarbamoyl, diethylcarbamoyl, diisopropylcarbamoyl, di-n-propylcarbamoyl, dibutylcarbamoyl, dipentylcarbamoyl, dihexylcarbamoyl and the like.

The term "C$_{3-8}$-cycloalkyl" as used herein represents a monocyclic, carbocyclic group having from from 3 to 8 carbon atoms. Representative examples are cyclopropyl, cyclobutyl, cyclopentyl, cyclohexyl, cycloheptyl, cyclooctyl and the like.

The term "C$_{5-8}$-cycloalkenyl" as used herein represents a monocyclic, carbocyclic, non-aromatic group having from 5 to 8 carbon atoms and at least one double bond. Representative examples are cyclopentenyl, cyclohexenyl, cycloheptenyl, cyclooctenyl, and the like.

The term "C$_{3-8}$-cycloalkanoyl" as used herein refers to the radical —C(═O)—C 3-8-cycloalkyl, wherein C 3-8-cycloalkyl is as defined above. Representative examples are cyclopropanoyl, cyclobutanoyl, cyclopentanoyl, cyclohexanoyl, cycloheptanoyl, cyclooctanoyl, and the like.

The term "C$_{3-8}$-cycloalkylcarbamoyl" as used herein refers to the radical —C(═O)NH—C$_{3-8}$-cycloalkyl, wherein C$_{3-8}$-cycloalkyl is as defined above. Representative examples are cyclopropylcarbamoyl, cyclobutylcarbamoyl, cyclopentylcarbamoyl, cyclohexylcarbamoyl, cycloheptylcarbamoyl, cyclooctylcarbamoyl, and the like.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "aryloxy" as used herein refers to the radical —O-aryl, wherein aryl is as defined above. Non-limiting examples are phenoxy, naphthoxy, anthracenyloxy, phenantrenyloxy, fluorenyloxy, indenyloxy and the like.

The term "aroyl" as used herein refers to the radical —C(═O)-aryl, wherein aryl is as defined above. Non-limiting examples are benzoyl, naphthoyl, anthracenylcarbonyl, phenantrenylcarbonyl, fluorenylcarbonyl, indenylcarbonyl and the like.

The term "heteroaryl" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzothiazolyl, benzoisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indanyl, indolinyl, oxazolidinyl, oxazolinyl, oxazepinyl and the like.

The term "heteroaroyl" as used herein refers to the radical —C(═O)-heteroaryl, wherein heteroaryl is as defined above.

The term "heteroaryloxy" as used herein refers to the radical —O-heteroaryl, wherein heteroaryl is as defined above.

The term "amine" or "amino" refer to a primary (—NH$_2$), secondary (—NHR), tertiary (—NRR') or quarternary amine (—NRR'R"$^+$) group wherein R, R' and R" are independently selected from H, straight or branched C$_{1-6}$ actyl, straight or branched C$_{1-6}$ alkyl, straight or branched C$_{2-6}$ alkenyl, straight or branched C$_{2-6}$ alkynyl, or form together with the N atom a heterocyclic ring selected from pyrrolidine, piperidine, morpholino and piperazino.

The term "amido" refer to an amide group (—C(═O)NRR') wherein R, R' and R" are independently selected from H, straight or branched C$_{1-6}$ actyl, straight or branched C$_{1-6}$ alkyl, straight or branched C$_{2-6}$ alkenyl, straight or branched C$_{2-6}$ alkynyl.

The term "morpholino" refers to a morpholine radical ring of either O(CH$_2$)$_4$N— or O(CH$_2$)$_3$NHCH—

The term "tetrazolyl" refers to a 5-member heterocyclic ring CHN$_4$ (either bonded through a nitrogen atom or a carbon atom).

The term "pentazolyl" refers to a 5-member heterocyclic ring —N$_4$.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question have more than one substituent the latter may be the same or different.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular, a human being.

The present invention also relates to pharmaceutical compositions comprising a compound of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The exact dose and regimen of administration of the composition will necessarily be dependent upon the therapeutic or nutritional effect to be achieved and may vary with the particular formula, the route of administration, and the age and condition of the individual subject to whom the composition is to be administered.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also included within the scope of the invention are the individual isomers of the compounds of the invention as well as any wholly or partially equilibrated mixtures thereof. The present invention also covers the individual isomers of the compounds represented by the formulas above as mixtures with isomers thereof in which one or more chiral centers are inverted.

It is also noted that the compounds of the invention may form tautomers. It is understood that all tautomers and mixtures of tautomers of the compounds of the present invention are included within the scope of the compounds of the present invention.

The invention also includes any salt of a compound of the invention, including any pharmaceutically acceptable salt, wherein a compound of the invention has a net charge (either positive or negative) and at least one counter ion (having a counter negative or positive charge) is added thereto to form said salt. The phrase "pharmaceutically acceptable salt(s)", as used herein, means those salts of compounds of the invention that are safe and effective for pharmaceutical use in mammals and that possess the desired biological activity.

Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts (See Berge et al., *J. Pharm. Sci.* 66, 1-19 (1977), incorporated herein by reference).

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 8A-8D show the effect of 689E (10.5 μmoles/kg) of the tosylate salt administered subcutaneously to mice with DSS (5%)-induced colitis on body weight loss (FIG. 8A), diarrhea (FIG. 8B), bleeding (FIG. 8C) and the composite DAI score (FIG. 8D). Data represent the mean±SEM from 10 mice per group. Significantly different from DSS alone * p<0.05; ** p<0.01.

DETAILED DESCRIPTION OF EMBODIMENTS

Synthetic Procedures

Figure 1:
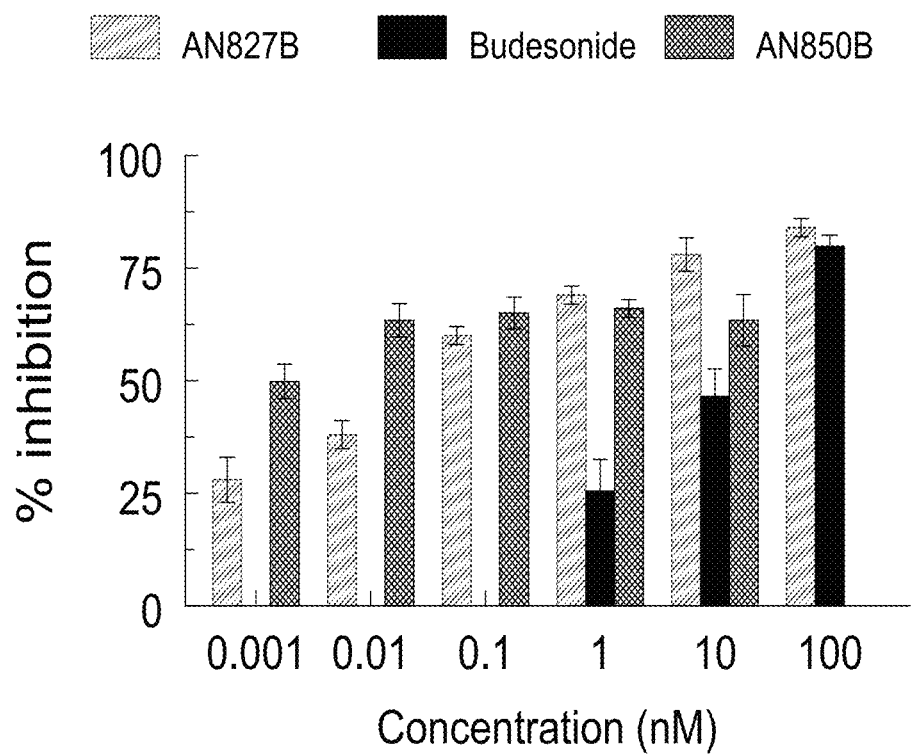
FIG. 1 shows the inhibition of LPS-induced release of NO from macrophage-like RAW cells by compounds AN-827B, AN-850B the methane sulfonic acid (mesylate salt) of AN-850 as compared with budesonide.

General $^1$H-NMR, $^{13}$C-NMR and $^{19}$F-NMR spectrum were obtained on Bruker Avance-200, Avance-DPX-300, Avance-DMX-600 and Avance-III-700 spectrometers. Chemical shifts are expressed in ppm downfield from Me$_3$Si (TMS) used as internal standard. The values are given in δ scale. The "t" is indicative of a multiplet similar to a triplet with second order characteristics. Mass spectra (MS) were obtained on a Varian Mat 731 spectrometer (CI$^+$=chemical ionization). HRMS were obtained on AutoSpec spectrometer (Water company-UK) (CI$^+$ CH$_4$). Electron Spray ionization (ESI) was obtained on a Micromass Q-TOF Micro mass spectrometer (Micromass (Waters) UK). MALDI were obtained on Autoflex III in TOFTOF mode (Bruker, Germany). Elemental analyses (EA) (CHNO) were obtained using a CHNS—O analyzer using a Flash EA model (Italy). Progress of the reactions was monitored by TLC on silica gel (Merck, Art. 5554). All the flash chromatographic procedures were carried out on silica gel (Merk, Art. 9385). All moisture sensitive reactions were carried out in flame-dried vessels. Melting points were determined on a Fisher-Johns apparatus.

Example 1

Procedure A

Synthesis of Carbamoyl Chlorides

To triphosgene (9.13 mmol) in dry CH$_2$Cl$_2$ (22 mL) at 0° C. was slowly added a solution of a secondary amine (23 mmol) and pyridine (3.77 mL, 50 mmol) in dry CH$_2$Cl$_2$ (11 mL). The mixture was stirred at room temperature for 30 min followed by addition of 0.1N HCl (21.5 mL). The organic layer was separate, dried over MgSO$_4$, filtered and concentrated to give the carbamoyl chloride.

Procedure B

Synthesis of Carbamates

Method I:

A carbamoyl chloride (15 mmol) was added to a solution of 4-, 5- or 6-hydroxyindole; or to 4-, 5-, 6- or 7-hydroxyindole-3-propanoic acid (or ester) (7.51 mmol) in dry CH$_2$Cl$_2$ (50 mL) containing NEt$_3$ (9.01 mmol) and 4-DMAP (10% mol). The mixture was stirred at room temperature for 24-72 h. Despite the use of 2 eq of carbamoyl chloride, starting phenolic material remained (determined by TLC analysis). The reaction was quenched by addition of water, and the mixture was extracted with CH$_2$Cl$_2$. The organic layer was washed with 5% NaHCO$_3$, brine, dried over MgSO$_4$ and evaporated to give the crude carbamates. The residual carbamates were purified either by chromatography, or by extraction with 2N NaOH and CH$_2$Cl$_2$ (in order to remove traces of unreacted hydroxyindoles and carbamoyl chlorides), followed by elution of the organic phase through a plug of silica gel, which was washed with EtOAc-Hex (1:1). The filtrate was evaporated and the residue was crystallized from CH$_2$Cl$_2$ and hexane.

Procedure C

Synthesis of Aldehydes by Vilsmeier Formylation

Phosphorus oxychloride (POCl$_3$) (5.38 mmol) was added dropwise with stirring to DMF (20 mmol) under N$_2$, the temperature being kept at 10-20° C. A carbamate (4.9 mmol) in DMF (3 mL) was slowly added with stirring, while maintaining the temperature of the mixture at 20-30° C. The mixture was then stirred at 35° C. for 45 min and was then cooled to room temperature. Cold water (10 mL) was added, followed by addition of a solution of 20% NaOH in water, until a pH~13. Although the reaction was exothermic, the mixture was further heated to its boiling point for 1 min, and was then stirred and allowed to cool to room temperature. In some cases, the product, which solidified at this stage, was filtered and the crystals were washed with water. In other cases, water was added followed by extraction with EtOAc. The organic phase was washed with water and brine, dried over MgSO$_4$ and evaporated to give the formylindoles.

Procedure D

Knoevenagel Condensation

To a solution of malonic acid monomethyl ester (2.18 mmol) in pyridine (8.09 mmol) containing a catalytic amount of piperidine (2-3 drops) was added a formylindole (1.46 mmol). The mixture was refluxed for 5-6 h, cooled to room temperature, diluted with EtOAc and acidified with 3N HCl to pH 7.0. The organic phase was separated, washed with brine, dried over MgSO$_4$ and evaporated to give the α,β-unsaturated ester.

Procedure E

Reduction of Indoles to Indolines

Method I:

NaBH$_3$CN (4.23 mmol) was added portion wise over 10 min at 0° C. to a solution of α,β-unsaturated system or to an indole (1.06 mmol) in AcOH (7.1 mL) and the mixture was stirred at room temperature from 1 h to overnight. Water (3 mL) was added and the solvent was removed under reduce pressure. The residue was dissolved in EtOAc and washed with saturated NaHCO$_3$ and brine, dried over MgSO$_4$ and evaporated to give the indoline.

The indoline hydrochloride was obtained after dissolving an indoline in EtOAc followed by extraction with 2N HCl. The aqueous phase was evaporated to give the reduced salt. An alternative method for the preparation of the indoline hydrochloride involved addition of HCl gas to a solution of indoline in dry ether.

Method II:

To an ice cold stirred solution of an indole (1.64 mmol) in TFA (12.5 mL) NaBH$_4$ (3.30 mmol) was added and the mixture was stirred for 22-77 h at room temperature. Water was then added followed by the addition of saturated NaHCO$_3$ until a pH=7-8. The mixture was then extracted with EtOAc, and brine, dried over Na$_2$SO$_4$ and concentrated to give the crude indoline, which was isolated by chromatography.

Procedure F

Deprotection of the Benzyloxy Group and Reduction of the α,β-Unsaturated System Method I:

To a solution of an α,β-unsaturated esteracidamide or/and compounds protected with a benzyl group (6.72 mmol) in EtOH (50 mL) was added 10% PdC (0.16 g) and HCO$_2$NH$_4$ (67 mmol). The mixture was refluxed for 1 h. The catalyst was removed by filtration through celite and concentrated to give the product.

Method II:

To a solution of an α,β-unsaturated esteracidamide or/and compounds protected with benzyl group or compounds containing a nitro group (1 eq) in EtOH, was added 10% PdC (10% ww). The mixture was stirred under H$_2$ at a 1-3 atm pressure for 4 h-2 d at room temperature. The mixture was then filtered through celite and concentrated.

Procedure G

Synthesis of N-Methyl Indoles

To a solution of methyl iodide (3 mmol) and an indole (3 mmol) in CH$_2$Cl$_2$ (50 mL) was added a solution of 50% NaOH (18 mmol) in water (0.72 mL). To the obtained mixture was added Bu$_4$N$^+$Br$^-$ (9 mmol). The mixture was stirred at room temperature for 16 h, extracted with CH$_2$Cl$_2$, washed with water and brine, dried over MgSO$_4$ and evaporated to give the methyl indole.

Procedure H

Hydrolysis of Methyl Esters

Method I:

To a solution of a methyl ester (0.133 mmol) in MeOH (3.36 mL) a 2 N solution of NaOH (0.46 mL) was added, and the obtained solution was stirred at room temperature overnight, evaporated and the residue was dissolved in EtOAc to which 1N HCl was added until a pH=1-2. The aqueous phase was separated, extracted with EtOAc (×3), and the organic layers were combined, washed with brine, dried over MgSO$_4$, filtered and evaporated to give the desired product.

Method II:

To a solution of a methyl ester (0.1 mmol) in MeOH (0.1 mL) and H$_2$O (0.5 mmol), KOH (0.5 mmol) was added and the mixture was stirred at room temperature for 18 h. The solution was concentrated to remove the MeOH and to the residue EtOAc was and the mixture was extracted with 1N HCl. The organic layer was washed with brine, dried over Na$_2$SO$_4$, filtered and evaporated to give the acid product.

Method III:

To an ice cold solution of a methyl ester (0.65 mmol) in MeOH (15 mL) and H$_2$O (2.5 mL), LiOH (6.5 mmol) was added. The obtained solution was refluxed for 3.5 h and was then diluted with EtOAc and extracted with 1N HCl. The organic layer was separated, washed with brine, dried over Na$_2$SO$_4$, filtered and evaporated to give the acid product.

Procedure I

Preparation of Carboxylic Acid Potassium Salts

To a solution of an acid (0.1 mmol) in EtOAc, Me$_3$SiO$^-$ K$^+$ (0.1 mmol) was added, and the solution obtained was stirred at room temperature for 15-20 min. The organic phase was extracted with H$_2$O (×2). The aqueous layers were combined and evaporated to give the K salts.

Procedure J

Protection of Phenols with TBSCl

To a solution of a phenol (0.9 mmol) in DMF (2 mL), under N$_2$ at room temperature was added imidazole (1.4 mmol). The mixture was stirred at room temperature for 10 min TBSCl (1.37 mmol) was then added and the obtained mixture was stirred at room temperature overnight. The solution was then diluted with EtOAc and extracted with water (2×30 mL). The organic layer was washed with brine, dried over MgSO$_4$, filtered and evaporated under reduced pressure to give the TBS-protected phenol.

Procedure K

Coupling with BOP

To a solution of an indole-3-propanoic acid (0.3 mmol) in DMF (6 mL), under N$_2$ at room temperature was added NEt$_3$ (0.3 mmol) and BOP (0.3 mmol). The mixture was stirred at room temperature for 45 min followed by addition of NaNH$_2$ (0.3 mmol). The mixture was stirred at room temperature overnight, diluted with EtOAc and washed with water (×2), 1N HCl (×2), NaHCO$_{3(aq)}$ (×2), brine, dried over MgSO$_4$, filtered and evaporated under reduced pressure to give the crude product.

Procedure L

Benzylation

To a suspension of a secondary amine or a phenol (1 eq) and Cs₂CO₃ (1 eq) in DMF (2.5 mL) was dropwise added benzyl bromide (1 eq) and the mixture was stirred at room temperature for 22-44 h. The solvent was evaporated and the crude residue was dissolved by EtOAc and extracted with water and the layers were separated. The organic phase was washed with brine, dried over Na₂SO₄, filtered and evaporated to give the benzylated amine or phenol.

Procedure M

Preparation of Citrate or Tartrate Salts

To a stirred solution of an amine (0.04 mmol) in EtOH/MeOH (1.5 mL) was added citric acid or L-(+)-tartaric acid (0.04 mmol). The mixture was stirred for 30 min at room temperature, and evaporated to give the citrate or tartrate salt.

Procedure N

Alkylation of Indoles with Methyl Acrylate

A stirred solution of an indole (0.46 mmol), methyl acrylate (0.69 mmol), and DBU (0.23 mmol) in CH₃CN (2 mL) was stirred at 50° C. for 19 h, extracted with EtOAc, washed with 1N HCl, dried over Na₂SO₄ and evaporated.

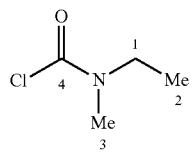

Ethylmethyl carbamoyl chloride, 2a

Compound 2a, prepared by procedure A, was isolated as a yellow liquid in 62% yield. $^1$H-NMR (300 MHz, CDCl₃) ppm δ 3.43+3.50 (q, J=21.4 Hz, 2H, H-1), 3.01+3.10 (s, 3H, H-3), 1.16+1.22 (m, 3H, H-2); $^{13}$C-NMR (75 MHz, CDCl₃) ppm δ 48.00, 46.47, 37.93, 36.14, 12.27, 13.00 (C-2).

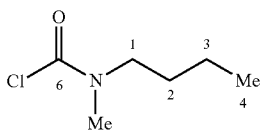

Butylmethyl Carbamoyl Chloride, 2b

Compound 2b, prepared by procedure A, was isolated as a yellow-brown liquid in 93% yield. $^1$H-NMR (300 MHz, CDCl₃) ppm δ 3.36 (m, 2H, H-1), 3.02 (m, 3H, H-5), 1.50 (m, 2H, H-2), 1.28 (m, 2H, H-3), 0.87 (m, 3H, H-4).

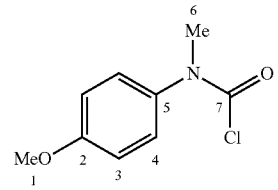

4-Methoxyphenyl(methyl) carbamoyl chloride, 2c

Compound 2c, prepared by procedure A, was isolated as a yellow-brown liquid in 57% yield. $^1$H-NMR (300 MHz, CDCl₃) ppm δ 7.14 (bd, J=8.4, 2.1 Hz, 2H, H-4), 6.91 (dd, J=8.4, 2.1 Hz, 2H, H-3), 3.79 (s, 3H, H-1), 3.31 (s, 3H, H-6); $^{13}$C-NMR (75 MHz, CDCl₃) ppm δ 159.31, 149.42, 136.11, 128.44, 114.63, 55.45, 40.48 (C-6).

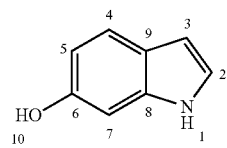

6-Hydroxyindole

6-Hydroxyindole was prepared from 6-benzyloxyindole by procedure F (Methods I or II), was isolated by chromatography eluted with EtOAc-hexane (1:1) to give white solid in 66% yield, mp 123-125° C. [128-129° C.]. $^1$H-NMR (300 MHz, CDCl₃) ppm δ 8.51 (bs, 1H, H-1), 7.41 (d, J=8.8 Hz, 1H, H-4), 6.94 (t, J=2.9 Hz, 1H, H-2), 6.80 (d, J=2.2 Hz, 1H, H-7), 6.71 (dd, J=8.8, 2.2 Hz, 1H, H-5), 6.38 (ddd, J=2.9, 1.5, 0.7 Hz, 1H, H-3); $^{13}$C-NMR (75 MHz, CDCl₃) ppm δ 152.19, 136.78, 123.09, 121.90, 120.87, 109.76, 101.74, 96.83 (C-7).

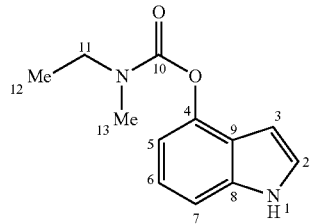 [SMILES: CCN(C)C(=O)Oc1cccc2[nH]ccc12]

1H-Indol-4-yl ethylmethylcarbamate, AN-651

Compound AN-651 was prepared from 4-hydroxyindole by procedure B, Method I, was isolated by chromatography eluted with EtOAc-hexane (1:3 to 1:2 to 1:1). It was also crystallized from EtOAc-hexane as white needle in 61% yield, mp 113-115° C. $^1$H-NMR (300 MHz, Acetone-d₆) ppm δ 10.31 (bs, 1H, H-1), 7.25-7.27 (m, 2H, H-2+H-7), 7.07 (t, J=7.2 Hz, 1H, H-6), 6.81 (d, J=2.0 Hz, 1H, H-5), 6.41 (bs, 1H, H-3), 3.37-3.59 (m, 2H, H-11), 3.18+2.99 (s, 3H, H-13), 1.18-1.31 (m, 3H, H-12). $^{13}$C-NMR (75 MHz, Acetone-d₆) ppm δ 154.75, 145.66, 139.02, 125.49, 122.85, 122.07, 112.25, 109.27, 99.30, 44.62, 28.78, 13.56, 12.72; MS (CI⁺) m/z 219.114 (MH⁺, 100.00), 218.109 (M, 31.30); HRMS calcd. for $C_{12}H_{15}N_2O_2$ (MH⁺, DCI⁺/CH₄) 219.1134. found 219.1138; Anal. Calcd. for $C_{12}H_{14}N_2O_2$ (218.25 g/mol): C, 66.04; H, 6.47; N, 12.84. Found C, 65.698; H, 6.636; N, 12.728.

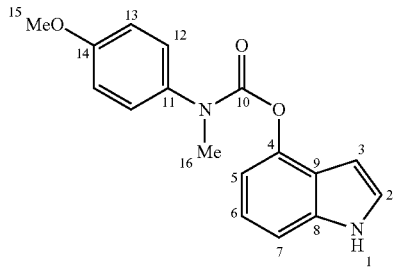

1H-indol-4-yl(4-methoxyphenyl)(methyl)carbamate, AN-807

Compound AN-807 was prepared from 4-hydroxyindole by procedure B, Method I, was isolated by chromatography eluted with EtOAc-hexane (1:2), as a white solid in 65% yield, mp 113-115° C. ¹H-NMR (600 MHz, CDCl₃) ppm δ 8.27 (bs, 1H, H-1), 7.32 (d, J=9.0 Hz, 2H, H-12), 7.14 (d, J=9.0 Hz, 1H, H-5), 7.08 (t, J=9.0 Hz, 1H, H-6), 7.05 (bs, 1H, H-7), 6.91 (d, J=9.0 Hz, 2H, H-13), 6.92-6.91 (m, 1H, H-2), 6.39 (bs, 1H, H-3), 3.80 (s, 3H, H-15), 3.42 (bs, 3H, H-16); ¹³C-NMR (150 MHz, CDCl₃) ppm δ 158.10, 155.28, 144.39, 137.68, 136.24, 127.49, 124.19, 122.05, 121.45, 114.32, 111.81, 108.59, 99.30, 55.48, 38.58; MS (CI⁺) m/z 296.116 (M⁺, 31.61); 297.121 (MH⁺, 19.73); HRMS calcd. for $C_{17}H_{16}N_2O_3$ (M⁺, DCI⁺/CH₄) 296.1161. found 296.1155.

1H-Indol-4-yl dimethylcarbamate, (3)

Compound (3) was prepared from 4-hydroxyindole 4-hydroxyindole by procedure B, Method I, was isolated by chromatography eluted with EtOAc-hexane (1:3 to 1:2 to 1:1), as a white needles in 48% yield, mp 140-143° C. ¹H-NMR (200 MHz, CDCl₃) ppm δ 8.74 (bs, 1H, H-1), 7.23-7.25 (m, 2H, H-2+H-7), 7.02-7.07 (m, 1H, H-6+H-5), 6.57 (bt, J=2.0 Hz, 1H, H-3), 3.36 (s, 3H, H-11), 3.22 (s, 3H, H-12); ¹³C-NMR (75 MHz, CDCl₃) ppm δ 155.22, 144.28, 137.75, 124.49, 121.77, 121.54, 111.71, 108.80, 98.68, 36.78, 36.59; MS (CI⁺) m/z 205.100 (MH⁺, 23.01), 204.094 (M⁺·, 48.45); HRMS calcd. for $C_{11}H_{12}N_2O_2$ (M⁺·, DCI⁺/CH₄) 204.0899. found 204.0942; Anal. Calcd. for $C_{11}H_{13}N_2O_2$*0.055 H₂O (MW 205.33 g/mol): C, 64.34; H, 6.43; N, 13.64. Found C, 63.933; H, 6.022; N, 13.594.

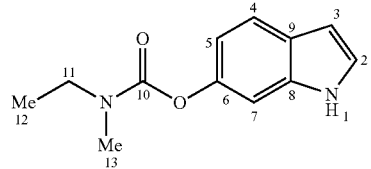

1H-Indol-6-yl ethylmethylcarbamate, AN-1106

Compound AN-1106 was prepared from 6-hydroxyindole by procedure B, Method I, was isolated by chromatography eluted with EtOAc-hexane (1:2), as a white solid in 57% yield, mp 105-108° C. ¹H-NMR (300 MHz, Acetone-d₆) ppm δ 10.23 (bs, 1H, H-1), 7.50 (d, J=8.9 Hz, 1H, H-4), 7.30 (t, J=3.3 Hz, 1H, H-2), 7.19 (bs, 1H, H-7), 6.80 (dd, J=8.9, 2.4 Hz, 1H, H-5), 6.44-6.46 (m, 1H, H-3), 3.36-3.51 (m, 2H, H-11), 3.09+2.95 (s, 3H, H-13), 1.14-1.24 (m, 3H, H-12); ¹³C-NMR (75 MHz, Acetone-d₆) ppm δ 156.12, 148.19, 137.04, 126.42, 126.07, 120.81, 115.01, 105.36, 102.31, 43.53, 33.12+33.13, 12.54, 11.74; MS (CI⁺) m/z 219.110 (MH⁺, 33.14), 134.061 ([MH⁺—C₄H₆NO], 24.44), 86.062 ([MH⁺—C₈H₆NO]⁺, 56.20); HRMS calcd. for $C_{12}H_{15}N_2O_2$ (MH⁺, DCI⁺/CH₄) 219.1134. found 219.1104, for C₈H₈NO ([MH⁺—C₄H₆NO], DCI⁺/CH₄) 134.0606. found 134.0608, for C₄H₈NO ([MH⁺—C₈H₆NO]⁺, DCI⁺/CH₄) 86.0606. found 86.0616; Anal. calcd. for $C_{12}H_{14}N_2O_2$ (MW 218.25 g/mol): C, 66.04; H, 6.47; N, 12.84; O, 14.66. Found C, 65.880; H, 6.706; N, 12.436.

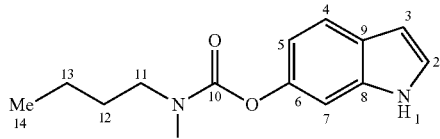

1H-Indol-6-yl-butylmethylcarbamate, AN-1100

Compound AN-1100 was prepared from 6-hydroxyindole by procedure B, Method I, was isolated by chromatography eluted with EtOAc-hexane (1:3), as a white solid in 62% yield, mp 84-87° C. ¹H-NMR (300 MHz, Acetone-d₆) ppm δ 10.15 (bs, 1H, H-1), 7.55 (d, J=8.1 Hz, 1H, H-4), 7.22-7.23 (m, 1H, H-7), 7.16 (t, J=3.0 Hz 1H, H-2), 6.86 (dd, J=8.1, 2.0 Hz, 1H, H-5), 6.45-6.47 (m, 1H, H-3), 3.36-3.50 (m, 2H, H-11), 3.10+2.99 (s, 3H, H-15), 1.52-1.68 (m, 2H, H-12), 1.32-1.44 (m, 2H, H-13), 0.91-1.00 (m, 3H, H-14); ¹³C-NMR (75 MHz, Acetone-d₆) ppm δ 155.86, 147.98, 136.89, 126.34, 125.99, 120.78, 114.84, 105.34, 102.12, 49.41, 49.31, 34.81, 34.57, 30.04, 29.31, 20.44, 14.15; MS (CI⁺) m/z 246.101 (M⁺, 13.20), 247.143 (MH⁺, 70.05), 114.077 ([MH⁺—C₈H₆NO]⁺, 95.53); HRMS calcd. for $C_{14}H_{19}N_2O_2$ (MH⁺, DCI⁺/CH₄) 247.1447. found 247.1432; Anal. calcd. for $C_{14}H_{18}N_2O_2$ (MW 246.30 g/mol): C, 68.27; H, 7.37; N, 11.37; O, 12.99. Found C, 68.110; H, 7.586; N, 11.055.

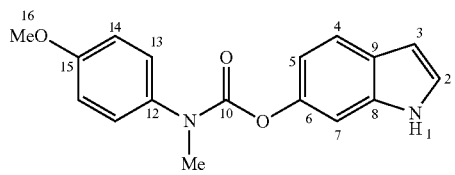

1H-Indol-6-yl 4-methoxyphenyl(methyl)carbamate, AN-1112

Compound AN-1112 prepared from 6-hydroxyindole by procedure B, Method I, was isolated by chromatography eluted with EtOAc-hexane (1:3 to 2:3 to 1:1 to EtOAc), as a white solid in 72% yield, mp 168-173° C. $^1$H-NMR (300 MHz, Acetone-$d_6$) ppm δ 10.24 (bs, 1H, H-1), 7.50 (bd, J=8.9 Hz, 1H, H-4), 7.37 (dd, J=6.4, 2.1 Hz, 2H, H-130, 7.28-7.31 (m, 1H, H-7), 7.19 (bs, 1H, H-2), 6.96 (dd, J=7.2, 2.4 Hz, 2H, H-14), 6.78 (bd, J=8.4 Hz, 1H, H-5), 6.44 (m, 1H, H-3), 3.80 (s, 3H, H-16), 3.34 (bs, 3H, H-11); $^{13}$C-NMR (75 MHz, Acetone-$d_6$) ppm δ 158.91, 155.09, 148.05, 137.38, 136.92, 128.24, 126.10, 125.94, 120.81, 114.90, 114.80, 105.21, 102.28, 55.67, 38.62; MS (CI$^+$) m/z 296.113 (M$^+$, 67.06), 164.068 ([M$^+$-C$_8$H$_6$NO]$^+$, 72.14), 136.074 ([M$^+$-C$_9$H$_6$NO$_2$]$^+$, 100); HRMS calcd. for C$_{17}$H$_{16}$N$_2$O$_3$ (M$^+$, DCI$^+$/CH$_4$) 296.1161. found 296.1135, for C$_9$H$_{10}$NO$_2$ ([M$^+$-C$_8$H$_6$NO]$^+$, DCI$^+$/CH$_4$) 164.0712. found 164.0683, for C$_8$H$_{10}$NO ([M$^+$-C$_9$H$_6$NO$_2$]$^+$, DCI$^+$/CH$_4$) 136.0762. found 136.0743; Anal. calcd. for C$_{17}$H$_{16}$N$_2$O$_3$ (MW 296.32 g/mol): C, 68.91; H, 5.44; N, 9.45; O, 16.20. Found C, 69.237; H, 5.768; N, 9.301.

3-Formyl-1H-indol-4-yl4-methoxyphenyl(methyl)carbamate, AN-809

Compound AN-809 was prepared from compound AN-807 by procedure C, was crystallized from EtOAc-hexane to give AN-809 as a white solid in 75% yield, mp 173-175° C. $^1$H-NMR (300 MHz, CDCl$_3$) ppm δ 9.87 (bs, 1H, H-1), 9.71 (bs, 1H, H-18), 7.51-7.43 (m, 2H, H-2+H-7), 7.25 (bs, 1H, H-6), 7.51-6.98 (m, 2H, H-12), 6.94-6.90 (m, 3H, H-13+H-5), 3.80 (s, 3H, H-15), 3.61+3.42 (bs, 3H, H-16); $^{13}$C-NMR (75 MHz, CDCl$_3$) ppm δ 184.20, 158.30, 155.04, 144.80, 138.82, 137.27, 136.15, 127.79, 127.27, 123.63, 118.14, 115.59, 114.31, 110.31, 55.44, 38.88; MS (CI$^+$) m/z 324.112 (M$^{.+}$, 1.77), 325.122 (MH$^+$, 0.85); HRMS calcd. for C$_{18}$H$_{16}$N$_2$O$_4$ (M$^{.+}$, DCI$^+$/CH$_4$) 324.1110. found 324.1118.

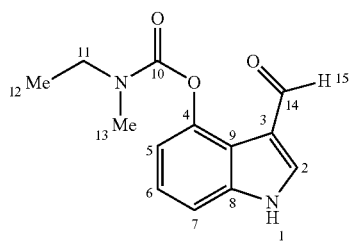 [SMILES: CCN(C)C(=O)Oc1cccc2[nH]cc(C=O)c12]

3-Formyl-1H-indol-4-yl ethyl(methyl)carbamate, AN-653

Compound AN-653, prepared from AN-651 by procedure C, was isolated as a brown oil in 97% yield, after extraction with EtOAc and water. $^1$H-NMR (300 MHz, CDCl$_3$) ppm δ 10.06 (bs, 1H, H-1), 9.78 (d, J=7.5 Hz, 1H, H-15), 7.15 (bs, 1H, H-2), 7.08 (t, J=7.5 Hz, 1H, H-6), 6.93-6.86 (m, 2H, H-7+H-5), 3.65+3.49 (q, J=6.7 Hz, 2H, H-11), 3.24+3.07 (s, 3H, H-13), 1.35+1.28 (t, J=6.7 Hz, 3H, H-12); $^{13}$C-NMR (75 MHz, CDCl$_3$) ppm δ 184.30, 184.17, 156.03, 155.96, 144.85, 139.16, 136.86, 136.47, 123.67, 118.55, 118.07, 115.99, 115.85, 110.68, 110.65, 44.53, 44.42, 34.49, 34.28, 13.27, 12.59; MS (CI$^+$) m/z 246.103 (M$^{.+}$, 12.55), 247.107 (M$^{.+}$, 3.05); HRMS calcd. for C$_{13}$H$_{14}$N$_2$O$_3$ (M$^{.+}$, DCI$^+$/CH$_4$) 246.1004. found 246.1027.

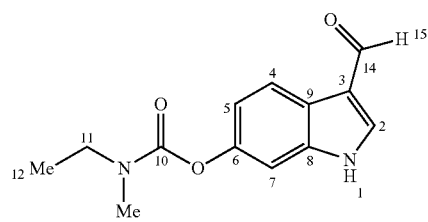

3-Formyl-1H-indol-6-ylethylmethylcarbamate, AN-1107

Compound AN-1107, prepared from AN-1106 by procedure C, was isolated as a bright pink solid in 92% yield, after extraction with EtOAc and water, mp 170-175° C. $^1$H-NMR (300 MHz, Acetone-$d_6$) ppm δ 11.23 (bs, 1H, H-1), 10.05 (s, 1H, H-15), 8.18 (dd, J=3.8, 0.9 Hz, 1H, H-4), 8.15 (s, 1H, H-2), 7.33 (d, J=1.9 Hz, 1H, H-7), 7.02 (dd, J=8.5, 1.9 Hz, 1H, H-5), 3.35-3.55 (m, 2H, H-11), 3.10+2.94+2.85 (s, 3H, H-13), 1.06-1.34 (m, 3H, H-12); $^{13}$C-NMR (75 MHz, Acetone-$d_6$) ppm δ 185.24, 155.17, 149.65, 138.48, 138.23, 122.67, 122.15, 119.93, 117.89, 106.41, 45.03, 44.56, 35.32, 34.35, 34.09, 12.67, 12.89, 13.53; MS (CI$^+$) m/z 247.107 (MH$^+$, 75.12), 246.100 (M, 20.38); HRMS calcd. for C$_{13}$H$_{15}$N$_2$O$_3$ (MH$^+$, DCI$^+$/CH$_4$) 247.1083. found 247.1074; Anal. calcd. for C$_{13}$H$_{14}$N$_2$O$_3$ (MW 246.26 g/mol): C, 63.40; H, 5.73; N, 11.38; O, 19.49. Found C, 63.680; H, 6.070; N, 11.385.

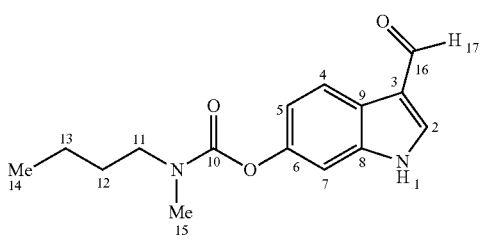 [SMILES: CCCCN(C)C(=O)Oc1ccc2c(C=O)c[nH]c2c1]

3-Formyl-1H-indol-6-yl butylmethylcarbamate, AN-1101

Compound AN-1101, prepared from AN-1100 by procedure C, was isolated as a brown viscous oil in 81% yield after extraction with EtOAc and water, and was used without further purification. $^1$H-NMR (300 MHz, Acetone-$d_6$) ppm δ 11.12 (bs, 1H, H-1), 9.95 (s, 1H, H-17), 8.17 (d, J=8.8 Hz, 1H, H-4), 7.97 (d, J=2.9 Hz, 1H, H-2), 7.31 (d, J=1.9 Hz, 1H, H-7), 7.04 (bd, J=8.8 Hz, 1H, H-5), 3.34-3.49 (m, 2H, H-11), 2.98+2.86 (s, 3H, H-15), 1.49-1.76 (m, 2H, H-12), 1.31-1.43 (m, 2H, H-13), 0.87-0.98 (m, 3H, H-14); $^{13}$C-NMR (75 MHz, Acetone-$d_6$) ppm δ 185.04, 155.39, 149.20, 138.36, 137.91, 122.35, 121.88, 119.41, 117.52, 106.24, 49.24, 49.13, 34.63, 34.37, 30.54, 30.35, 20.17, 13.86; MS (CI$^+$) m/z 275.137 (MH$^+$, 100.00), 274.129 (M, 12.48), 114.097 ([M-C$_9$H$_6$NO$_2$]$^+$, 44.73); HRMS calcd. for C$_{15}$H$_{19}$N$_2$O$_3$ (MH$^+$, DCI$^+$/CH$_4$) 275.1396. found 275.1367.

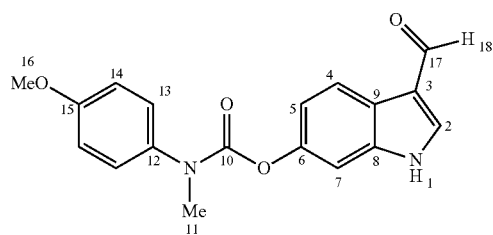 [SMILES: COc1ccc(N(C)C(=O)Oc2ccc3c(C=O)c[nH]c3c2)cc1]

3-Formyl-1H-indol-6-yl 4-methoxyphenyl(methyl)carbamate, AN-1113

Compound AN-1113, prepared from AN-1112 by procedure C, was isolated as a yellow solid in 66% yield, after extraction with EtOAc and water, and was isolated by chromatography eluted with EtOAc-hexane (1:1), mp 218-220° C. $^1$H-NMR (300 MHz, Acetone-$d_6$) ppm δ 11.16 (bs, 1H, H-1), 9.98 (s, 1H, H-18), 8.19 (s, 1H, H-7), 8.13 (d, J=8.4 Hz, 1H, H-4), 7.40 (dd, J=7.0, 1.4 Hz, 2H, H-13), 7.32 (bs, 1H, H-2), 7.01 (bd, J=8.4 Hz, 1H, H-5), 6.95 (dd, J=7.0, 1.4 Hz, 2H, H-14), 3.81 (s, 3H, H-16), 3.35 (bs, 3H, H-11); $^{13}$C-NMR (75 MHz, Acetone-$d_6$) ppm δ 185.23, 154.78, 149.55, 138.52, 138.18, 137.22, 128.33, 122.78, 122.18, 119.96, 117.77, 114.98, 106.31, 55.72, 38.72; MS (CI$^+$) m/z 324.111 (M$^+$, 31.16), 296.115 ([M$^+$-CO], 10.11), 164.072 ([M$^+$-C$_9$H$_6$NO$_2$]$^+$, 69.50), 136.078 ([M$^+$-C$_{10}$H$_6$NO$_3$]$^+$, 99.95); HRMS calcd. for C$_{18}$H$_{16}$N$_2$O$_4$ (M$^+$, DCI$^+$/CH$_4$) 324.1110. found 324.1111, for C$_{17}$H$_{16}$N$_2$O$_3$ ([M$^+$-CO], DCI$^+$/CH$_4$) 296.1161. found 296.1153, for C$_9$H$_{10}$NO$_2$ ([M$^+$-C$_9$H$_6$NO$_2$]$^+$, DCI$^+$/CH$_4$) 164.0712. found 164.0716, for C$_8$H$_{10}$NO ([M$^+$-C$_{10}$H$_6$NO$_3$]$^+$, DCI$^+$/CH$_4$) 136.0762. found 136.0777; Anal. calcd. for C$_{18}$H$_{16}$N$_2$O$_4$ (MW 324.33 g/mol): C, 66.66; H, 4.97; N, 8.64; O, 19.73. Found C, 66.785; H, 5.338; N, 8.769.

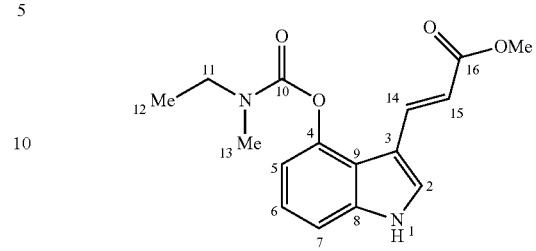

3-((E)-2-(Methoxycarbonyl)vinyl)-1H-indol-4-yl ethylmethylcarbamate, AN-803

Compound AN-803 was prepared from AN-653 by procedure D, was crystallized from EtOAc-hexane and then was washed with cold ether to give AN-803 as an off-white solid in 61% yield, mp 128-131° C. $^1$H-NMR (300 MHz, DMSO) ppm δ 11.94 (bs, 1H, H-1), 8.09 (bs, 1H, H-2), 7.90 (d, J=16.9 Hz, 1H, H-14), 7.31 (d, J=7.5 Hz, 1H, H-7), 7.13 (t, J=7.5 Hz, 1H, H-6), 6.79-6.83 (m, 1H, H-5), 6.35 (d, J=16.9 Hz, 1H, H-15), 3.68 (s, 3H, H-17), 3.30-3.60 (m, 2H, H-11), 3.19+2.94 (s, 3H, H-13), 1.08+1.31 (m, 3H, H-12); $^{13}$C-NMR (75 MHz, DMSO) ppm δ 167.44, 154.00, 144.51, 138.63, 138.24, 128.08, 122.30, 119.23, 114.46, 114.10, 112.04, 110.57, 109.81, 51.04, 44.07, 33.93, 33.64, 13.11, 12.19; MS (CI$^+$) m/z 302.130 (MH$^+$, 25.65), 271.113 ([M-CH$_3$OH], 38.63); HRMS calcd. for C$_{16}$H$_{18}$N$_2$O$_4$ (MH$^+$, DCI$^+$/CH$_4$) 302.1267. found 302.1304, for C$_{15}$H$_{15}$N$_2$O$_3$ ([M-CH$_3$OH], DCI$^+$/CH$_4$) 271.1083. found 271.1129; Anal. Calcd. for C$_{16}$H$_{18}$N$_2$O$_4$ (302.32 g/mol): C, 63.56; H, 6.00; N, 9.27. Found C, 63.3715; H, 6.1755; N, 8.904.

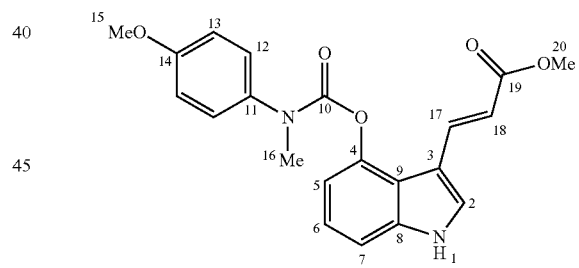

(E)-methyl 3-(4-((4-methoxyphenyl)(methyl)carbamoyloxy)-1H-indol-3-yl)acrylate, AN-811

Compound AN-811 prepared from AN-809 by procedure D, was crystallized from EtOH to give AN-811 as a pale bright solid in 52% yield, mp 155-157° C. $^1$H-NMR (300 MHz, CDCl$_3$) ppm δ 7.34 (bd, J=8.0 Hz, 1H, H-17), 7.17-7.04 (m, 3H, H-2+H-12), 6.98 (m, 5H, H-7+H-6+H-5+H-13), 6.64 (bd, J=8.0 Hz, 1H, H-18) 3.81 (s, 3H, H-20), 3.58 (bs, 3H, H-15), 3.26+3.43 (bs, 3H, H-16); $^{13}$C-NMR (75 MHz, CDCl$_3$) ppm δ 172.77, 158.30, 154.69, 144.51, 138.35, 131.10, 127.77, 127.08, 122.28, 121.65, 114.31, 113.06, 109.37, 55.48, 52.305, 39.68, 38.91; MS (CI$^+$) m/z 380.133 (M$^{·+}$, 100.00), 381.157 (MH$^+$, 52.05); HRMS calcd. for C$_{21}$H$_{20}$N$_2$O$_5$ (M$^{·+}$, DCI$^+$/CH$_4$) 380.1372. found 380.1330.

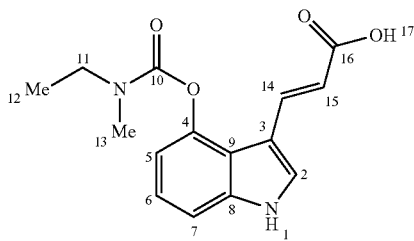 [SMILES: CCN(C)C(=O)Oc1cccc2[nH]cc(/C=C/C(=O)O)c12]

(E)-3-(4-(Ethyl(methyl)carbamoyloxy)-1H-indol-3-yl)acrylic acid, AN-865

Compound AN-865 prepared from AN-803 by procedure H using KOH as a base, was isolated by chromatography eluted with EtOAc-hexane (1:1), as a white solid in 43% yield, mp. 164-166° C. $^1$H-NMR (300 MHz, MeOD) ppm δ 11.36 (bs, 1H, H-17), 8.00 (d, J=16.9 Hz, 1H, H-14), 7.77 (bs, 1H, H-2), 7.3 (d, J=7.5 Hz, 1H, H-7), 7.16 (t, J=7.5 Hz, 1H, H-6), 6.82 (d, J=7.5 Hz, 1H, H-5), 6.22 (d, J=16.9 Hz, 1H, H-15), 3.42-3.68 (q, J=7.4 Hz, 2H, H-11), 3.28+3.03 (s, 3H, H-13), 1.18+1.39 (m, 3H, H-12); $^{13}$C-NMR (75 MHz, DMSO) ppm δ 171.42, 156.55, 145.92, 140.50, 140.36, 127.94, 127.63, 123.35, 120.40, 115.42, 115.08, 113.96, 113.86, 112.60, 110.89, 45.39, 34.47, 13.51, 12.64; MS (ES$^+$) mass 311 ([M+Na]$^+$, 5.86).

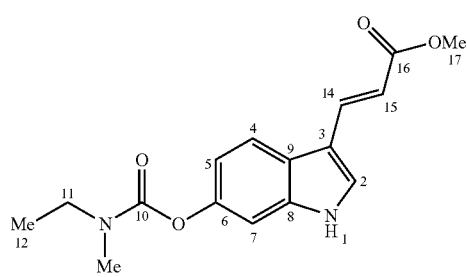

3-((E)-2-Methoxy carbonyl)vinyl)-1H-indol-6-yl ethylmethylcarbamate, AN-863

Compound AN-863 prepared from AN-1107 by procedure D, was isolated by chromatography eluted with EtOAc-hexane (1:1), as a bright yellow solid in 67% yield, mp 142-145° C. $^1$H-NMR (300 MHz, Acetone-d$_6$) ppm δ 10.76 (bs, 1H, H-1), 7.88 (d, J=16.8 Hz, 1H, H-14), 7.87 (d, J=7.8 Hz, 1H, H-4), 7.70 (d, J=2.2 Hz, 1H, H-2), 7.27 (d, J=2.2 Hz, 1H, H-7), 7.00 (dd, J=8.9, 2.2 Hz, 1H, H-5), 6.40 (d, J=16.8 Hz, 1H, H-15), 3.74 (s, 3H, H-17), 3.36-3.54 (m, 2H, H-11), 3.01+2.97 (bs, 3H, H-13), 1.13-1.27 (m, 3H, H-12); $^{13}$C-NMR (75 MHz, Acetone-d$_6$) ppm δ 168.62, 155.40, 148.95, 139.33, 138.57, 132.07, 123.54, 120.85, 116.68, 113.33, 112.62, 106.45, 51.30, 44.56, 34.37, 34.08, 13.50, 12.71; MS (CI$^+$) m/z 302.123 (M$^+$, 27.48); 303.133 (MH$^+$, 26.26); HRMS calcd. for C$_{16}$H$_{18}$N$_2$O$_4$ (M$^+$, DCI$^+$/CH$_4$), 302.1267. found 302.1227, for C$_{16}$H$_{19}$N$_2$O$_4$ (MH$^+$, DCI$^+$/CH$_4$), 303.1345. found 303.1332; Anal. calcd. for C$_{16}$H$_{18}$N$_2$O$_4$ (MW 302.32 g/mol): C, 63.56; H, 6.00; N, 9.27; O, 21.17. Found C, 63.626; H, 6.190; N, 9.143.

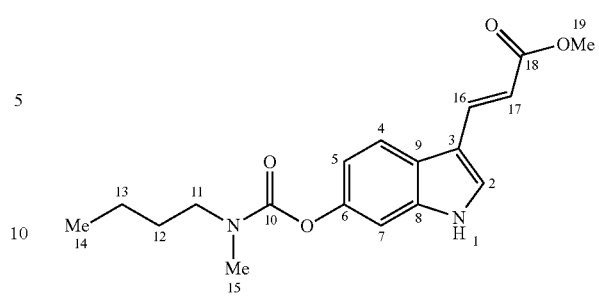

3-((E)-2-Methoxycarbonyl)vinyl)-1H-indol-6-yl butylmethylcarbamate, AN-1102

Compound AN-1102, prepared from AN-1101 by procedure D, was isolated by chromatography eluted with EtOAc-hexane (1:2 to 1:1), as a yellow oil in 45% yield. $^1$H-NMR (300 MHz, CDCl$_3$) ppm δ 9.80 (bs, 1H, H-1), 7.67 (d, J=15.8 Hz, 1H, H-16), 7.60 (d, J=7.9 Hz, 1H, H-4), 6.94 (s, 1H, H-2), 6.80-6.86 (m, 2H, H-5+H-7), 6.20 (d, J=15.8 Hz, 1H, H-17), 3.76 (s, 3H, H-19), 3.34-3.45 (m, 2H, H-11), 3.07+3.00 (s, 3H, H-15), 1.55-1.63 (m, 2H, H-12), 1.33-1.42 (m, 2H, H-13), 0.94-0.98 (m, 3H, H-14); $^{13}$C-NMR (75 MHz, CDCl$_3$) ppm δ 168.79, 156.21, 147.31, 138.75, 137.37, 130.62, 122.74, 120.21, 115.08, 112.20, 111.69, 105.98, 51.24, 49.18, 49.01, 34.81, 34.42, 30.08, 29.49, 19.89, 19.83, 13.82; MS (CI$^+$) m/z 331.163 (MH$^+$, 9.97); HRMS calcd. for C$_{18}$H$_{23}$N$_2$O$_4$ (MH$^+$, DCI$^+$/CH$_4$) 331.1658. found 331.1627.

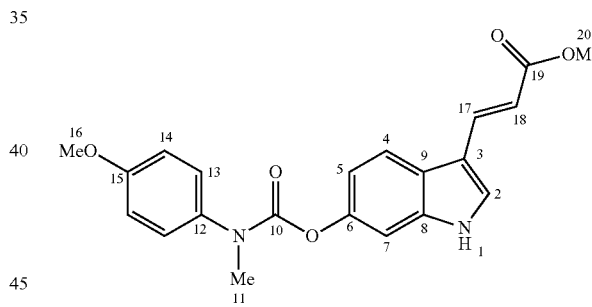

(E)-Methyl 3-(6-((4-methoxyphenyl)(methyl)carbamoyloxy)-1H-indol-3-yl)acrylate, AN-1118

Compound AN-1118 prepared from AN-1113 by procedure D, was isolated by chromatography eluted with EtOAc-hexane (2:1), as a colourless oil in 64% yield. $^1$H-NMR (300 MHz, Acetone-d$_6$) ppm δ 10.80 (bs, 1H, H-1), 7.90 (d, J=15.5 Hz, 1H, H-17), 7.88 (d, J=7.7 Hz, 1H, H-4), 7.74 (d, J=3.1 Hz, 1H, H-7), 7.38 (dd, J=6.2, 3.1 Hz, 2H, H-13), 7.29 (bs, 1H, H-2), 6.94-6.98 (m, 1H, H-5), 6.95 (J=6.2, 3.1 Hz, 2H, H-14), 6.41 (d, J=15.5 Hz, 1H, H-18), 3.78 (s, 3H, H-20), 3.73 (s, 3H, H-16), 3.36 (bs, 3H, H-11); $^{13}$C-NMR (75 MHz, Acetone-d$_6$) ppm δ 168.60, 154.99, 148.87, 139.28, 138.50, 137.10, 132.10, 128.31, 123.64, 120.89, 116.57, 114.93, 113.36, 112.70, 106.32, 55.67, 51.30, 38.72; MS (CI$^+$) m/z 380.136 (M$^+$, 24.27), 164.073 ([M$^+$-C$_{12}$H$_{10}$NO$_3$], 82.06), 136.078 ([M$^+$-C$_{13}$H$_{10}$NO$_4$], 100.04); HRMS calcd. for C$_{21}$H$_{20}$N$_2$O$_5$ (M$^+$, DCI$^+$/CH$_4$) 380.1372. found 380.1362, for C$_9$H$_{10}$NO$_2$ ([M$^+$-C$_{12}$H$_{10}$NO$_3$], DCI$^+$/

CH₄) 164.0712. found 164.0733, for C₈H₁₀NO ([M⁺-C₁₃H₁₀Na₄], DCI⁺/CH₄) 136.0762. found 136.0782.

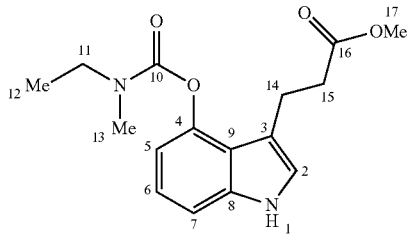

3-(2-(Methoxycarbonyl)ethyl)-1H-indol-4-yl ethyl-methylcarbamate, AN-1146

Compound AN-1146 was prepared from AN-803 or from AN-843 by procedure F, was crystallized from EtOAc-hexane to give AN-1146 as a white solid in 92% yield, mp 122-124° C. ¹H-NMR (300 MHz, Acetone-d₆) ppm δ 10.16 (bs, 1H, H-1), 7.22 (d, J=7.5 Hz, 1H, H-7), 7.09 (bs, 1H, H-2), 7.03 (t, J=7.5 Hz, 1H, H-6), 6.70 (d, J=7.5 Hz, 1H, H-5), 3.67 (s, 3H, H-17), 3.37-3.56 (m, 2H, H-11), 3.17+3.03 (s, 3H, H-13), 3.08 (t, J=6.7 Hz, 2H, H-14), 2.65 (t, J=6.7 Hz, 2H, H-15), 1.22-1.31 (m, 3H, H-12); ¹³C-NMR (75 MHz, Acetone-d₆) ppm δ 173.74, 155.24, 145.98, 139.89, 123.50, 123.34, 122.17, 113.81, 113.14, 112.93, 109.54, 51.47, 44.59, 44.42, 36.18, 36.05, 34.16, 34.09, 22.61, 13.56, 12.66; MS (CI⁺) m/z 305.149 (MH⁺, 90.07), 304.139 (M⁺, 81.83), 333.180 ([M+C₂H₅]⁺, 9.63), 273.120 ([MH—CH₃OH]⁺, 18.86), 231.105 ([M⁺·-C₃H₅O₂], 8.38); HRMS calcd. for C₁₆H₂₀N₂O₄ (M⁺·, DCI⁺/CH₄) 304.1423. found 304.1385, for C₁₆H₂₁N₂O₄ (MH⁺, DCI⁺/CH₄) 305.1501. found 305.1488; Anal. Calcd. for C₁₆H₂₀N₂O₄ (304.34 g/mol): C, 63.14; H, 6.62; N, 9.20. Found C, 63.299; H, 6.822; N, 8.966.

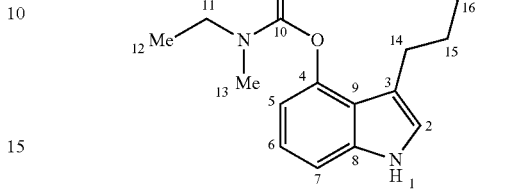

138.25, 135.96, 127.75, 122.15, 121.84, 114.29, 113.78, 112.20, 108.63, 55.45, 51.42, 38.69, 35.05, 21.62; MS (CI⁺) m/z 382.152 (M⁺, 29.87), 383.158 (MH⁺, 31.74); HRMS calcd. for C₂₁H₂₃N₂O₅ (MH⁺, DCI⁺/CH₄) 382.1607. found 383.1583.

3-(4-(Ethyl(methyl)carbamoyl)-1H-indol-3-yl)pro-panoic acid, AN-805

Compound AN-805 was prepared from AN-1146 by procedure H, was crystallized from EtOAc-hexane to give AN-805 as a white solid in 75% yield, mp 118-121° C. ¹H-NMR (300 MHz, CDCl₃) ppm δ 8.35 (bs, 1H, H-1), 7.04-7.05 (m, 2H, H-7+H-2), 6.76 (bs, 1H, H-6), 6.64 (s, 1H, H-5), 3.42-3.58 (m, 2H, H-12), 3.13+3.01 (s, 3H, H-13), 3.01 (t, J=9.0 Hz, 2H, H-14), 2.60 (t, J=9.0 Hz, 2H, H-15), 1.18+1.33 (m, 3H, H-11); ¹³C-NMR (75 MHz, CDCl₃) ppm δ 178.63, 155.20, 144.85, 138.75, 122.02, 120.24, 112.88, 112.61, 109.17, 44.35, 35.31, 34.00, 21.73, 13.35, 12.54; MS (CI⁺) m/z 291.134 (MH⁺, 12.58), 290.130 (M⁺, 13.66), 231.109 ([MH⁺—C₂H₄O₂], 7.57); HRMS calcd. for C₁₅H₁₉N₂O₄ (MH⁺, DCI⁺/CH₄) 291.1345. found 291.1336, for C₁₅H₁₉N₂O₄ (M⁺·, DCI⁺/CH₄) 290.1267. found 290.1300; Anal. Calcd. for C₁₅H₁₈N₂O₄ (290.31 g/mol): C, 62.06; H, 6.25; N, 9.65. Found C, 61.712; H, 6.381; N, 9.232.

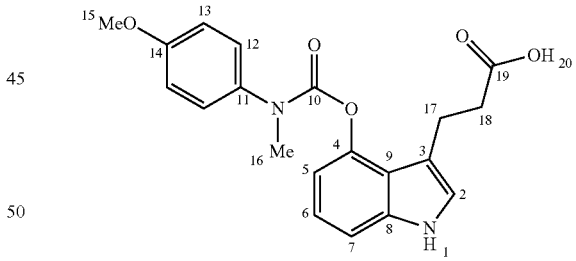

(E)-methyl 3-(4-((4-methoxyphenyl)(methyl)car-bamoyloxy)-1H-indol-3-yl)propanoate, AN-813

Compound AN-813 prepared from AN-811 or from AN-843 by procedure F, was dissolved in EtOAc and filtered through silica gel and the filtrate was evaporated to provide AN-813 as a colourless oil in 97% yield. ¹H-NMR (300 MHz, CDCl₃) ppm 8.16 (bs, 1H, H-1), 7.47 (dd, J=9.0, 3.0 Hz, 2H, H-12), 7.39 (s, 1H, H-2), 7.26-7.23 (m, 2H, H-7+H-6), 7.04 (dd, J=9.0, 3.0 Hz, 2H, H-13), 6.98 (bs, 1H, H-5) 3.94 (s, 3H, H-15), 3.81 (s, 3H, H-20), 3.53 (bs, 3H, H-16), 3.06 (bs, 2H, H-17), 2.66 (bs, 2H, H-17); ¹³C-NMR (75 MHz, CDCl₃) ppm δ 173.80, 158.26, 154.64, 144.95, (E)-methyl 3-(4-((4-methoxyphenyl)(methyl)car-bamoyloxy)-1H-indol-3-yl)propanoic acid, AN-815

Compound AN-815 prepared from AN-813 by procedure H, was crystallized from EtOAc-hexane to give AN-815 as a white solid in 72% yield, mp 194-196° C. ¹H-NMR (300 MHz, CDCl₃) ppm 7.99 (bs, 1H, H-1), 7.33 (dd, J=10.2, 2.5 Hz, 2H, H-12), 7.27 (bs, 1H, H-2), 7.17-7.09 (m, 2H, H-7+H-6), 6.92 (dd, J=10.2, 2.5 Hz, 2H, H-13), 6.88-6.85 (m, 1H, H-5) 3.80 (s, 3H, H-15), 3.39 (bs, 3H, H-16), 2.92 (bs, 2H, H-17), 2.51 (bs, 2H, H-18); ¹³C-NMR (75 MHz, CDCl₃) ppm δ 175.92, 158.40, 155.23, 144.60, 138.73, 135.73, 127.73, 122.24, 121.63, 114.38, 113.00, 111.67, 108.90, 55.41, 38.58, 35.29, 21.62; MALDI (DHB+Na⁺/RP_PepMix) m/z 369 (MH⁺), 391 (M+Na⁺), 413 (M+2Na—H⁺); HRMS calcd. for $C_{20}H_{20}N_2O_5Na$ (M+Na⁺) 391.1264. found 391.169.

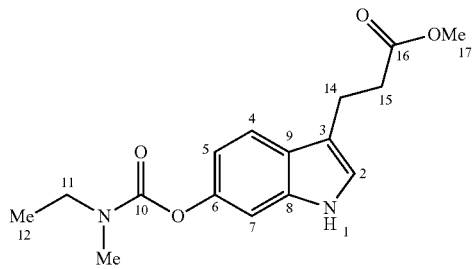

3-(2-(Methoxycarbonyl)ethyl)-1H-indol-6-yl ethyl-methylcarbamate, AN-679

Compound AN-679 prepared from AN-863 or from AN-678 by procedure F, was isolated by chromatography eluted with EtOAc-hexane (1:1) to give AN-679 as a colourless oil in 92% yield. ¹H-NMR (300 MHz, CDCl₃) ppm δ 8.64 (bs, 1H, H-1), 7.45 (d, J=8.4 Hz, 1H, H-4), 7.01 (d, J=1.7 Hz, 1H, H-7), 6.82 (dd, J=8.4, 1.7 Hz, 1H, H-5), 6.68 (bs, 1H, H-2), 3.66 (s, 3H, H-17), 3.41-3.49 (m, 2H, H-11), 2.98+3.10 (s, 3H, H-13), 3.00 (t, J=7.5 Hz, 2H, H-14), 2.64 (t, J=7.5 Hz, 2H, H-15), 1.22-1.28 (m, 3H, H-12); ¹³C-NMR (75 MHz, CDCl₃) ppm δ 173.97, 155.64, 147.02, 136.25, 124.82, 122.23, 118.57, 114.00, 113.48, 104.73, 51.57, 44.09, 34.77, 34.30, 33.85, 20.62, 13.24, 12.56; MS (CI⁺) m/z 304.139 (M⁺, 90.36), 305.151 (MH⁺, 73.01), 273.129 ([MH⁺—CH₃OH], 14.71), 231.117 ([M⁺-C₃H₅O₂]⁺, 36.92), 86.045 ([M⁺-C₁₂H₁₂NO₃]⁺, 32.56); HRMS calcd. for $C_4H_8NO$ ([M⁺-C₁₂H₁₂NO₃]⁺, DCI⁺/CH₄) 86.0606. found 86.0595, for $C_{13}H_{15}N_2O_2$ ([M⁺-C₃H₅O₂]⁺, DCI⁺/CH₄) 231.1134. found 231.1165, for $C_{16}H_{20}N_2O_4$ 304.1423. found 304.1389, for $C_{16}H_{21}N_2O_4$ 305.1501. found 305.1510.

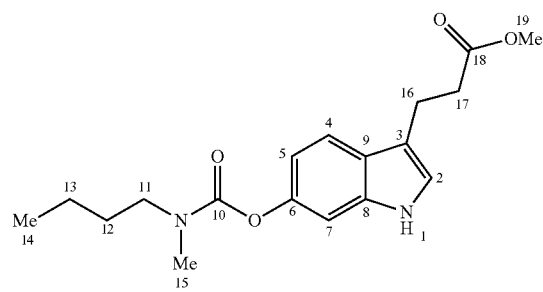 [SMILES: CCCCN(C)C(=O)Oc1ccc2c(CCC(=O)OC)c[nH]c2c1]

3-(2-(Methoxy carbonyl)ethyl)-1H-indol-6-yl butyl-methylcarbamate, AN-676

Compound AN-676 prepared from AN-1102 by procedure F, was isolated by chromatography eluted with EtOAc-hexane (1:2), as a yellow oil in 52% yield. ¹H-NMR (300 MHz, Acetone-d₆) ppm δ 9.98 (bs, 1H, H-1), 7.51 (d, J=8.52 Hz, 1H, H-4), 7.14 (d, J=1.70 Hz 1H, H-7), 7.08 (m, 1H, H-2), 6.80 (dd, J=8.52, 1.70 Hz 1H, H-2), 3.61 (s, 3H, H-19), 3.30-3.50 (m, 2H, H-11), 3.09+2.96 (s, 3H, H-15), 3.04 (t, J=8.06 Hz 2H, H-16), 2.68 (t, J=8.06 Hz, 2H, H-17), 1.57-1.67 (m, 2H, H-12), 1.29-1.42 (m, 2H, H-13), 0.89-0.99 (m, 3H, H-14); ¹³C-NMR (75 MHz, Acetone-d₆) ppm δ 173.84, 155.70, 148.37, 137.46, 125.65, 123.32, 118.99, 114.48, 105.40, 51.55, 49.40, 34.40, 33.67, 33.87, 29.32, 21.31, 20.51, 14.15; MS (CI⁺) m/z 332.171 (M⁺, 81.29); HRMS calcd. for $C_{18}H_{24}N_2O_4$ (M⁺, DCI⁺/CH₄) 332.1736. found 332.1707.

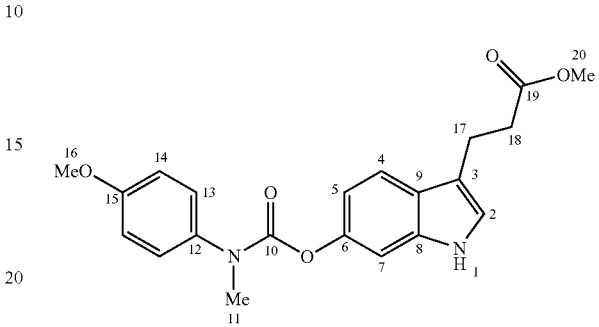

Methyl 3-(6-((4-methoxyphenyl)(methyl)carbamoyloxy)-1H-indol-3-yl)propanoate, AN-683

Compound AN-683 prepared from AN-1118 or from AN-678 by procedure F, was isolated by chromatography eluted with EtOAc-hexane (1:1), as a white solid in 63% yield, mp 120-124° C. ¹H-NMR (300 MHz, Acetone-d₆) ppm δ 10.00 (bs, 1H, H-1), 7.50 (d, J=8.4 Hz, 1H, H-4), 7.37 (dd, J=6.7, 2.5 Hz, 2H, H-13), 7.12-7.13 (m, 2H, H-2+H-7), 6.96 (dd, J=6.7, 2.5 Hz, 2H, H-14), 6.80 (bd, J=8.4 Hz, 1H, H-5), 3.80 (s, 3H, H-16), 3.60 (s, 3H, H-20), 3.34 (bs, 3H, H-11), 3.02 (t, J=7.3 Hz, 2H, H-17), 2.67 (J=7.3 Hz, 2H, H-18); ¹³C-NMR (75 MHz, Acetone-d₆) ppm δ 173.83, 158.92, 155.12, 148.23, 137.39, 128.29, 127.77, 125.74, 123.41, 119.03, 114.91, 114.67, 114.33, 105.30, 55.69, 51.55, 38.64, 35.31, 21.27; MS (CI⁺) m/z 382.151 (M⁺, 56.01), 164.072 ([M⁺-C₁₂H₁₂NO₃]⁺, 93.42), 136.077 ([M⁺-C₁₃H₁₂Na₄]⁺, 99.97); HRMS calcd. for $C_9H_{10}NO_2$ ([M⁺-C₁₂H₁₂NO₃]⁺, DCI⁺/CH₄) 164.0712. found 164.0724, for $C_8H_{10}NO$ ([M⁺-C₁₃H₁₂NO₄]⁺, DCI⁺/CH₄) 136.0762. found 136.0773; Anal. calcd. for $C_{21}H_{22}N_2O_5$ (MW 382.41 g/mol): C, 65.96; H, 5.80; N, 7.33; O, 20.92. Found C, 65.848; H, 5.968; N, 6.959.

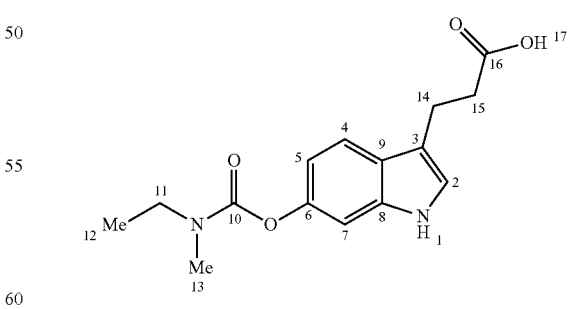

3-(6-(Ethyl(methyl)carbamoyloxy)-1H-indol-3-yl)propanoic acid, AN-1138

Compound AN-1138 prepared from AN-679 by procedure H, was obtained as an off-white solid in 80% yield after crystallization from EtOAc-hexane, mp 132-136° C. $^1$H-NMR (300 MHz, MeOD) ppm δ 10.23 (bs, 1H, H-1), 7.51 (d, J=8.8 Hz, 1H, H-4), 7.05 (d, J=2.4 Hz, 1H, H-7), 7.07 (bs, 1H, H-2), 6.76 (dd, J=8.8, 2.4 Hz, 1H, H-5), 3.38-3.61 (m, 2H, H-11), 3.10+2.97 (bs, 3H, H-13), 3.01 (t, J=7.9 Hz, 2H, H-14), 2.66 (t, J=7.9 Hz, 2H, H-15), 1.16-1.28 (m, 3H, H-12); $^{13}$C-NMR (75 MHz, MeOD) ppm δ 177.27, 157.37, 148.19, 137.92, 123.81, 123.64, 119.41, 115.24, 114.28, 105.38, 45.10, 35.99, 34.28, 21.73, 13.44, 12.68; MS (CI) m/z 289.120 ([M−H]$^−$, 32.42); HRMS calcd. for $C_{15}H_{17}N_2O_4$ ([M−H]$^−$, DCI$^−$/CH$_4$) 289.1188. found 289.1196.

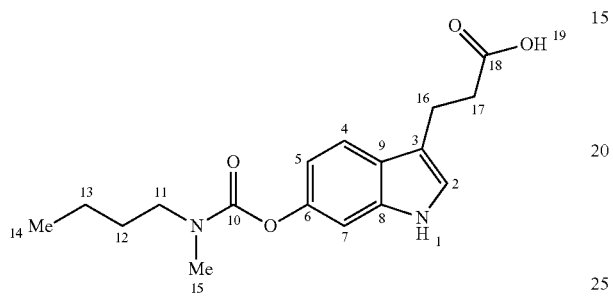

3-(6-(Butyl(methyl)carbamoyloxy)-1H-indol-3-yl) propanoic acid, AN-1137

Compound AN-1137 prepared from AN-676 by procedure H, was obtained as a colourless oil in 87% yield. $^1$H-NMR (300 MHz, Acetone-d$_6$) ppm δ 9.93 (bs, 1H, H-1), 7.53 (d, J=8.4 Hz, 1H, H-4), 7.14 (d, J=1.7 Hz, 1H, H-7), 7.04-7.08 (m, 1H, H-2), 6.81 (dd, J=8.4, 1.7 Hz, 1H, H-5), 3.35-3.47 (m, 2H, H-11), 3.09+2.96 (bs, 3H, H-15), 3.05 (t, J=6.8 Hz, 2H, H-16), 2.69 (t, J=6.8 Hz, 2H, H-17), 1.59-1.67 (m, 2H, H-12), 1.30-1.40 (m, 2H, H-13), 0.95-0.97 (m, 3H, H-14); $^{13}$C-NMR (75 MHz, Acetone-d$_6$) ppm δ 174.75, 155.85, 148.28, 137.43, 125.72, 123.31, 119.05, 115.05, 114.40, 105.37, 49.41, 35.18, 34.83, 34.63, 30.90, 30.61, 21.29, 20.48, 14.14; MS (CI$^+$) m/z 319.163 (MH$^+$, 80.00), 318.156 (M$^+$, 55.00), 272.143 ([M$^+$-CH$_2$O$_2$], 52.50); HRMS calcd. for $C_{17}H_{22}N_2O_4$ (M$^+$, DCI$^+$/iBu) 318.1580. found 318.1561, for $C_{17}H_{23}N_2O_4$ ([MH$^+$—C$_9$H$_8$NO]$^+$, DCI$^+$/iBu) 319.1658. found 319.1632.

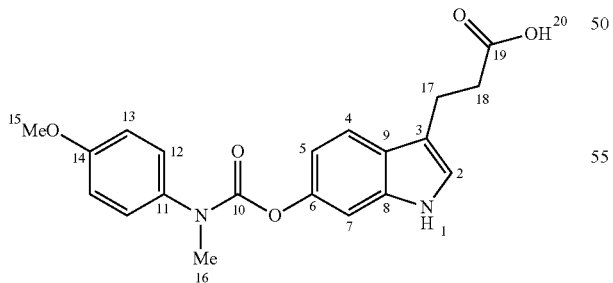

3-(6-(((4-Methoxyphenyl)(methyl)carbamoyl)oxy)-1H-indol-3-yl)propanoic acid, AN-1141

Compound AN-1141 prepared from AN-683 by procedure H, was obtained as a colourless oil in 60% yield. $^1$H-NMR (300 MHz, MeOD) ppm δ 10.25 (bs, 1H, H-1), 7.46 (d, J=8.7 Hz, 1H, H-4), 7.32 (dd, J=6.9, 2.6 Hz, 2H, H-13), 7.05 (bs, 2H, H-2+H-7), 6.96 (dd, J=6.9, 2.6 Hz, 2H, H-14), 6.75 (bd, J=6.9 Hz, 1H, H-5), 3.80 (s, 3H, H-16), 3.36 (s, 3H, H-11), 3.06 (t, J=7.9 Hz, 2H, H-17), 2.65 (J=7.9 Hz, 2H, H-18); $^{13}$C-NMR (75 MHz, MeOD) ppm δ 175.95, 158.47, 155.70, 146.78, 136.47, 127.11, 125.02, 122.29, 118.01, 113.99, 113.87, 112.72, 103.85, 54.55, 37.54, 34.65, 20.33.

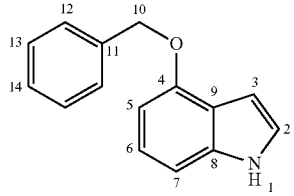

4-(Benzyloxy)-1H-indole, (2)

Compound 2, prepared from 4-hydroxyindole by procedure P, was isolated by chromatography eluted with EtOAc-hexane (1:14 to 1:12), and was isolated as a yellow oil in 30-54% yields. $^1$H-NMR (300 MHz, CDCl$_3$) ppm δ 8.15 (bs, 1H, H-1), 7.57-7.60 (m, 2H, H-12), 7.38-7.49 (m, 3H, H-13+H-14), 7.16 (t, J=8.1 Hz, 1H, H-6), 7.09-7.02 (m, 2H, H-7+H-5), 6.81-6.78 (m, 1H, H-3), 6.67 (d, J=8.1 Hz, 1H, H-2), 5.30 (s, 2H, H-10); $^{13}$C-NMR (75 MHz, CDCl$_3$) ppm δ 152.56, 137.64, 137.36, 128.56, 127.81, 127.42, 122.82, 122.73, 118.94, 104.81, 101.16, 100.02, 69.99.

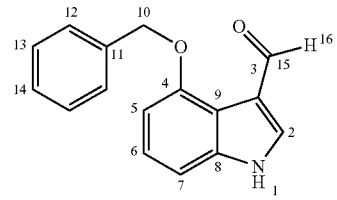

4-(Benzyloxy)-1H-indole-3-carbaldehyde AN-1193

Compound AN-1193, prepared from 2 by procedure C, was isolated as an off-white solid in 62% yield, after quickly boiling the solution for 1 min. The precipitated solid was filtered and washed with water and was recrystallized from EtOAc-hexane, mp 153-156° C. $^1$H-NMR (300 MHz, CDCl$_3$) ppm δ 10.49 (s, 1H, H-16), 9.14 (bs 1H, H-1), 7.93 (d, J=2.0 Hz, 1H, H-2), 7.48 (d, J=8.0 Hz, 2H, H-12), 7.39 (t, J=8.0 Hz, 2H, H-13), 7.34 (d, J=8.0 Hz, 1H, H-14), 7.18 (t, J=8.0 Hz, 1H, H-6), 7.09 (d, J=8.0 Hz, 1H, H-7), 6.79 (d, J=8.0 Hz, 1H, H-5), 5.25 (s, 2H, H-10); $^{13}$C-NMR (75 MHz, CDCl$_3$) ppm δ 188.61, 153.56, 137.74, 136.72, 128.74, 128.21, 128.09, 127.51, 124.28, 119.56, 116.28, 105.46, 103.70, 70.29; MS (CI$^+$) m/z 252.100 (MH$^+$, 100.00); HRMS calcd. for $C_{16}H_{14}NO_2$ (MH$^+$, DCI$^+$/CH$_4$) 252.1025. found 252.0998.

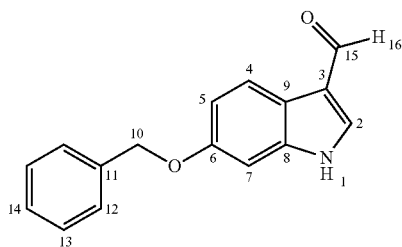 [SMILES: O=Cc1c[nH]c2cc(OCc3ccccc3)ccc12]

6-(Benzyloxy)-1H-indole-3-carbaldehyde, 99

Compound 99, prepared from 6-Benzyloxyindole 91 by procedure C, was isolated as a yellow crystals in 86% yield, after quickly boiling the solution for 1 min. The precipitated crystals were filtered, washed with water and dried, mp dec.>150° C. $^1$H-NMR (300 MHz, Acetone-$d_6$) ppm δ 9.96 (s, 1H, H-16), 8.08 (d, J=8.8 Hz, 1H, H-4), 8.06 (s, 1H, H-2), 7.50+7.36 (m, 5H, H-12, H-13, H-14), 7.14 (d, J=2.4 Hz, 1H, H-7), 7.00 (dd, J=8.9, 2.4 Hz, 1H, H-5), 5.15 (s, 2H, H-10) $^{13}$C-NMR (75 MHz, Acetone-$d_6$) ppm δ 185.13, 157.44, 138.49, 137.39, 137.21, 129.23, 128.53, 128.35, 122.79, 122.40, 113.52, 113.36, 97.48, 70.76.

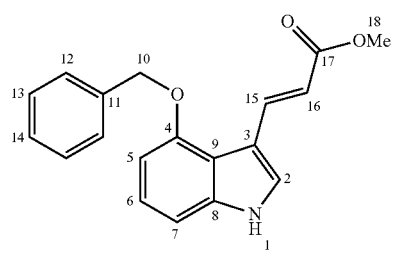 [SMILES: COC(=O)/C=C/c1c[nH]c2cccc(OCc3ccccc3)c12]

(E)-Methyl 3-(4-(benzyloxy)-1H-indol-3-yl)acrylate, AN-830

Compound AN-830 prepared from AN-1193 by procedure D, was recrystallized from EtOH to give AN-830 as a creamy solid in 57% yield, mp 153-156° C. $^1$H-NMR (300 MHz, Acetone-$d_6$) ppm δ 10.84 (bs, 1H, H-1), 8.49 (d, J=16.8 Hz, 1H, H-15), 7.90 (d, J=2.1 Hz, 1H, H-2), 7.65-7.61 (m, 2H, H-12), 7.47-7.35 (m, 3H, H-13+H-6), 7.12-7.09 (m, 2H, H-14+H-7), 6.80-6.75 (m, 1H, H-5), 6.39 (d, J=16.8 Hz, 1H, H-16), 5.31 (s, 2H, H-10), 3.66 (s, 3H, H-18); $^{13}$C-NMR (75 MHz, Acetone-$d_6$) ppm δ 168.42, 154.50, 140.64, 139.62, 138.38, 129.32, 128.41, 128.18, 125.96, 125.79, 124.09, 113.73, 113.16, 106.42, 103.35, 70.56, 51.10.

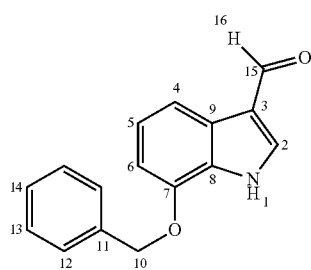

7-(Benzyloxy)-1H-indole-3-carbaldehyde, AN-1148

Compound AN-1148, prepared from 7-benzyloxyindole by procedure C, was isolated as a brown crystals in 96% yield, after quickly boiling the solution for 1 min. The precipitated crystals were filtered, washed with water and dried. mp 153-155° C. [156.3-157.3° C.]. $^1$H-NMR (300 MHz, Acetone-$d_6$) ppm δ 11.50 (bs, 1H, H-1), 10.03 (s, 1H, H-16), 8.13 (s, 1H, H-2), 7.82 (d, J=7.5 Hz, 1H, H-6), 7.55 (d, J=6.0 Hz, 2H, H-12), 7.35-7.45 (m, 3H, H-13-H-14), 7.15 (t, J=7.5 Hz, 1H, H-5), 6.94 (d, J=7.5 Hz, 1H, H-4), 5.27 (s, 2H, H-10); $^{13}$C-NMR (75 MHz, Acetone-$d_6$) ppm δ 185.45, 146.44, 138.06, 137.07, 129.27, 128.74, 128.65, 127.08, 123.80, 120.55, 114.93, 106.14, 70.71; MS (CE) m/z 280.136 ([M+$C_2H_5$]$^+$, 17.24), 252.102 (MH$^+$, 100.00); HRMS calcd. for $C_{16}H_{14}NO_2$ (MH$^+$, DCI$^+$/CH$_4$) 252.1025. found 252.1020.

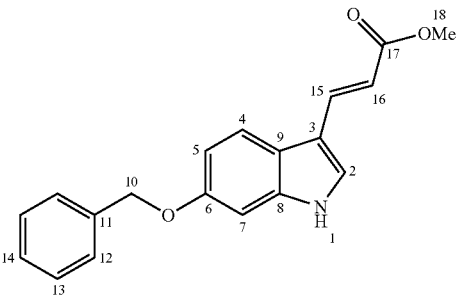 [SMILES: COC(=O)/C=C/c1c[nH]c2cc(OCc3ccccc3)ccc12]

(E)-Methyl 3-(6-(benzyloxy)-1H-indole-3-yl)acrylate, AN-1104

Compound AN-1104 prepared from 99 by procedure D, was isolated by chromatography eluted with EtOAc-hexane (1:2), as a yellow solid in 60% yield, mp 174-178° C. $^1$H-NMR (300 MHz, Acetone-$d_6$) ppm δ 10.78 (bs, 1H, H-1), 7.87 (d, J=15.2 Hz, 1H, H-15), 7.82 (d, J=8.2 Hz, 1H, H-4), 7.72 (bs, 1H, H-2), 7.29-7.51 (m, 5H, H-12, H-13, H-14), 7.12 (d, J=2.3 Hz, 1H, H-7), 6.98 (dd, J=8.2, 2.3 Hz, 1H, H-5), 6.38 (d, J=15.2 Hz, 1H, H-16), 5.15 (s, 2H, H-10), 3.67 (s, 3H, H-18); $^{13}$C-NMR (75 MHz, Acetone-$d_6$) ppm δ 168.65, 156.92, 139.63, 139.57, 138.60, 130.99, 129.23, 128.50, 128.32, 121.58, 120.70, 113.57, 112.33, 112.20, 97.70, 70.77, 51.20; MS (CI$^+$) m/z 307.121 (M$^+$, 100.00), 308.131 (WE, 80.02), 276.105 ([MH$^+$—CH$_3$OH]$^+$, 37.70); HRMS calcd. for $C_{19}H_{17}NO_3$ (M$^+$, DCI$^+$/CH$_4$) 307.1208. found 307.1212, for $C_{19}H_{18}NO_3$ (MH$^+$, DCI$^+$/CH$_4$) 308.1287. found 308.1309, for ([MH$^+$—CH$_3$OH]$^+$, DCI$^+$/CH$_4$) 276.1025. found 276.1051; Anal. calcd. for $C_{19}H_{17}NO_3$ (MW 307.34 g/mol): C, 74.25; H, 5.58; N, 4.56; O, 15.62. Found C, 73.918; H, 5.680; N, 4.557.

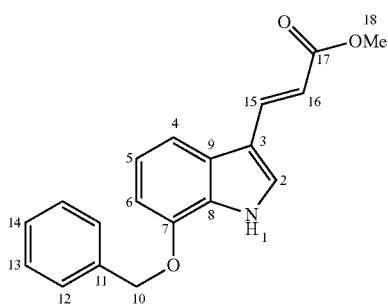 [SMILES: COC(=O)/C=C/c1c[nH]c2c(OCc3ccccc3)cccc12]

(E)-Methyl 3-(7-(benzyloxy)-1H-indole-3-yl)acrylate, AN-1149

Compound AN-1149 prepared from AN-1148 by procedure D, was recrystallized from MeOH to give AN-1149 as a yellow solid in 47% yield, mp 134-137° C. $^1$H-NMR (300 MHz, CDCl$_3$) ppm δ 8.86 (bs, 1H, H-1), 7.92 (d, J=16.6 Hz, 1H, H-15), 7.36-7.53 (m, 7H, H-2+H-6+H-12+H-13+H-14), 7.16 (t, J=7.6 Hz, 1H, H-5), 6.80 (d, J=7.6 Hz, 1H, H-4), 6.45 (d, J=16.6 Hz, 1H, H-16), 5.19 (s, 2H, H-10), 3.80 (s, 3H, H-18); $^{13}$C-NMR (75 MHz, CDCl$_3$) ppm δ 168.82, 145.56, 138.77, 136.71, 128.75, 128.38, 127.96, 126.78, 122.12, 114.06, 113.36, 113.00, 104.55, 70.42, 51.51; MS (CI$^+$) m/z 308.128 (MH$^+$, 82.41), 307.123 (M$^{\cdot+}$, 63.67), 276.101 ([MH$^+$—CH$_3$OH], 54.12); HRMS calcd. for C$_{18}$H$_{14}$NO$_2$ ([MH$^+$—CH$_3$OH], DCI$^+$/CH$_4$) 276.1025. found 276.1006, for C$_{19}$H$_{17}$NO$_3$ (M$^{\cdot+}$, DCI$^+$/CH$_4$) 307.1208. found 307.1229, for C$_{19}$H$_{18}$NO$_3$ (MH$^+$, DCI$^+$/CH$_4$) 308.1287. found 308.1283; Anal. calcd. for C$_{19}$H$_{17}$NO$_3$*1H$_2$O (MW 309.14 g/mol): C, 73.82; H, 5.61; N, 4.53. Found C, 73.629; H, 5.715; N, 4.352.

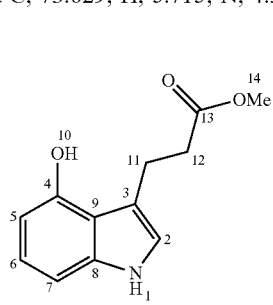

Methyl 3-(4-hydroxy-1H-indol-3-yl)propanoate, AN-843

Compound AN-843 prepared from AN-830 by procedure D, was isolated by chromatography eluted with EtOAc-hexane (1:3), as a white solid in 85% yield, mp. 93-95° C. $^1$H-NMR (300 MHz, CDCl$_3$) ppm δ 7.96 (bs, 1H, H-1), 7.00 (t, J=8.2 Hz, 1H, H-6), 6.93-6.88 (m, 2H, H-2+H-5), 6.48 (dd, J=8.2, 1.65 Hz, 1H, H-7), 3.66 (s, 3H, H-14), 3.22 (t, J=6.7 Hz, 2H, H-11), 2.80 (t, J=6.7 Hz, 2H, H-12); $^{13}$C-NMR (75 MHz, CDCl$_3$) ppm δ 175.03, 150.38, 138.49, 122.87, 120.94, 116.76, 114.74, 105.09, 104.15, 51.77, 36.42, 21.63; MS (CI$^+$) m/z 220.097 (WE, 96.56), 219.090 (NV, 74.22), 188.067 ([MH-MeOH]$^+$, 67.22); HRMS calcd. for C$_{12}$H$_{14}$NO$_3$ (MH$^+$, DCI$^+$/CH$_4$) 220.0974. found 220.0973, for C$_{12}$H$_{13}$NO$_3$ (M$^{\cdot+}$, DCI$^+$/CH$_4$) 219.0895. found 219.0896, for C$_{11}$H$_{10}$NO$_2$ ([MH-MeOH]$^+$, DCI$^+$/CH$_4$) 188.0712. found 188.0669.

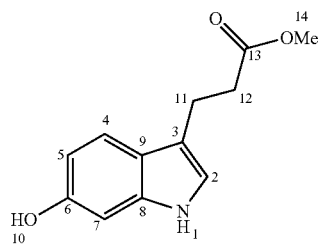

Methyl 3-(6-hydroxy-1H-indol-3-yl) propanoate, AN-678

Compound AN-678 prepared from AN-1104 by procedure F, was isolated by chromatography eluted with EtOAc-hexane (1:2), as a white solid in 83% yield, mp 93-96° C. $^1$H-NMR (300 MHz, Acetone-d$_6$) ppm δ 9.63 (bs, 1H, H-1), 7.35 (d, J=8.4 Hz, 1H, H-4), 6.93 (dt, J=2.5, 1.0 Hz, 1H, H-2), 6.82 (dd, J=2.2, 0.5 Hz, 1H, H-7), 6.64 (dd, J=8.4, 2.2 Hz, 1H, H-5), 5.08 (br, 1H, H-10), 3.61 (s, 3H, H-14), 2.98 ("t", 2H, H-11), 2.66 ("t", 2H, H-11); $^{13}$C-NMR (75 MHz, Acetone-d$_6$) ppm δ 173.91, 154.20, 138.76, 122.06, 120.78, 119.49, 114.72, 109.75, 97.39, 51.49, 35.34, 21.42; MS (CI$^+$) m/z 219.090 (M$^{\cdot+}$, 86.05), 220.102 (MH$^+$, 17.55); HRMS calcd. for C$_{12}$H$_{13}$NO$_3$ (M$^{\cdot+}$, CH$_4$) 219.0895 found 219.0904; Anal. calcd. for C$_{12}$H$_{13}$NO$_3$ (MW 219.23 g/mol): C, 65.74; H, 5.98; N, 6.39; O, 21.89. Found C, 65.711; H, 6.142; N, 6.070.

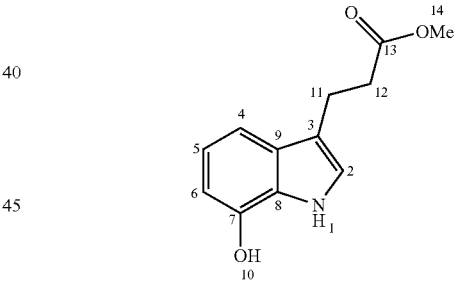

Methyl 3-(7-hydroxy-1H-indol-3-yl) propanoate, AN-1150

Compound AN-1150 prepared from AN-1149 by procedure F, was crystallized from CH$_2$Cl$_2$-hexane to give AN-1150 as a white solid in 61% yield, mp 89-94° C. $^1$H-NMR (300 MHz, CDCl$_3$) ppm δ 8.38 (bs, 1H, H-1), 7.18 (d, J=7.9 Hz, 1H, H-6), 6.95 (t, J=7.9 Hz, 1H, H-5), 6.89 (bs, 1H, H-2), 6.62 (d, J=7.9 Hz, 1H, H-4), 6.50 (bs, 1H, H-10), 3.70 (s, 3H, H-14), 3.07 (t, J=5.6 Hz, 2H, H-11), 2.75 (t, J=5.6 Hz, 2H, H-12); $^{13}$C-NMR (75 MHz, CDCl$_3$) ppm δ 174.94, 141.91, 129.41, 126.29, 121.61, 119.93, 115.11, 111.38, 106.83, 52.01, 34.96, 20.92; MS (CI$^+$) m/z 219.087 (MH$^+$, 48.55), 188.068 ([MH$^+$-MeOH], 19.66), 146.06 (C$_9$H$_8$NO$^+$, 100.01); HRMS calcd. for C$_{12}$H$_{13}$NO$_3$ (MH$^+$, DCI$^+$/CH$_4$) 219.0895. found 219.0866, for C$_9$H$_8$NO ([MH$^+$-MeOH], DCI$^+$/CH$_4$) 146.0606. found 146.0598; Anal. calcd.

for $C_{12}H_{13}NO_3$ (MW 219.23 g/mol): C, 65.74; H, 5.98; N, 6.39; O, 21.89. Found C, 65.386; H, 6.146; N, 6.136.

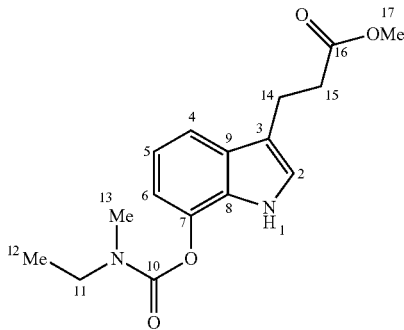 [SMILES: CCN(C)C(=O)Oc1cccc2c(CCC(=O)OC)c[nH]c12]

Methyl 3-(7-(ethyl(methyl)carbamoyloxy)-1H-indol-3-yl)propanoate, AN-1151

Compound AN-1151 prepared from AN-1150 and 2a by procedure B, was isolated by chromatography eluted with EtOAc-hexane (1:2), as a pale bright oil in 78% yield. $^1$H-NMR (300 MHz, CDCl$_3$) ppm δ 8.49 (bs, 1H, H-1), 7.42 (d, J=7.9 Hz, 1H, H-6), 7.06 (t, J=7.9 Hz, 1H, H-5), 6.96 (d, J=5.6 Hz, 1H, H-4), 6.89 (bs, 1H, H-2), 3.67 (s, 3H, H-17), 3.39-3.53 (m, 2H, H-11), 3.01+3.10 (s, 3H, H-13), 3.08 (t, J=9.0 Hz, 2H, H-14), 2.70 (t, J=9.0 Hz, 2H, H-15), 1.18-1.28 (m, 3H, H-12); $^{13}$C-NMR (75 MHz, CDCl$_3$) ppm δ 173.79, 153.70, 137.10, 130.21, 128.96, 122.16, 119.25, 115.80, 115.23, 113.79, 51.54, 44.28, 44.21, 34.68, 34.35, 33.98, 20.65, 13.26, 12.44; MS (CI$^+$) m/z 305.145 (MH$^+$, 100.00), 304.140 (M$^{+}$, 73.51), 273.119 ([M$^+$-CH$_3$OH], 17.82), 231.108 ($C_9H_{15}N_2O_2^+$, 50.50), 86.056 ($C_4H_8NO^+$, 87.68); HRMS calcd. for $C_{16}H_{21}N_2O_4$ (MH$^+$, DCI$^+$/CH$_4$) 305.1501. found 305.1454, for $C_{16}H_{20}N_2O_4$ (M$^+$, DCI$^+$/CH$_4$) 304.1423. found 304.1403, for $C_{13}H_{15}N_2O_2$ ($C_9H_{15}N_2O_2^+$, DCI$^+$/CH$_4$) 231.1134. found 231.1084.

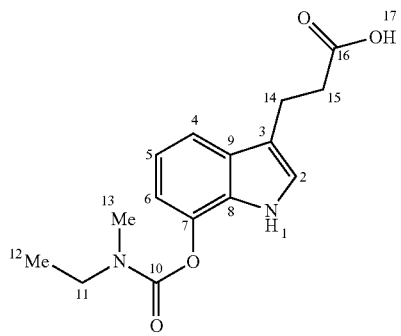 [SMILES: CCN(C)C(=O)Oc1cccc2c(CCC(=O)O)c[nH]c12]

Methyl 3-(7-(ethyl(methyl)carbamoyloxy)-1H-indol-3-yl)propanoic acid, AN-1152

Compound AN-1152 prepared from AN-1151 by procedure H, was crystallized from EtOAc-hexane to give AN-1152 as a white solid in 59% yield, mp 98-101° C. $^1$H-NMR (300 MHz, CDCl$_3$) ppm δ 8.50 (bs, 1H, H-1), 7.43 (d, J=8.2 Hz, 1H, H-6), 7.06 (t, J=8.2 Hz, 1H, H-5), 6.93 (bs, 2H, H-4+H-2), 3.51-3.33 (m, 2H, H-11), 3.08 (t, J=7.0 Hz, 2H, H-14), 3.14+3.02 (s, 3H, H-13), 2.74 (t, J=7.0 Hz, 2H, H-15), 1.19-1.32 (m, 3H, H-12); $^{13}$C-NMR (75 MHz, CDCl$_3$) ppm δ 178.61, 154.48, 154.27, 137.01, 130.28, 128.93, 122.31, 119.35, 115.96, 115.09, 113.85, 44.43, 44.28, 34.53, 34.44, 34.08, 20.36, 13.27, 12.46; MS (CI$^+$) m/z 291.135 (MH$^+$, 88.74), 290.128 (M$^{*+}$, 56.23), 231.111 ($C_{13}H_{15}N_2O_2^+$, 24.30), 86.058 ($C_4H_8NO^+$, 99.99); HRMS calcd. for $C_{15}H_{19}N_2O_4$ (MH$^+$, DCI$^+$/CH$_4$) 291.1345. found 291.1350, for $C_{15}H_{18}N_2O_4$ (M$^a$, DCI$^+$/CH$_4$) 290.1267. found 290.1284, for $C_{13}H_{15}N_2O_2$ ($C_{13}H_{15}N_2O_2^+$, DCI$^+$/CH$_4$) 231.1134. found 231.1108; Anal. calcd. for $C_{15}H_{18}N_2O_4$ (MW 290.31 g/mol): C, 62.06; H, 6.25; N, 9.65. Found C, 61.9595; H, 6.3035; N, 9.261.

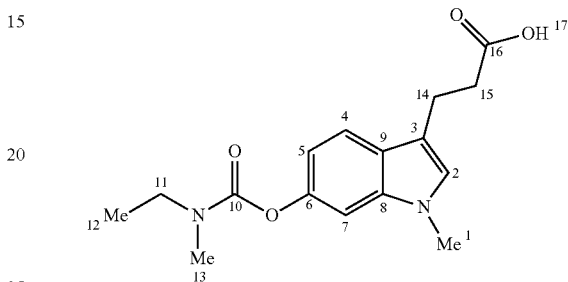

3-(6-(Ethyl(methyl)carbamoyloxy)-1-methyl-1H-indol-3-yl)propanoic acid, AN-1139

Compound AN-1139 prepared from AN-1138 by procedure H, was obtained as a colourless oil in 95% yield. $^1$H-NMR (300 MHz, MeOD) ppm δ 7.50 (d, J=8.4 Hz, 1H, H-4), 7.05 (d, J=2.3 Hz, 1H, H-7), 6.93 (s, 1H, H-2), 6.8 (dd, J=8.42, 2.30 Hz, 1H, H-5), 3.63 (s, 3H, H-1), 3.38-3.56 (m, 2H, H-11), 3.10+2.97 (bs, 3H, H-13), 3.01 (t, J=8.3 Hz, 2H, H-14), 2.63 (t, J=8.3 Hz, 2H, H-15), 1.16-1.27 (m, 3H, H-12); $^{13}$C-NMR (75 MHz, MeOD) ppm δ 177.09, 157.50, 148.31, 138.44, 128.20, 126.75, 119.77, 114.75, 114.31, 103.60, 45.10, 35.96, 34.53, 34.28, 32.67, 21.53, 13.46, 12.70; MS (CI$^-$) m/z 303.138 ([M–H]$^-$, 100.00); HRMS calcd. for $C_{16}H_{19}N_2O_4$ ([M–H]$^-$, DCI$^-$/CH$_4$) 303.1345. found 303.1279.

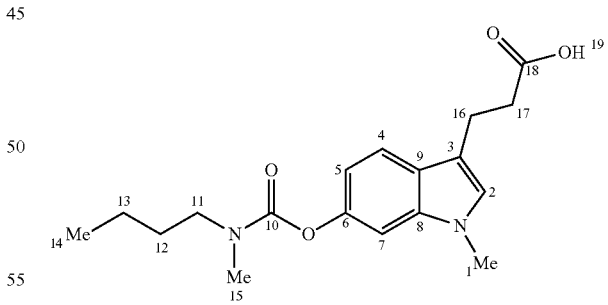

3-(6-(Butyl(methyl)carbamoyloxy)-1-methyl-1H-indol-3-yl)propanoic acid, AN-1140

Compound AN-1140 prepared from AN-1137 by procedure H, was obtained as a colourless oil in 82% yield. $^1$H-NMR (300 MHz, MeOD) ppm δ 7.50 (d, J=8.1 Hz, 1H, H-4), 7.05 (bs, 1H, H-7), 6.95 (s, 1H, H-2), 6.77 (bd, J=8.1 Hz, 1H, H-5), 3.66 (s, 3H, H-1), 3.32-3.51 (m, 2H, H-11), 3.11+2.97 (s, 3H, H-15), 3.01 (t, J=6.4 Hz, 2H, H-16), 2.64

(t, J=6.4 Hz, 2H, H-17), 1.55-1.73 (m, 2H, H-12), 1.24-1.46 (m, 2H, H-13), 0.79-1.03 (m, 3H, H-14); $^{13}$C-NMR (75 MHz, MeOD) ppm δ 177.11, 157.50, 148.35, 138.47, 128.21, 126.781, 119.78, 114.80, 114.35, 114.22, 103.53, 49.85, 49.95, 35.99, 35.04, 34.83, 32.69, 31.22, 30.57, 22.18, 20.89, 14.19.

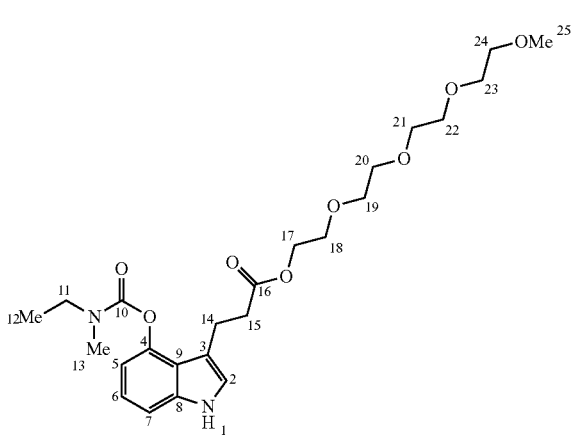 [SMILES: CCN(C)C(=O)Oc1cccc2[nH]cc(CCC(=O)OCCOCCOCCOCCOC)c12]

2,5,8,11-Tetraoxatridecan-13-yl 3-(4-((ethyl(methyl)carbamoyl)oxy)-1H-indol-3-yl)propanoate, AN-889

To a stirred solution of acid AN-805 (96 mg, 0.33 mmol) in CH$_2$Cl$_2$ (2.5 mL) was added 2,4,6-trichlorobenzoyl chloride (0.057 mL, 0.33 mmol) and NEt$_3$ (0.055 mL, 0.33 mmol). After stirring for 2.5 h at room temperature, a solution of tetraethyleneglycol monomethyl ether (0.072 mL, 0.33 mmol) in CH$_2$Cl$_2$ (2.5 mL) was added. To this mixture were added NEt$_3$ (0.055 mL, 0.33 mmol) and 4-DMAP (44 mg, 0.33 mmol) and the solution was stirred at room temperature for 1 h. The mixture was diluted with CH$_2$Cl$_2$ and washed with water. The organic layers were washed with brine, dried over Na$_2$SO$_4$, filtered and evaporated to give the ester, which was isolated by chromatography eluted with CHCl$_3$-EtOAc (10:2 to 10:3 to 10:5 to EtOAc) to give AN-889 as a yellow oil in 69% yield. $^1$H-NMR (300 MHz, CDCl$_3$) ppm δ 8.84 (bs, 1H, H-1), 7.11-7.01 (m, 2H, H-6+H-7), 6.83 (bs, 1H, H-2), 6.74 (bt, J=6.7 Hz, 1H, H-5), 4.21 ("bt", J=4.5 Hz, 2H, H-17), 3.63 (s, 2H, H-24), 3.63-3.42 (m, 14H, H-11+H-18+H-19+H-20+H-21+H-22+H-23), 3.33 (s, 3H, H-25), 3.14+3.01 (s, 3H, H-13), 3.06 (t, J=6.9 Hz, 2H, H-15), 2.67 (t, J=6.9 Hz, 2H, H-14), 1.27+1.19 (bt, J=6.9 Hz, 3H, H-12); $^{13}$C-NMR (75 MHz, CDCl$_3$) ppm δ 173.37, 155.27, 138.75, 122.69, 121.69, 120.25, 112.84, 112.33, 112.10, 108.97, 71.88, 70.63, 70.57, 70.48, 69.19, 58.97, 44.21, 43.97, 35.46, 35.32, 34.18, 33.89, 21.93, 13.34, 12.53; MS (CI$^+$) m/z 480.238 (M$^+$·, 0.26), 481.225 (MH$^+$, 0.18); HRMS calcd. for C$_{21}$H$_{32}$N$_3$O$_4$ (MH$^+$, DCI$^+$/CH$_4$) 481.2250. found 480.2552.

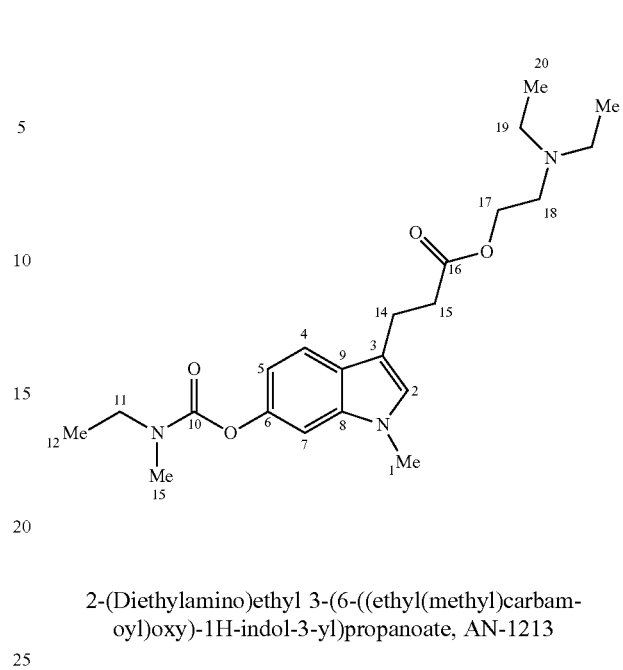

2-(Diethylamino)ethyl 3-(6-((ethyl(methyl)carbamoyl)oxy)-1H-indol-3-yl)propanoate, AN-1213

To a stirred solution of AN-1139 (50 mg, 0.17 mmol) in dry CH$_3$CN (3 mL), DBU (0.05 mL, 0.34 mmol) and diethylaminoethylchloride hydrochloride (32 mg, 0.19 mmol) were added. The mixture was stirred at room temperature for 1 h and was then dissolved in EtOAc and was extracted with water. The organic layers were washed with brine dried over Na$_2$SO$_4$, filtered and evaporated. The residue was isolated by chromatography eluted with CH$_2$Cl$_2$-MeOH (10:0.3 to 10:0.4), to give AN-1213 as a colourless oil in 23% yield. $^1$H-NMR (600 MHz, CDCl$_3$) ppm δ 8.05 (bs, 1H, H-1), 7.50 (d, J=9.0 Hz, 1H, H-4), 7.11 (bs, 1H, H-2), 6.94 (d, J=3.0 Hz, 1H, H-7), 6.86 (bd, J=9.0 Hz, 1H, H-5), 4.16 (t, J=6.0 Hz, 2H, H-17), 3.50+3.42 (q, J=9.0 Hz, 2H, H-11), 3.09+3.00 (s, 3H, H-13), 3.06 (t, J=9.0 Hz, 2H, H-14), 2.70 (t, J=9.0 Hz, 4H, H-15+H-18), 2.57 (q, J=9.0 Hz, 4H, H-19), 1.29+1.20 (bt, J=7.2 Hz, 3H, H-12), 1.02 (t, J=7.5 Hz, 6H, H-20); $^{13}$C-NMR (150 MHz, CDCl$_3$) ppm δ 173.34, 155.38, 155.20, 147.49, 136.25, 124.88, 121.83, 118.84, 114.92, 113.03, 104.42, 62.38, 50.90, 47.58, 44.07, 34.95, 34.28, 33.83, 20.66, 13.26, 12.53, 11.60; MS (co m/z 390.245 (MH$^+$, 46.02); HRMS calcd. for C$_{21}$H$_{32}$N$_3$O$_4$ (MH$^+$, DCI$^+$/CH$_4$) 390.2393. found 390.2451.

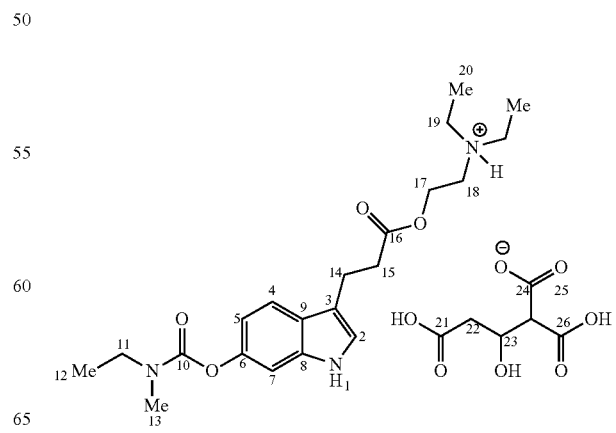

N,N-diethyl-2-((3-(6-((ethyl(methyl)carbamoyl)oxy)-1H-indol-3-yl)propanoyl)oxy) ethanaminium citrate AN-791

Compound AN-791 prepared from AN-1213 by procedure R, gave the citrate salt AN-791 as a colourless oil in quantitative yield. $^1$H-NMR (300 MHz, MeOD) ppm δ 7.50 (d, J=9.0 Hz, 1H, H-4), 7.08 (bs, 2H, H-2+H-7), 6.77 (dd, J=9.0, 2.2 Hz, 1H, H-5), 4.29 (bs, 2H, H-17), 3.53+3.40 (q, J=6.0 Hz, 2H, H-11), 3.20 (bs, 2H, H-18), 3.12+2.98 (s, 3H, H-13), 3.10 (t, J=6.0 Hz, 2H, H-15), 2.93 (bq, J=6.0 Hz, 4H, H-19), 2.76 (ABq, J=15.0 Hz, 4H, H-22+H-25), 2.74 (t, J=6.0 Hz, 2H, H-14), 1.29-1.16 (m, 3H, H-12), 1.14 (bt, J=6.0 Hz, 6H, H-20); $^{13}$C-NMR (75 MHz, MeOD) ppm δ 179.55, 175.16, 174.43, 157.20, 148.37, 137.89, 126.25, 124.16, 119.54, 114.86, 114.61, 114.55, 105.64, 74.21, 59.64, 51.23, 45.12, 44.92, 36.29, 34.55, 34.27, 21.89, 13.45, 12.68, 9.09; MS (CI$^+$) m/z 390.235 (MH$^+$, 23.57); HRMS calcd. for $C_{21}H_{32}N_3O_4$ (MH$^+$, DCI$^+$/CH$_4$) 390.2393. found 390.2353.

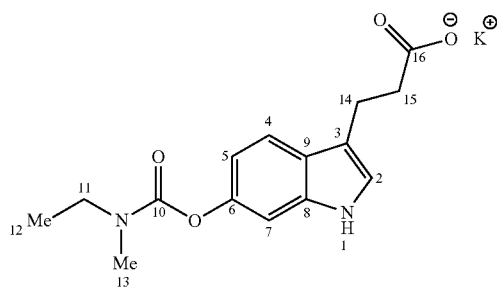 [SMILES: CCN(C)C(=O)Oc1ccc2c(CCC(=O)[O-])c[nH]c2c1 ; [K+]]

Pottassium 3-(6-(Butyl(propyl)carbamoyloxy)-1H-indol-3-yl)propanoate, AN-840

Compound AN-840 prepared from AN-1139 by procedure I, was obtained as a bright brown oil in 78% yield. $^1$H-NMR (300 MHz, MeOD) ppm δ 7.55 (d, J=8.9 Hz, 1H, H-4), 7.06 (bs, 1H, H-2+H-7), 6.74 (dd, J=8.9, 1.8 Hz, 1H, H-5), 3.38-3.53 (m, 2H, H-11), 3.11+2.98 (bs, 3H, H-13), 3.02 (t, J=8.3 Hz, 2H, H-14), 2.54 (t, J=8.3 Hz, 2H, H-15), 1.16-1.27 (m, 3H, H-12); $^{13}$C-NMR (75 MHz, MeOD) ppm δ 182.58, 157.36, 148.04, 137.88, 126.69, 123.32, 119.63, 116.77, 113.96, 105.21, 45.09, 40.10, 34.51, 34.26, 23.37, 13.44, 12.69.

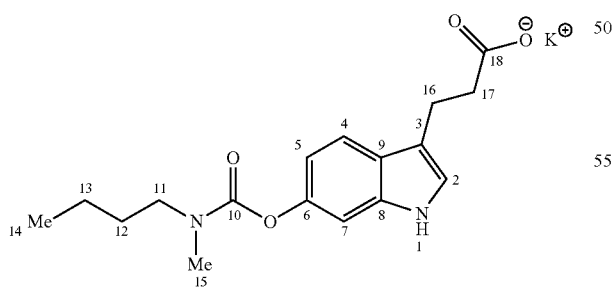

Pottassium 3-(6-(Butyl(propyl)carbamoyloxy)-1H-indol-3-yl)propanoate, AN-824

Compound AN-824 prepared from AN-1140 by procedure I, was obtained as a brown oil in 84% yield. $^1$H-NMR (300 MHz, MeOD) ppm δ 7.56 (d, J=8.0 Hz, 1H, H-4), 7.05-7.06 (m, 2H, H-2+H-7), 6.74 (bd, J=8.0 Hz, 1H, H-5), 3.30-3.49 (m, 2H, H-11), 3.09+2.96 (s, 3H, H-13), 3.04 (t, J=8.1 Hz, 2H, H-16), 2.56 (t, J=8.1 Hz, 2H, H-17), 1.56-1.68 (m, 2H, H-12), 1.32-1.45 (m, 2H, H-13), 0.94-1.02 (m, 3H, H-14); $^{13}$C-NMR (75 MHz, MeOD) ppm δ 182.58, 157.59, 148.02, 137.86, 125.55, 123.36, 119.64, 116.71, 114.00, 105.21, 49.85, 40.09, 35.03, 34.81, 31.17, 30.54, 23.37, 20.85, 14.21; MS (CI$^+$) m/z 346.214 ([M+C$_2$H$_5$]$^+$, 3.11), 319.161 (MH$^+$, 25.47); HRMS calcd. for $C_{17}H_{23}N_2O_4$ (MH$^+$, DCI$^+$/CH$_4$) 319.1658. found 319.1613.

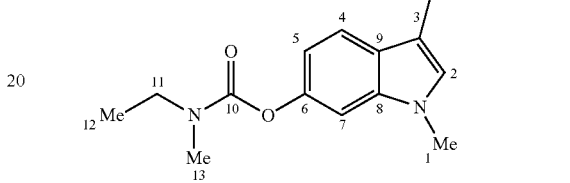

Pottassium 3-(6-(Ethyl(methyl)carbamoyloxy)-1-methyl-1H-indol-3-yl)propanoate, AN-841

Compound AN-841a prepared from AN-1139 by procedure I, was obtained as viscous white solid in 78% yield. $^1$H-NMR (300 MHz, MeOD) ppm δ 7.55 (d, J=8.8 Hz, 1H, H-4), 7.04 (d, J=1.7 Hz, 1H, H-7), 6.97 (s, 1H, H-2), 6.76 (dd, J=8.8, 1.7 Hz, 1H, H-5), 3.68 (s, 3H, H-1), 3.40-3.60 (m, 2H, H-11), 3.12+2.98 (bs, 3H, H-13), 3.01 (t, J=8.2 Hz, 2H, H-14), 2.53 (t, J=8.2 Hz, 2H, H-15), 1.13-1.35 (m, 3H, H-12); $^{13}$C-NMR (75 MHz, MeOD) ppm δ 182.41, 157.50, 148.20, 138.45, 127.95, 127.10, 120.00, 116.33, 113.98, 103.41, 45.10, 40.07, 34.53, 32.67, 23.18, 13.46+12.71; MS (CI$^+$) m/z 304.145 (MH$^+$, 33.78), 286.138 ([MH$^+$—H$_2$O], 42.76), 258.126 ([MH$^+$—CH$_2$O$_2$], 42.75); HRMS calcd. for $C_{16}H_{20}N_2O_4$ (MH$^+$, DCI$^+$/CH$_4$) 304.1463. found 304.1452.

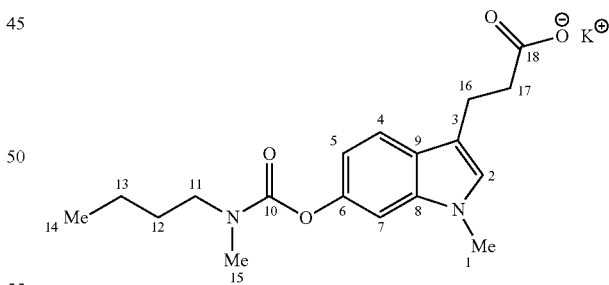

Pottassium 3-(6-(Butyl(methyl)carbamoyloxy)-1-methyl-1H-indol-3-yl)propanoate, AN-842

Compound AN-842 prepared from AN-1140 by procedure I, was obtained as a colourless oil in 90% yield. $^1$H-NMR (300 MHz, MeOD) ppm δ 7.56 (d, J=8.5 Hz, 1H, H-4), 7.03 (bd, J=2.5 Hz, 1H, H-7), 6.98 (s, 1H, H-2), 6.75 (bd, J=8.5 Hz, 1H, H-5), 3.68 (s, 3H, H-1), 3.33-3.52 (m, 2H, H-11), 3.11+2.98 (s, 3H, H-15), 3.02 (t, J=8.0 Hz, 2H, H-16), 2.53 (t, J=8.0 Hz, 2H, H-17), 1.58-1.71 (m, 2H, H-12), 1.33-1.47

(m, 2H, H-13), 0.95-1.03 (m, 3H, H-14); $^{13}$C-NMR (75 MHz, MeOD) ppm δ 182.43, 157.54, 148.17, 138.40, 127.93, 127.06, 119.99, 116.30, 114.01113.88, 103.30, 49.83, 40.07, 35.03, 34.82, 32.66, 31.18, 30.55, 23.16, 20.86, 14.17; MS (CI$^+$) m/z 332.175 (MH, 7.22); HRMS calcd. for $C_{18}H_{24}N_2O_4$ (MH, DCI$^+$/CH$_4$) 332.1736. found 332.1750.

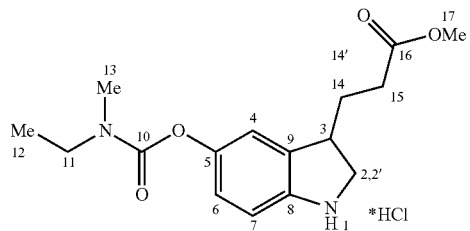 [SMILES: CCN(C)C(=O)Oc1ccc2c(c1)C(CCC(=O)OC)CN2]

3-(2-(Methoxycarbonyl)ethyl) indolin-5-yl ethylmethylcarbamate, AN-669

Compound AN-669 prepared from AN-785 or AN-789 by procedure E, was stirred at room temperature over night, was isolated as a white crystals in 23% yield, mp 108-113° C. $^1$H-NMR (300 MHz, D$_2$O) ppm δ 7.52 (d, J=8.4 Hz, 1H, H-4), 7.17-7.25 (m, 2H, H-7+H-6), 4.01-4.16 (m, 1H, H-2'), 3.66 (s, 3H, H-17), 3.55-3.67 (m, 2H, H-2+H-3), 3.31-3.52 (m, 2H, H-11), 3.08+2.95 (s, 3H, H-13), 2.48-2.52 (m, 2H, H-15), 2.14 (ddd, J=21.5, 14.7, 7.8 Hz, 1H, H-14), 1.91 (ddd, J=21.5, 14.7, 7.8 Hz, 1H, H-14'), 1.09-1.24 (m, 3H, H-12); $^{13}$C-NMR (75 MHz, D$_2$O) ppm δ 176.03, 152.30, 145.98, 140.24, 126.94, 122.68, 119.33, 115.81, 51.57, 51.28, 44.24, 40.52, 33.64, 33.91, 30.94, 27.54, 11.54, 12.19.

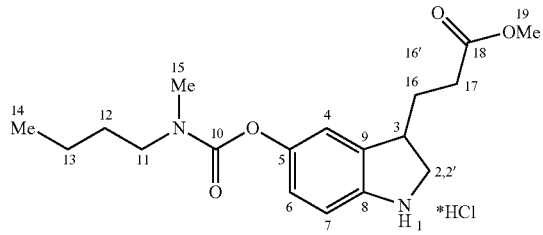 [SMILES: CCCCN(C)C(=O)Oc1ccc2c(c1)C(CCC(=O)OC)CN2]

3-(2-Methoxycarbonyl)ethyl)-1-indol-5-yl-butylmethylcarbamate hydrochloride, AN-668

Compound AN-668 prepared from AN-786 or AN-790 by procedure E, was stirred at room temperature over night, and was isolated as white crystals in 12% yield, mp 114-117° C. $^1$H-NMR (300 MHz, D$_2$O) ppm δ 7.60 (d, J=8.8 Hz, 1H, H-7), 7.29 (bs, 1H, H-4), 7.23 (bd, 1H, H-6), 4.14-4.26 (m, 1H, H-2'), 3.71 (bs, 3H, H-19), 3.67-3.72 (m, 1H, H-3), 3.50 (t, J=7.3 Hz, 1H, H-2), 3.19-3.40 (m, 1H, H-11), 3.12+3.00 (s, 3H, H-15), 2.55 (m, 1H, H-17), 2.13-2.28 (m, 1H, H-16), 1.93-1.98 (m, 1H, H-16'), 1.50-1.70 (m, 2H, H-12), 1.20-1.44 (m, 2H, H-13), 0.88-0.98 (m, 3H, H-14); $^{13}$C-NMR (75 MHz, D$_2$O) ppm δ 175.78, 156.07, 152.35, 140.37, 132.35, 121.08, 119.14, 114.10, 52.26, 51.45, 48.96, 40.60, 34.52, 34.26, 31.18, 29.22, 28.10, 19.22, 13.06.

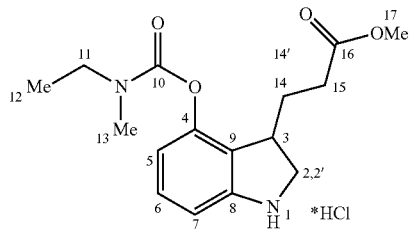

3-(2-(Methoxycarbonyl)ethyl)indolin-4-yl ethylmethylcarbamate hydrochloride, AN-827

Compound AN-827 prepared from AN-803 or AN-1146 or from AN-1167 according to method E, was stirred at room temperature over night, and was isolated as a yellow oil in 40% yield. $^1$H-NMR (300 MHz, CD$_3$CN) ppm δ 7.16-7.48 (m, 3H, H-6+H-5+H-7), 3.70-3.86 (m, 1H, H-2), 3.60 (s, 3H, H-17), 3.46-3.62 (m, 3H, H-2'+H-11), 3.35+3.37 (m, 1H, H-3), 3.06+2.95 (s, 3H, H-13), 2.36-2.40 (m, 2H, H-15), 2.05-2.11 (m, 1H, H-14), 1.80-1.85 (m, 1H, H-14'), 1.15-1.36 (m, 3H, H-12); $^{13}$C-NMR (75 MHz, CD$_3$CN) ppm δ 173.79, 153.98, 149.63, 138.13, 131.93, 130.78, 124.69, 125.29, 118.24, 117.68, 52.14, 50.45, 44.92, 44.78, 40.52, 34.64, 34.35, 31.73, 28.51, 13.45, 12.61; MS (CI$^+$) m/z 335.204 ([M+C$_2$H$_5$]$^+$, 28.34), 307.170 (MH$^+$, 100.00), 306.164 (M, 46.78), 275.143 ([MH$^+$—CH$_3$OH], 27.57); HRMS calcd. for $C_{16}H_{23}N_2O_4$ (MH$^+$, DCI$^+$/CH$_4$) 307.1658. found 307.1702.

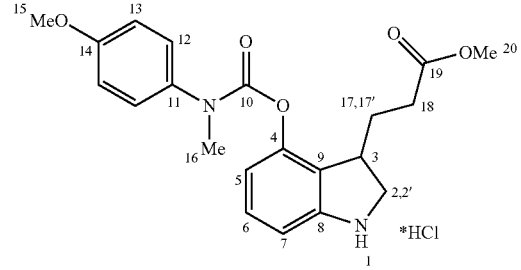 [SMILES: COC(=O)CCC1CNc2cccc(OC(=O)N(C)c3ccc(OC)cc3)c21]

3-(3-methoxy-3-oxopropyl)-4-(((4-methoxyphenyl)(methyl)carbamoyl)oxy) indolin-1-ium hydrochloride, AN-819

Compound AN-819 was isolated as a hygroscopic yellow solid in quantitative yield upon addition of HCl gas to a solution of AN-1222 in ether. $^1$H-NMR (300 MHz, MeOD) ppm δ 7.47 (bt, J=7.3 Hz, 1H, H-6), 7.36 (d, J=9.3 Hz, 2H, H-12), 7.37-7.32 (m, 2H, H-5+H-7), 6.97 (d, J=9.3 Hz, 2H, H-13), 3.93-3.81 (m, 1H, H-2), 3.81 (s, 3H, H-15) 3.67 (s, 3H, H-20), 3.62-3.54 (m, 2H, H-2'+H-3), 3.33 (bs, 3H, H-16), 2.27 (bt, J=5.5 Hz, 2H, H-18), 1.89 (bs, 1H, H-17), 1.66 (bs, 1H, H-17'); $^{13}$C-NMR (75 MHz, CDCl$_3$) ppm δ 174.60, 160.37, 154.37, 149.99, 138.37, 136.48, 131.84, 131.35, 128.91, 124.88, 117.54, 115.58, 55.96, 52.24, 51.35, 41.21, 39.19, 31.96, 28.69; MS (CI$^+$) m/z 384 (M$^{.+}$, 10.22), 385 (MH$^+$, 22.77), 386 (MH$_2^+$, 6.92).

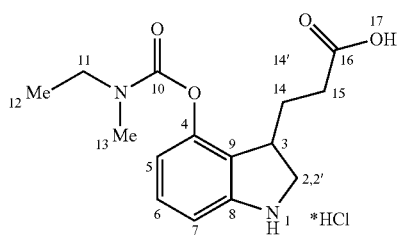 [SMILES: CCN(C)C(=O)Oc1cccc2c1C(CCC(=O)O)CN2]

3-(3-Oxobutyl)indolin-4-yl ethyl(methyl) carbamate hydrochloride, AN-850

Compound AN-850 prepared from AN-805 by procedure E, was stirred at room temperature over night, and was isolated as off-white hygroscopic crystals in 56% yield. $^1$H-NMR (300 MHz, CD$_3$CN) ppm δ 7.17-7.46 (m, 3H, H-6+H-5+H-7), 3.82 ("t", J=9.90 Hz, 1H, H-2), 3.62-3.63 (m, 1H, H-3), 3.58 ("t", J=9.9 Hz 1H, H-2'), 3.38+2.99 (bs, 5H, H-11+H-13), 2.35 ("t", J=7.4 Hz, 2H, H-15), 2.02-2.09 (m, 1H, H-14), 1.73-1.85 (m, 1H, H-14'), 1.15+1.34 (m, 3H, H-12); $^{13}$C-NMR (75 MHz, CD$_3$CN) ppm δ 175.37, 154.36, 149.38, 137.70, 131.99, 130.96, 124.93, 118.33, 50.97, 44.96, 39.46, 34.59, 31.84, 28.34, 13.30, 12.73; MS (CI$^+$) m/z 293.150 (MH$^+$, 100.00), 292.144 (M$^+$, 76.31), 275.138 ([MH—H$_2$O]$^+$, 56.34), 219.115 ([M$^+$-C$_3$H$_5$O$_2$], 13.73); HRMS calcd. for C$_{15}$H$_{20}$N$_2$O$_4$ (M$^+$·, DCI$^+$/CH$_4$) 292.1423. found 292.1438, for C$_{15}$H$_{21}$N$_2$O$_4$ (MH$^+$, DCI$^+$/CH$_4$) 293.1501. found 293.1497, for C$_{15}$H$_{19}$N$_2$O$_3$ ([MH—H$_2$O]$^+$, DCI$^+$/CH$_4$) 275.1396. found 275.1384.

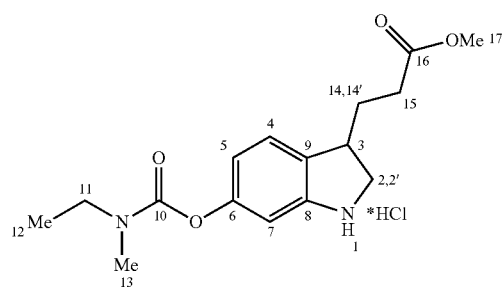 [SMILES: CCN(C)C(=O)Oc1ccc2c(c1)NCC2CCC(=O)OC]

3-(2-(Methoxycarbonyl)ethyl)-1-indoline-6-yl ethylmethylcarbamate hydrochloride, AN-680

A solution of compound AN-681 in MeOH containing a few drops of 1N HCl was stirred over night. The solvent was evaporated to give brown crystals in 43% yield, mp 100-105° C. Another possible way for getting the HCl salt is by bubbling HCl gas to a solution of indoline AN-1171 in ether or CH$_2$Cl$_2$. $^1$H-NMR (300 MHz, MeOD) ppm δ 7.53 (bd, J=6.4 Hz, 1H, H-4), 7.35 (bs, 1H, H-7), 7.18 (bd, J=6.4 Hz, 1H, H-5), 4.05 (m, 1H, H-2), 3.68 (s, 3H, H-17), 3.56-3.64 (m, 1H, H-2), 3.35-3.52 (m, 2H, H-11), 3.35-3.41 (m, 1H, H-3), 3.11+2.99 (s, 3H, H-13), 2.52 ("t", J=7.3 Hz, 2H, H-15), 2.21 (bs, 1H, H-14), 1.94 (bs, 1H, H-14'), 1.18+1.26+1.41 (m, 3H, H-12); $^{13}$C-NMR (75 MHz, MeOD) ppm δ 174.74, 155.43, 152.85, 136.84, 127.09, 125.83, 124.97, 114.95, 52.56, 52.33, 45.21, 41.75, 34.72, 34.46, 32.15, 29.99, 12.62, 13.47; MS (CE) m/z 219.100 ([M$^+$-C$_4$H$_7$O$_2$]$^+$, 62.63), 306.157 (M$^+$, 100); HRMS calcd. for C$_{16}$H$_{22}$N$_2$O$_4$ (M$^+$, DCI$^+$/CH$_4$) 306.1580. Found 306.1567.

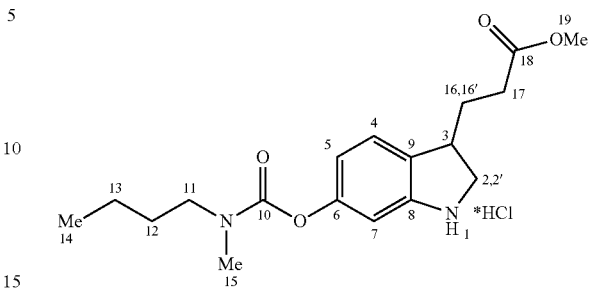

3-(2-(Methoxy carbonyl)ethyl)-1-indoline-6-yl butylmethylcarbamate hydrochloride, AN-677

Compound AN-677 prepared from AN-676 by procedure E, was stirred at room temperature for 1 h, was isolated as white hygroscopic crystals in 60% yield, mp hygroscopic salt. $^1$H-NMR (300 MHz, D$_2$O) ppm δ 7.53 (d, J=8.0 Hz, 1H, H-4), 7.28 (d, J=1.8 Hz 1H, H-7), 7.25 (dd, J=3.0, 1.8 Hz, 1H, H-7), 4.05-4.12 (m, 1H, H-2'), 3.66 (s, 3H, H-19), 3.60-3.73 (m, 1H, H-3), 3.47 (t, J=7.4 Hz, 1H, H-2), 3.14-3.34 (m, 1H, H-11), 3.08+2.95 (s, 3H, H-15), 2.52 (t, J=7.9 Hz, 2H, H-17), 2.13-2.20 (m, 2H, H-16), 1.89-1.99 (m, 2H, H-16') 1.45-1.65 (m, 2H, H-12), 1.19-1.38 (m, 2H, H-13), 0.83-0.94 (m, 3H, H-14); $^{13}$C-NMR (75 MHz, D$_2$O) ppm δ 177.50, 150.97, 147.5, 126.36, 124.00, 113.67, 109.16, 51.35, 49.74, 48.87, 40.06, 31.04, 29.11, 28.60, 28.19, 19.16, 13.05; MS (CI$^+$) m/z 334.188 (M$^+$, 6.29), 335.198 (WE, 4.36); HRMS calcd. for C$_{18}$H$_{26}$N$_2$O$_4$ (M$^+$, CH$_4$), 334.1893. found 334.1877, for C$_{18}$H$_{27}$N$_2$O$_4$ (WE, CH$_4$) 335.1971. found 335.1976.

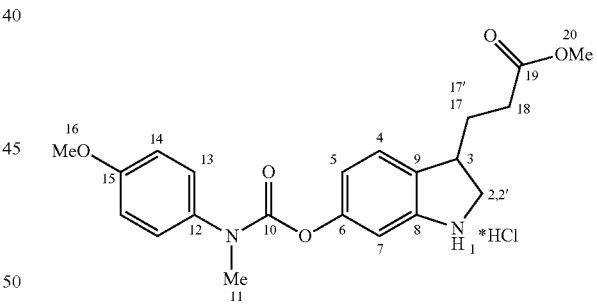

Methyl 3-(6-((4-methoxyphenyl)(methyl)carbamoyloxy)indolin-3-yl)propanoate hydrochloride, AN-685

Compound AN-685 prepared from AN-683 by procedure E, was stirred at room temperature over night, and was isolated as white crystals in 18% yield, mp dec.>150° C. Another possible way for getting the HCl salt is by bubbling HCl gas to a solution of indoline AN-1223 in ether or CH$_2$Cl$_2$. $^1$H-NMR (300 MHz, MeOD) ppm δ 7.51 (bd, J=7.4 Hz, 1H, H-4), 7.41 (bs, 1H, H-7), 7.31 (dd, J=8.9, 2.2 Hz, 2H, H-13), 7.20 (bs, 1H, H-5), 6.96 (dd, J=8.9, 2.2 Hz, 2H, H-14), 4.01-4.13 (m, 1H, H-2'), 3.81 (s, 3H, H-16), 3.68 (s, 3H, H-20), 3.46-3.61 (m, 5H, H-2+H-3+H-11), 2.52 (t, dd, J=7.7 Hz, 2H, H-18), 2.10-2.29 (m, 1H, H-17), 1.78-1.94 (m, 1H, H-17'); $^{13}$C-NMR (75 MHz, MeOD) ppm δ 173.51, 158.50, 151.64, 136.04, 135.62, 135.20, 127.33, 127.10, 125.83, 123.54, 114.08, 113.42, 54.62, 51.35, 50.92, 40.51, 37.74, 30.77, 28.65; MS (CI$^+$) m/z 385.179 (M$^+$, 3.5); HRMS calcd. for $C_{21}H_{25}N_2O_5$ (M$^+$, DCI$^+$/CH$_4$) 385.1763. found 385.1786.

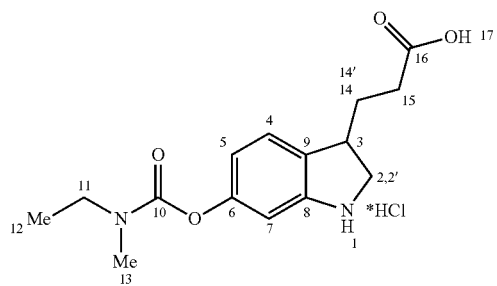 [SMILES: CCN(C)C(=O)Oc1ccc2c(c1)NCC2CCC(=O)O]

3-(6-(Ethyl(methyl) carbamoyloxy) indolin-3-yl) propanoic acid hydrochloride, AN-681

Compound AN-681 prepared from AN-1138 by procedure E, was stirred at room temperature for 2 h, and was isolated as a white crystals in 23% yield, mp 117-119° C. $^1$H-NMR (300 MHz, D$_2$O) ppm δ 7.51 (bd, J=8.1 Hz, 1H, H-4), 7.31 (bd, 1H, H-7), 7.24 (dd, J=8.1, 1.8 Hz, 1H, H-5), 4.05-4.15 (m, 1H, H-2'), 3.59+3.68 (m, 2H, H-3+H-2), 3.30-3.48 (m, 1H, H-11), 3.06+2.94 (s, 3H, H-13), 2.50 ("t", J=7.7 Hz, 2H, H-15), 2.11-2.16 (m, 1H, H-14), 1.87-1.94 (m, 1H, H-14'), 1.11-1.36 (m, 3H, H-12); $^{13}$C-NMR (75 MHz, D$_2$O) ppm δ 177.44, 155.79, 151.27, 150.97, 135.95, 126.34, 124.04, 113.73, 51.35, 44.23; MS (CI$^+$) m/z 219.096 ([M$^+$-C$_3$H$_5$O$_2$]$^+$, 17.24), 292.142 (M$^+$, 18.23); HRMS calcd. for $C_{15}H_{20}N_2O_4$ (M$^+$, DCI$^+$/CH$_4$) 292.1423. found 292.1424.

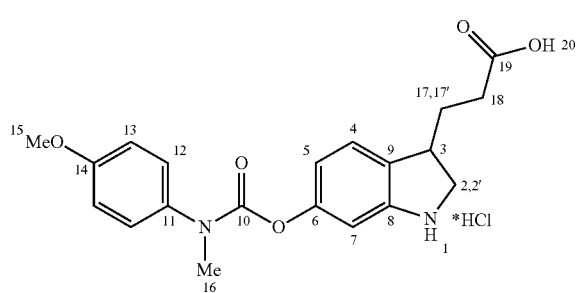 [SMILES: COc1ccc(N(C)C(=O)Oc2ccc3c(c2)NCC3CCC(=O)O)cc1]

3-(6-(((4-Methoxyphenyl)(methyl)carbamoyl)oxy) indolin-3-yl)propanoic acid hydrochloride, AN-684

Compound AN-685 was dissolved in MeOH, stirred with 3N HCl at room temperature over night. Then the solvents were evaporated to give AN-684 as a brown solid. $^1$H-NMR (300 MHz, D$_2$O) ppm δ 7.22-7.44 (m, 4H, H-4+H-13+H-7), 7.06 (bd, J=8.6 Hz, 1H, H-5), 6.93 (dd, J=6.2, 2.3 Hz, 2H, H-14), 3.98-4.06 (m, 1H, H-2'), 3.71 (s, 3H, H-16), 3.45-3.61 (m, 2H, H-2+H-3), 3.25+3.61 (bs, 3H, H-11), 2.35 (bt, J=7.2 Hz, 2H, H-18), 1.98-2.11 (m, 1H, H-17), 1.80-1.84 (m, 1H, H-17'); $^{13}$C-NMR (75 MHz, D$_2$O) ppm δ 177.40, 157.97, 155.21, 150.59, 136.18, 127.67, 126.35, 123.84, 114.63, 113.58, 55.48, 51.28, 39.97, 38.19, 30.94, 28.08.

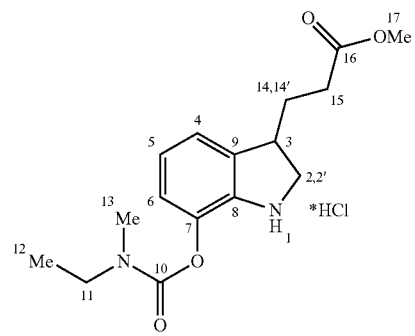 [SMILES: CCN(C)C(=O)Oc1cccc2c1NCC2CCC(=O)OC]

Methyl 3-(7-(ethyl(methyl)carbamoyloxy)indolin-3-yl)propanoate hydrochloride, AN-852

Compound AN-852 prepared from AN-1151 according to procedure E, was stirred at room temperature over night, and was crystallized from MeOH-ether to give AN-1151 as a white solid in 4.2% yield, mp dec.>180° C. $^1$H-NMR (300 MHz, D$_2$O) ppm δ 7.44-7.48 (m, 1H, H-6), 7.38 (t, J=8.2 Hz, 1H, H-5), 7.23 (d, J=8.2 Hz, 1H, H-4), 4.09-3.98 (m, 1H, H-2), 3.79-3.67 (m, 1H, H-2'), 3.69 (s, 3H, H-17), 3.64-3.50 (m, 2H, H-11), 3.46-3.33 (s, 1H, H-3), 3.01+3.14 (s, 3H, H-13), 2.53 (qd, J=8.1, 2.7 Hz, 2H, H-15), 2.24-2.16 (m, 1H, H-14), 1.93-2.04 (m, 1H, H-14'), 1.24-1.19 (t, J=7.4 Hz 3H, H-12); $^{13}$C-NMR (75 MHz, CD$_3$CN) ppm δ 173.86, 153.37, 143.84, 141.93, 131.60, 128.16, 122.87, 122.42, 118.20, 52.18, 51.47, 44.99, 41.93, 34.69, 31.85, 29.65, 13.54, 12.61; MS (CI$^+$) m/z 335.207 ([M+C$_2$H$_5$]$^+$, 9.77), 307.169 (MH$^+$, 100.00), 306.163 (M$^{.+}$, 36.98), 275.147 ([M$^{.+}$-MeOH], 12.94); HRMS calcd. for $C_{16}H_{23}N_2O_4$(MH$^+$, DCI$^+$/CH$_4$) 307.1658. found 307.1690.

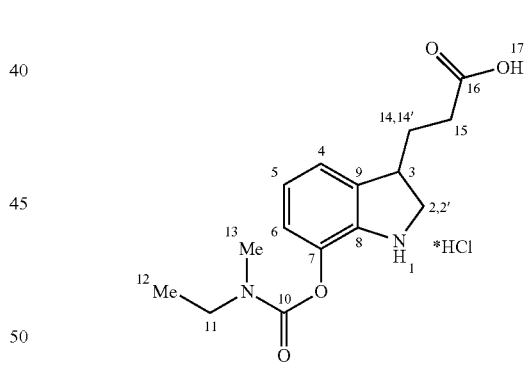

Methyl 3-(7-(ethyl(methyl)carbamoyloxy)indolin-3-yl)propanoic acid hydrochloride, AN-853

Compound AN-853 prepared from AN-1152 according to procedure E, was stirred at room temperature over night and was isolated as a colourless oil in 45% yield. $^1$H-NMR (300 MHz, CD$_3$CN) ppm δ 7.43 (t, J=7.6 Hz, 1H, H-5), 7.24-7.20 (m, 2H, H-6+H-4), 3.84 ("t", J=9.0 Hz, 1H, H-2), 3.56-3.32 (m, 4H, H-2'+H-11+H-3), 2.92+3.05 (s, 3H, H-13), 2.37 ('t', J=9.0 Hz, 2H, H-15), 2.11-2.04 (m, 1H, H-14), 1.82-1.77 (m, 1H, H-14'), 1.20-1.11 (m, 3H, H-12); $^{13}$C-NMR (75 MHz, CD$_3$CN) ppm δ 174.91, 153.57, 143.88, 142.13, 131.98, 121.97, 121.75, 118.31, 51.78, 45.11, 42.02, 34.77, 31.94, 29.60, 13.53, 12.66; MS (CI$^+$) m/z 293.148 (MH$^+$, 74.59), 292.142 (M·+, 100.00), 275.138 ([MH+—H₂O], 55.06), 231.117 ($C_{13}H_{15}N_2O_2^+$, 52.30); HRMS calcd. for $C_{15}H_{21}N_2O_4$ (MH+, DCI+/CH₄) 293.1501. found 293.1484, for $C_{15}H_{20}N_2O_4$ (M·+, DCI+/CH₄) 292.1423. found 292.1419, for $C_{15}H_{19}N_2O_3$ ([MH+—H₂O], DCI+/CH₄) 275.1396. found 275.1379, for $C_{13}H_{15}N_2O_2$ ($C_{13}H_{15}N_2O_2^+$, DCI+/CH₄) 231.1134. found 231.1173.

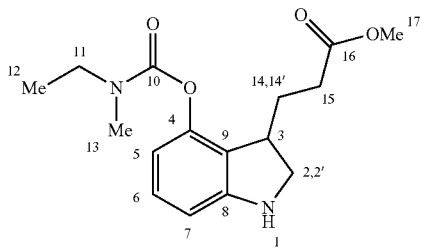

Note:

Compound AN-1167 was obtained by procedure E, Method I in 30-32% yield. When Method II was used, compound AN-1167 was obtained in 79% yield.

3-(2-(Methoxycarbonyl)ethyl)indolin-4-yl ethylmethylcarbamate, AN-1167

Compound AN-1167 was prepared from AN-803 according to procedure E, Method I (stirred at room temperature overnight) or according Method II, and was isolated by chromatography eluted with EtOAc-hexane (1:3 to 1:2), as a colourless oil (it solidified in the refrigerator) in 30-32% yield, mp 42-45° C. According procedure E, method II, compound AN-1167 was obtained in 79% yield (after using the same method of purification); ¹H-NMR (300 MHz, CDCl₃) ppm δ 6.92 (t, J=8.2 Hz, 1H, H-6), 6.36-6.33 (m, 2H, H-5+H-7), 3.75 (s, 1H, H-2'), 3.57 (s, 3H, H-17), 3.52 (t, J=9.0 Hz, 1H, H-2), 3.43-3.34 (m, 2H, H-11), 3.16-3.12 (m, 1H, H-3), 3.02+2.93 (s, 3H, H-13), 2.28 (t, J=9.0 Hz, 2H, H-15), 2.04-1.93 (m, 1H, H-14), 1.90-1.76 (m, 1H, H-14'), 1.21-1.13 (m, 3H, H-12); ¹³C-NMR (75 MHz, CDCl₃) ppm δ 173.68, 153.40, 153.29, 148.29, 128.58, 122.85, 112.06, 111.91, 106.38, 52.07, 51.25, 43.82, 43.88, 39.45, 33.98, 33.60, 31.03, 28.03, 12.99, 12.26; MS (CI+) m/z 306.156 (M*+, 50.49), 307.160 (MH+, 18.50); HRMS calcd. for $C_{16}H_{22}N_2O_4$ (M·+, DCI+/CH₄) 306.1580. found 306.1556; Anal. calcd. for $C_{16}H_{22}N_2O_4$ (MW 306.357 g/mol): C, 62.73; H, 7.24; N, 9.14. Found C, 62.554; H, 7.251; N, 9.093.

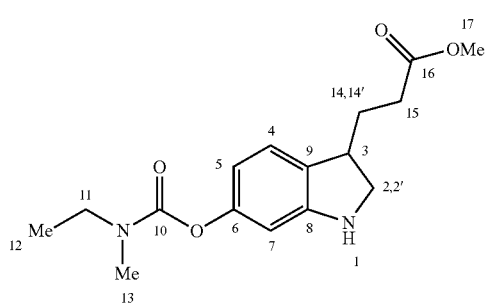 [SMILES: CCN(C)C(=O)Oc1ccc2c(c1)NCC2CCC(=O)OC]

Note:

Compound AN-1171 was obtained using procedure E, Method I in 6% yield. When Method II was used, compound AN-1171 was obtained in 75% yield.

Methyl 3-(6-(ethyl(methyl)carbamoyloxy)indolin-3-yl)propanoate, AN-1171

Compound AN-1171 was prepared from AN-679 according to procedure E, Method I or II, was isolated by chromatography eluted with EtOAc-hexane (1:4 to 1:3 to 1:2), as a colourless oil in 75% yield (after Method II). ¹H-NMR (300 MHz, CDCl₃) ppm δ 7.00 (d, J=7.9 Hz, 1H, H-4), 6.39 (bd, J=7.9 Hz, 1H, H-5), 6.36 (bs, 1H, H-7), 3.67-3.59 (m, 1H, H-2'), 3.65 (s, 3H, H-17), 3.42-3.36 (m, 2H, H-11), 3.24-3.14 (m, 2H, H-2+H-3), 3.01+2.95 (s, 3H, H-13), 2.36 (t, J=9.0 Hz, 2H, H-15), 2.10-2.01 (m, 1H, H-14), 1.89-1.79 (m, 1H, H-14'), 1.21-1.13 (m, 3H, H-12); ¹³C-NMR (75 MHz, CDCl₃) ppm δ 173.91, 155.00, 152.35, 151.64, 128.87, 124.05, 111.42, 103.71, 53.55, 51.65, 44.06, 40.67, 34.26, 33.81, 31.64, 29.26, 13.22, 12.51; MS (CI+) m/z 306.155 (M·+, 70.51), 307.164 (MH+, 100.00); SOLID INS. HRMS calcd. for $C_{16}H_{22}N_2O_4$ (M·+, DCI+/CH₄) 306.1580. found 306.1553, for $C_{16}H_{23}N_2O_4$ (MH+, DCI+/CH₄) 307.1658. found 307.1635; TOF MS (ES+) m/z 307 (MH+, 100.00).

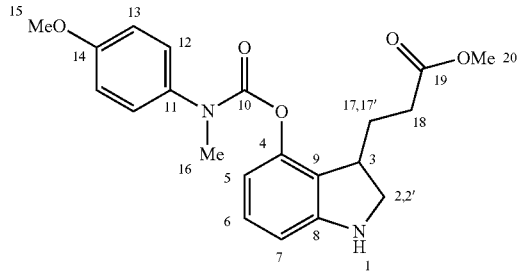

Methyl 3-(4-(((4-methoxyphenyl)(methyl)carbamoyl)oxy)indolin-3-yl) propanoate, AN-1222

Compound AN-1222 prepared from AN-683 by procedure E, Method II, was isolated by chromatography eluted with EtOAc-hexane (1:2), as a colourless oil, which solidified in the freezer, in 76% yield, mp 65-67° C. ¹H-NMR (300 MHz, CDCl₃) ppm δ 7.27 (bd, J=7.5 Hz, 2H, H-12), 6.99 (t, J=7.5 Hz, 1H, H-6), 6.89 (dd, J=7.5, 1.5 Hz, 2H, H-13), 6.51 (d, J=7.5 Hz, 1H, H-5), 6.43 (d, J=7.5 Hz, 1H, H-7), 3.80 (s, 3H, H-15), 3.64 (s, 3H, H-20), 3.57-3.64 (m, 2H, H-2+H-3), 3.39-3.20 (m, 4H, H-16+H-2'), 2.16 (bs, 2H, H-18), 1.83 (bs, 1H, H-17), 1.70 (bs, 1H, H-17'); ¹³C-NMR (75 MHz, CDCl₃) ppm δ 173.81, 158.30, 153.71, 152.85, 148.41, 135.91, 128.86, 127.64, 123.04, 114.30, 112.49, 106.87, 55.43, 52.23, 51.48, 39.72, 38.50, 31.35, 28.11; MS (CI+) m/z 385.180 (MH+, 0.49); HRMS calcd. for $C_{21}H_{25}N_2O_5$ (MH+, DCI+/CH₄) 385.1763. found 385.1803.

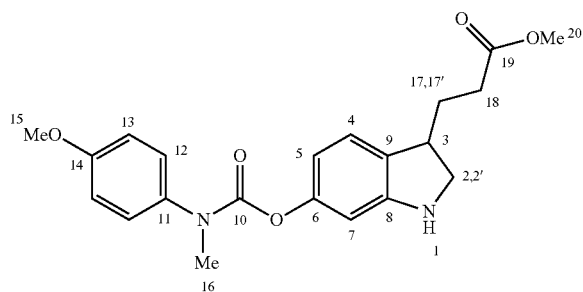 [SMILES: COC(=O)CCC1CNc2cc(OC(=O)N(C)c3ccc(OC)cc3)ccc21]

Methyl 3-(4-(((4-methoxyphenyl)(methyl)carbamoyl)oxy)indolin-3-yl)propanoate, AN-1223

Compound AN-1223 was prepared from AN-683 by procedure E, Method II, was isolated by chromatography eluted with EtOAc-hexane (1:3 to 1:2), as a colourless oil in 62% yield. $^1$H-NMR (300 MHz, CDCl$_3$) ppm δ 7.23 (bd, J=8.4 Hz, 2H, H-13), 6.98 (bd, J=7.8 Hz, 1H, H-11), 6.88 (d, J=8.4 Hz, 2H, H-12), 6.36 (bs, 2H, H-5+H-7), 3.79 (s, 3H, H-15), 3.64 (s, 3H, H-20) 3.34 (bs, 3H, H-16), 3.27-3.17 (m, 3H, H-2+H-2'+H-3), 2.36 (t, J=7.5 Hz, 2H, H-18), 2.16-2.01 (m, 1H, H-17), 1.90-1.78 (m, 1H, H-17'); $^{13}$C-NMR (75 MHz, CDCl$_3$) ppm δ 173.94, 158.15, 154.57, 152.42, 151.61, 136.09, 128.97, 127.34, 124.10, 114.31, 111.31, 103.48, 55.55, 53.62, 51.71, 40.71, 38.53, 31.66, 29.30; MS (CI$^+$) m/z 384.172 (M$^{.+}$, 3.70), 385.173 (MH$^+$, 6.44); HRMS calcd. for C$_{21}$H$_{25}$N$_2$O$_5$ (MH$^+$, DCI$^+$/CH$_4$) 385.1763. found 385.1725; TOF MS (ES$^+$) m/z 385 (MIE, 100.00).

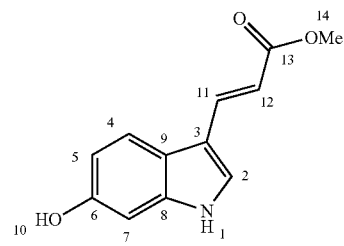

(E)-Methyl-3-(6-hydroxy-1H-indol-3-yl)acrylate, AN-1111

Compound AN-1111 prepared from AN-1110 by procedure D, was isolated by chromatography eluted with EtOAc-hexane (1:1), as a bright yellow solid in 56% yield, mp 195-200° C. $^1$H-NMR (300 MHz, Acetone-d$_6$) ppm δ 10.55 (bs, 1H, H-1), 8.25 (bs, 1H, H-10), 7.87 (d, J=15.6 Hz, 1H, H-11), 7.74 (d, J=8.2 Hz, 1H, H-4), 7.66 (d, J=2.2 Hz, 1H, H-2), 6.96 (d, J=2.0 Hz, 1H, H-7), 6.81 (dd, J=8.7, 2.0 Hz, 1H, H-5), 6.36 (d, J=16.4 Hz, 1H, H-12), 3.73 (s, 3H, H-14); $^{13}$C-NMR (75 MHz, Acetone-d$_6$) ppm δ 168.82, 155.17, 140.00, 139.89, 130.78, 121.53, 119.74, 113.63, 112.04, 111.81, 98.44, 51.24; MS (co m/z 218.084 (WE, 39.35), 217.076 (M$^+$, 37.23), 186.057 ([MH$^+$—CH$_3$OH], 37.73); HRMS calcd. for C$_{12}$H$_{12}$NO$_3$ (MH$^+$, DCI$^+$/CH$_4$) 218.0817. found 218.0841, for C$_{12}$H$_{11}$NO$_3$ (M$^+$, DCI$^+$/CH$_4$) 217.0739. found 217.0761, for C$_{11}$H$_8$NO$_2$ ([MH$^+$—CH$_3$OH], DCI$^+$/CH$_4$) 186.0555. found 186.0573; Anal. calcd. for C$_{12}$H$_{11}$NO$_3$ (MW 217.22 g/mol): C, 66.35; H, 5.10; N, 6.45; O, 22.10. Found C, 66.214; H, 5.312; N, 6.385.

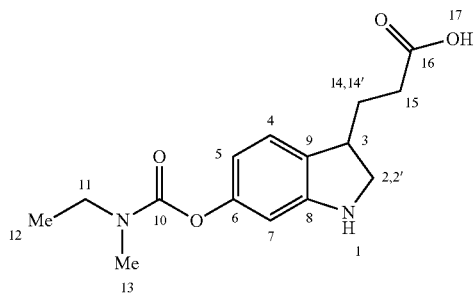 [SMILES: CCN(C)C(=O)Oc1ccc2c(c1)NCC2CCC(=O)O]

3-(6-((Ethyl(methyl)carbamoyl)oxy)indolin-3-yl)propanoic acid, AN-1238

Compound AN-1238, prepared from AN-1138 by procedure E, method II, was isolated by chromatography eluted with EtOAc-hexane (2:1), and was isolated as a yellow oil in 92% yield. $^1$H-NMR (300 MHz, CDCl$_3$+MeOD) ppm δ 7.07 (bd, J=8.7 Hz, 1H, H-4), 6.61 (bs, 2H, H-5+H-7), 3.69 (t, J=8.1 Hz, 1H, H-2), 3.42-3.21 (m, 4H, H-11+H-2'+H-3), 2.98+2.90 (s, 3H, H-13), 2.32 (t, J=7.5 Hz, 2H, H-5), 2.07-1.98 (m, 1H, H-14'), 1.85-1.73 (m, 1H, H-14), 1.22-1.09 (m, 3H, H-12); $^{13}$C-NMR (75 MHz, CDCl$_3$+MeOD) ppm δ 176.29, 154.99, 154.79, 151.39, 146.93, 131.34, 124.61, 115.92, 115.62, 107.44, 107.21, 52.57, 44.14, 40.58, 34.17, 33.79, 31.54, 28.98, 13.02, 12.27; MS (co ms 293.158 (MIE, 2.27); HRMS calcd. for C$_{15}$H$_{21}$N$_2$O$_4$ (MIE, DCI$^+$/CH$_4$) 293.1501. found 293.1576.

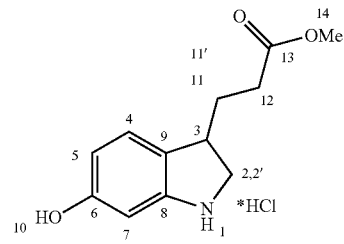

Methyl 3-(6-hydroxyindolin-3-yl)propanoate hydrochloride, AN-682

Compound AN-682 prepared from AN-1111 (or from indoline AN-1219) by procedure E, was stirred at room temperature for 2 h. The residue was crystallized from MeOH/Et$_2$O to provide the AN-682 as a green hygroscopic solid in 68% yield. $^1$H-NMR (300 MHz, MeOD) ppm δ 7.29 (bd, J=8.4 Hz, 1H, H-4), 6.92 (dd, J=8.4, 1.8 Hz, 1H, H-5), 6.91 (s, 1H, H-7), 3.96 (ABq, J=0.8 Hz, 1H, H-2'), 3.66 (s, 3H, H-14), 3.51-3.53 (m, 2H, H-2+H-3), 2.45 (t, J=7.7 Hz, 2H, H-12), 2.13 (td, J=14.0, 7.4 Hz, 1H, H-11), 1.89 (J=14.0, 7.4 Hz, 1H, H-11'); $^{13}$C-NMR (75 MHz, MeOD) ppm δ 174.93, 159.60, 137.60, 129.79, 127.13, 118.46, 107.34, 52.48, 52.25, 41.53, 32.31, 30.28; MS (CI$^+$) m/z 222.110 (MH$^+$, 100.00), 221.103 (M$^+$, 46.37), 190.087 ([MH$^+$—CH$_3$OH], 26.79); 134.076 ([M$^+$-C$_4$H$_7$O$_2$]$^+$, 42.54); HRMS calcd. for C$_{12}$H$_{16}$NO$_3$ (MH$^+$, DCI$^+$/CH$_4$) 222.1130. found 222.1104.

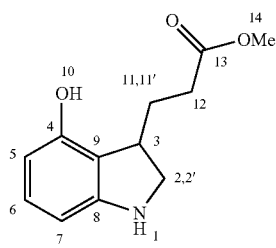

Methyl 3-(4-hydroxyindolin-3-yl)propanoate, AN-1196

Compound AN-1196 prepared from AN-843 by procedure E, Method I, was isolated by chromatography eluted with EtOAc-hexane (1:4 to 1:3 to 1:2), as a colourless oil in 79% yield. $^1$H-NMR (300 MHz, CDCl$_3$) ppm δ 6.93 (t, J=7.8 Hz, 1H, H-6), 6.26 (d, J=7.8 Hz, 1H, H-5), 6.25 (d, J=7.8 Hz, 1H, H-7), 3.73 (s, 3H, H-14), 3.67 (t, J=9.4 Hz, 1H, H-3), 3.36 (qd, J=5.63, 1.9 Hz, 1H, H-2), 3.25 (dd, J=9.4, 1.87 Hz, 1H, H-2'), 2.44 (t, J=7.5 Hz, 2H, H-12), 2.14-2.03 (m, 1H, H-11), 1.93-1.81 (m, 1H, H-11'); $^{13}$C-NMR (75 MHz, CDCl$_3$) ppm δ 175.99, 153.62, 152.69, 129.46, 116.96, 107.46, 102.53, 53.82, 52.25, 38.65, 31.89, 29.13; MS (CI$^+$) m/z 221.106 (NV, 41.04), 222.111 (MH$^+$, 100.00); SOLID INS. HRMS calcd. for C$_{12}$H$_{16}$NO$_3$ (WE, DCI$^+$/CH$_4$) 222.1130. found 222.1112.

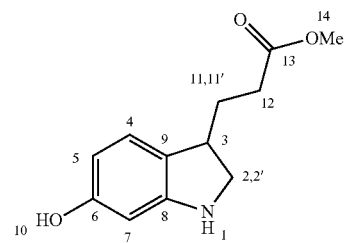

Methyl 3-(6-hydroxyindolin-3-yl)propanoate, AN-1219

Compound AN-1219 prepared from AN-678 by procedure E, Method I, was isolated by chromatography eluted with EtOAc-hexane (1:4 to 1:3 to 1:2), as a white solid in 67% yield, mp 97-98° C. $^1$H-NMR (300 MHz, CDCl$_3$) ppm δ 6.91 (d, J=7.5 Hz, 1H, H-5), 6.16 (dd, J=7.5, 2.2 Hz, 1H, H-4), 6.15 (s, 1H, H-7), 3.69-3.66 (m, 1H, H-2), 3.67 (s, 3H, H-14), 3.24-3.18 (m, 2H, H-2'+H-3), 2.38 (t, J=9.0 Hz, 2H, H-12), 2.10-2.01 (m, 1H, H-11), 1.88-1.81 (m, 1H, H-11'); $^{13}$C-NMR (75 MHz, CDCl$_3$) ppm δ 173.98, 155.91, 152.74, 124.49, 124.32, 105.10, 97.41, 53.53, 51.63, 40.45, 31.65, 29.47; MS (CI$^+$) m/z 222.111 (MH$^+$, 8.61), 221.106 (NV, 4.98); HRMS calcd. for C$_{12}$H$_{16}$NO$_3$ (MH$^+$, DCI$^+$/CH$_4$) 222.1130. found 222.1110.

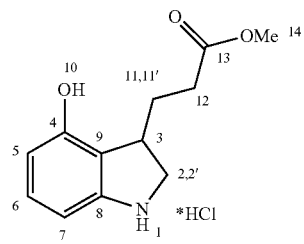 [SMILES: COC(=O)CCC1CNc2cccc(O)c21]

Methyl 3-(4-hydroxyindolin-3-yl)propanoate hydrochloride, AN-832

Upon addition of HCl gas to a solution of AN-1196 in ether, compound AN-832 was obtained as a hygroscopic white solid in quantitative yield. $^1$H-NMR (300 MHz, MeOD) ppm δ 7.27 (t, J=9.6 Hz, 1H, H-6), 6.89 (t, J=9.6 Hz, 1H, H-5+H-7), 3.87 (ABq, J=14.5, 4.8 Hz, 1H, H-2), 3.72-3.69 (m, 1H, H-3), 3.67 (s, 3H, H-14), 3.60 (dd, J=14.5, 4.8 Hz, 1H, H-2'), 2.48 (t, J=9.6 Hz, 2H, H-12), 2.28-2.24 (m, 1H, H-11), 1.97-1.92 (m, 1H, H-11'); $^{13}$C-NMR (75 MHz, MeOD) ppm δ 175.27, 156.69, 138.97, 131.38, 131.28, 131.17, 125.24, 117.06, 110.46, 52.17, 51.88, 40.87, 32.39, 28.99.

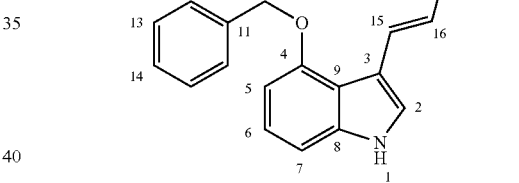

(E)-3-(4-(benzyloxy)-1H-indol-3-yl)acrylic acid, AN-1202

Compound AN-1202 prepared from AN-830 by procedure H, Method III, was crystallized from EtOAc-hexane and was isolated as a yellow solid in 87% yield, mp 163-164° C. $^1$H-NMR (300 MHz, Acetone-d$_6$) ppm δ 10.82 (bs, 1H, H-1), 8.58 (d, J=16.8 Hz, 1H, H-15), 7.90 (d, J=2.1 Hz, 1H, H-2), 7.63 (bd, J=8.4 Hz, 2H, H-12), 7.43-7.35 (m, 2H, H-13), 7.29 (t, J=8.4 Hz, 1H, H-6), 7.09-7.08 (m, 2H, H-14+H-7), 6.76 (ABq J=4.2 Hz, 1H, H-5), 6.36 (d, J=16.8 Hz, 1H, H-16), 5.34 (s, 2H, H-10); $^{13}$C-NMR (75 MHz, Acetone-d$_6$) ppm δ 168.79, 156.11, 140.96, 139.50, 138.48, 129.31, 128.29, 127.90, 126.81, 125.68, 125.51, 124.03, 118.10, 113.49, 106.40, 106.35, 103.36, 70.41; MS (CI$^+$) m/z 293.105 (M$^+$, 15.02), 294.115 (MH$^+$, 27.33), 249.109 (M$^-$, 84.27), 250.120 (MH$^+$, 100.00); SOLID INS. HRMS calcd. for C$_{18}$H$_{16}$NO$_3$ (MH$^+$, DCI$^+$/CH$_4$) 294.1130. found 294.1146, for C$_{17}$H$_{16}$NO (MH$^+$, DCI$^+$/CH$_4$) 250.1232. found 250.1200.

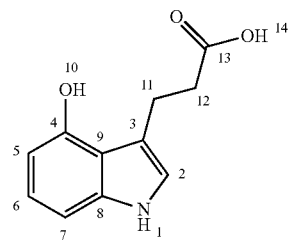 [SMILES: O=C(O)CCc1c[nH]c2cccc(O)c12]

3-(4-Hydroxy-1H-indol-3-yl) propanoic acid, AN-1201

Compound AN-1201 prepared from AN-1202 or from AN-1200 by procedure F, Method I, was isolated by chromatography eluted with $CH_2Cl_2$-MeOH (10:0.2) or by crystallization with EtOAc-hexane, as a white solid in 60% yield, mp 118-120° C. $^1$H-NMR (300 MHz, $CDCl_3$) ppm δ 7.92 (bs, 1H, H-1), 6.99 (t, J=8.2 Hz, 1H, H-6), 6.92 (d, J=8.2 Hz, 1H, H-5), 6.91 (bs, 1H, H-2), 6.43 (d, J=8.2 Hz, 1H, H-7), 3.22 (t, J=7.5 Hz, 2H, H-11), 2.82 (t, J=7.5 Hz, 2H, H-12); $^{13}$C-NMR (75 MHz, $CDCl_3$) ppm δ 176.97, 151.22, 138.63, 122.47, 122.35, 120.58, 116.80, 114.53, 103.88, 103.48, 36.34, 22.05; MS ($CI^+$) m/z 205.072 ($M^{+\cdot}$, 26.68), 206.080 ($MH^+$, 100.00); SOLID INS. HRMS calcd. for $C_{11}H_{12}NO_3$ ($MH^+$, $DCI^+/CH_4$) 206.0817. found 206.0802.

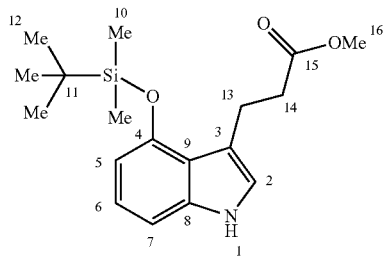 [SMILES: COC(=O)CCc1c[nH]c2cccc(O[Si](C)(C)C(C)(C)C)c12]

Methyl 3-(4-(tert-butyldimethylsilyloxy)-1H-indol-3-yl) propanoate, AN-1200

Compound AN-1200 prepared from AN-843 by procedure J, was isolated by chromatography eluted with EtOAc-hexane (1:7), as a colourless oil in 75% yield. $^1$H-NMR (300 MHz, $CDCl_3$) ppm δ 8.05 (bs, 1H, H-1), 7.03 (t, J=7.8 Hz, 1H, H-6), 6.93 (dd, J=7.8, 1.2 Hz, 1H, H-5), 6.84-6.85 (m, 1H, H-2), 6.53 (dd, J=7.8, 1.2 Hz, 1H, H-7), 3.70 (s, 3H, H-16), 3.28 (t, J=6.0 Hz, 2H, H-13), 2.79 (t, J=6.0 Hz, 2H, H-14), 1.08 (s, 9H, H-12), 0.37 (s, 6H, H-10); $^{13}$C-NMR (75 MHz, $CDCl_3$) ppm δ 174.19, 150.33, 138.85, 122.55, 120.53, 119.22, 115.10, 107.66, 104.60, 51.43, 36.00, 22.40, 18.67, 14.25, -3.77; MS ($CI^+$) m/z 333.188 ($M^{+\cdot}$, 93.29), 334.188 ($MH^+$, 100.00); SOLID INS. HRMS calcd. for $C_{18}H_{28}NO_3Si$ ($MH^+$, $DCI^+/CH_4$) 334.1838. found 334.1880.

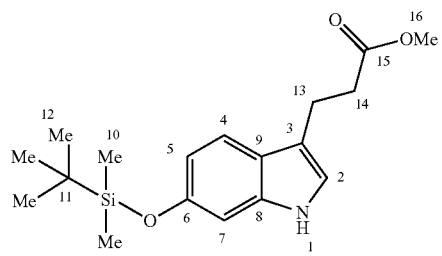 [SMILES: COC(=O)CCc1c[nH]c2cc(O[Si](C)(C)C(C)(C)C)ccc12]

Methyl 3-(6-(tert-butyldimethylsilyloxy)-1H-indol-3-yl) propanoate, AN-1142

Compound AN-1142 prepared from AN-678 by procedure J, was isolated by chromatography eluted with EtOAc-hexane (1:5), as a colourless oil in 76% yield. $^1$H-NMR (300 MHz, $CDCl_3$) ppm δ 7.80 (bs, 1H, H-1), 7.40 (d, J=8.2 Hz, 1H, H-4), 6.88 (bs, 1H, H-2), 6.80 (bd, J=1.2 Hz, 1H, H-7), 6.70 (dd, J=8.2, 1.2 Hz, 1H, H-5), 3.68 (s, 3H, H-16), 3.06 (t, J=7.8 Hz, 2H, H-13), 2.71 (t, J=7.8 Hz, 2H, H-14), 1.01 (s, 9H, H-12), 0.20 (s, 6H, H-10); $^{13}$C-NMR (75 MHz, $CDCl_3$) ppm δ 174.05, 152.01, 137.20, 122.29, 120.40, 119.03, 115.03, 114.01, 101.89, 51.72, 34.85, 25.91, 20.82, 18.37, -4.26; MS ($CI^+$) m/z 334.180 ($MH^+$, 72.59), 333.176 ($M^{+\cdot}$, 80.31), 260.145 ($[M^{+\cdot}-C_3H_5O_2]$, 23.26); HRMS calcd. for $C_{18}H_{28}NO_3Si$ ($MH^+$, $DCI^+/CH_4$) 334.1838. found 334.1798, for $C_{18}H_{27}NO_3Si$ ($M^{+\cdot}$, $DCI^+/CH_4$) 334.1760. found 333.1757.

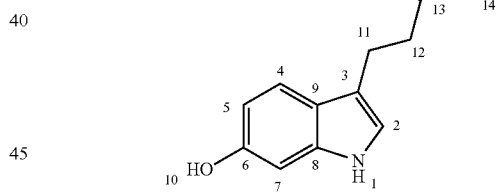

3-(6-Hydroxy-1H-indol-3-yl) propanoic acid, AN-1144

Compound AN-1144 prepared from AN-1142 by procedure H, was isolated by chromatography eluted with $CH_2Cl_2$-MeOH (1:10), as a bright brown solid in 31% yield, mp 197-200° C. $^1$H-NMR (300 MHz, MeOD) ppm δ 7.32 (dd, J=8.5, 0.6 Hz, 1H, H-4), 6.85 (s, 1H, H-2), 6.75 (dd, J=2.6, 0.6 Hz, 1H, H-7), 6.60 (dd, J=8.5, 2.6 Hz, 1H, H-5), 2.98 (t, J=7.3 Hz, 2H, H-11), 2.64 (t, J=7.3 Hz, 2H, H-12); $^{13}$C-NMR (75 MHz, MeOD) ppm δ 177.53, 153.99, 139.10, 122.61, 121.19, 119.61, 115.00, 109.78, 97.57, 36.03, 21.87; MS ($CI^+$) m/z 206.080 ($MH^+$, 34.98), 205.076 ($M^{+\cdot}$, 48.22), 160.077 ($[M-CO_2]^+$, 64.02) 146.062 ($[M^{+\cdot}-C_3H_3O_2]$, 100.00); HRMS calcd. for $C_{11}H_{21}NO_3$ ($M^{+\cdot}$, $DCI^+/CH_4$) 205.0739. found 205.0762.

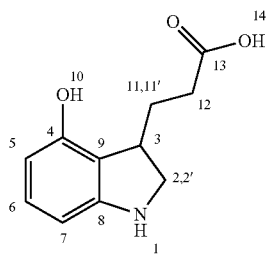 [SMILES: O=C(O)CCC1CNc2cccc(O)c21]

3-(4-Hydroxyindolin-3-yl)propanoic acid, AN-1205

Compound AN-1205 prepared from AN-1201 by procedure E, Method I, was isolated by chromatography eluted with CHCl$_3$-MeOH (20:0.5 to 15:0.5), as a yellow oil in 36% yield. $^1$H-NMR (300 MHz, MeOD+CDCl$_3$) ppm δ 6.86 (t, J=7.9 Hz, 1H, H-6), 6.25 (d, J=7.9 Hz, 1H, H-7), 6.24 (dd, J=7.9, 1.1 Hz, 1H, H-5), 3.58 (t, J=9.0 Hz, 1H, H-2), 3.46-3.37 (m, 1H, H-3), 3.22 (dd, J=9.0, 3.7 Hz, 1H, H-2), 2.37 ("t", J=7.5 Hz, 2H, H-12), 2.23-2.09 (m, 1H, H-11'), 1.92-1.80 (m, 1H, H-11); $^{13}$C-NMR (75 MHz, MeOD+CDCl$_3$) ppm δ 178.10, 155.02, 152.85, 129.65, 119.08, 108.46, 103.99, 53.00, 40.44, 32.65, 29.29.

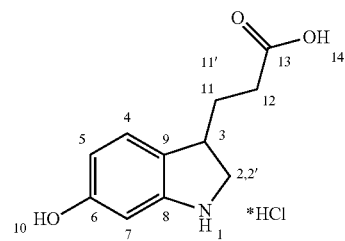 [SMILES: O=C(O)CCC1CNc2cc(O)ccc21]

3-(6-Hydroxyindolin-3-yl) propanoic acid hydrochloride, AN-848

Compound AN-848 prepared from AN-1144 or from AN-1219 by procedure E, was isolated as a brown hygroscopic oil in 23% yield. $^1$H-NMR (300 MHz, MeOD) ppm δ 7.31 (d, J=8.0 Hz, 1H, H-4), 6.88-6.97 (m, 2H, H-5+H-7), 3.97 (m, 1H, H-2), 3.46-3.68 (m, 2H, H-2'+H-3), 2.45 (t, J=8.0 Hz, 2H, H-12), 2.01-2.18 (m, 1H, H-11'), 1.77-1.95 (m, 1H, H-11); $^{13}$C-NMR (75 MHz, MeOD) ppm δ 173.62, 158.39, 136.34, 128.40, 125.75, 117.14, 116.88, 105.89, 51.50, 51.24, 40.26, 39.04, 30.80, 28.94, 28.58; MS (CI$^-$) m/z 207.090 (M$^{+\cdot}$, 69.86), 148.033 (C$_9$H$_{10}$NO$^-$, 34.36); HRMS calcd. for C$_{11}$H$_{13}$NO$_3$ (M$^+$, DCI$^-$/CH$_4$) 207.0895. found 207.0904.

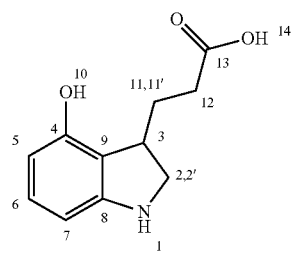 [SMILES: O=C(O)CCC1CNc2cccc(O)c21]

3-(4-hydroxyindolin-3-yl)propanoic acid hydrochloride, AN-834

Compound AN-834 was isolated as a yellow oil in quantitative yield from AN-1196 upon addition of 3N HCl to a solution of AN-1196 in MeOH. $^1$H-NMR (300 MHz, MeOD) ppm δ 7.27 (t, J=8.2 Hz, 1H, H-6), 6.92 (bt, J=8.2 Hz, 2H, H-5+H-7), 3.89 (bt, J=8.1 Hz, 1H, H-2), 3.71-3.61 (m, 2H, H-2'+H-3), 2.44 (t, J=8.1 Hz, 2H, H-12), 2.35-2.20 (m, 1H, H-11'), 1.97-1.87 (m, 1H, H-11); $^{13}$C-NMR (75 MHz, MeOD) ppm δ 173.72, 154.58, 137.98, 131.32, 125.59, 117.49, 110.91, 51.68, 40.84, 32.49, 28.98.

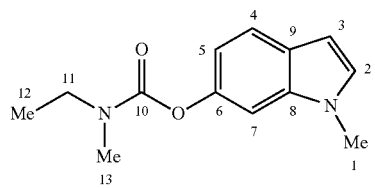

1-Methyl-1H-indol-6-yl ethyl(methyl)carbamate, AN-1120

Compound AN-1120 prepared from AN-1106 by procedure G, was isolated by chromatography eluted with EtOAc-hexane (1:3), as a yellow oil in 83% yield. $^1$H-NMR (300 MHz, Acetone-d$_6$) ppm δ 7.53 (d, J=8.5 Hz, 1H, H-4), 7.11-7.18 (m, 2H, H-2+H-7), 6.86 (dd, J=8.5, 2.3 Hz, 1H, H-5), 6.44 (dd, J=2.8, 0.9 Hz, 1H, H-3), 3.74 (s, 3H, H-1), 3.39-3.52 (m, 2H, H-11), 2.97+3.11 (s, 3H, H-13), 1.15-1.32 (m, 3H, H-12); $^{13}$C-NMR (75 MHz, Acetone-d$_6$) ppm δ 155.37, 148.17, 137.57, 130.37, 126.78, 121.09, 114.94, 103.55, 101.33, 44.44, 34.28, 34.03, 32.85, 13.53, 12.75; MS (CI$^+$) m/z 233.133 (MH$^+$, 39.57); HRMS calcd. for C$_{13}$H$_{17}$N$_2$O$_2$ (MH$^+$, DCI$^+$/CH$_4$) 233.1290. found 233.1326.

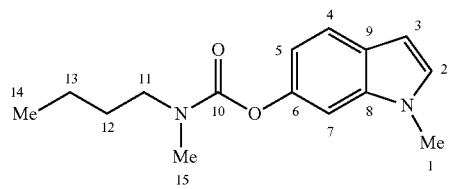

1-Methyl-1H-indol-6-yl butyl(methyl)carbamate, AN-1124

Compound AN-1124 prepared from AN-1100 by procedure G, was isolated by chromatography eluted with EtOAc-hexane (1:3), as an off-white oil in 77% yield. $^1$H-NMR (300 MHz, Acetone-d$_6$) ppm δ 7.53 (d, J=9.0 Hz, 1H, H-4), 7.16-7.18 (m, 2H, H-2+H-7), 6.86 (bd, J=9.0 Hz, 1H, H-5), 6.44 (d, J=2.7 Hz, 1H, H-3), 3.73 (s, 3H, H-1), 3.35-3.51 (m, 2H, H-11), 3.11+2.98 (s, 3H, H-15), 1.53-1.72 (m, 2H, H-12), 1.34-1.47 (m, 2H, H-13), 0.92-1.03 (m, 3H, H-14); $^{13}$C-NMR (75 MHz, Acetone-d$_6$) ppm δ 155.60, 148.22, 137.57, 130.36, 126.78, 121.10, 114.97, 103.52, 101.34, 49.39, 34.84, 34.62, 32.86, 30.92, 30.36, 20.50, 14.52, 14.19; MS (CI$^+$) m/z 261.159 (WE, 91.40), 260.155 (M$^+$, 35.75), 114.092 ([M$^+$-C$_9$H$_8$NO], 52.02); HRMS calcd. for C$_{15}$H$_{21}$N$_2$O$_2$ (MH$^+$, DCI$^+$/CH$_4$) 261.1603. found 261.1585, for C$_6$H$_{12}$NO ([M$^+$-C$_9$H$_8$NO], DCI$^+$/CH$_4$) 114.0919. found 114.0919.

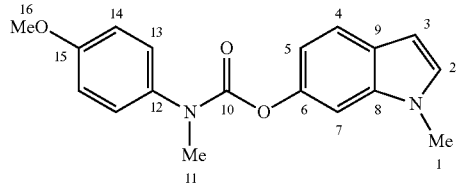

1-Methyl-1H-indol-6-yl 4-methoxyphenyl(methyl)carbamate, AN-1116

Compound AN-1116 prepared from AN-1112 by procedure G, was isolated by chromatography eluted with EtOAc-hexane (1:2), as a colourless viscous oil in 56% yield. $^1$H-NMR (300 MHz, Acetone-d$_6$) ppm δ 7.52 (d, J=8.1 Hz, 1H, H-4), 7.40 (dd, J=6.3, 2.7 Hz, 2H, H-13), 7.17 (bs, 1H, H-2), 7.16 (d, J=2.7 Hz, 1H, H-7), 6.96 (dd, J=6.3, 2.7 Hz, 2H, H-14), 6.85 (bd, J=8.1 Hz, 1H, H-5), 6.43 (d, J=3.2 Hz, 1H, H-3), 3.78 (s, 3H, H-16), 3.72 (s, 3H, H-1), 3.37 (bs, 3H, H-11); $^{13}$C-NMR (75 MHz, Acetone-d$_6$) ppm δ 158.89, 155.10, 148.06, 137.52, 137.27, 130.46, 128.21, 126.89, 121.15, 114.89, 114.77, 103.46, 101.36, 55.67, 38.66, 32.86; MS (CI$^+$) m/z 310.134 (M$^+$, 3.74), 311.140 (MH$^+$, 8.75), 164.067 ([MH$^+$—C$_9$H$_8$NO]$^+$, 3.45); HRMS calcd. for C$_{18}$H$_{19}$N$_2$O$_3$ (MH$^+$, DCI$^+$/CH$_4$) 311.1396. found 311.1403, for C$_9$H$_{10}$NO$_2$ ([M$^+$-C$_9$H$_8$NO]$^+$, DCI$^+$/CH$_4$) 164.0712. found 164.0674.

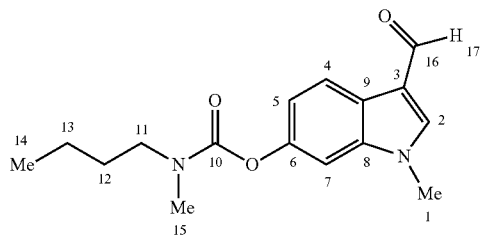

3-Formyl-1-methyl-1H-indol-6-yl butyl(methyl)carbamate, AN-1125

Compound AN-1125, prepared from AN-1124 by procedure C, was isolated after extraction with EtOAc and water, as a yellow solid in 89% yield, mp 90-95° C. $^1$H-NMR (300 MHz, Acetone-d$_6$) ppm δ 9.87 (s, 1H, H-17), 8.17 (d, J=9.2 Hz, 1H, H-4), 7.94 (s, 1H, H-2), 7.27 (d, J=1.8 Hz, 1H, H-7), 7.06 (bd, J=9.2 Hz, 1H, H-5), 3.81 (s, 3H, H-1), 3.34-3.50 (m, 2H, H-11), 3.11+2.98 (s, 3H, H-15), 1.55-1.73 (m, 2H, H-12), 1.29-1.51 (m, 2H, H-13), 0.88-1.01 (m, 3H, H-14); $^{13}$C-NMR (75 MHz, Acetone-d$_6$) ppm δ 184.54, 155.31, 149.62, 141.79, 138.99, 123.09, 122.21, 118.56, 118.16, 104.80, 49.46, 34.88, 34.64, 33.73, 30.87, 30.18, 20.48, 14.15; MS (CI$^+$) m/z 289.152 (MH$^+$, 100.00), 288.147 (M$^+$, 25.08), 114.097 ([M$^+$-C$_9$H$_8$NO]$^+$, 27.21); HRMS calcd. for C$_{16}$H$_{20}$N$_2$O$_3$ (M$^+$, CH$_4$$^+$/DCI) 288.1474. found 288.1468, for C$_{16}$H$_{21}$N$_2$O$_3$ (MH$^+$, DCI$^+$/CH$_4$) 289.1552. found 289.1524; Anal. calcd. for C$_{16}$H$_{20}$N$_2$O$_3$ (MW 288.34 g/mol): C, 66.65; H, 6.99; N, 9.72; O, 16.65. Found C, 66.878; H, 7.114; N, 9.765.

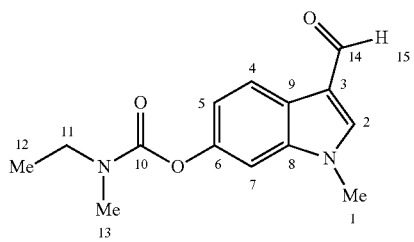 [SMILES: CCN(C)C(=O)Oc1ccc2c(C=O)cn(C)c2c1]

3-Formyl-1-methyl-1H-indol-6-yl ethyl(methyl)carbamate, AN-1121

Compound AN-1121, prepared from AN-1120 by procedure C, after extraction with EtOAc and water, was isolated as a yellow solid in 84% yield, mp 124-128° C. $^1$H-NMR (300 MHz, Acetone-d$_6$) ppm δ 9.87 (s, 1H, H-15), 8.15 (d, J=9.3 Hz, 1H, H-4), 8.05 (s, 1H, H-2), 7.30 (d, J=1.8 Hz, 1H, H-7), 7.05 (dd, J=9.3, 1.8 Hz, 1H, H-5), 3.91 (s, 3H, H-1), 3.36-3.56 (m, 2H, H-11), 3.11+2.97 (s, 3H, H-13), 1.14-1.28 (m, 3H, H-12); $^{13}$C-NMR (75 MHz, Acetone-d$_6$) ppm δ 184.54, 149.69, 141.83, 139.11, 123.17, 122.27, 118.69, 118.18, 104.88, 44.55, 34.36, 34.08, 33.84, 13.52, 12.71; MS (CI$^+$) m/z 261.121 (MH$^+$, 94.88); HRMS calcd. for C$_{14}$H$_{17}$N$_2$O$_3$ (MH$^+$, DCI$^+$/CH$_4$) 261.1239. found 261.1214; Anal. calcd. for C$_{14}$H$_{16}$N$_2$O$_3$ (MW 260.28 g/mol): C, 64.60; H, 6.20; N, 10.76; O, 18.44. Found C, 64.266; H, 6.483; N, 10.426.

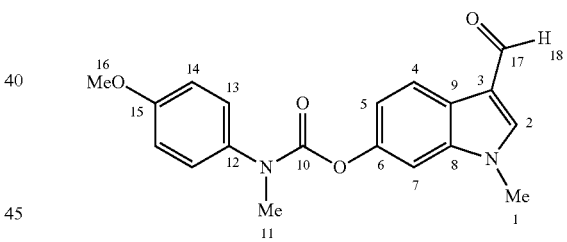

3-Formyl-1-methyl-1H-indol-6-yl 4-methoxyphenyl(methyl)carbamate, AN-1117

Compound AN-1117 prepared from AN-1116 by procedure C, was isolated after extraction with EtOAc and water, as a bright yellow solid in 91% yield, mp 110-115° C. $^1$H-NMR (300 MHz, Acetone-d$_6$) ppm δ 9.91 (s, 1H, H-18), 8.15 (d, J=8.8 Hz, 1H, H-4), 8.00 (s, 1H, H-7), 7.40 (dd, J=8.9, 2.1 Hz, 2H, H-13), 7.28 (bs, 1H, H-2), 7.03 (bd, J=8.4 Hz, 1H, H-5), 6.97 (dd, J=8.9, 2.1 Hz, 2H, H-14), 3.86 (s, 3H, H-16), 3.80 (s, 3H, H-1), 3.36 (bs, 3H, H-11); $^{13}$C-NMR (75 MHz, Acetone-d$_6$) ppm δ 184.56, 154.81, 149.52, 141.86, 139.02, 137.20, 128.35, 123.24, 122.29, 118.61, 118.00, 114.96, 104.79, 55.70, 38.73, 33.80; MS (CI$^+$) m/z 339.134 (WE, 100.00); HRMS calcd. for C$_{19}$H$_{19}$N$_2$O$_4$ (MH$^+$, DCI$^+$/CH$_4$) 339.1345. found 339.1337; Anal. calcd. for C$_{19}$H$_{18}$N$_2$O$_4$ (MW 338.35 g/mol): C, 67.44; H, 5.36; N, 8.28; O, 18.91. Found C, 67.458; H, 5.689; N, 8.021.

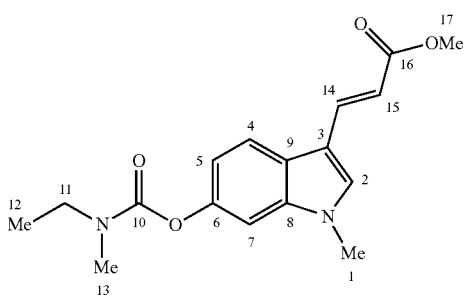 [SMILES: CCN(C)C(=O)Oc1ccc2c(/C=C/C(=O)OC)cn(C)c2c1]

(E)-Methyl 3-(6-(ethyl(methyl)carbamoyloxy)-1-methyl-1H-indol-3-yl)acrylate, AN-1122

Compound AN-1122 prepared from AN-1121 or from AN-863 by procedure D, was isolated by chromatography eluted with EtOAc-hexane (1:1), as a bright yellow solid in 62% yield, mp 105-110° C. $^1$H-NMR (300 MHz, Acetone-$d_6$) ppm δ 7.87 (d, J=7.6 Hz, 1H, H-4), 7.84 (d, J=15.2 Hz, 1H, H-14), 7.70 (s, 1H, H-2), 7.26 (d, J=2.5 Hz, 1H, H-7), 7.02 (dd, J=7.6, 2.5 Hz, 1H, H-5), 6.38 (d, J=15.2 Hz, 1H, H-15), 3.81 (s, 3H, H-1), 3.73 (s, 3H, H-17), 3.54-3.86 (m, 2H, H-11), 3.11+2.97 (s, 3H, H-13), 1.14-1.28 (m, 3H, H-12); $^{13}$C-NMR (75 MHz, Acetone-$d_6$) ppm δ 168.55, 155.11, 149.15, 139.26, 138.83, 135.73, 124.05, 120.97, 116.94, 112.40, 104.73, 51.27, 44.54, 34.34, 34.08, 33.36, 13.53, 12.72; MS (CI$^+$) m/z 317.147 (WE, 31.02), 316.140 (M$^+$, 28.78), 285.123 ([MH$^+$—CH$_3$OH], 14.18), 86.071 ([M$^+$-C$_{13}$H$_{12}$NO$_3$], 31.78); HRMS calcd. for C$_{17}$H$_{20}$N$_2$O$_4$ (M$^+$, DCI$^+$/CH$_4$) 316.1423. found 316.1402, for C$_{17}$H$_{21}$N$_2$O$_4$ (WE, DCI$^+$/CH$_4$) 317.1501. found 317.1468, for C$_{16}$H$_{17}$N$_2$O$_3$ ([MH$^+$—CH$_3$OH], DCI$^+$/CH$_4$) 285.1239. found 285.1226; Anal. calcd. for C$_{17}$H$_{20}$N$_2$O$_4$ (MW 316.35 g/mol): C, 64.54; H, 6.37; N, 8.86; O, 20.23. Found C, 64.391; H, 6.537; N, 8.214.

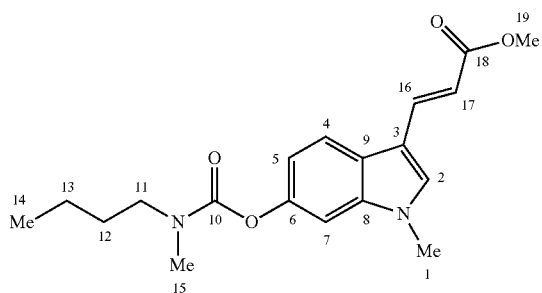 [SMILES: CCCCN(C)C(=O)Oc1ccc2c(/C=C/C(=O)OC)cn(C)c2c1]

(E)-Methyl 3-(6-(butyl(methyl)carbamoyloxy)-1-methyl-1H-indol-3-yl) acrylate, AN-1126

Compound AN-1126 prepared from AN-1125 or from AN-1102 by procedure D, was isolated by chromatography eluted with EtOAc-hexane (1:1), as a white solid in 74% yield, mp 65-70° C. $^1$H-NMR (300 MHz, Acetone-$d_6$) ppm δ 7.75 (d, J=15.6 Hz, 1H, H-16), 7.70 (d, J=7.8 Hz, 1H, H-4), 7.38 (s, 1H, H-2), 7.10 (bs, 1H, H-7), 6.91 (bd, J=7.8 Hz, 1H, H-5), 6.28 (d, J=15.6 Hz, 1H, H-17), 3.75 (s, 3H, H-19), 3.57 (s, 3H, H-1), 3.30-3.35 (m, 2H, H-11), 2.95+ 3.07 (s, 3H, H-15), 1.52-1.67 (m, 2H, H-12), 1.28-1.42 (m, 2H, H-13), 0.93-1.00 (m, 3H, H-14); $^{13}$C-NMR (75 MHz, Acetone-$d_6$) ppm δ 174.05, 156.88, 149.02, 139.74, 139.55, 136.10, 124.66, 121.28, 116.90, 112.72, 112.15, 104.77, 51.82, 50.04, 49.92, 35.07, 34.86, 33.22, 31.16, 30.51, 20.86, 14.47, 14.24; MS (CE) m/z 345.182 (MH$^+$, 100.00), 344.173 (M$^+$, 66.85), 313.155 ([MH$^+$—CH$_3$OH], 31.61), 114.093 ([M$^+$-C$_{13}$H$_{12}$NO$_3$], 24.54); HRMS calcd. for C$_{19}$H$_{24}$N$_2$O$_4$ (M$^+$, DCI$^+$/CH$_4$) 344.1736. found 344.1734, for C$_{19}$H$_{25}$N$_2$O$_4$ (MH$^+$, DCI$^+$/CH$_4$) 345.1814. found 345.1818; Anal. calcd. for C$_{19}$H$_{24}$N$_2$O$_4$ (MW 344.40 g/mol): C, 66.26; H, 7.02; N, 8.13; O, 18.58. Found C, 66.579; H, 7.314; N, 8.073.

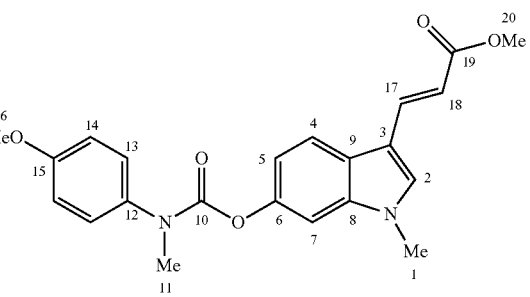

(E)-Methyl 3-(6-((4-methoxyphenyl)(methyl)carbamoyloxy)-1-methyl-1H-indol-3-yl)acrylate, AN-1119

Compound AN-1119 prepared from AN-1117 or from AN-1118 by procedure D, was isolated by chromatography eluted with EtOAc-hexane (1:1), as a yellow solid in 69% yield, mp 120-125° C. $^1$H-NMR (300 MHz, Acetone-$d_6$) ppm δ 7.86 (d, J=8.3 Hz, 1H, H-4), 7.84 (d, J=16.7 Hz, 1H, H-17), 7.70 (s, 1H, H-7), 7.40 (dd, J=8.3, 2.4 Hz, 2H, H-13), 7.27 (bs, 1H, H-2), 6.98-6.95 (m, 1H, H-5), 6.97 (dd, J=8.3, 2.4 Hz, 2H, H-14), 6.36 (d, J=16.7 Hz, 1H, H-18), 3.81 (s, 3H, H-16), 3.80 (s, 3H, H-1), 3.72 (s, 3H, H-20), 3.36 (bs, 3H, H-11); $^{13}$C-NMR (75 MHz, Acetone-$d_6$) ppm δ 168.55, 158.96, 154.87, 149.01, 139.21, 138.79, 137.21, 135.78, 128.26, 124.15, 121.02, 116.77, 114.96, 112.45, 112.34, 104.65, 55.71, 51.28, 38.73, 33.38; MS (CI$^+$) m/z 394.153 (M$^+$, 1.54); HRMS calcd. for C$_{22}$H$_{22}$N$_2$O$_5$ (M$^+$, DCI$^+$/CH$_4$) 394.1529. found 394.1534; Anal. calcd. for C$_{22}$H$_{22}$N$_2$O$_5$*0.1H$_2$O (MW 396.22 g/mol):C, 66.69; H, 5.65; N, 7.07; O, 20.59. Found C, 66.415; H, 5.920; N, 6.806.

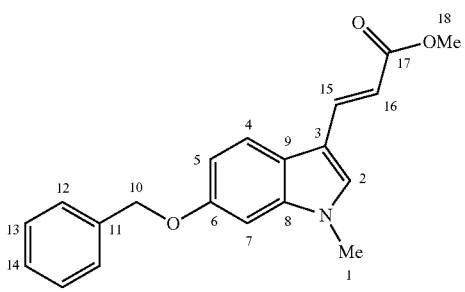 [SMILES: COC(=O)/C=C/c1cn(C)c2cc(OCc3ccccc3)ccc12]

(E)-Methyl 3-(6-(benzyloxy)-1-methyl-1H-indol-3-yl)acrylate, AN-1128

Compound AN-1128 prepared from AN-1104 by procedure D, was isolated by chromatography eluted with EtOAc-hexane (1:3 to 1:1), as a yellow solid in 85% yield, mp 150-155° C. $^1$H-NMR (300 MHz, Acetone-$d_6$) ppm δ 7.80 (d, J=16.0 Hz, 1H, H-15), 7.77 (d, J=8.8 Hz, 1H, H-4), 7.58 (s, 1H, H-2), 7.50-7.27 (m, 5H, H-12+H-13+H-14), 7.11 (d, J=2.3 Hz, 1H, H-7), 6.96 (dd, J=9.2, 2.3 Hz, 1H, H-5), 6.32 (d, J=15.3 Hz, 1H, H-16), 5.16 (s, 2H, H-10), 3.79 (s, 3H, H-18), 3.71 (s, 3H, H-1); $^{13}$C-NMR (150 MHz, Acetone-$d_6$) ppm δ 168.62, 157.11, 140.21, 139.11, 138.58, 134.68, 129.25, 128.57, 128.47, 121.75, 112.10, 112.53, 112.25, 111.99, 96.19, 70.96, 51.18, 33.27; MS (CI$^+$) m/z 322.143 (WE, 100.00), 321.145 (M, 52.78), 230.082 ([M−C$_7$H$_7$]$^+$, 28.61); HRMS calcd. for C$_{20}$H$_{20}$NO$_3$ (MH$^+$, DCI$^+$/CH$_4$) 322.1443. found 322.1434; Anal. calcd. for C$_{20}$H$_{19}$NO$_3$*0.1H$_2$O (MW 323.17 g/mol): C, 74.33; H, 5.99; N, 4.33; O, 15.35. Found C, 73.953; H, 6.231; N, 3.949.

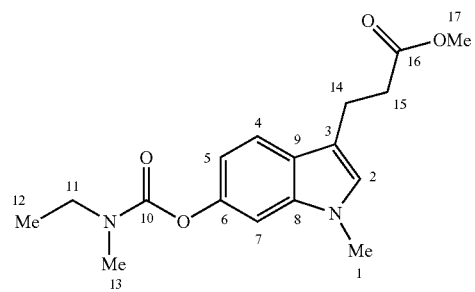 [SMILES: CCN(C)C(=O)Oc1ccc2c(CCC(=O)OC)cn(C)c2c1]

Methyl 3-(6-(ethyl(methyl)carbamoyloxy)-1-methyl-1H-indol-3-yl) propanoate, AN-688

Compound AN-688 prepared from AN-1122 by procedure F, was isolated by chromatography eluted with EtOAc-hexane (1:2), as a white solid in 84% yield, mp 49-52° C. $^1$H-NMR (300 MHz, Acetone-$d_6$) ppm δ 7.52 (d, J=8.9 Hz, 1H, H-4), 7.12 (d, J=1.9 Hz, 1H, H-7), 6.98 (bs, 1H, H-2), 6.84 (dd, J=8.9, 1.9 Hz, 1H, H-5), 3.68 (s, 3H, H-1), 3.63 (s, 3H, H-17), 3.38-3.52 (m, 2H, H-11), 3.10+2.96 (s, 3H, H-13), 3.03 (t, J=5.6 Hz, 2H, H-14), 2.67 (t, J=5.6 Hz, 2H, H-15), 1.28-1.43 (m, 3H, H-12); $^{13}$C-NMR (75 MHz, Acetone-$d_6$) ppm δ 173.76, 155.39, 148.39, 137.91, 127.77, 125.94, 119.25, 114.45, 114.12, 103.55, 51.56, 44.46, 35.38, 34.29, 34.05, 32.65, 21.13, 13.54, 12.75; MS (CI$^+$) m/z 319.163 (MH$^+$, 100.00), 318.157 (M$^+$, 65.21), 245.117 ([MH$^+$—C$_3$H$_5$O$_2$], 44.91); HRMS calcd. for C$_{17}$H$_{22}$N$_2$O$_4$ ([M$^+$, DCI$^+$/CH$_4$) 318.1580. found 318.1573, for C$_{17}$H$_{23}$N$_2$O$_4$ ([MH$^+$, DCI$^+$/CH$_4$) 319.1658. found 319.1631; Anal. calcd. for C$_{17}$H$_{22}$N$_2$O$_4$ (318.37 g/mol): C, 64.13; H, 6.97; N, 8.80; O, 20.10. Found C, 64.077; H, 7.168; N, 8.474.

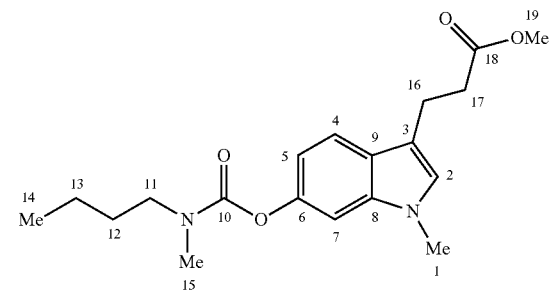 [SMILES: CCCCN(C)C(=O)Oc1ccc2c(CCC(=O)OC)cn(C)c2c1]

Methyl 3-(6-(butyl(methyl)carbamoyloxy)-1-methyl-1H-indol-3-yl) propanoate, AN-690

Compound AN-690 prepared from AN-1126 by procedure F, was isolated by chromatography eluted with EtOAc-hexane (1:2), as a colourless oil in 81% yield. $^1$H-NMR (300 MHz, Acetone-$d_6$) ppm δ 7.53 (d, J=9.0 Hz, 1H, H-4), 7.12 (d, J=1.7 Hz, 1H, H-7), 6.97 (s, 1H, H-2), 6.86 (bd, J=9.0 Hz, 1H, H-5), 3.65 (s, 3H, H-1), 3.64 (s, 3H, H-19), 3.34-3.51 (m, 2H, H-11), 3.11+2.97 (s, 3H, H-15), 3.04 (t, J=8.3 Hz, 2H, H-17), 2.68 (t, J=8.3 Hz, 2H, H-16), 1.56-1.71 (m, 2H, H-12), 1.32-1.46 (m, 2H, H-13), 0.96-1.03 (m, 3H, H-14); $^{13}$C-NMR (75 MHz, Acetone-$d_6$) ppm δ 173.71, 155.57, 148.38, 137.86, 127.72, 125.90, 119.22, 114.44, 114.07, 103.48, 51.55, 49.37, 35.35, 34.81, 34.60, 32.61, 30.90, 30.23, 21.11, 20.49, 14.18; MS (CI$^+$) m/z 347.197 (MH$^+$, 100.00), 346.189 (M$^+$, 60.55), 273.163 ([M$^+$-C$_3$H$_5$O$_2$]$^+$, 20.90), 233.106 ([MH$^+$—C$_6$H$_{12}$NO], 11.43), 160.076 ([MH$^+$—C$_9$H$_{17}$NO$_3$], 16.29), 114.097 ([M$_4$-C$_{13}$H$_{14}$NO$_3$], 28.23); HRMS calcd. for C$_{19}$H$_{27}$N$_2$O$_4$ ([MH$^+$, DCI$^+$/CH$_4$) 347.1971. found 347.1966.

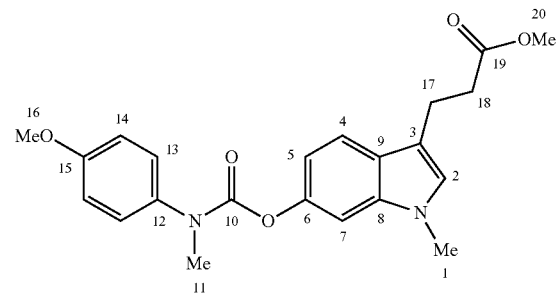 [SMILES: COC(=O)CCc1cn(C)c2cc(OC(=O)N(C)c3ccc(OC)cc3)ccc12]

Methyl 3-(6-((4-methoxyphenyl)(methyl)carbamoyloxy)-1-methyl-1H-indol-3-yl)propanoate, AN-686

Compound AN-686 prepared from AN-1119 by procedure F, was isolated by chromatography eluted with EtOAc-hexane (1:2), as a colourless oil in 60% yield. $^1$H-NMR (300 MHz, Acetone-$d_6$) ppm δ 7.50 (d, J=8.3 Hz, 1H, H-4), 7.38 (dd, J=8.3, 2.5 Hz, 2H, H-13), 7.10 (bs, 1H, H-2), 7.00 (s, 1H, H-7), 6.96 (dd, J=8.3, 2.5 Hz, 2H, H-14), 6.81 (bd, J=8.3 Hz, 1H, H-5), 3.80 (s, 3H, H-16), 3.70 (s, 3H, H-1), 3.60 (s, 3H, H-20), 3.01 (t, J=7.4 Hz, 2H, H-17), 2.66 (t, J=7.4 Hz, 2H, H-18); $^{13}$C-NMR (75 MHz, Acetone-$d_6$) ppm δ 173.76, 158.79, 155.13, 148.31, 137.89, 137.34, 128.25, 127.88, 126.06, 119.31, 114.92, 114.28, 114.18, 103.47, 55.70, 51.55, 38.66, 35.38, 32.71, 21.11; MS (CI$^+$) m/z 397.168

(MH⁺, 1.78), 396.167 (M⁺, 2.41), 323.150 ([M⁺-C₃H₅O₂], 0.32); HRMS calcd. for C₂₂H₂₄N₂O₅ ([M⁺, DCI⁺/CH₄) 396.1685. found 396.1674.

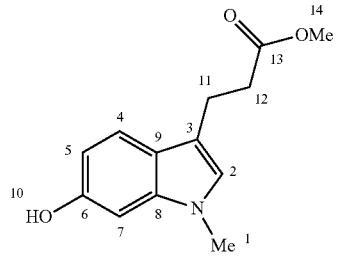 [SMILES: COC(=O)CCc1cn(C)c2cc(O)ccc12]

Methyl 3-(6-hydroxy-1-methyl-1H-indol-3-yl)propanoate, AN-697

Compound AN-697 prepared from AN-1128 by procedure F, was isolated by chromatography eluted with EtOAc-hexane (1:2), as a white solid in 69% yield, mp 35-40° C. ¹H-NMR (300 MHz, CDCl₃) ppm δ 7.27 (dd, J=9.0, 1.2 Hz, 1H, H-4), 6.59-6.62 (m, 3H, H-7+H-2+H-5), 6.26 (bs, 1H, H-10), 3.62 (s, 3H, H-1), 3.44 (s, 3H, H-14), 2.97 (t, J=7.4 Hz, 2H, H-11), 2.63 (t, J=7.4 Hz, 2H, H-12); ¹³C-NMR (75 MHz, CDCl₃) ppm δ 174.63, 152.18, 137.99, 125.10, 122.01, 119.44, 113.32, 108.95, 95.23, 51.85, 35.08, 32.44, 20.66; MS (CI⁺) m/z 234.112 (MH⁺, 87.28), 233.105 (M⁺, 69.29), 160.084 ([M⁺-C₃H₅O₂]⁺, 100.00); HRMS calcd. for C₁₃H₁₅NO₃ ([M⁺, DCI⁺/CH₄) 233.1052. found 233.1046, for C₁₃H₁₆NO₃ ([MH⁺, DCI⁺/CH₄) 234.1130. found 234.1120; Anal. calcd. for C₁₃H₁₅NO₃*0.1H₂O (MW 235.06 g/mol): C, 66.42; H, 6.52; N, 5.96; O, 21.10. Found C, 66.0175; H, 6.7045; N, 6.2335.

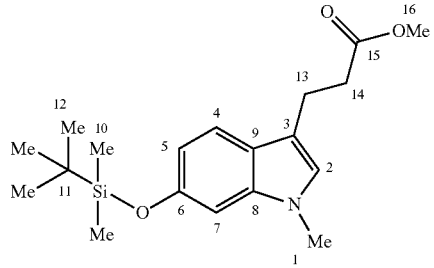 [SMILES: COC(=O)CCc1cn(C)c2cc(O[Si](C)(C)C(C)(C)C)ccc12]

Methyl 3-(6-(tert-butyldimethylsilyloxy)-1-methyl-1H-indol-3-yl)propanoate, AN-1143

Compound AN-1143 prepared from AN-1142 by procedure G, was isolated by chromatography eluted with EtOAc-hexane (1:8), as a colourless oil in 42% yield. ¹H-NMR (300 MHz, CDCl₃) ppm δ 7.45 (dd, J=8.8, 0.7 Hz, 1H, H-4), 6.76-6.77 (m, 2H, H-2+H-7), 6.74 (dd, J=8.8, 2.2 Hz, 1H, H-5), 3.72 (s, 3H, H-1), 3.67 (s, 3H, H-16), 3.10 (t, J=7.3 Hz, 2H, H-13), 2.74 (t, J=7.3 Hz, 2H, H-14), 1.08 (s, 9H, H-12), 0.28 (s, 6H, H-10); ¹³C-NMR (75 MHz, CDCl₃) ppm δ 173.89, 151.73, 137.90, 125.27, 122.62, 119.10, 113.45, 113.26, 99.98, 51.57, 34.99, 32.54, 25.38, 20.66, 18.32, −4.28; MS (CI⁺) m/z 348.205 (MH⁺, 53.56), 347.195 (M⁺, 100.00), 274.164 ([M⁺-C₃H₅O₂], 22.88); HRMS calcd. for C₁₉H₂₉NO₃Si (M⁺, DCI⁺/CH₄) 347.1917. found 347.1948.

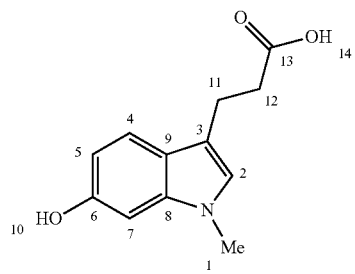 [SMILES: Cn1cc(CCC(=O)O)c2ccc(O)cc21]

3-(6-Hydroxy-1-methyl-1H-indol-3-yl) propanoic acid, AN-1145

Compound AN-1145 prepared from AN-1143 by procedure H, was isolated by chromatography eluted with EtOAc-hexane (1:1), as a white solid in 45% yield, mp 157-161° C. ¹H-NMR (300 MHz, MeOD) ppm δ 7.32 (dd, J=8.1, 0.6 Hz, 1H, H-4), 6.72 (s, 1H, H-2), 6.67 (dd, J=2.3, 0.6 Hz, 1H, H-7), 6.60 (dd, J=8.1, 2.3 Hz, 1H, H-5), 3.56 (s, 3H, H-1), 2.96 (t, J=7.1 Hz, 2H, H-11), 2.61 (t, J=7.1 Hz, 2H, H-12); ¹³C-NMR (75 MHz, MeOD) ppm δ 177.41, 154.26, 139.61, 125.79, 122.96, 120.04, 114.54, 109.71, 95.60, 36.03, 32.44, 21.68; MS (CI⁺) m/z 220.097 (MH⁺, 85.91), 219.089 (M⁺·, 100.00), 160.077 ([M⁺-C₂H₃O₂], 92.42); HRMS calcd. for C₁₂H₁₄NO₃ (MH⁺, DCI⁺/CH₄) 220.0974. found 220.0971, for C₁₂H₁₃NO₃ (M⁺·, DCI⁺/CH₄) 219.0895. found 219.0891, for C₁₀H₁₀NO ([M⁺·-C₂H₃O₂], DCI⁺/CH₄) 160.0762. found 160.0772.

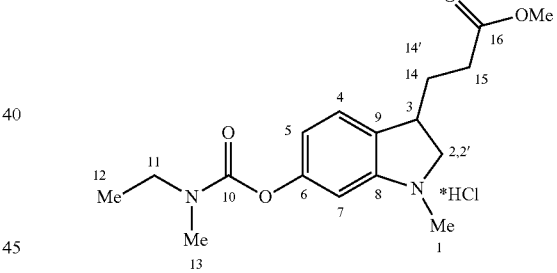

Methyl 3-(6-(ethyl(methyl)carbamoyloxy)-1-methyl-indolin-3-yl)propanoate hydrochloride, AN-689

Compound AN-689 prepared from AN-688 by procedure E, was stirred at room temperature over night, and was isolated as white hygroscopic crystals in 47% yield. ¹H-NMR (300 MHz, MeOD) ppm δ 7.55 (d, J=8.5 Hz, 1H, H-4), 7.51 (d, J=2.0 Hz, 1H, H-7), 7.31 (bd, J=8.5 Hz, 1H, H-5), 4.12 (m, 1H, H-2'), 3.71-3.79 (m, 1H, H-2), 3.69 (s, 3H, H-17), 3.37-3.56 (m, 2H, H-11), 3.30 (s, 3H, H-1), 3.30-3.32 (m, 1H, H-3), 2.99+3.11 (s, 3H, H-13), 2.52 (t, J=7.1 Hz, 2H, H-15), 2.18-2.33 (m, 1H, H-14'), 1.87-2.04 (m, 1H, H-14), 1.14-1.30 (m, 3H, H-12); ¹³C-NMR (75 MHz, MeOD) ppm δ 174.77, 155.56, 153.38, 142.41, 136.36, 127.19, 125.67, 114.22, 63.65, 52.29, 45.31, 43.18, 40.73, 34.67, 34.37, 32.20, 29.51, 13.44, 12.60; MS (co m/z 321.179 (MH⁺, 100.00), 320.171 (M⁺, 53.45), 289.153 ([MH⁺—CH₃OH], 13.26), 233.123 ([M⁺-C₄H₇O₂]⁺, 14.03); HRMS calcd. for C₁₇H₂₄N₂O₄ (M⁺, DCI⁺/CH₄) 320. 1736.

found 320.1708, for C$_{17}$H$_{25}$N$_2$O$_4$ (WE, DCI$^+$/CH$_4$) 321.1814. found 321.1792, for C$_{16}$H$_{21}$N$_2$O$_3$ ([MH$^+$—CH$_3$OH], DCI$^+$/CH$_4$) 289.1552. found 289.1528.

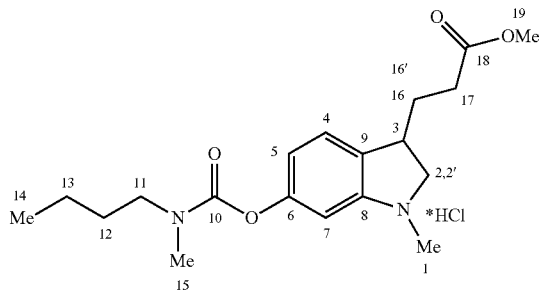 [SMILES: CCCCN(C)C(=O)Oc1ccc2c(c1)N(C)CC2CCC(=O)OC]

Methyl 3-(6-(butyl(methyl)carbamoyloxy)-1-methylindolin-3-yl)propanoate hydrochloride, AN-691

Compound AN-691 prepared from AN-690 by procedure E, was stirred at room temperature over night, and was isolated as white hygroscopic crystals in 34% yield. $^1$H-NMR (300 MHz, MeOD) ppm δ 7.48-7.53 (m, 2H, H-4+H-7), 7.29 (bs, 1H, H-5), 4.15 (bs, 1H, H-2'), 3.68-3.81 (m, 1H, H-2), 3.68 (s, 3H, H-19), 3.35-3.48 (m, 2H, H-11), 3.21-3.26 (m, 4H, H-1+H-3), 3.12+2.99 (s, 3H, H-15), 2.53 (bs, 2H, H-17), 2.27 (bs, 1H, H-16'), 1.95 (bs, 1H, H-16), 1.61-1.67 (m, 2H, H-12), 1.28-1.39 (m, 2H, H-13), 0.97-0.99 (m, 3H, H-14); $^{13}$C-NMR (75 MHz, MeOD) ppm δ 174.61, 155.60, 153.20, 142.40, 136.18, 127.18, 125.52, 114.21, 63.82, 52.45, 50.16, 43.61, 40.71, 35.37, 35.21, 32.34, 31.09, 30.38, 29.53, 20.78, 14.17; MS (CI$^+$) m/z 348.208 (M$^+$, 82.42), 349.214 (MH$^+$, 100.00), 261.168 ([M$^+$-C$_4$H$_7$O$_2$]$^+$, 30.49), 114.107 ([MH$^+$—C$_{13}$H$_{17}$NO$_3$]$^+$, 38.56); HRMS calcd. for C$_{19}$H$_{28}$N$_2$O$_4$ (M$^+$, DCI$^+$/CH$_4$) 348.2049. found 348.2080, for C$_{19}$H$_{29}$N$_2$O$_4$ (MH$^+$, DCI$^+$ CH$_4$) 349.2127. found 349.2141.

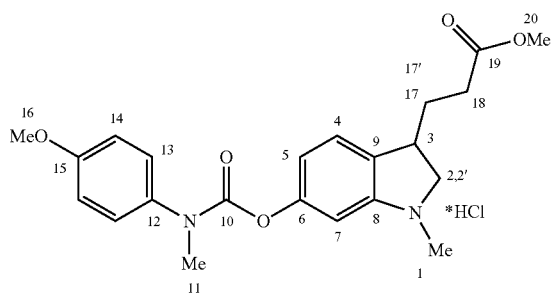 [SMILES: COC(=O)CCC1CN(C)c2cc(OC(=O)N(C)c3ccc(OC)cc3)ccc21]

Methyl 3-(6-((4-methoxyphenyl)(methyl)carbamoyloxy)-1-methylindolin-3-yl)propanoate hydrochloride, AN-687

Compound AN-687 prepared from AN-686 by procedure E, was stirred at room temperature over night, and was isolated as white crystals in 47% yield, mp dec.>150° C. $^1$H-NMR (300 MHz, MeOD) ppm δ 7.42-7.55 (m, 2H, H-4+H-7), 7.33 (bd, J=8.4 Hz, 2H, H-13), 7.25 (bs, 1H, H-5), 6.96 (bd, J=8.4 Hz, 2H, H-14), 4.12 (m, 1H, H-2'), 3.79 (s, 3H, H-16), 3.67 (s, 3H, H-20), 3.56-3.37 (m, 1H, H-2), 3.43-3.45 (m, 1H, H-3), 3.25-3.35 (m, 6H, H-1+H-11), 2.51 (t, J=6.7 Hz, 2H, H-18), 2.15-2.30 (m, 1H, H-17), 1.85-2.01 (m, 1H, H-17'); $^{13}$C-NMR (75 MHz, MeOD) ppm δ 174.74, 159.80, 153.24, 142.32, 136.95, 136.43, 128.73, 128.13, 127.17, 125.48, 115.42, 114.04, 63.56, 56.01, 52.28, 43.17, 40.68, 39.12, 32.18, 29.47; MS (CI$^+$) m/z 400.195 (MD$^+$, 100.00), 399.190 (MH$^+$, 72.16), 164.078 ([MH$^+$—C$_{13}$H$_{17}$NO$_3$]$^+$, 71.13), 136.083 ([MH$^+$—C$_{14}$H$_{17}$NO$_4$]$^+$, 57.04); HRMS calcd. for C$_{22}$H$_{27}$N$_2$O$_5$ (MH$^+$, DCI$^+$/CH$_4$) 399.1920. found 399.1898, for C$_{22}$H$_{26}$N$_2$O$_5$D (MD$^+$, DCI$^+$/CH$_4$) 400.1983. found 400.1952, for C$_9$H$_{10}$NO$_2$ ([MH$^+$—C$_{13}$H$_{17}$NO$_3$]$^+$, DCI$^+$CH$_4$) 164.0712. found 164.0784, for C$_8$H$_{10}$NO ([MH$^+$—C$_{14}$H$_{17}$NO$_4$]$^+$, DCI$^+$CH$_4$) 136.0762. found 136.0831.

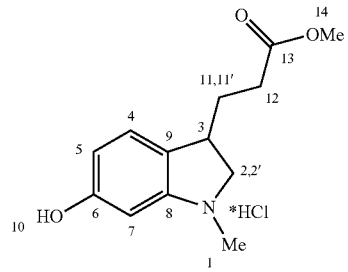

Methyl 3-(6-hydroxy-1-methylindolin-3-yl)propanoate hydrochloride, AN-802

Compound AN-802 prepared from AN-1128 by procedure E, was stirred at room temperature for 2 h, and was isolated as a bright brown hygroscopic solid in 70% yield, mp 104-108° C. $^1$H-NMR (300 MHz, CD$_3$CN) ppm δ 7.18 (d, J=10 Hz, 1H, H-4), 6.97 (s, 1H, H-7), 6.95 (d, J=10 Hz, 1H, H-5), 6.39 (bs, 1H, H-10), 3.86-3.44 (m, 2H, H-2+H-2'), 3.62 (s, 3H, H-14), 3.44-3.37 (m, 1H, H-3), 3.05 (s, 3H, H-1), 2.45-2.37 (m, 2H, H-12), 2.10 (bs, 1H, H-11), 1.82 (bs, 1H, H-11'); $^{13}$C-NMR (75 MHz, CD$_3$CN) ppm δ 174.03, 159.00, 142.26, 129.23, 126.88, 118.29, 106.39, 62.88, 52.22, 42.80, 39.87, 32.07, 29.47; MS (CI$^+$) m/z 235.125 (M$^+$, 21.49), 236.130 (MH$^+$, 42.45); HRMS calcd. for C$_{13}$H$_{18}$NO$_3$ (MH$^+$, DCI$^+$/CH$_4$) 236.1287. found 236.1296.

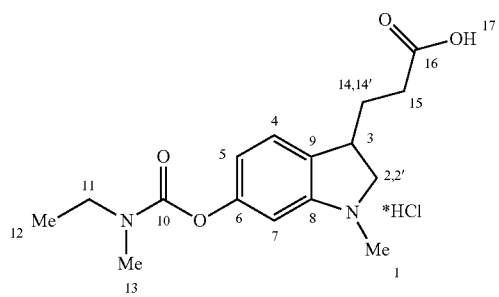 [SMILES: CCN(C)C(=O)Oc1ccc2c(c1)N(C)CC2CCC(=O)O]

3-(6-((Ethyl(methyl)carbamoyl)oxy)-1-methylindolin-3-yl)propanoic acid hydrochloride, AN-893

Compound AN-1237 was dissolved with CH$_2$Cl$_2$ and stirred with 3N HCl at room temperature for 2 d. The aqueous phase was evaporated to provide AN-893 as a colourless oil in quantitative yield. $^1$H-NMR (300 MHz, MeOD) ppm δ 7.52 (d, J=8.4 Hz, 1H, H-4), 7.41 (bs, 1H, H-7), 7.24 (bd, J=8.4 Hz, 1H, H-5), 4.11 (ABq, J=7.4 Hz, 1H, H-2'), 3.74-3.63 (m, 2H, H-3+H-2), 3.52+3.41 (q, J=7.4 Hz, 2H, H-11), 3.26 (s, 3H, H-1), 2.99+3.11 (s, 3H, H-13), 2.49 (t, J=7.4 Hz, 2H, H-15), 2.26-2.22 (m, 1H, H-14), 1.95-1.89 (m, 1H, H-14'), 1.27+1.19 (t, J=7.4 Hz, 3H, H-12); $^{13}$C-NMR (75 MHz, MeOD) ppm δ 174.88, 155.73, 153.41, 143.67, 135.85, 126.89, 113.13, 113.04, 63.73, 45.32, 45.22, 42.56, 40.78, 34.63, 34.32, 32.21, 29.56, 13.40, 12.57; MS (co ms 307.168 (MH$^+$, 6.29); HRMS calcd. for $C_{16}H_{23}N_2O_4$ (MH$^+$, DCI$^+$/CH$_4$) 307.1658. found 307.1684.

hexane (1:3), as a white solid in 86% yield, mp 62-64° C. $^1$H-NMR (300 MHz, CDCl$_3$) ppm δ 7.18-7.09 (m, 2H, H-6+H-5), 8.23-6.77 (m, 2H, H-2+H-7), 3.74 (s, 3H, H-1), 3.67 (s, 3H, H-17), 3.58+3.44 (q, J=7.6 Hz, 2H, H-11), 3.16+3.02 (s, 3H, H-13), 3.08 (t, J=7.6 Hz, 2H, H-14), 2.67 (t, J=7.6 Hz, 2H, H-15), 1.30+1.21 (t, J=7.6 Hz, 3H, H-12); $^{13}$C-NMR (75 MHz, CDCl$_3$) ppm δ 173.71, 155.06, 154.84, 145.09, 144.89, 139.31, 126.81, 121.79, 120.50, 112.35, 112.11, 112.21, 106.75, 51.41, 44.14, 43.90, 35.66, 35.50, 34.12, 33.78, 32.84, 21.74, 13.27, 12.43; MS (CI+) m/z 318.159 (M$^+$, 55.78), 319.166 (MH$^+$, 100.00); HRMS calcd. for $C_{17}H_{22}N_2O_4$ (M$^+$, DCI$^+$/CH$_4$) 318.1580. found 318.1589, for $C_{17}H_{23}N_2O_4$ (MH$^+$, DCI$^+$/CH$_4$) 319.1658. found 319.1658.

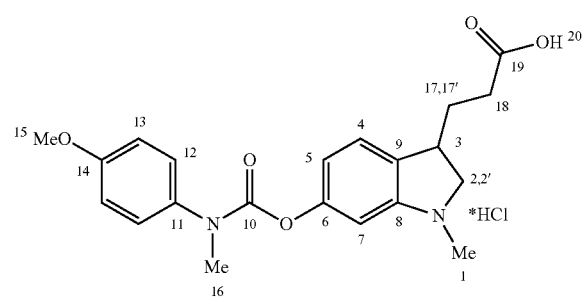 [SMILES: COc1ccc(N(C)C(=O)Oc2ccc3c(c2)N(C)CC3CCC(=O)O)cc1]

3-(6-(((4-Methoxyphenyl)(methyl)carbamoyl)oxy)-1-methylindolin-3-yl) propanoic acid hydrochloride, AN-892

Compound AN-1234 was dissolved in a few drops of MeOH or CH$_2$Cl$_2$ and stirred with 3N HCl at room temperature for 2-3 d. The solvent was evaporated to provide AN-892 as a yellow oil in quantitative yield. $^1$H-NMR (300 MHz, MeOD) ppm δ 7.60-7.45 (bm, 2H, H-5+H+-7), 7.32 (bd, J=9.0 Hz, 2H, H-12), 7.25 (bs, 1H, H-4), 6.96 (bd, J=9.0 Hz, 2H, H-13), 4.13 ("t", J=10.2 Hz, 1H, H-2), 3.80 (s, 3H, H-15), 3.79-3.60 (m, 2H, H-3+H-2'), 3.28+3.43 (bs, 3H, H-16), 3.32 (s, 3H, H-1), 2.48 (t, J=7.5 Hz, 2H, H-18), 2.25-2.15 (m, 1H, H-17), 1.93-1.84 (m, 1H, H-17'); $^{13}$C-NMR (75 MHz, MeOD) ppm δ 174.81, 160.16, 153.33, 142.57, 136.32, 128.70, 127.20, 127.10, 125.37, 115.46, 113.88, 63.73, 55.99, 43.16, 40.77, 39.11, 32.19, 29.50; MALDI (DHB_MeOH+Na$^+$RP_PepMix) m/z 421.160 (M+H)$^+$; HRMS calcd. for $C_{21}H_{24}N_3O_5Na$ 421.1608 (M+H)$^+$ found 421.160.

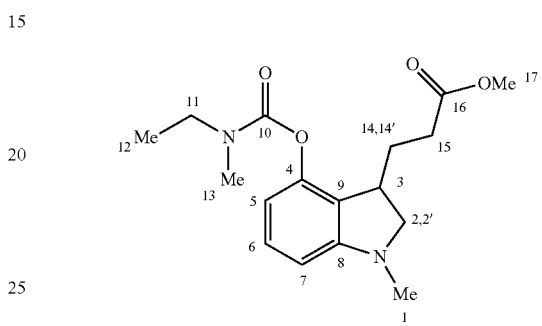

Methyl 3-(4-((ethyl(methyl)carbamoyl)oxy)-1-methylindolin-3-yl) propanoate, AN-1235

Compound AN-1235, prepared from AN-629 by procedure E, method II, was isolated by chromatography eluted with EtOAc-hexane (1:3), as a yellow oil in 90% yield. $^1$H-NMR (300 MHz, CDCl$_3$) ppm δ 7.05 (t, J=7.5 Hz, 1H, H-6), 6.42+6.40 (d, J=7.5 Hz, 1H, H-5), 6.28 (d, J=7.5 Hz, 1H, H-7), 3.62 (s, 3H, H-17), 3.47-3.29 (m, 4H, H-11+H-2+H-3), 3.12-3.06 (bm, 1H, H-2'), 3.06+2.97 (s, 3H, H-13), 2.71 (s, 3H, H-1), 2.34 (t, J=8.4 Hz, 2H, H-15), 2.10-2.00 (m, 1H, H-14), 1.93-1.81 (m, 1H, H-14'), 1.25-1.15 (m, 3H, H-12); $^{13}$C-NMR (75 MHz, CDCl$_3$) ppm δ 173.91, 154.87, 148.14, 129.02, 123.62, 111.91, 111.77, 104.41, 61.02, 60.90, 51.51, 44.09, 38.35, 35.88, 34.25, 33.84, 31.40, 28.13, 13.24, 12.51; MS (CI$^+$) m/z 320.178 (M$^+$, 0.68), 321.181 (MH$^+$, 2.38); HRMS calcd. for $C_{17}H_{25}N_2O_4$ (M$^+$, DCI$^+$/CH$_4$) 321.1814. found 321.1815.

Methyl 3-(4-((ethyl(methyl)carbamoyl)oxy)-1-methyl-1H-indol-3-yl) propanoate, AN-629

Compound AN-629, prepared from AN-803 by procedure G, was isolated by chromatography eluted with EtOAc-

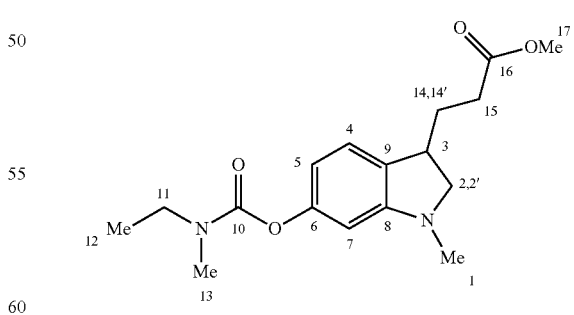

Methyl 3-(6-((ethyl(methyl)carbamoyl)oxy)-1-methylindolin-3-yl)propanoate, AN-1237

Compound AN-1237, prepared from AN-688 by procedure E, method II, was purified by silica gel chromatography eluted with EtOAc-hexane (1:3), as a colourless oil in 89% yield. $^1$H-NMR (300 MHz, CDCl$_3$) ppm δ 6.80 (d, J=8.1 Hz, 1H, H-4), 6.35 (bd, J=8.1 Hz, 1H, H-5), 6.19 (bs, 1H, H-7), 3.65 (s, 3H, H-17), 3.43 (t, J=8.4 Hz, 1H, H-2), 3.46-3.36 (m, 2H, H-11), 3.19-3.10 (m, 1H, H-3), 3.01+2.91 (s, 3H, H-13), 2.98 (ABq, J=8.4 Hz, 1H, H-2'), 2.68 (s, 3H, H-1), 2.37 (t, J=8.4 Hz, 2H, H-15), 2.12-2.00 (m, 1H, H-14), 1.88-1.76 (m, 1H, H-14'), 1.23-1.16 (m, 3H, H-12); $^{13}$C-NMR (75 MHz, CDCl$_3$) ppm δ 173.81, 154.69, 154.05, 152.02, 129.55, 123.58, 110.26, 101.37, 62.01, 51.58, 43.98, 39.49, 35.62, 34.17, 33.74, 31.64, 28.98, 13.19, 12.48; MS (CI$^+$) m/z 321.179 (MH$^+$, 100.00), 320.173 (M$^{+\cdot}$, 61.81), 319.168 ([M−H]$^+$, 42.09); HRMS calcd. for C$_{17}$H$_{25}$N$_2$O$_4$ (MH$^+$, DCI$^+$/CH$_4$) 321.1814. found 321.1793, for C$_{17}$H$_{24}$N$_2$O$_4$ (M$^{+\cdot}$, DCI$^+$/CH$_4$) 320.1736. found 320.1729, for C$_{17}$H$_{23}$N$_2$O$_4$ ([M−H]$^\pm$, DCI$^+$/CH$_4$) 319.1658. found 319.1683.

3-(4-((Ethyl(methyl)carbamoyl)oxy)-1-methylindolin-3-yl)propanoic acid hydrochloride, AN-699

Compound AN-1235 was dissolved in CH$_2$Cl$_2$ and stirred with 3N HCl at room temperature for 2 d. The aqueous phase was evaporated to provide AN-699 as a colourless oil in quantitative yield. $^1$H-NMR (300 MHz, MeOD) ppm δ 7.59-7.50 (m, 2H, H-6+H-5), 7.31 (d, J=7.5 Hz, 1H, H-7), 4.04-3.97 (m, 1H, H-2), 3.92-3.85 (m, 1H, H-2'), 3.79-3.77 (bs, 1H, H-3), 3.56+3.42 (q, J=7.2 Hz, 2H, H-11), 3.40 (s, 3H, H-1), 3.15+3.01 (s, 3H, H-13), 2.44 (t, J=7.2 Hz, 2H, H-15), 2.30-2.20 (m, 1H, H-14), 1.92-1.84 (m, 1H, H-14'), 1.28+1.20 (t, J=7.2 Hz, 3H, H-12); $^{13}$C-NMR (175 MHz, MeOD) ppm δ 174.58, 154.87, 149.91, 149.87, 143.40, 143.34, 131.81, 131.63, 131.54, 131.53, 125.91, 125.74, 116.83, 62.35, 62.24, 45.51, 45.30, 43.35, 40.20, 34.72, 34.49, 32.98, 31.91, 28.52, 28.45, 13.50, 12.61; MS (co ms 306.159 (M$^{+\cdot}$, 57.80), 307.167 (MH$^+$, 100.00); HRMS calcd. for C$_{16}$H$_{23}$N$_2$O$_4$ (MH$^+$ DCI$^+$/CH$_4$) 307.1658. found 307.1668.

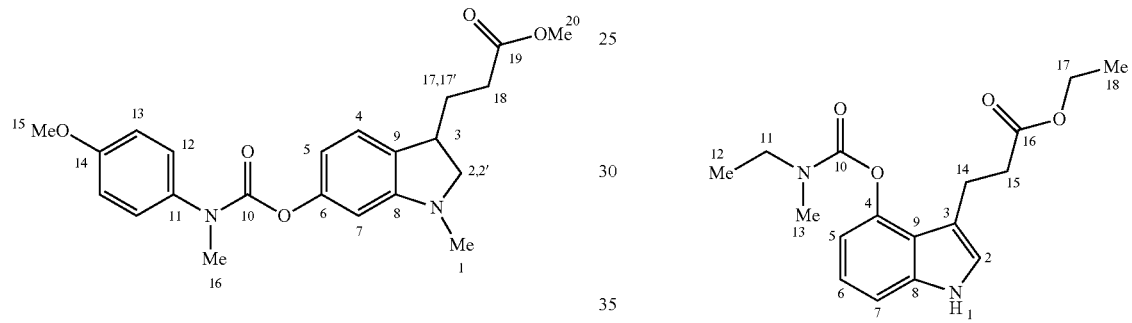

Methyl 3-(6-(((4-methoxyphenyl)(methyl)carbamoyl)oxy)-1-methylindolin-3-yl)propanoate, AN-1234

Ethyl 3-(4-(ethyl(methyl)carbamoyloxy)-1H-indol-3-yl)propanoate, AN-1191

Compound AN-1234, prepared from AN-1223 by procedure G, was isolated by chromatography eluted with EtOAc-hexane (1:3), as a white solid in 37% yield. $^1$H-NMR (300 MHz, CDCl$_3$) ppm δ 7.24 (bd, J=7.8 Hz, 2H, H-12), 6.95 (d, J=7.8 Hz, 1H, H-4), 6.89 (d, J=7.8 Hz, 2H, H-13), 6.36 (bs, 1H, H-5), 6.17 (bs, 1H, H-7), 3.79 (s, 3H, H-15), 3.66 (s, 3H, H-20), 3.44 (t, J=7.5 Hz, 1H, H-2'), 3.35 (bs, 3H, H-16), 3.15 (quintet, J=7.5 Hz, 1H, H-3), 3.00 (ABq, J=7.5 Hz, 1H, H-2), 2.69 (s, 3H, H-1), 2.37 (t, J=7.5 Hz, 2H, H-18), 2.12-2.01 (m, 1H, H-17), 1.89-1.76 (m, 1H, H-17').

To a stirred solution of AN-805 (0.31 g, 0.01 mmol) in EtOH was added a few drops of con. H$_2$SO$_4$ and activated molecular scieves 4 Å. The mixture was refluxed for 1.5 h and the EtOH was evaporated. The residue was dissolved in EtOAc, filtered through celite and the filtrate was evaporated. The residue was isolated by chromatography eluted with EtOAc-hexane (1:2), as a white solid. Alternative way of purification is crystallization from EtOAc-hexane to provide AN-1191 in quantitative yield, mp 85-87° C. $^1$H-NMR (300 MHz, CDCl$_3$) ppm δ 8.47 (bs, 1H, H-1), 7.04-6.99 (m, 2H, H-7+H-2), 6.77 (t, J=5.8 Hz, 1H, H-6), 6.66 (bs, 1H, H-5), 4.14 (q, J=7.9 Hz, 2H, H-17), 3.58+3.46 (q, J=7.9 Hz, 2H, H-12), 3.17+3.04 (s, 3H, H-13), 3.06 (t, J=7.9 Hz, 2H, H-14), 2.64 (t, J=7.9 Hz, 2H, H-15), 1.24 (t, J=7.9 Hz, 3H, H-18), 1.27-1.22 (m, 3H, H-11); $^{13}$C-NMR (75 MHz, CDCl$_3$) ppm δ 173.47, 155.23, 144.72, 138.74, 122.36, 121.77, 120.21, 113.04, 112.41, 112.20, 109.06, 60.28, 44.26, 44.02, 35.79, 35.67, 34.21, 33.90, 22.96, 14.32, 13.33, 12.53; MALDI (DHB+Na$^+$/RP_PepMix) m/z 341.148 (M+Na$^+$), 319.156 (M+H$^+$); HRMS calcd. for C$_{17}$H$_{22}$N$_2$O$_4$Na (M+Na$^+$) 341.1472. found 341.148; HPLC impurity 98%.

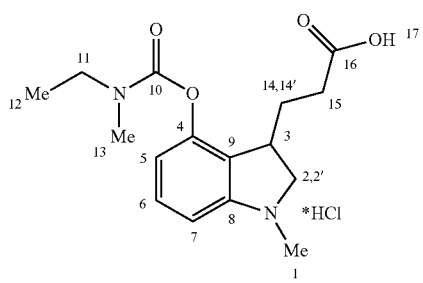 [SMILES: CCN(C)C(=O)Oc1cccc2c1C(CCC(=O)O)CN2C]

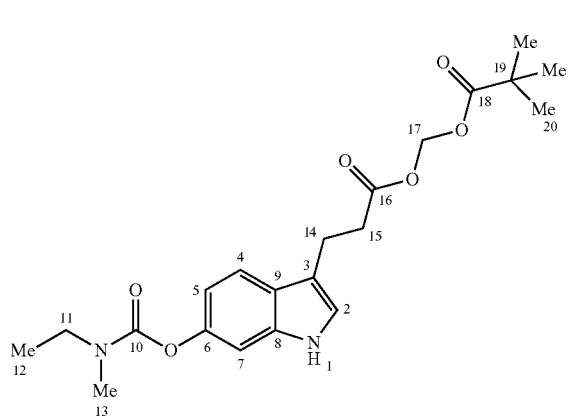 [SMILES: CCN(C)C(=O)Oc1ccc2c(CCC(=O)OCOC(=O)C(C)(C)C)c[nH]c2c1]

(3-(6-(Ethyl(methyl)carbamoyloxy)-1H-indol-3-yl)propanotloxy)methyl pivalate, AN-860

To a solution of acid (0.34 mmol) in of dry DMF (0.2 mL) was added $K_2CO_3$ (0.52 mmol) at room temperature, and the reaction mixture was stirred for 2 h, after which 0.68 mmol of pivaloyloxymethyl chloride was added. The mixture was stirred overnight, diluted with $CHCl_3$, washed with water and brine, dried over $MgSO_4$, evaporated, and was isolated by chromatography eluted with EtOAc-hexane (1:4) to give the product AN-860 as a yellow oil in 27% yield. $^1$H-NMR (300 MHz, $CDCl_3$) ppm δ 8.09 (bs, 1H, H-1), 7.48 (d, J=8.0 Hz, 1H, H-4), 7.10 (d, J=2.4 Hz, 1H, H-7), 6.91-6.92 (m, 1H, H-2), 6.78 (dd, J=8.0, 2.4 Hz, 1H, H-5), 5.75 (s, 2H, H-17), 3.38-3.52 (m, 2H, H-11), 3.01-3.10 (m, 5H, H-13, H-14), 2.73 (t, J=7.5 Hz, 2H, H-15), 1.18-1.20 (m, 3H, H-12), 1.18 (s, 9H, H-20); $^{13}$C-NMR (75 MHz, $CDCl_3$) ppm δ 177.44, 172.18, 155.50, 147.68, 136.45, 124.99, 122.12, 118.94, 114.62, 114.24, 104.70, 79.73, 44.29, 38.96, 34.83, 34.00, 34.65, 27.07, 20.55, 13.46, 12.75; MS (co m/z 404.196 (M'·, 23.72), 405.198 (MH$^+$, 5.73); HRMS calcd. for $C_{21}H_{28}N_2O_6$ (M$^{+·}$, DCI$^+$/CH$_4$) 404.1947. found 404.1962.

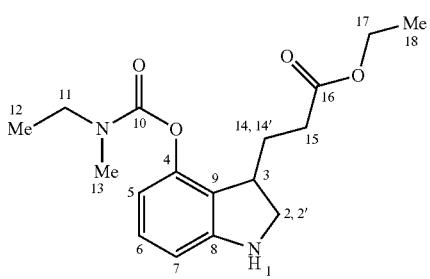 [SMILES: CCOC(=O)CCC1CNc2cccc(OC(=O)N(C)CC)c21]

Ethyl 3-(4-(ethyl(methyl)carbamoyloxy)indolin-3-yl)propanoate, AN-1192

Compound AN-1192 was prepared from AN-1191 by procedure E, was stirred at room temperature over night, and was isolated by chromatography eluted with EtOAc-hexane (1:4), as a colourless oil in 31% yield. $^1$H-NMR (300 MHz, $CDCl_3$) ppm δ 7.01 (t, J=7.9 Hz, 1H, H-6), 6.48 (bd, J=7.9 Hz, 2H, H-5+H-7), 4.08 (q, J=7.2 Hz, 2H, H-17), 3.74 (bs, 1H, H-2'), 3.65 (t, J=7.2 Hz, 1H, H-2), 3.48-3.39 (m, 2H, H-11), 3.29-3.24 (m, 1H, H-3), 3.07+2.98 (s, 3H, H-13), 2.32 ("t", J=7.2 Hz, 2H, H-15), 2.10-2.03 (m, 1H, H-14), 1.95-1.85 (m, 1H, H-14'), 1.23 (t, J=7.2 Hz, 3H, H-18), 1.24-1.16 (m, 3H, H-12); $^{13}$C-NMR (75 MHz, $CDCl_3$) ppm δ 173.51, 153.98, 152.50, 148.65, 129.03, 123.57, 113.62, 113.02, 107.24, 60.37, 52.33, 44.22, 39.88, 34.35, 33.83, 31.69, 28.35, 14.31, 13.33, 12.58; MS (CI$^+$) m/z 320.175 (M$^{+·}$, 39.72), 321.186 (MH$^+$, 23.20), 275.139 ([MH-EtOH]$^+$, 12.49), 217.107 ([MH—$C_4H_9NO_2$]$^+$, 14.17); HRMS calcd. for $C_{17}H_{24}N_2O_4$ (M$^{+·}$, DCI$^+$/CH$_4$) 320.1736. found 320.1753.

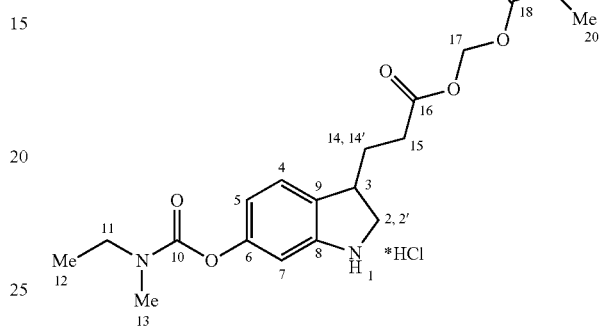

(3-(6-(Ethyl(methyl)carbamoyloxy)indolin-3-yl)propanotloxy)methyl pivalate hydrochloride, AN-862

Compound AN-862 prepared from AN-860 by procedure E, was stirred at room temperature over night, and was isolated as white hygroscopic solid in 28% yield. $^1$H-NMR (300 MHz, MeOD) ppm δ 7.51 (d, J=8.2 Hz, 1H, H-4), 7.29 (bs, 1H, H-7), 7.23 (bd, J=8.2 Hz, 1H, H-5), 5.76 (d, J=2.2 Hz 2H, H-17), 3.96-4.03 (m, 1H, H-2), 3.58-3.66 (m, 2H, H-2', H-3), 3.48-3.56+3.37-3.44 (m, 1H, H-11), 3.10-2.99 (s, 3H, H-13), 2.45-2.59 (m, 2H, H-15), 2.15-2.24 (m, 1H, H-14), 1.88-2.00 (m, 1H, H-14'), 1.19-1.34 (m, 3H, H-12'), 1.19 (s, 9H, H-20); $^{13}$C-NMR (75 MHz, MeOD) ppm δ 178.41, 172.93, 153.16, 138.40, 136.45, 127.11, 124.49, 124.39, 114.47, 80.99, 52.82, 45.31, 45.21, 41.79, 34.63, 34.31, 32.10, 29.82, 27.21, 13.40, 12.56; MS (CI$^+$) m/z 406.210 (M$^{+·}$, 17.42), 407.222 (MH$^+$, 5.40), 275.143 ($C_{15}H_{19}N_2O_3^+$, 28.34), 219.047 ([$C_{12}H_{15}N_2O_2$]$^+$, 19.74); HRMS calcd. for $C_{21}H_{30}N_2O_6$ (M$^{+·}$, DCI$^+$/CH$_4$) 406.2104. found 406.2096.

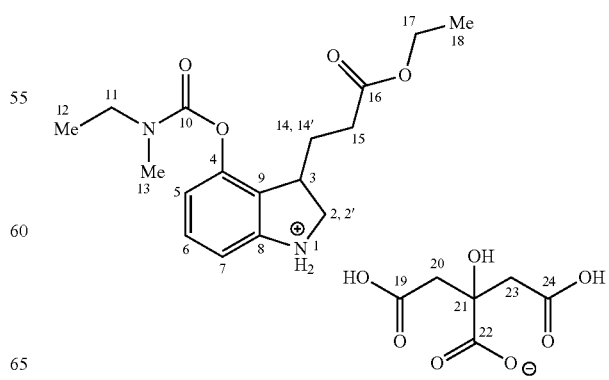

Ethyl 3-(4-(ethyl(methyl)carbamoyloxy)indolinium citrate, AN-871

Compound AN-871 prepared from AN-1192 by procedure R was isolated as a yellow oil in quantitative yield. $^1$H-NMR (300 MHz, MeOD) ppm δ 7.05 (t, J=7.9 Hz, 1H, H-6), 6.59 (d, J=7.9 Hz, 1H, H-5), 6.47 (bd, J=7.9 Hz, 1H, H-7), 4.10 (q, J=7.6 Hz, 2H, H-17), 3.66-3.59 (m, 1H, H-2), 3.57-3.48 (m, 1H, H-2'), 3.43-3.36 (m, 2H, H-11), 3.30-3.25 (m, 1H, H-3), 2.98+3.11 (s, 3H, H-13), 2.85 (ABq, J=14.0 Hz, 4H, H-20+H-23), 2.34 (t, J=7.9 Hz, 2H, H-15), 2.10-1.99 (m, 1H, H-14), 1.87-1.75 (m, 1H, H-14'), 1.23 (t, J=6.7 Hz, 3H, H-18), 1.33-1.15 (m, 3H, H-12); $^{13}$C-NMR (75 MHz, MeOD) ppm δ 176.84, 174.97, 173.48, 153.31, 149.68, 141.50, 130.04, 125.78, 114.82, 114.60, 110.21, 109.48, 74.13, 61.46, 52.89, 52.79, 45.24, 45.15, 43.84, 41.19, 34.54, 34.38, 32.35, 29.31, 29.23, 14.54, 13.52, 12.69; MS (CI$^+$) m/z 320.178 (M$^{+\cdot}$, 67.08), 321.178 (MH$^+$, 38.14); HRMS calcd. for C$_{17}$H$_{24}$N$_2$O$_4$ (M$^{+\cdot}$, DCI$^+$/CH$_4$) 320.1736. found 320.1775.

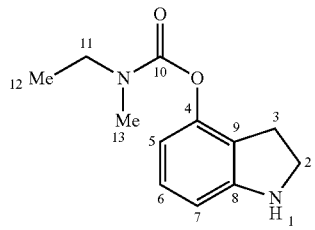 [SMILES: CCN(C)C(=O)Oc1cccc2c1CCN2]

Indolin-4-yl ethyl(methyl)carbamate, AN-1195

Compound AN-1195 prepared from AN-651 by procedure E, Method I. The crude was isolated by chromatography eluted with EtOAc-hexane (1:3 to 1:2) or with CH$_2$Cl$_2$-EtOAc (20:1 to 15:1), as a colourless oil which is solidified in the freezer to a white solid in 58% yield, mp 47-49° C. $^1$H-NMR (300 MHz, CDCl$_3$) ppm δ 6.98 (t, J=7.8 Hz, 1H, H-6), 6.45 (d, J=7.8 Hz, 2H, H-5+H-7), 3.79 (bs, 1H, H-1), 3.52 (t, J=9.0 Hz, 2H, H-2), 3.45-3.38 (m, 2H, H-11), 3.04+2.98 (s, 3H, H-13), 2.95 (J=9.0 Hz, 2H, H-3), 1.24-1.15 (m, 3H, H-12); $^{13}$C-NMR (75 MHz, CDCl$_3$) ppm δ 153.36, 148.30, 128.30, 121.34, 112.09, 106.62, 47.11, 44.06, 34.26, 33.81, 27.15, 13.13, 12.46; MS (CI$^+$) m/z 220.120 (M$^{+\cdot}$, 62.96), 221.127 (MH$^+$, 58.45); HRMS calcd. for C$_{12}$H$_{17}$N$_2$O$_2$ (MH$^+$, DCI$^+$/CH$_4$) 221.1290. found 221.1274, for C$_{12}$H$_{16}$N$_2$O$_2$ (M$^{+\cdot}$, DCI$^+$/CH$_4$) 220.1212. found 220.1198.

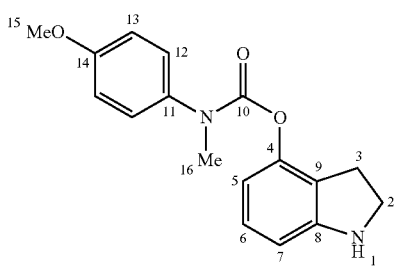

Indolin-4-yl(4-methoxyphenyl)(methyl)carbamate, AN-1176

Compound AN-1176 prepared from AN-807 by procedure E, Method I. The crude was obtained as a hygroscopic white solid in 70% yield after crystallization from CH$_2$Cl$_2$-hexane. $^1$H-NMR (300 MHz, CDCl$_3$) ppm δ 7.22 (bd, J=7.5 Hz, 2H, H-12), 7.18-7.05 (m, 2H, H-5+H-6), 6.92 (bd, J=7.5 Hz, 2H, H-13), 6.83 (bd, J=7.5 Hz, 1H, H-7) 3.82 (s, 3H, H-15), 3.66-3.58 (m, 2H, H-2), 3.09 (bs, 3H, H-16), 3.09-3.00 (bs, 2H, H-3); $^{13}$C-NMR (75 MHz, CDCl$_3$) ppm δ 158.39, 153.36, 148.33, 147.81, 135.35, 129.10, 126.87, 121.55, 116.75, 114.51, 113.45, 55.50, 53.82, 46.08, 38.73.

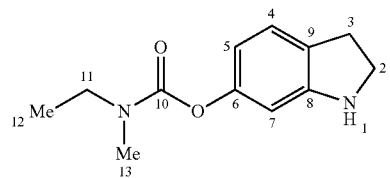

Indolin-6-yl ethyl(methyl)carbamate, AN-1156

Compound AN-1156 prepared from AN-1106 by procedure B, was isolated by chromatography eluted with EtOAc-hexane (1:2), as a white solid in 60% yield, mp 101-104° C. $^1$H-NMR (300 MHz, CDCl$_3$) ppm δ 7.01 (d, J=7.9 Hz, 1H, H-4), 6.40 (d, J=7.9 Hz, 1H, H-5), 6.38 (bs, 1H, H-7), 3.53 (t, J=9.0 Hz, 2H, H-2), 3.44-3.38 (m, 2H, H-11), 3.03+2.98 (s, 3H, H-13), 2.96 (t, J=9.0 Hz, 2H, H-3), 1.23-1.17 (m, 3H, H-12); $^{13}$C-NMR (75 MHz, CDCl$_3$) ppm δ 155.00, 152.54, 151.30, 126.30, 124.50, 111.50, 103.64, 47.92, 44.04, 34.19, 29.24, 13.22, 12.53; MS (CI$^+$) m/z 220.120 (M$^{+\cdot}$, 80.36), 221.128 (MH$^+$, 30.52); HRMS calcd. for C$_{12}$H$_{16}$N$_2$O$_2$ (M$^{+\cdot}$, DCI$^+$/CH$_4$) 220.1212. found 220.1202.

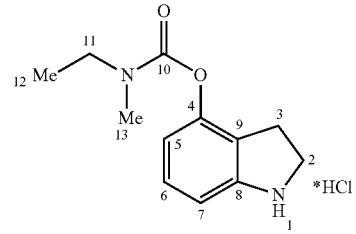 [SMILES: CCN(C)C(=O)Oc1cccc2c1CCN2]

Indolin-4-yl ethyl(methyl)carbamate hydrochloride, AN-854

Compound AN-854 prepared from AN-651 or from AN-1195 by procedure E, was stirred at room temperature for 2 h, and was isolated as a colourless hygroscopic oil in 63% yield. $^1$H-NMR (300 MHz, CD$_3$CN) ppm δ 7.35 (t, J=7.6 Hz, 1H, H-6), 7.26 (d, J=7.6 Hz, 1H, H-5), 7.18 (d, J=7.6 Hz, 1H, H-7) 3.73 (t, J=7.9 Hz, 2H, H-2), 3.36-3.43 (m, 2H, H-11), 3.11 (t, J=7.9 Hz, 2H, H-3), 2.97+3.04 (s, 3H, H-13), 1.18 (bs, 3H, H-12); $^{13}$C-NMR (75 MHz, CD$_3$CN) ppm δ 153.94, 149.60, 138.31, 130.33, 129.91, 123.93, 118.28, 117.63, 46.40, 44.89, 34.63, 27.62, 13.38, 12.67; MS (CI$^+$) m/z 221.126 (MH$^+$, 100.00), 220.120 (M$^{+\cdot}$, 58.49);

HRMS calcd. for $C_{12}H_{17}N_2O_2$ (MH$^+$, DCI$^+$/CH$_4$) 221.1290. found 221.1260, for $C_{12}H_{16}N_2O_2$ (M$^{+\cdot}$, DCI$^+$/CH$_4$) 220.1212. found 220.1203.

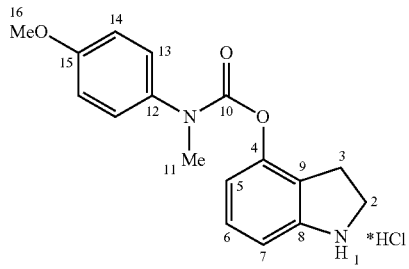 [SMILES: COc1ccc(N(C)C(=O)Oc2cccc3c2CCN3)cc1]

Indolin-4-yl 4-methoxyphenyl(methyl)carbamate hydrochloride, AN-857

Compound AN-857 prepared from AN-807 or from AN-1176 by procedure E, was stirred at room temperature for 2 h, and was isolated as a colourless oil in 69% yield. $^1$H-NMR (300 MHz, D$_2$O) ppm δ 7.12-7.23 (m, 4H, H-5, H-6, H13), 6.77-6.79 (m, 3H, H-14, H-7), 3.68 ("t", J=9.0 Hz, 2H, H-2), 3.55 (s, 3H, H-16), 3.06 (bs, 3H, H-11), 2.91 ("t", J=9.0 Hz, 2H, H-3); $^{13}$C-NMR (75 MHz, D$_2$O) ppm δ 158.03, 153.93, 136.68, 129.90, 128.50, 127.55, 123.09, 117.18, 114.47, 55.39, 45.90, 38.22, 26.29; MS (CI$^+$) m/z 298.132 (M$^{+\cdot}$, 74.38), 299.141 (MH$^+$, 100.00); HRMS calcd. for $C_{17}H_{19}N_2O_3$ (MH$^+$, DCI$^+$/CH$_4$) 299.1396. found 299.1414.

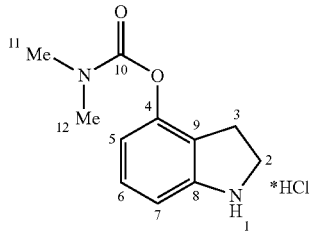 [SMILES: CN(C)C(=O)Oc1cccc2c1CCN2]

Indolin-4-yl dimethylcarbamate hydrochloride, AN-856

Compound AN-856 prepared from 3 by procedure E, was stirred at room temperature for 2 h, and was isolated as a colourless oil in 69% yield. $^1$H-NMR (300 MHz, D$_2$O) ppm δ 7.35-7.29 (m, 2H, H-6+H-5), 7.09 (bd, J=7.1 Hz, 1H, H-7), 3.78 (bt, J=7.9 Hz, 2H, H-2), 3.10 (bt, J=7.9 Hz, 2H, H-3), 2.97 (s, 3H, H-11), 2.83 (s, 3H, H-12); $^{13}$C-NMR (75 MHz, D$_2$O) ppm δ 155.17, 147.77, 136.63, 129.86, 128.80, 123.41, 116.97, 46.00, 36.20, 26.29; MS (CI$^+$) m/z 207.117 (MH$^+$, 54.82), 206.106 (M$^{+\cdot}$, 100.00); HRMS calcd. for $C_{11}H_{14}N_2O_2$ (M$^{+\cdot}$, DCI$^+$/CH$_4$) 206.1055. found 206.1062.

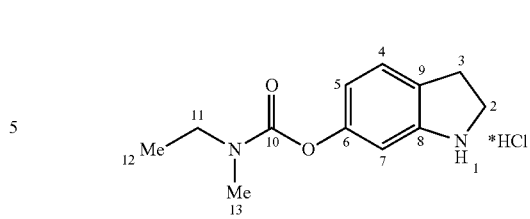

Indolin-6-yl ethyl(methyl)carbamate hydrochloride, AN-885

Compound AN-885 prepared from AN-1106 or from AN-1156 after dissolving of indoline in EtOAc and extraction with 1N HCl. Separation and evaporation of the water phase in high vacuum gave 110a as a yellow oil in quantitative yield. $^1$H-NMR (300 MHz, MeOD) ppm δ 7.51 (d, J=8.2 Hz, 1H, H-4), 7.33 (d, J=2.2 Hz, 1H, H-7), 7.24 (dd, J=8.2, 2.2 Hz, 1H, H-5), 3.92 (t, J=7.8 Hz, 2H, H-2), 3.52+3.41 (q, J=7.8 Hz, 2H, H-11), 3.33 (t, J=7.8 Hz, 2H, H-3), 3.11+2.99 (s, 3H, H-13), 1.26+1.19 (t, J=7.5 Hz, 3H, H-12); $^{13}$C-NMR (75 MHz, MeOD) ppm δ 155.70, 152.70, 137.58, 133.89, 127.26, 124.28, 114.84, 47.89, 45.30, 45.20, 34.64, 34.34, 29.71, 13.42, 12.58; MS (CI$^+$) m/z 220 (M$^{+\cdot}$, 92.36), 221 (MH$^+$, 1.89).

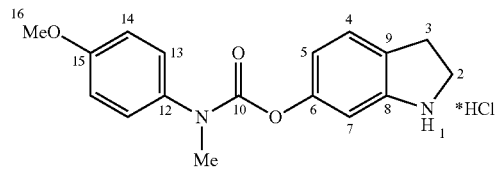

Indolin-6-yl 4-methoxyphenyl(methyl)carbamate hydrochloride, AN-858

Compound AN-858 prepared from AN-1112 by procedure E, was stirred at room temperature for 2 h, and was isolated as a colourless oil in 85% yield. $^1$H-NMR (300 MHz, D$_2$O) ppm δ 7.09-7.33 (m, 4H, H-4, H-7, H13), 6.76-6.83 (m, 3H, H-14, H-5), 3.76 ("t", J=6.3 Hz, 2H, H-2), 3.57 (s, 3H, H-15), 3.07-3.19 (m, 5H, H-3, H-11); $^{13}$C-NMR (75 MHz, D$_2$O) ppm δ 157.85, 150.07, 135.65, 133.45, 127.50, 126.75, 123.44, 114.47, 113.40, 55.39, 46.70, 38.16, 28.21; MS (CI$^+$) m/z 298.137 (M$^{+\cdot}$, 99.78), 299.144 (MH$^+$, 84.31); HRMS calcd. for $C_{17}H_{19}N_2O_3$ (MH$^+$, DCI$^+$/CH$_4$) 299.1396. found 299.1436, for $C_{17}H_{18}N_2O_3$ (M$^{+\cdot}$, DCI$^+$/CH$_4$) 298.1317. found 298.1372.

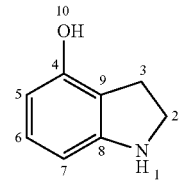

4-Hydroxyindolin, AN-1194

Compound AN-1194 prepared from 4-Hydroxyindole by procedure E, was isolated by chromatography eluted with EtOAc-hexane (1:3 to 1:2), as a white solid in 32% yield, mp 148-150° C. $^1$H-NMR (300 MHz, CDCl$_3$) ppm δ 6.90 (t, J=7.5 Hz, 1H, H-6), 6.27 (bd, J=7.5 Hz, 1H, H-7), 6.18 (bd, J=7.5 Hz, 1H, H-5), 4.34-4.11 (bs, 2H, H-1+H-10), 3.60 (bt, J=6.0 Hz, 2H, H-2), 2.96 (bt, J=6.0 Hz, 2H, H-3); $^{13}$C-NMR (75 MHz, CDCl$_3$) ppm δ 153.84, 152.94, 128.76, 113.06, 106.20, 102.70, 47.39, 26.31; MS (CI$^+$) m/z 135.064 (M$^{+\cdot}$, 100.00), 136.072 (MH$^+$, 85.83); HRMS calcd. for C$_8$H$_{10}$NO (MH$^±$, DCI$^+$/CH$_4$) 136.0762. found 136.0719, for C$_8$H$_9$NO (M$^{+\cdot}$, DCI$^+$/CH$_4$) 135.0684. found 135.0645.

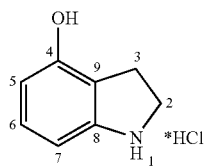

Indolin-4-ol hydrochloride, AN-855

Compound AN-855 prepared from 4-hydroxyindole or from AN-1194 by procedure E, was stirred at room temperature for 2 h, and was isolated as green solid in 60% yield, mp 168-170° C. $^1$H-NMR (300 MHz, MeOD) ppm δ 7.24 (t, J=8.3 Hz, 1H, H-6) 6.95 (d, J=8.3 Hz, 1H, H-5), 6.90 (d, J=8.3 Hz, 1H, H-7), 3.84 (t, J=9.0 Hz, 2H, H-2), 3.23 (t, J=9.0 Hz, 2H, H-3); $^{13}$C-NMR (75 MHz, MeOD) ppm δ 156.21, 138.21, 130.78, 122.80, 117.15, 110.86, 46.90, 27.37; MS (CI$^+$) m/z 136.073 (MH$^+$, 99.98), 135.066 (M$^{+\cdot}$, 85.67), 118.066 ([MH$^+$—H$_2$O], 18.51); HRMS calcd. for C$_8$H$_{10}$NO (MH$^+$, DCI$^+$/CH$_4$) 136.0762. found 136.0735, for C$_8$H$_9$NO (M$^{+\cdot}$, DCI$^+$/CH$_4$) 135.0684. found 135.0656.

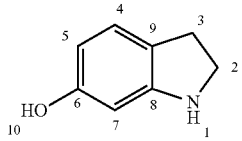

Indolin-6-ol, AN-1155.[104]

Compound AN-1155 prepared from 6-Hydroxyindole by procedure E, was stirred at room temperature for 2 h, and was isolated by chromatography eluted with EtOAc-hexane (1:2), as a colourless oil in 33% yield. $^1$H-NMR (300 MHz, CDCl$_3$) ppm δ 6.90 (d, J=7.5 Hz, 1H, H-4), 6.19 (dd, J=7.5, 1.5 Hz, 1H, H-5), 6.14 (s, 1H, H-7), 5.38 (bs, 2H, H-1, H-10), 3.45 (t, J=8.2 Hz, 2H, H-2), 2.88 (t, J=8.2 Hz, 2H, H-3); $^{13}$C-NMR (75 MHz, CDCl$_3$) ppm δ 155.92, 151.95, 125.18, 121.81, 106.81, 99.05, 47.87, 29.10; MS (CI$^+$) m/z 134.058 ([M–H]$^+$, 51.07), 135.065 (M$^{+\cdot}$, 100.00), 136.072 (MH$^+$, 43.45); HRMS calcd. for C$_8$H$_9$NO (M$^+$, DCI$^+$/CH$_4$) 135.0684. found 135.0650.

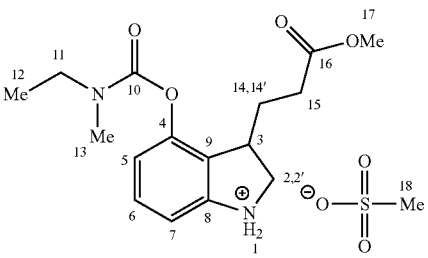

4-(Ethyl(methyl)carbamoyloxy)-3-(3-methoxy-3-oxopropyl)indolinium methanesulfonate, AN-867

Compound AN-1167 (0.037 g, 0.12 mmol) was treated with a solution of methanesulfonic acid (0.008 mL, 0.12 mmol) in dry CH$_2$Cl$_2$ (1.5 mL), to give AN-867 as a colourless oil in quantitative yield. $^1$H-NMR (300 MHz, MeOD) ppm δ 7.51 (t, J=8.2 Hz, 1H, H-6), 7.40 (d, J=8.2 Hz, 1H, H-7), 7.27 (d, J=8.2 Hz, 1H, H-5), 3.99-3.92 (m, 1H, H-2), 3.80-3.73 (m, 2H, H-2'+H-3), 3.66 (s, 3H, H-17), 3.56+3.41 (q, J=6.7 Hz, 2H, H-11), 3.15+3.01 (s, 3H, H-13), 2.74 (s, 3H, H-18), 2.43 (t, J=7.6 Hz, 2H, H-15), 2.26-2.16 (m, 1H, H-14), 1.92-1.79 (m, 1H, H-14'), 1.28+1.20 (t, J=7.6 Hz, 3H, H-12); $^{13}$C-NMR (75 MHz, MeOD) ppm δ 174.59, 154.92, 150.08, 138.42, 132.46, 131.42, 125.55, 125.40, 117.94, 51.52, 51.41, 45.48, 45.28, 41.29, 39.52, 34.69, 34.45, 31.84, 31.78, 28.72, 28.68, 13.49, 12.60; MS (CI$^+$) m/z 306.160 (M$^{+\cdot}$, 5.99), 307.162 (MH$^+$, 4.40); HRMS calcd. for C$_{13}$H$_{24}$NO$_7$ (M$^+$, DCI$^+$/CH$_4$) 306.1553. found 306.1595.

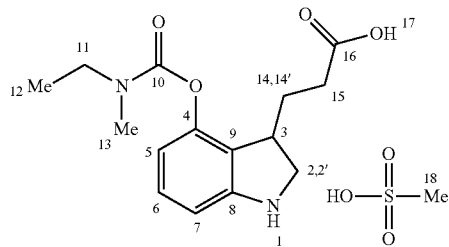

3-(4-((Ethyl(methyl)carbamoyl)oxy)indolin-3-yl) propanoic acid methanesulfonate, AN-894

Compound AN-867 was stirred with 3N HCl at room temperature for 2 d. The aqueous phase was evaporated to provide AN-894 as a yellow oil in quantitative yield. $^1$H-NMR (300 MHz, MeOD) ppm δ 7.51 (t, J=8.2 Hz, 1H, H-6), 7.40 (d, J=8.2 Hz, 1H, H-5), 7.28 (d, J=8.2 Hz, 1H, H-7), 3.96 (ABq, J=7.2 Hz, 1H, H-2), 3.77 (bs, 1H, H-3), 3.71-3.67 (m, 1H, H-2'), 3.56+3.42 (q, J=7.2 Hz, 2H, H-11), 3.15+3.01 (s, 3H, H-13), 2.71 (s, 3H, H-18), 2.46+2.42 (t, J=7.2 Hz, 2H, H-15), 2.30-2.10 (m, 1H, H-14), 1.89-1.85 (m, 1H, H-14'), 1.28+1.20 (t, J=7.2 Hz, 3H, H-12); $^{13}$C-NMR (75 MHz, MeOD) ppm δ 174.59, 154.91, 150.09, 138.38, 132.45, 131.42, 125.54, 125.39, 117.94, 51.50, 51.39, 45.49, 45.29, 41.30, 39.48, 34.71, 34.47, 32.87, 31.81, 28.76, 28.72, 13.50, 12.61; TOF MS ES$^+$ m/s 293 (MH$^+$, 23.35).

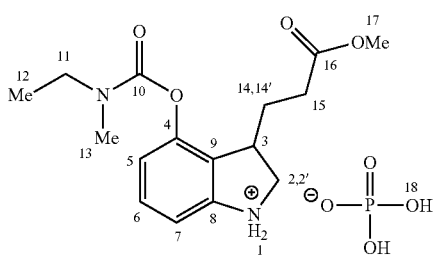 [SMILES: CCN(C)C(=O)Oc1cccc2c1C(CCC(=O)OC)C[NH2+]2 ; O=P([O-])(O)O]

4-(Ethyl(methyl)carbamoyloxy)-3-(3-methoxy-3-oxopropyl)indolinium dihydrogenphosphate, AN-869

Compound AN-1167 (0.094 g, 0.30 mmol) was stirred with a solution of phosphoric acid (0.018 mL, 0.30 mmol) in dry H$_2$O (1 mL) and a few drops of MeOH for 30 min in room temperature to give the phosphate salt AN-869 as a creamy hygroscopic solid in quantitative yield, mp 101-105° C. $^1$H-NMR (300 MHz, MeOD) ppm δ 7.14 (t, J=7.5 Hz, 1H, H-6), 6.79 (bd, J=7.5 Hz, 1H, H-5), 6.64 (dd, J=7.5, 4.5 Hz, 1H, H-7), 3.70-3.64 (m, 1H, H-2'), 3.64 (s, 3H, H-17), 3.53-3.31 (m, 4H, H-2+H-3+H-11), 3.11+2.98 (s, 3H, H-13), 2.37 (t, J=6.7 Hz, 2H, H-15), 2.13-2.01 (m, 1H, H-14), 1.88-1.75 (m, 1H, H-14'), 1.26+1.18 (t, J=6.7 Hz, 3H, H-12); $^{13}$C-NMR (75 MHz, MeOD) ppm δ 175.18, 155.57, 149.68, 130.29, 127.39, 117.32, 117.03, 111.66, 111.52, 52.35, 52.27, 52.07, 45.26, 45.14, 41.15, 34.56, 34.37, 31.96, 29.05, 13.48, 12.66; MS (CI$^+$) m/z 307.167 (MH$^+$, 71.31); HRMS calcd. for C$_{16}$H$_{23}$N$_2$O$_4$ (MH$^+$, DCI$^+$/CH$_4$) 307.1658. found 307.1668.

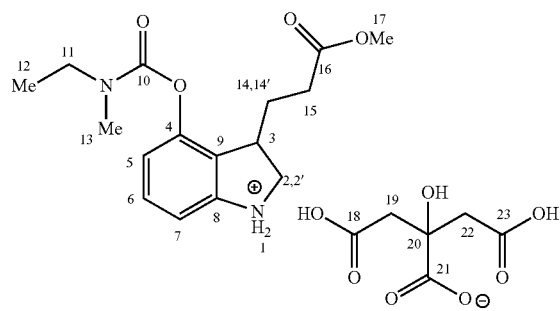 [SMILES: CCN(C)C(=O)Oc1cccc2c1C(CCC(=O)OC)C[NH2+]2 ; O=C(O)CC(O)(CC(=O)O)C(=O)[O-]]

4-(Ethyl(methyl)carbamoyloxy)-3-(3-methoxy-3-oxopropyl)indolinium citrate, AN-868

Compound AN-868 prepared from AN-1167 by procedure R, was obtained as an off-white hygroscopic foamy solid in quantitative yield. $^1$H-NMR (300 MHz, MeOD) ppm δ 7.06 (t, J=7.9 Hz, 1H, H-6), 6.26 (bd, J=7.9 Hz, 1H, H-5), 6.50 (bd, J=7.9 Hz, 1H, H-7), 3.99-3.92 (m, 1H, H-2), 3.64 (s, 3H, H-17), 3.64-3.50 (m, 2H, H-2'+H-2), 3.41-3.39 (m, 2H, H-11), 3.28-3.25 (m, 1H, H-3), 2.98+3.11 (s, 3H, H-13), 2.85 (ABq, J=14.6 Hz, 4H, H-19+H-22), 2.36 (t, J=6.7 Hz, 2H, H-15), 2.15-1.99 (m, 1H, H-14), 1.87-1.75 (m, 1H, H-14'), 1.17+1.26 (t, J=6.7 Hz, 3H, H-12); $^{13}$C-NMR (75 MHz, MeOD) ppm δ 176.98, 176.11, 175.33, 173.52, 155.75, 152.72, 149.58, 130.03, 125.97, 115.16, 114.93, 109.85, 74.10, 52.76, 52.66, 52.08, 45.20, 45.08, 43.89, 41.07, 34.55, 34.36, 32.00, 29.11, 13.50, 12.69; MS (CI$^+$) m/z 307.167 (MH$^+$, 100.00), 306.164 (M$^{·+}$, 83.72); HRMS calcd. for C$_{16}$H$_{23}$N$_2$O$_4$ (MH$^+$, DCI$^+$/CH$_4$) 307.1658. found 307.1669.

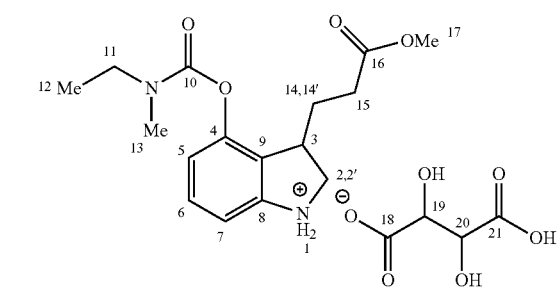 [SMILES: CCN(C)C(=O)Oc1cccc2c1C(CCC(=O)OC)C[NH2+]2 ; O=C([O-])C(O)C(O)C(=O)O]

4-(Ethyl(methyl)carbamoyloxy)-3-(3-methoxy-3-oxopropyl)indolinium tartrate, AN-881

Compound AN-881 prepared from AN-1167 by procedure R, was obtained as a yellow oil in quantitative yield. $^1$H-NMR (300 MHz, MeOD) ppm δ 7.03 (t, J=7.9 Hz, 1H, H-6), 6.56 (d, J=7.9 Hz, 1H, H-5), 6.43 (bd, J=7.9 Hz, 1H, H-7), 4.54 (s, 2H, H-19+H-20), 3.63 (s, 3H, H-17), 3.64-3.58 (m, 1H, H-2), 3.56-3.48 (m, 1H, H-11), 3.43-3.36 (m, 2H, H-11+H-2'), 3.28-3.25 (m, 1H, H-3), 3.11+2.98 (s, 3H, H-13), 2.36 (t, J=7.9 Hz, 2H, H-15), 2.09-1.98 (m, 1H, H-14), 1.87-1.75 (m, 1H, H-14'), 1.26, 1.18 (t, J=6.7 Hz, 3H, H-12); $^{13}$C-NMR (75 MHz, MeOD) ppm δ 175.42, 174.92, 155.84, 153.95, 149.63, 129.86, 125.49, 114.95, 114.14, 109.13, 73.47, 52.93, 52.83, 52.04, 45.22, 45.12, 41.13, 34.53, 34.35, 32.04, 29.22, 13.49, 12.68; MS (CI$^+$) m/z 306.163 (M$^{··±}$, 64.16), 307.171 (MH$^±$, 74.25); HRMS calcd. for C$_{16}$H$_{23}$N$_2$O$_4$ (MH$^±$, DCI$^+$/CH$_4$) 307.1658. found 307.1714, for C$_{16}$H$_{22}$N$_2$O$_4$ (M$^{·+}$, DCI$^+$/CH$_4$) 306.1580. found 306.1631.

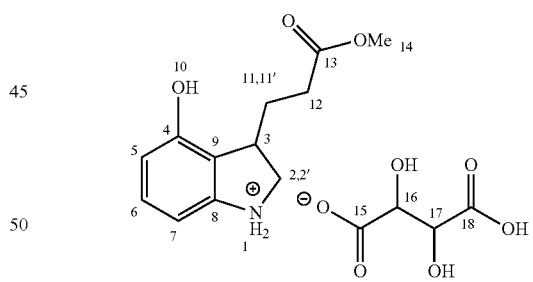

4-Hydroxy-3-(3-methoxy-3-oxopropyl)indolinium tartrate, AN-884

Compound AN-884 prepared from AN-1196 by procedure R gave the citrate salt as a colourless oil in quantitative yield. $^1$H-NMR (300 MHz, MeOD) ppm δ 6.97 (bs, 1H, H-6), 6.46-6.53 (bs, 1H, H-5), 6.42 (d, J=7.9 Hz, 1H, H-7), 4.52 (bs, 2H, H-16+H-17), 3.60-3.75 (m, 1H, H-2), 3.64 (s, 3H, H-14), 3.48 (bs, 1H, H-3), 3.30-3.35 (m, 1H, H-2'), 2.41 (bt, J=7.8 Hz, 2H, H-12), 2.10-2.20 (m, 1H, H-11), 1.83-1.95 (m, 1H, H-11'); $^{13}$C-NMR (75 MHz, MeOD) ppm δ 175.93, 175.59, 155.80, 148.87, 130.30, 121.30, 106.48, 73.69, 52.70, 52.07, 40.79, 32.52, 29.31; MS (CI$^+$) m/z 222.116

(MH⁺, 1.87); HRMS calcd. for $C_{12}H_{16}NO_3$ (MH⁺, DCI⁺/CH₄) 222.1130. found 222.1163; TOF MS (ES⁺) m/z 222 (MH⁺, 100.00), 223 (MH₂⁺, 45.21).

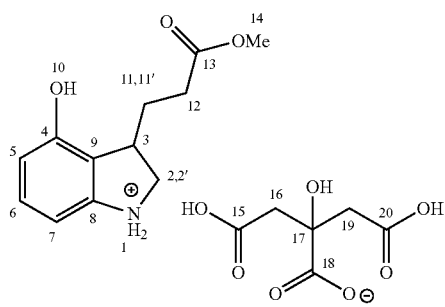 [SMILES: COC(=O)CCC1C[NH2+]c2cccc(O)c21 ; O=C(O)CC(O)(CC(=O)O)C(=O)[O-]]

4-Hydroxy-3-(3-methoxy-3-oxopropyl)indolinium citrate, AN-876

Compound AN-876 prepared from AN-1196 by procedure R gave the citrate salt as a brown oil in quantitative yield. ¹H-NMR (300 MHz, MeOD) ppm δ 6.97 (t, J=8.1 Hz, 1H, H-6), 6.45 (d, J=8.1 Hz, 1H, H-5), 6.42 (d, J=8.1 Hz, 1H, H-7), 3.65 (s, 3H, H-14), 3.65-3.62 (m, 1H, H-3), 3.51-3.47 (m, 1H, H-2), 3.33 (dd, J=9.0, 4.5 Hz, 1H, H-2'), 2.89 (ABq, J=13.5 Hz, 4H, H-16+H-19), 2.42 (t, J=9.0 Hz, 2H, H-12), 2.20-2.12 (m, 1H, H-11), 1.92-1.85 (m, 1H, H-11'); ¹³C-NMR (75 MHz, MeOD) ppm δ 177.33, 175.90, 173.7, 155.79, 130.28, 130.18, 121.09, 111.08, 106.21, 74.13, 52.74, 52.04, 43.99, 40.78, 32.49, 29.30.

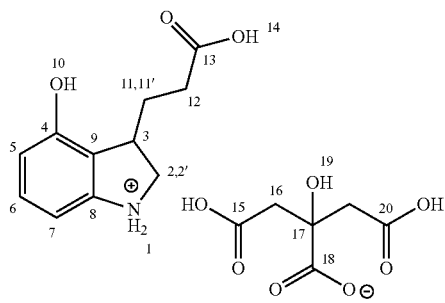 [SMILES: O=C(O)CCC1C[NH2+]c2cccc(O)c21 ; O=C(O)CC(O)(CC(=O)O)C(=O)[O-]]

3-(2-Carboxyethyl)-4-hydroxyindolinium citrate, AN-877

Compound AN-877 prepared from AN-1205 by procedure R gave the citrate salt as a yellow oil in quantitative yield. ¹H-NMR (300 MHz, MeOD) ppm δ 7.04 (t, J=7.9 Hz, 1H, H-6), 6.56 (d, J=7.9 Hz, 1H, H-7), 6.52 (d, J=7.9 Hz, 1H, H-5), 3.71 (t, J=9.0 Hz, 1H, H-2), 3.64-3.52 (m, 1H, H-3), 3.40 (dd, J=9.0, 4.5 Hz, 1H, H-2'), 2.84 (ABq, J=15.7 Hz, 4H, H-16+H-19), 2.40 (t, J=9.0 Hz, 2H, H-12), 2.23-2.16 (m, 1H, H-11), 1.92-1.84 (m, 1H, H-11'); ¹³C-NMR (75 MHz, MeOD) ppm δ 177.18, 173.68, 155.99, 146.79, 130.50, 122.29, 112.50, 107.26, 74.16, 52.56, 43.96, 40.89, 32.68, 29.36.

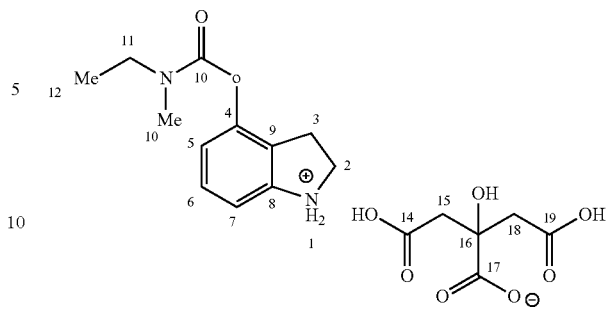

4-(Ethyl(methyl)carbamoyloxy)indolinium citrate, AN-875.

Compound AN-875 prepared from AN-1195 by procedure R gave the citrate salt as a colourless foamy oil in quantitative yield. ¹H-NMR (300 MHz, MeOD) ppm δ 7.07 (t, J=8.1 Hz, 1H, H-6), 6.70 (d, J=8.1 Hz, 1H, H-7), 6.56 (bd, J=8.1 Hz, 1H, H-5), 3.56 (t, J=7.8 Hz, 2H, H-2), 3.49+3.38 (q, J=6.8 Hz, 2H, H-11), 3.08+2.97 (s, 3H, H-13), 2.06 (t, J=7.8 Hz 2H, H-3), 2.84 (ABq, J=15.6 Hz, 4H, H-15+H-18), 1.25+1.17 (t, J=7.1 Hz, 3H, H-12); ¹³C-NMR (75 MHz, CDCl₃) ppm δ 177.14, 173.61, 155.54, 151.69, 149.44, 129.59, 124.46, 115.46, 115.36, 110.37, 74.09, 47.74, 45.12, 43.93, 34.57, 34.31, 28.01, 13.38, 12.62; MS (CI⁺) m/z 220.120 (M, 38.70), 221.129 (MH⁺, 100.00); SOLID INS. HRMS calcd. for $C_{12}H_{17}N_2O_2$ (MH⁺, DCI⁺/CH₄) 221.1290. found 221.1291; TOF MS (ES⁻) m/z 191 ([$C_6H_7O_7$]⁻, 100.00); TOF MS (ES⁺) m/z 221 (MH⁺, 99.99).

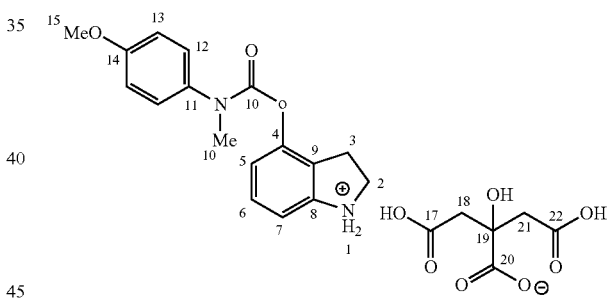

4-((4-Methoxyphenyl)(methyl)carbamoyloxy)indolinium citrate, AN-870

Compound AN-870 prepared from AN-1176 by procedure R gave the citrate salt as a white hygroscopic foamy solid in 86% yield, mp 76-80° C. ¹H-NMR (300 MHz, MeOD) ppm δ 7.30 (dd, J=9.0, 2.7 Hz, 2H, H-13), 7.03 (t, J=8.1 Hz, 1H, H-6), 6.95 (dd, J=9.0, 2.7 Hz, 2H, H-12), 6.65 (bd, J=8.1 Hz, 1H, H-5), 6.54 (bs, 1H, H-7), 3.79 (s, 3H, H-15), 3.56 (t, J=7.9 Hz, 2H, H-2), 3.32 (bs, 3H, H-16), 2.84 (ABq, J=14.6 Hz, 4H, H-18+H-21); ¹³C-NMR (75 MHz, MeOD) ppm δ 181.27, 176.93, 173.55, 159.99, 152.18, 149.51, 143.25, 137.05, 129.64, 129.54, 128.58, 115.42, 115.06, 110.15, 74.15, 55.95, 47.91, 43.88, 43.73, 43.19, 38.97, 28.12; MS (CI⁺/CH₄) m/z 298.134 (M·⁺, 100.00), 299.158 (MH⁺, 43.74); HRMS calcd. for $C_{17}H_{18}N_2O_3$ (Mᵃ, DCI⁺/CH₄) 298.1317. found 298.1340; TOF MS (ES⁺) m/z 299 (MH⁺, 100.00); TOF MS (ES⁻) m/z 191 ($C_6H_7O_7^-$, 100.00).

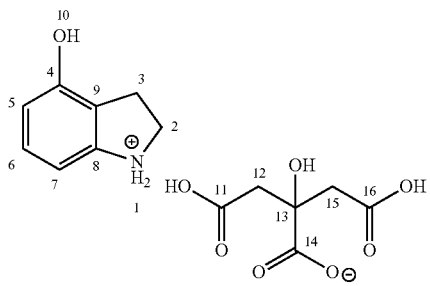 [SMILES: Oc1cccc2c1CC[NH2+]2 ; O=C(O)CC(O)(CC(=O)O)C(=O)[O-]]

4-Hydroxyindolinium citrate, AN-874

Compound AN-874 prepared from AN-1194 by procedure R gave the citrate salt as a colourless foamy oil in quantitative yield. $^1$H-NMR (300 MHz, MeOD) ppm δ 7.03 (t, J=8.1 Hz, 1H, H-6), 6.64 (d, J=7.2 Hz, 1H, H-7), 6.56 (dd, J=8.1, 0.9 Hz, 1H, H-5), 3.64 (t, J=6.7 Hz, 2H, H-2), 3.06 (t, J=6.7 Hz, 2H, H-3), 2.80 (ABq, J=15.7 Hz, 4H, H-12+H-15); $^{13}$C-NMR (75 MHz, CDCl$_3$) ppm δ 178.40, 174.32, 155.49, 145.82, 130.00, 129.90, 112.93, 107.88, 74.25, 47.38, 44.31, 27.49; MS (CI$^+$) m/z 135.066 (M$^{+\cdot}$, 69.81), 136.073 (MH$^+$, 100.00); SOLID INS. HRMS calcd. for C$_8$H$_{10}$NO (MH$^+$, DCI$^+$/CH$_4$) 136.0762. found 136.0732; TOF MS (ES$^-$) m/z 191 ([C$_6$H$_7$O$_7$]$^-$, 100.00); TOF MS (ES$^+$) m/z 136 ([C$_8$H$_{10}$NO]$^+$, 100.00).

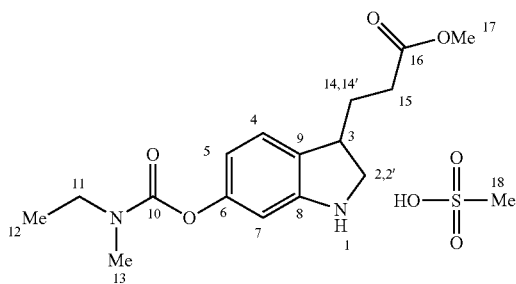

Methyl 3-(6-((ethyl(methyl)carbamoyl)oxy)indolin-3-yl)propanoate methanesulfonate, AN-680D Compound AN-1171 (23 mg, 0.07 mmol) was treated with a solution of methanesulfonic acid (5 L, 70 mol) in dry CH$_2$Cl$_2$ (1 mL) to give salt AN-680D as a brown oil in quantitative yield. $^1$H-NMR (300 MHz, MeOD) ppm δ 7.53 (d, J=8.2 Hz, 1H, H-4), 7.34 (d, J=2.2 Hz, 1H, H-7), 7.27 (dd, J=8.2, 2.2 Hz, 1H, H-5), 4.09-4.01 (m, 1H, H-2), 3.68 (s, 3H, H-17), 3.65-3.57 (m, 2H, H-2'+H-3), 3.51+3.40 (q, J=7.2 Hz, 2H, H-11), 3.10+2.98 (s, 3H, H-13), 2.69 (s, 3H, H-18), 2.52 (t, J=8.6 Hz, 2H, H-15), 2.26-2.15 (m, 1H, H-14), 1.99-1.87 (m, 1H, H-14'), 1.26+1.18 (t, J=7.2 Hz, 3H, H-12); $^{13}$C-NMR (75 MHz, MeOD) ppm δ 174.80, 153.02, 137.45, 136.86, 127.11, 125.05, 114.96, 52.71, 52.22, 45.25, 45.15, 41.81, 39.43, 34.59, 34.28, 32.05, 29.91, 13.37, 12.53; MS (CI$^+$) m/z 97.006 ([CH$_5$SO$_3$]$^+$, 100.00), 275.143 ([MH-MeOH]$^+$, 47.64), 293.144 ([MH$^+$—CH$_2$], 62.55), 307.166 (MH$^+$, 16.01); HRMS calcd. for C$_{16}$H$_{23}$N$_2$O$_4$ (MH$^+$, DCI$^+$/CH$_4$) 307.1658. found 307.1660, for C$_{15}$H$_{21}$N$_2$O$_4$ (MH$^+$—CH$_2$], DCI$^+$/CH$_4$) 293.1501. found 293.1441, for C$_{15}$H$_{19}$N$_2$O$_3$ ([MH-MeOH]$^+$, DCI$^+$/CH$_4$) 275.1396. found 275.1431.

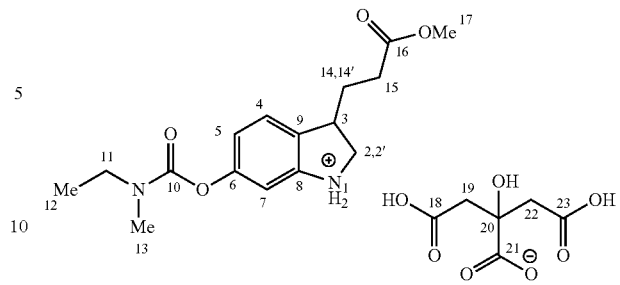

6-(Ethyl(methyl)carbamoyloxy)-3-(3-methoxy-3-oxopropyl)indolinium citrate, AN-878

Compound AN-878 prepared from AN-1171 by procedure R, was obtained as a yellow hygroscopic foamy solid in quantitative yield. $^1$H-NMR (300 MHz, MeOD) ppm δ 7.07 (dd, J=9.0, 1.1 Hz, 1H, H-4), 6.47 (bs, 1H, H-5+H-7), 3.66 (s, 3H, H-17), 3.64-3.60 (m, 1H, H-2), 3.50-3.36 (q, J=6.7 Hz, 2H, H-11), 3.27-3.18 (m, 2H, H-3+H-2'), 3.05-2.95 (bs, 3H, H-13), 2.85 (ABq, J=15.7 Hz, 4H, H-19+H-22), 2.41 ("t", J=7.9 Hz, 2H, H-15), 2.12-2.00 (m, 1H, H-14), 1.86-1.74 (m, 1H, H-14'), 1.25+1.15 (m, 3H, H-12); $^{13}$C-NMR (75 MHz, MeOD) ppm δ 177.05, 175.53, 173.55, 156.49, 152.75, 152.21, 131.52, 125.09, 113.81, 113.68, 106.11, 106.01, 74.10, 54.03, 52.13, 45.03, 43.91, 41.87, 34.50, 34.23, 32.32, 30.35, 13.40, 12.64; MS (CI$^+$) m/z 306.158 (M, 52.81), 307.163 (MH$^+$, 100.00); HRMS calcd. for C$_{16}$H$_{23}$N$_2$O$_4$ (MH$^+$, DCI$^+$/CH$_4$) 307.1658. found 307.1633.

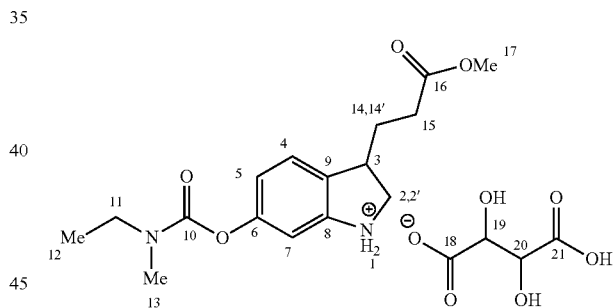

6-(Ethyl(methyl)carbamoyloxy)-3-(3-methoxy-3-oxopropyl)indolinium tartrate, AN-882

Compound AN-882 prepared from AN-1171 by procedure R, was obtained as a yellow oil in quantitative yield. $^1$H-NMR (300 MHz, MeOD) ppm δ 7.06 (d, J=9.0 Hz, 1H, H-5), 6.42 (d, J=9.0 Hz, 1H, H-4), 6.41 (s, 1H, H-7), 4.53 (s, 2H, H-19+H-20), 3.70-3.62 (m, 1H, H-2), 3.66 (s, 3H, H-17), 3.47+3.37 (q, J=7.1 Hz, 2H, H-11), 3.27-3.18 (m, 2H, H-3+H-2'), 3.06+2.96 (s, 3H, H-13), 2.41 (t, J=7.9 Hz, 2H, H-15), 2.13-2.01 (m, 1H, H-14), 1.87-1.75 (m, 1H, H-14'), 1.23+1.16 (t, J=6.7 Hz, 3H, H-12); $^{13}$C-NMR (75 MHz, MeOD) ppm δ 175.58, 174.88, 153.10, 152.83, 131.26, 125.03, 115.39, 113.26, 105.52, 73.50, 54.16, 52.08, 45.05, 41.96, 34.46, 34.20, 32.34, 30.43, 13.37, 12.61; MS (CI$^+$) m/z 306.159 (M$^{\cdot+}$, 8.70), 307.167 (MH$^+$, 10.17); HRMS calcd. for C$_{16}$H$_{23}$N$_2$O$_4$(MH$^+$, DCI$^+$/CH$_4$) 307.1658. found 307.1665.

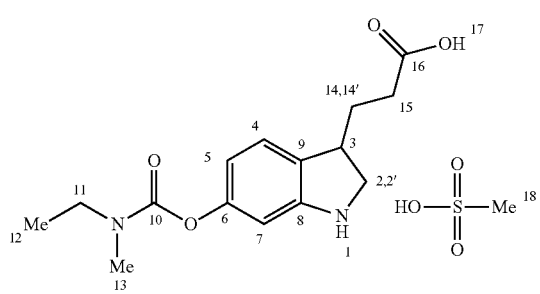

3-(6-((Ethyl(methyl)carbamoyl)oxy)indolin-3-yl) propanoic acid methanesulfonate, AN-895

Compound AN-1238 was dissolved in CH$_2$Cl$_2$ and stirred with MeSO$_3$H at room temperature for 30 min. The CH$_2$Cl$_2$ was evaporated to provide AN-895 as a yellow oil in quantitative yield. $^1$H-NMR (300 MHz, MeOD) ppm δ 7.53 (d, J=8.2 Hz, 1H, H-4), 7.34 (d, J=2.2 Hz, 1H, H-7), 7.27 (bd, J=8.2 Hz, 1H, H-5), 4.06-4.03 (m, 1H, H-2), 3.65-3.58 (m, 2H, H-3+H-2'), 3.51+3.40 (q, J=7.2 Hz, 2H, H-11), 3.10+2.98 (s, 3H, H-13), 2.71 (s, 3H, H-18), 2.48 (t, J=7.2 Hz, 2H, H-15), 2.23-2.14 (m, 1H, H-14), 1.97-1.85 (m, 1H, H-14'), 1.26+1.18 (t, J=7.2 Hz, 3H, H-12); $^{13}$C-NMR (75 MHz, MeOD) ppm δ 176.41, 155.70, 152.99, 146.90, 137.51, 137.03, 127.15, 125.06, 114.99, 52.78, 45.29, 45.20, 41.87, 39.51, 34.65, 34.33, 32.24, 30.06, 13.41, 12.57; TOF MS ES$^+$ m/s 293 (MH$^+$, 100).

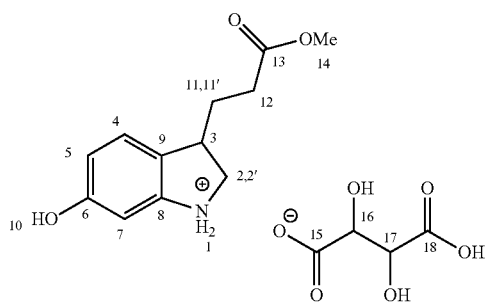 [SMILES: COC(=O)CCC1C[NH2+]c2cc(O)ccc21 ; O=C([O-])C(O)C(O)C(=O)O]

6-Hydroxy-3-(3-methoxy-3-oxopropyl)indolinium tartrate, AN-883

Compound AN-883 prepared from AN-1219 by procedure R, was obtained as a colourless oil in quantitative yield. $^1$H-NMR (300 MHz, MeOD) ppm δ 6.96 (d, J=9.0 Hz, 1H, H-4), 6.34-6.31 (m, 2H, H-5+H-7), 4.51 (s, 2H, H-16+H-17), 3.66-3.57 (m, 1H, H-2'), 3.64 (s, 3H, H-14), 3.25-3.17 (m, 2H, H-3+H-2), 2.40 (t, J=6.7 Hz, 2H, H-12), 2.08-2.01 (m, 1H, H-11), 1.83-1.76 (m, 1H, H-11'); $^{13}$C-NMR (75 MHz, MeOD) ppm δ 175.65, 175.26, 158.73, 150.33, 126.23, 125.59, 125.50, 109.47, 101.28, 73.67, 53.86, 52.11, 41.88, 32.45, 30.64; MS (CI$^+$) m/z 221.104 (M$^{*+}$, 51.81), 222.116 (MH$^+$, 100.00), 223.117 (MH$_2^+$, 38.22); HRMS calcd. for C$_{12}$H$_{16}$NO$_3$ (MH$^+$, DCI$^+$/CH$_4$) 222.1130. found 222.1162.

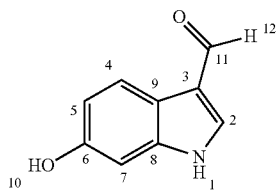

6-Hydroxy-1H-indole-3-carbaldehyde, AN-1110

Compound AN-1110 prepared from 6-Hydroxyindole by procedure C, was isolated by chromatography eluted with EtOAc-hexane (1:2) to give AN-1110 as an off-white solid in 70% yield, mp dec.>180° C. $^1$H-NMR (300 MHz, Acetone-d$_6$) ppm δ 10.87 (bs, 1H, H-1), 9.94 (s, 1H, H-12), 8.30 (bs, 1H, H-10), 8.013 (s, 1H, H-2), 8.01 (d, J=8.9 Hz, 1H, H-4), 6.96 (d, J=2.0 Hz, 1H, H-7), 6.84 (dd, J=8.6, 2.05 Hz, 1H, H-5); $^{13}$C-NMR (75 MHz, Acetone-d$_6$) ppm δ 185.03, 155.76, 139.52, 122.73, 120.25, 118.71, 113.00, 98.23; MS (CI$^+$) m/z 161.049 (M$^+$, 60.83), 162.053 (MH$^+$, 100), 134.060 ([MH$^+$—CO], 29.49); HRMS calcd. for C$_9$H$_7$NO$_2$ (M$^+$, DCI$^+$/CH$_4$) 161.0477. found 161.0486, for C$_9$H$_8$NO$_2$ 162.0555. found 162.0530; Anal. calcd. for C$_9$H$_7$NO$_2$*0.1H$_2$O (MW 162.9589): C, 66.33; H, 4.45; N, 8.60; O, 20.62. Found C, 66.208; H, 4.599; N, 8.267.

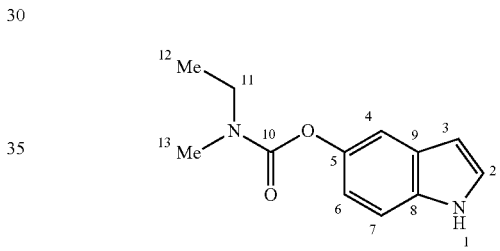

Methyl-ethyl-carbamic acid 1H-indol-5-yl ester, AN-780

Compound AN-780 was obtained from 5-Hydroxyindole and methyl-ethyl carbamoyl chloride 2a (procedure A) and purified by column chromatography (hexane/EtOAc 10:1) to provide AN-780 as a colourless solid in 80% yield. $^1$H-NMR (200 MHz, CDCl$_3$ ppm 7.4-7.3 (m, 2H, H-7, H-2), 7.15 (d, 1H, J=2.2 Hz, H-4), 6.9 (dd, 1H, J=8.5, 2.2 Hz, H-6), 6.5 (m, 1H, H-3), 3.55-3.45 (m, 2H, H-11), 3.1-3 (m, 3H, H-13), 1.3-1.1 (m, 3H, H-12); $^{13}$C-NMR (50 MHz, CDCl$_3$) ppm 155.72, 145.31, 133.57, 128.21, 128.2, 116.55, 111.66, 111.23, 102.76, 44.06, 34.17, 12.61; MS (ES$^+$) m/z 219 (MH$^+$, 100), 241 (MNa$^+$, 80).

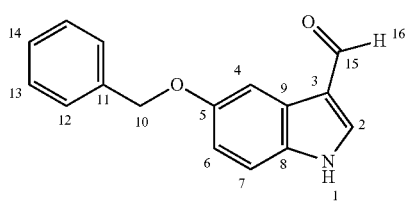 [SMILES: O=Cc1c[nH]c2ccc(OCc3ccccc3)cc12]

5-Benzyloxy-1H indol-3-carbaldehyde, AN-696

Compound AN-696 was obtained from indole 5-Benzyloxyindole (procedure C) as a yellow solid in 80% yield. $^1$H NMR (200 MHz, DMSO-$d_6$) ppm 9.9 (s, 1H, H-16), 8.2 (s, 1H, H-2), 7.7 (s, 1H, H-4), 7.5-7.2 (m, 6H, H-12+H-13+H-14+H-7), 6.95 (d, 1H, J=9.6 Hz, H-6), 5.1 (s, 2H, H-10); $^{13}$C NMR (50 MHz, DMSO-$d_6$) ppm 185.53, 154.69, 138.1, 137.44, 132.02, 128.22, 127.5, 127.41, 124.9, 118.09, 113.70, 113.0, 104.23, 69.72; MS (ES$^+$) m/z 252 (MH$^+$, 35), 274 (MNa$^+$, 80), 290 (MK$^+$, 100).

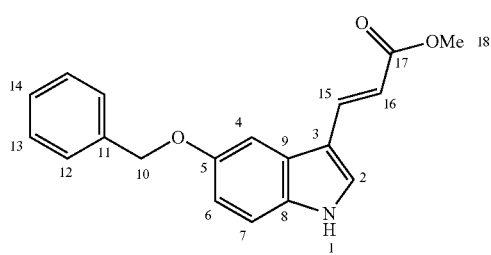 [SMILES: COC(=O)/C=C/c1c[nH]c2ccc(OCc3ccccc3)cc12]

3-(5-Benzyloxy-1H indol-3-yl)-acrylic acid methyl ester, AN-787.[128]

Compound AN-787 was obtained from AN-696 (procedure D) as a yellow-brown solid in 80% yield. $^1$H NMR (200 MHz, DMSO-$d_6$) ppm 11.7 (bs, 1H, H-1), 7.91 (s, 1H, H-2), 7.86 (d, 1H, J=16.1 Hz, H-15), 7.55-7.3 (m, 7H, H-12+H-13+H-14, H-7+H-4), 6.95 (dd, 1H, J=9.6, 1.9 Hz, H-6), 6.31 (d, 1H, J=16.1 Hz, H-16), 5.2 (s, 2H, H-10), 3.7 (s, 3H, H-18); $^{13}$C NMR (150 MHz, DMSO-$d_6$) ppm 167.82, 153.81, 139.04, 137.65, 132.33, 132.08, 127.85, 127.67, 127.65, 127.57, 125.52, 113.05, 111.51, 110.07, 103.36, 69.83, 50.9; MS (ES$^+$) m/z 308 (MH$^+$, 50), 330 (MNa$^+$, 30), 346 (MK$^+$, 20).

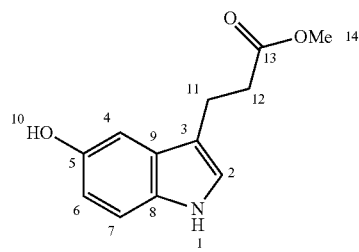 [SMILES: COC(=O)CCc1c[nH]c2ccc(O)cc12]

3-(5-Hydroxy-1H indol-3-yl)-propionic acid methyl ester, AN-788

Compound AN-788 was obtained from AN-787 (procedure F) as a yellow oil in 85% yield. $^1$H NMR (200 MHz, acetone-$d_6$) ppm 9.72 (bs, 1H, H-1), 7.18 (d, 1H, J=8.79 Hz, H-7), 7.06 (s, 1H, H-2), 6.95 (d, 1H, J=2.3 Hz, H-4), 6.7 (dd, 1H, J=8.8, 2.3 Hz, H-5), 3.62 (s, 3H, H-14), 2.95 (t, 2H, J=7.7 Hz, H-12), 2.65 (t, 2H, J=7.7 Hz, H-11); $^{13}$C NMR (50 MHz, acetone-$d_6$) ppm 173.92, 151.54, 132.56, 129.02, 126.02, 123.55, 112.49, 112.38, 103.35, 51.60, 35.40, 21.53; MS (ES$^+$): m/z 146 ([M-CH$_2$CO$_2$Me], 100), 242 (MNa$^+$, 30), 258 (MK$^+$, 10).

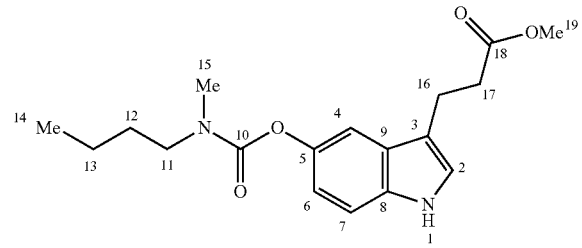 [SMILES: CCCCN(C)C(=O)Oc1ccc2[nH]cc(CCC(=O)OC)c2c1]

3-(5-(Butyl-methyl-carbamoyloxy)-1H indol-3-yl)-propionic acid methyl ester, AN-790

Compound AN-788 was carbamoylated (procedure A) with butyl-methyl carbamoyl chloride 2b and the crude mixture was chromatographed (hexane:EtOAc (4:1)) to provide pure AN-790 as yellow oil in 85% yield. $^1$H NMR (200 MHz, CDCl$_3$) ppm 8.37 (bs, 1H, H-1), 7.17 (m, 1H, H-4), 6.98 (d, 1H, J=8.6 Hz, H-7), 6.77-6.71 (m, 2H, H-6, H-2), 3.56 (s, 3H, H-19), 3.41-3.19 (m, 2H, H-11), 3.02-2.87 (m, 5H, H-17+H-15), 2.55 (t, 2H, J=7.0 Hz, H-16), 1.6-1.5 (m, 2H, H-12), 1.42-1.3 (m, 2H, H-13), 0.95-0.83 (m, 3H, H-14); $^{13}$C NMR (50 MHz, CDCl$_3$) ppm 173.73, 155.92, 144.74, 133.94, 127.27, 122.81, 116.24, 114.53, 111.41, 110.63, 51.37, 48.98, 34.67, 34.42, 30.12, 29.56, 20.55, 13.81; MS (DCI/CH$_4$) m/z 332.177 (M$^+$, 30); HRMS calcd. for C$_{18}$H$_{24}$N$_2$O$_4$ (M$^+$, DCI/CH$_4$) 332.173608. found 332.177477.

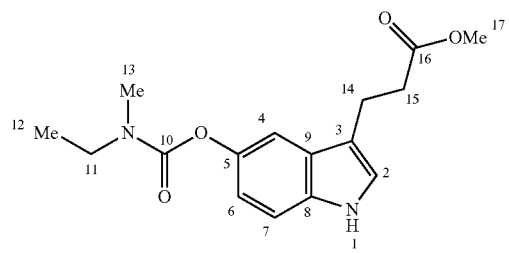

3-(5-(Ethyl-methyl-carbamoyloxy)-1H indol-3-yl)-propionic acid methyl ester, AN-789

Compound AN-788 was carbamoylated (procedure B) by ethyl-methyl carbamoyl chloride 2a and the residue was chromatographed (hexane:EtOAc 4:1) to provide AN-789 as yellow oil in 83% yield. $^1$H NMR (200 MHz, CDCl$_3$) ppm 8.3 (bs, 1H, H-1), 7.26 (s, 1H, H-4), 7.13 (d, 1H, J=8.3 Hz, H-7), 6.89-6.83 (m, 2H, H-6+H-2), 3.63 (s, 3H, H-17), 3.55-3.4 (m, 2H, H-11), 3.1-2.92 (m, 5H, H-15+H-13), 2.65 (t, 2H, J=6.6 Hz, H-14), 1.33-1.2 (m, 3H, H-12); $^{13}$C NMR (50 MHz, CDCl$_3$) ppm 173.73, 155.87, 144.86, 133.98, 127.39, 122.77, 116.45, 114.79, 111.39, 110.78, 51.437, 44.06, 34.73, 34.1, 20.61, 13.15; MS (DCI/CH$_4$) m/z 304.144 (M$^+$, 100); HRMS calcd. for C$_{16}$H$_{20}$N$_2$O$_4$ (M$^+$, DCI/CH$_4$) 304.142307. found 304.143557.

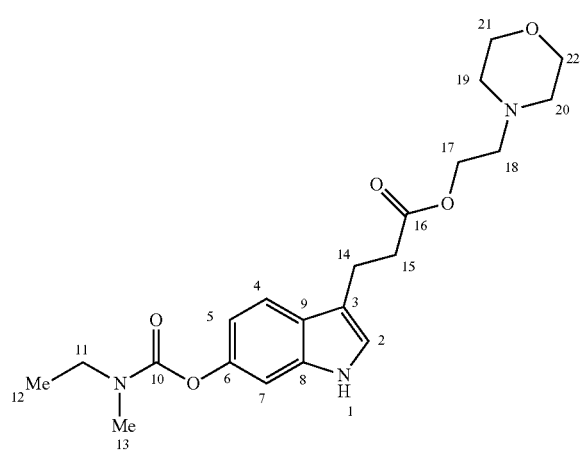 [SMILES: CCN(C)C(=O)Oc1ccc2c(CCC(=O)OCCN3CCOCC3)c[nH]c2c1]

2-Morpholinoethyl 3-(6-((ethyl(methyl)carbamoyl)
oxy)-1H-indol-3-yl)propanoate, AN-1240

A mixture of acid AN-1138 (50 mg, 0.17 mmol) in dry DMF (0.5 mL) was added N-methylmorpholine (0.057 mL, 0.51 mmol), 4-(2-Hydroxyethyl)-morpholine (0.023 mL, 0.19 mmol) and BOP (84 mg, 0.19 mmol). The mixture was stirred for 4 h at room temperature then it was diluted with EtOAc, washed with water and brine, dried over $Na_2SO_4$, evaporated, and was isolated by chromatography eluted with EtOAc-hexane (2:1 to 4:1 to EtOAc to EtOAc:MeOH (1:1)) to give the ester as a yellow oil in 80.7% yield. $^1$H-NMR (300 MHz, $CDCl_3$) ppm δ 8.63 (bs, 1H, H-1), 7.43 (d, J=7.5 Hz, 1H, H-4), 7.04 (bs, 1H, H-2), 6.81 (bd, J=7.5 Hz, 1H, H-5), 6.80 (bs, 1H, H-7), 4.16 ("t", J=2.8 Hz, 2H, H-17), 3.66-3.63 (m, 4H, H-21+H-22), 3.50-3.41 (m, 2H, H-11), 3.08+3.03 (bs, 3H, H-13), 3.01 (bs, 2H, H-14), 2.67-2.54 (m, 4H, H-15+H-18), 2.44-2.42 (m, 4H, H-19+H-20), 1.25-1.19 (m, 3H, H-12); $^{13}$C-NMR (75 MHz, $CDCl_3$) ppm δ 173.40, 155.50, 147.25, 136.31, 124.88, 122.17, 118.69, 114.31, 113.72, 104.65, 66.92, 61.58, 57.10, 53.81, 44.13, 34.99, 34.35, 33.89, 20.70, 13.31, 12.61; MS (CI$^+$) m/z 404.217 (MH$^+$, 0.25); HRMS calcd. for $C_{21}H_{30}N_3O_5$ (MH$^+$, DCI$^+$/$CH_4$) 404.2185. found 404.2167.

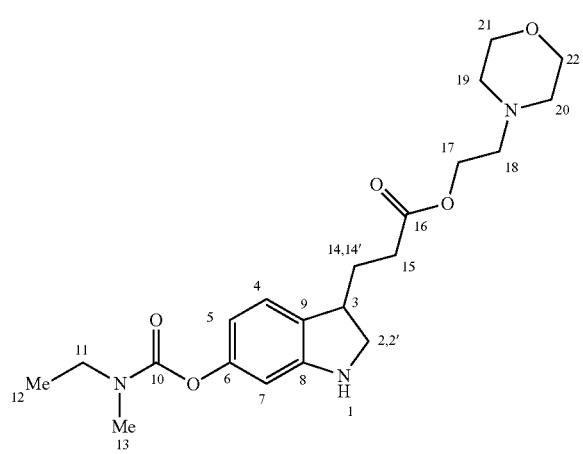 [SMILES: CCN(C)C(=O)Oc1ccc2c(c1)NCC2CCC(=O)OCCN1CCOCC1]

2-Morpholinoethyl 3-(6-((ethyl(methyl)carbamoyl)
oxy)indolin-3-yl)propanoate, AN-1242

Compound AN-1242 was prepared from AN-1240 according to procedure E, Method I (stirred at room temperature for 1 h), and was isolated by chromatography eluted with EtOAc:MeOH (10:0.5 to 10:1), as a yellow oil in 58.7% yield; $^1$H-NMR (300 MHz, $CDCl_3$) ppm δ 7.00 (d, J=7.8 Hz, 1H, H-4), 6.40 (d, J=7.8 Hz, 1H, H-5), 6.37 (bs, 1H, H-7), 4.20 (t, J=6.0 Hz, 2H, H-17), 3.70-3.67 (m, 5H, H-2+H-21+H-22), 3.45-3.36 (m, 2H, H-11), 3.29-3.19 (m, 2H, H-2'+H-3), 3.02+2.96 (bs, 3H, H-13), 2.61 (t, J=6.0 Hz, 2H, H-18), 2.51 (m, 4H, H-19+H-20), 2.38 (t, J=15.0 Hz, 2H, H-15), 2.11-2.04 (m, 1H, H-14), 1.88-1.82 (m, 1H, H-14'), 1.24-1.14 (m, 3H, H-12); $^{13}$C-NMR (75 MHz, $CDCl_3$) ppm δ 173.39, 154.80, 152.44, 151.71, 128.78, 124.13, 111.46, 103.67, 66.92, 61.39, 57.21, 53.65, 52.32, 44.09, 40.64, 33.80, 34.30, 31.84, 29.28, 13.25.

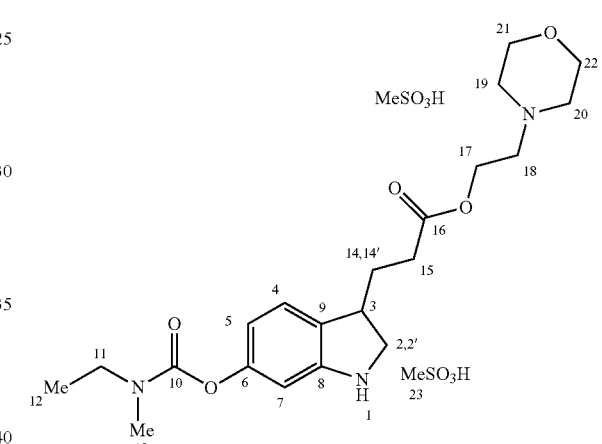

2-Morpholinoethyl 3-(6-((ethyl(methyl)carbamoyl)
oxy)indolin-3-yl)propanoate di-methanesulfonic
acid, AN-896

Compound AN-1242 (1 eq) was treated with a solution of methanesulfonic acid (1 eq) in dry $CH_2Cl_2$ to give AN-896 as a yellow oil in quantitative yield. $^1$H-NMR (300 MHz, MeOD) ppm δ 7.54 (d, J=8.1 Hz, 1H, H-4), 7.33 (d, J=2.1 Hz, 1H, H-7), 7.27 (bd, J=8.1 Hz, 1H, H-5), 4.47 ("t", J=5.1 Hz, 2H, H-17), 4.09-4.03+3.78-3.92 (m, 5H, H-2+H-21+H-22), 3.74-3.61 (m, 2H, H-2+H-3), 3.55-3.50 (m, 5H, H-19+H-20+H-12), 3.41 (q, J=7.8 Hz, 1H, H-12), 3.20-3.30 (m, 2H, H-18), 3.11+2.99 (s, 3H, H-13), 2.70 (s, 6H, H-23), 2.63 (t, J=7.8 Hz, 2H, H-15), 2.30-2.14 (m, 1H, H-14), 2.07-1.88 (m, 1H, H-14'), 1.26+1.19 (t, J=6.9 Hz, 3H, H-12); $^{13}$C-NMR (75 MHz, $CDCl_3$) ppm δ 173.78, 153.19, 137.95, 136.72, 127.21, 124.90, 114.74, 64.89, 59.00, 57.06, 53.61, 52.83, 45.34, 45.23, 41.88, 39.55, 34.64, 34.32, 31.96, 29.64, 13.41, 12.57; MS (CI$^+$) m/z 406.234 (MH$^+$, 23.16); HRMS calcd. for $C_{21}H_{32}N_3O_5$ (MH$^+$, DCI$^+$/$CH_4$) 406.2342. found 406.2337.

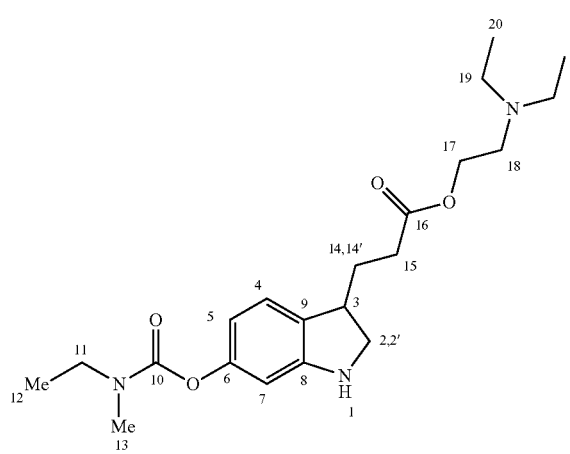 [SMILES: CCN(CC)CCOC(=O)CCC1CNc2cc(OC(=O)N(C)CC)ccc21]

2-(Diethylamino)ethyl 3-(6-((ethyl(methyl)carbamoyl)oxy)indolin-3-yl)propanoate, AN-1241

Compound AN-1241 was prepared from AN-1213 according to procedure E, Method I (stirred at room temperature for 1 h), and was isolated by chromatography eluted with EtOAc:MeOH (10:2), as a colourless oil; $^1$H-NMR (300 MHz, CDCl$_3$) ppm δ 7.01 (bd, J=7.5 Hz, 1H, H-4), 6.41 (bd, J=7.5 Hz, 1H, H-5), 6.38 (bs, 1H, H-7), 4.16 ("t", J=6.0 Hz, 2H, H-17), 3.69-3.68 (m, 1H, H-2), 3.40-3.18 (m, 4H, H-2'+H-3+H-12), 3.02+2.96 (s, 3H, H-13), 2.74 (t, J=6.0 Hz, 2H, H-18), 2.63 (q, J=8.0 Hz, 4H, H-19), 2.38 (t, J=8.0 Hz, 2H, H-15), 2.01-1.78 (m, 2H, H-14+H-14'), 1.24-1.17 (m, 3H, H-12), 1.04 (t, J=8.0 Hz, 6H, H-20); $^{13}$C-NMR (125 MHz, CDCl$_3$) ppm δ 173.35, 154.86, 154.69, 152.33, 151.64, 128.75, 124.07, 111.40, 103.57, 58.67, 53.56, 50.95, 47.57, 44.01, 40.65, 34.20, 33.76, 31.78, 29.16, 13.17, 12.46, 11.54; MS (CI$^+$) m/z 391.247 (M$^+$, 14.27), 392.256 (MH$^+$, 21.71); HRMS calcd. for C$_{21}$H$_{34}$N$_3$O$_4$ (MH$^+$, DCI$^+$/CH$_4$) 392.2549. found 392.2557.

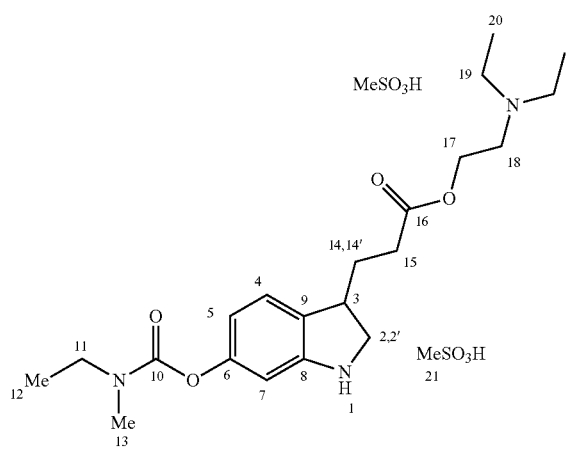 [SMILES: "MeSO3H" ; "MeSO3H" ; CCN(CC)CCOC(=O)CCC1CNc2cc(OC(=O)N(C)CC)ccc21]

2-(diethylamino)ethyl 3-(6-((ethyl(methyl)carbamoyl)oxy)indolin-3-yl) propanoate, di-methanesulfonic acid, AN-897

Compound AN-1241 (1 eq) was treated with a solution of methanesulfonic acid (1 eq) in dry CH$_2$Cl$_2$ to give AN-897 as a green oil in quantitative yield. $^1$H-NMR (300 MHz, MeOD) ppm δ 7.54 (d, J=8.2 Hz, 1H, H-4), 7.34 (d, J=2.2 Hz, 1H, H-7), 7.26 (dd, J=8.2, 2.2 Hz, 1H, H-5), 4.43 ("t", J=5.2 Hz, 2H, H-17), 4.11-4.03 (m, 1H, H-2), 3.72-3.61 (m, 2H, H-2'+H-3), 3.54-3.47 (m, 3H, H-18+H-11), 3.43 (q, J=7.0 Hz, 1H, H-11), 3.237-3.33 (m, 4H, H-19), 3.11+2.99 (s, 3H, H-13), 2.70 (s, 6H, H-21), 2.62 (t, J=7.0 Hz, 2H, H-15), 2.30-2.18 (m, 1H, H-14), 2.04-1.92 (m, 1H, H-14'), 1.35 (t, J=7.0 Hz, 6H, H-20), 1.27+1.19 (t, J=7.0 Hz, 3H, H-12); $^{13}$C-NMR (75 MHz, MeOD) ppm δ 173.73, 153.11, 137.76, 136.82, 127.17, 124.90, 114.87, 59.63, 52.74, 51.72, 49.18, 45.31, 45.22, 41.83, 39.56, 34.64, 34.32, 31.98, 29.63, 13.42, 12.57, 9.02; TOF MS (ES+) m/z 392 (MH$^+$, 92.34).

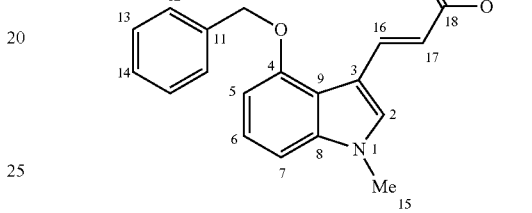

(E)-Methyl 3-(4-(benzyloxy)-1-methyl-1H-indol-3-yl)acrylate, AN-831

Compound AN-831 was prepared from AN-830 according to procedure G. The product was purified by chromatography (hexane:EtOAc 3:1) to give a yellow solid (yield 76%), mp 122-125° C.; $^1$H-NMR (300 MHz, acetone-d$_6$) ppm 8.48 (d, J=16 Hz, 1H, H-16), 7.77 (s, 1H, H-2), 7.61 (dm, J=7.5 Hz, 2H, H-13), 7.47-7.35 (m, 3H, H-12+H-14), 7.15 (t, J=8 Hz, 1H, H-6), 7.04 (d, J=8 Hz, 1H, H-7), 6.78 (d, J=8 Hz, 1H, H-5), 6.33 (d, J=16 Hz, 1H, H-17), 5.28 (s, 2H, H-10), 3.82 (s, 3H, H-15), 3.67 (s, 3H, H-19); $^{13}$C-NMR (75 MHz, acetone-d$_6$) ppm 168.41, 154.51, 140.29, 140.16, 138.32, 129.87, 129.33, 128.44, 128.17, 124.05, 117.64, 112.75, 112.59, 104.54, 103.58, 70.59, 51.14, 33.58; MS (CI+) m/z 322.141 (MH$^+$, 66.88), 321.135 (M$^+$, 99.99), 171.069 (C$_{11}$H$_{10}$NO$^+$, 78.85), 91.061 (C$_7$H$_7^+$, 35.50); HRMS calcd. for C$_{20}$H$_{19}$NO$_3$$^{+\cdot}$ (M$^{+\cdot}$) 321.1365. found 321.1352.

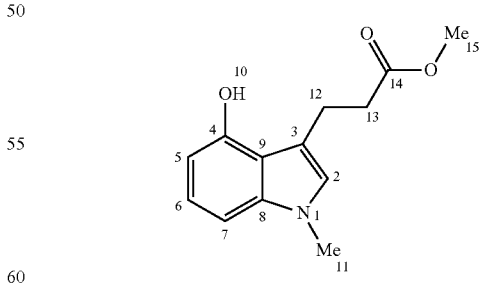

Methyl 3-(4-hydroxy-1-methyl-1H-indol-3-yl)propanoate, AN-844

Compound AN-844 was prepared from AN-831 according to procedure F. The product was purified by chromatography (hexane:EtOAc 5:1) to give a bright yellow solid (yield 54%), mp 123-124° C.; $^1$H-NMR (300 MHz, acetone-$d_6$) ppm 8.46 (broad 1H, H-10), 6.96 (t, J=8 Hz, 1H, H-6), 6.80 (dd, J=8, 0.5 Hz, 1H, H-7), 6.79 (s, 1H, H-2), 6.48 (dd, J=8, 0.5 Hz, 1H, H-5), 3.63 (s, 3H, H-15), 3.62 (s, 3H, H-11), 3.21 ("t", J=7.5 Hz, 2H, H-12), 2.77 ("t", J=7.5 Hz, 2H, H-13); $^{13}$C-NMR (75 MHz, acetone-$d_6$) ppm 174.24, 152.52, 140.49, 125.93, 123.07, 117.81, 114.31, 104.11, 102.19, 51.42, 36.78, 32.67, 23.02.

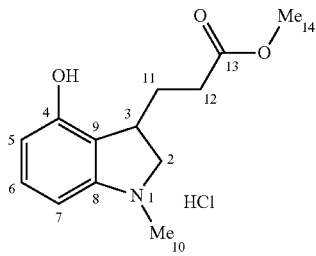 [SMILES: COC(=O)CCC1CN(C)c2cccc(O)c21 ; Cl]

Methyl 3-(4-hydroxy-1-methylindolin-3-yl)propanoate hydrochloride, AN-833

Compound AN-833 was prepared from AN-844 according to procedure E, Method I. The crude was a mixture of the methyl ester and the acid. Thus, it was dissolved in MeOH and few drops of concentrated HCl were added. The mixture was stirred over night. The solution was evaporated to give an oil (yield 69%); $^1$H-NMR (300 MHz, CD$_3$OD) ppm 7.34 (t, J=8 Hz 1H, H-6), 7.05 (d, J=8 Hz, 1H, H-7), 6.94 (d, J=8 Hz, 1H, H-5), 3.97-3.91 (bm, 1H, H-2), 3.84-3.81+3.60 (m, 2H, H-2+H-3), 3.67 (s, 3H, H-14), 3.26 (s, 3H, H-10), 2.51 ("t", J=7.5 Hz, 2H, H-12), 2.40-2.29+2.00-1.88 (m, 2H, H-11); $^{13}$C-NMR (75 MHz, CD$_3$OD) ppm 175.11, 156.62, 143.14, 131.74, 125.04, 118.05, 109.90, 62.76, 52.18, 43.31, 39.79, 32.48, 28.68.

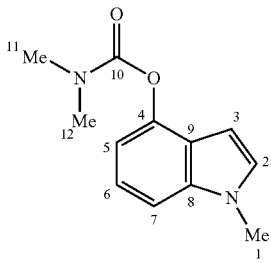 [SMILES: CN(C)C(=O)Oc1cccc2c1ccn2C]

Dimethyl carbamic acid 1-methyl-1H indol-4-yl ester, AN-618

Compound AN-618 was obtained from indole 3 (procedure G) as a colourless solid in 60% yield; $^1$H NMR (200 MHz, CDCl$_3$) ppm 7.3-7.12 (m, 2H, H-7+H-2), 7.15 (m, 1H, H-6), 6.9-6.86 (m, 1H, H-5), 6.4 (d, 1H, J=3.14 Hz, H-3), 3.174 (s, 3H, H-1), 3.17+3.03 (s, 6H, H-11+H-12); $^{13}$C NMR (50 MHz, CDCl$_3$) ppm 154.92, 144.61, 138.69, 128.70, 122.13, 121.76, 111.63, 106.60, 97.83, 36.78, 36.77, 30; MS (ES$^+$): m/z 219 (MH$^+$, 60), 241 (MNa$^+$, 100), 257 (MH$^+$, 20).

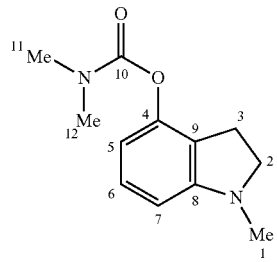 [SMILES: CN(C)C(=O)Oc1cccc2c1CCN2C]

Dimethyl-carbamic acid 1-methyl-2,3-dihydro-1H-indol-4-yl ester, AN-619

Compound AN-619 was obtained from compound AN-618 (procedure E, method I) as colourless oil in 80% yield; $^1$H NMR (200 MHz) CDCl$_3$, ppm 7.06 (t, 1H, J=7.89 Hz, H-6), 6.45 (d, 1H, J=7.89 Hz, H-5), 6.3 (d, 1H, J=7.89 Hz, H-7), 3.37 (t, 2H, J=7.81 Hz, H-2), 3.06+3.00 (s, 6H, H-11+H-12), 2.87 (t, 2H, J=7.81 Hz, H-3), 2.75 (s, 3H, H-1); $^{13}$C NMR (75 MHz, CDCl$_3$) ppm 155.17, 154.37, 147.91, 128.47, 121.77, 111.41, 104.32, 55.94, 36.69, 36.47, 36.17, 25.98; MS (ES$^+$): m/z 221 (MH$^+$, 100).

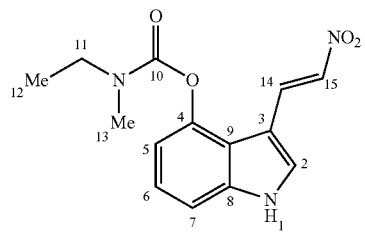 [SMILES: CCN(C)C(=O)Oc1cccc2[nH]cc(/C=C/[N+](=O)[O-])c12]

(E)-3-(2-Nitrovinyl)-1H-indol-4-yl ethyl(methyl) carbamate, AN-1199

Compound AN-1199 was prepared from AN-653 by procedure S. The residue was isolated by chromatography eluted with EtOAc-hexane (1:2), as an orange solid in 70% yield, mp 171-174° C. $^1$H-NMR (300 MHz, CDCl$_3$) ppm δ 9.54 (bs, 1H, H-1), 8.23 (d, J=13.5 Hz, 1H, H-15), 7.47+7.50 (d, J=13.5 Hz, 1H, H-14), 7.09 (t, J=6.7 Hz, 1H, H-6), 6.96-6.87 (m, 4H, H-2+H-5+H-7), 3.73+3.51 (q, J=6.7 Hz, 2H, H-11), 3.33+3.11 (s, 3H, H-13), 1.41+1.26 (t, J=6.7 Hz, 3H, H-12); $^{13}$C-NMR (75 MHz, CDCl$_3$) ppm δ 155.35, 155.62, 144.66, 144.45, 139.00, 137.94, 137.86, 129.71, 125.28, 124.39, 123.56, 115.88, 115.65, 113.06, 112.85, 110.53, 110.40, 109.95, 109.88, 106.86, 44.97, 44.72, 44.17, 34.72, 33.65, 13.87, 12.20; MS (CI$^+$) m/z 290.113 (MH$^+$, 78.07); SOLID INS. HRMS calcd. for C$_{14}$H$_{16}$N$_3$O$_4$(MH$^+$, DCI$^+$/CH$_4$) 290.1141. found 290.1127.

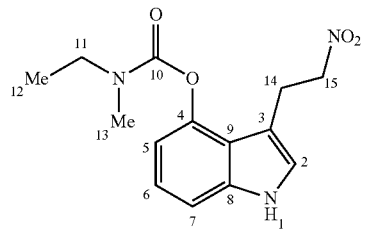 [SMILES: CCN(C)C(=O)Oc1cccc2[nH]cc(CC[N+](=O)[O-])c12]

3-(2-Nitroethyl)-1H-indol-4-yl ethyl(methyl)carbamate, AN-1215

Compound AN-1215, prepared from AN-1199 by procedure U, was isolated by chromatography eluted with EtOAc-hexane (1:3 to 1:1), as a yellow oil in 66% yield. $^1$H-NMR (300 MHz, CDCl$_3$) ppm δ 8.52 (bs, 1H, H-1), 7.10-7.00 (m, 2H, H-5+H-2), 6.78 (bt, J=6.9 Hz, 1H, H-6), 6.64 (bs, 1H, H-7), 4.57 (t, J=6.9 Hz, 2H, H-15), 3.58+3.47 (q, J=6.9 Hz, 2H, H-11), 3.40 (bt, J=6.9 Hz, 2H, H-14), 3.17+3.05 (s, 3H, H-13), 1.30+1.23 (bt, J=6.9 Hz, 3H, H-12); $^{13}$C-NMR (75 MHz, CDCl$_3$) ppm δ 155.42, 155.20, 144.60, 144.43, 138.64, 123.72, 122.31, 119.87, 112.84, 112.66, 109.38, 109.38, 107.83, 107.73, 72.42, 44.38, 44.15, 34.33, 33.96, 25.07, 24.98, 13.37, 12.51; MS (CI$^+$) m/z 291.137 (M$^{+\cdot}$, 14.37), 292.136 (MH$^+$, 18.27), 245.143 ([M$^{+\cdot}$-NO$_2$], 30.19); HRMS calcd. for C$_{15}$H$_{20}$N$_2$O$_4$ (MH$^+$, DCI$^+$/CH$_4$) 292.1423. found 292.136.

3-(2-Nitroethyl)indolin-4-yl ethyl(methyl)carbamate, AN-1216

Compound AN-1216, prepared from AN-1215 by procedure E, Method II, was isolated by chromatography eluted with EtOAc-hexane (1:2), as a yellow oil in 73% yield. $^1$H-NMR (300 MHz, CDCl$_3$) ppm δ 7.04 (t, J=7.8 Hz, 1H, H-6), 7.46 (d, J=7.8 Hz, 1H, H-7), 6.45 (bd, J=7.8 Hz, 1H, H-5), 4.49-4.33 (m, 2H, H-15), 3.85 (bs, 1H, H-1), 3.70 (t, J=9.0 Hz, 1H, H-2), 3.52-3.45 (m, 1H, H-3), 3.41+3.48 (q, J=7.2 Hz, 2H, H-11), 3.27 (t, J=9.0 Hz, 1H, H-2'), 3.07+2.99 (s, 3H, H-13), 2.44-2.18 (m, 2H, H-14+H-14'), 1.27-1.17 (m, 3H, H-12); $^{13}$C-NMR (175 MHz, CDCl$_3$) ppm δ 154.00, 153.80, 152.99, 148.53, 148.50, 129.46, 129.42, 121.74, 112.72, 112.60, 106.75, 73.15, 73.10, 52.47, 52.35, 44.18, 44.04, 37.22, 34.23, 33.78, 30.61, 13.20, 12.40; MS (CI$^+$) m/z 293.138 (M$^{+\cdot}$, 13.10), 294.145 (MH$^+$, 57.11); HRMS calcd. for C$_{14}$H$_{20}$N$_3$O$_4$ (MH$^+$, DCI$^+$/CH$_4$) 294.1454. found 294.1448.

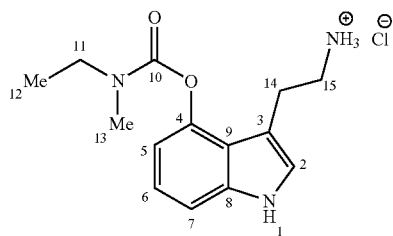 [SMILES: CCN(C)C(=O)Oc1cccc2[nH]cc(CC[NH3+])c12 ; [Cl-]]

2-(4-((ethyl(methyl)carbamoyl)oxy)-1H-indol-3-yl) ethanaminium hydrochloride, AN-886

To a solution of nitroethane AN-1215 (0.05 g, 0.17 mmol) in MeOH (5 mL) was added 10% PdC (10% ww), and the mixture was stirred under 1-1.5 atm of H$_2$ for 24 h at room temperature. The mixture was filtered through celite and was concentrated to give the amine, which was dissolved in EtOAc and extracted with 1N HCl, separation of the layers and evaporation of the aqueous gave the amine hydrochloric. The residue was crystallized from MeOH and ether, mp dec.>190° C. $^1$H-NMR (300 MHz, MeOD) ppm δ 7.27 (dd, J=8.1, 0.7 Hz, 1H, H-7), 7.16 (bs, 1H, H-2), 7.11 (t, J=8.2 Hz, 1H, H-6), 6.71+6.68 (d, J=7.4 Hz, 1H, H-5), 3.58+3.45 (q, J=8.4 Hz, 2H, H-11), 3.23 (t, J=6.3 Hz, 2H, H-15), 3.21+3.03 (s, 3H, H-13), 3.11 (t, J=6.3 Hz, 2H, H-14), 1.33+1.21 (t, J=6.3 Hz, 3H, H-12); $^{13}$C-NMR (75 MHz, CDCl$_3$) ppm δ 157.15, 156.97, 145.92, 145.75, 140.83, 125.50, 125.43, 123.00, 121.21, 113.31, 113.07, 110.46, 108.99, 45.36, 45.25, 41.34, 41.27, 34.59, 34.53, 25.69, 13.68, 12.75; MS (CI$^+$) m/z 262.156 (MH$^+$, 70.60), 245.132 ([MH$^+$—NH$_3$], 100.00); HRMS calcd. for C$_{14}$H$_{20}$N$_3$O$_2$ (MH$^+$, DCI$^+$/CH$_4$) 262.1556. found 292.1563.

3-(2-aminoethyl)indolin-4-yl ethyl(methyl)carbamate, AN-1217

Compound AN-1217, prepared from AN-1216 by procedure F, Method II, was isolated by chromatography eluted with CHCl$_3$-MeOH (10:1), as a colourless oil in 36% yield. $^1$H-NMR (300 MHz, CDCl$_3$) ppm δ 6.95 (t, J=7.8 Hz, 1H, H-6), 6.40 (bd, J=7.8 Hz, 1H, H-5), 6.39 (d, J=7.8 Hz, 1H, H-7), 3.57 (t, J=8.8 Hz, 1H, H-2), 3.41-3.35 (m, 3H, H-11+H-3), 3.22 (bm, 1H, H-2'), 3.01+2.94 (s, 3H, H-13), 2.88 (t, J=7.3 Hz, 2H, H-15), 2.02-1.87 (m, 1H, H-14), 1.78-1.67 (m, 1H, H-14'), 1.19-1.12 (m, 3H, H-12); $^{13}$C-NMR (75 MHz, CDCl$_3$) ppm δ 154.21, 153.98, 153.27, 148.41, 128.70, 129.65, 112.36, 106.67, 52.69, 52.58, 51.46, 44.05, 38.35, 34.22, 33.82, 30.45, 13.24, 12.50; MS (co m/z 263.163 (M$^{+\cdot}$, 1.71), 264.171 (WE, 3.21); HRMS calcd. for C$_{14}$H$_{22}$N$_3$O$_2$ (MH$^+$, DCI$^+$/CH$_4$) 264.1712. found 264.1706.

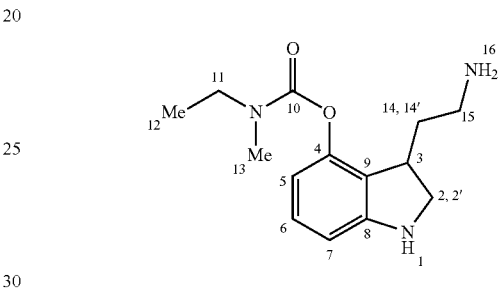

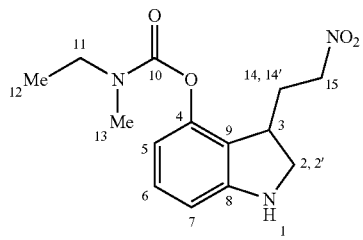 [SMILES: CCN(C)C(=O)Oc1cccc2c1C(CC[N+](=O)[O-])CN2]

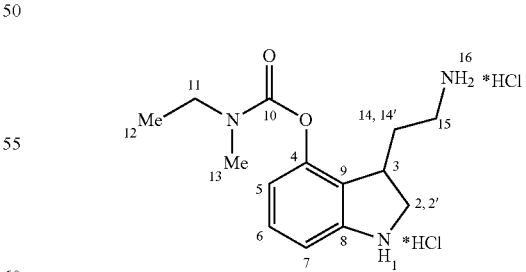

3-(2-Aminoethyl)indolin-4-yl ethyl(methyl)carbamate dihydrochloride, AN-890

Compound AN-890 was prepared from AN-1217 by procedure F, Method II. The amine was converted to HCl salt after work-up with 2N HCl and evaporation of the aqueous phase at high vacuum to give AN-890 as an off-white solid in quantitative yield. $^1$H-NMR (300 MHz, MeOD) ppm δ 7.54 (t, J=8.1 Hz, 1H, H-6), 7.42 (d, J=8.1 Hz, 1H, H-7), 7.30+7.28 (d, J=8.1 Hz, 1H, H-5), 4.05-3.95 (m, 1H, H-2'), 3.88-3.73 (m, 2H, H-2+H-3), 3.65-3.40 (m, 2H, H-11), 3.17+3.02 (s, 3H, H-13), 3.10-3.00 (m, 2H, H-15), 2.22 (bs, 1H, H-14), 2.02 (m, 1H, H-14'), 1.30+1.22 (t, J=6.9 Hz, 3H, H-12); $^{13}$C-NMR (75 MHz, MeOD) ppm δ 153.25, 153.12, 148.36, 136.62, 130.03, 129.69, 123.70, 116.23, 49.71, 43.82, 43.75, 37.71, 37.65, 36.87, 33.09, 32.98, 30.14, 11.92, 10.93; MS (CI$^+$) m/z 263.163 (M$^+$·, 1.52), 264.171 (MH$^+$, 22.59); HRMS calcd. for $C_{14}H_{22}N_3O_2$ (MH$^+$, DCI$^+$/CH$_4$) 264.1712. found 264.1706.

85-88° C.; $^1$H-NMR (600 MHz, acetone-d$_6$) ppm 9.91+9.93 (s, 1H, H-15), 8.02 (s, 1H, H-2), 7.36 (d, J=8 Hz, 1H, H-7), 7.28 (t, J=8 Hz, 1H, H-6), 6.97 (d, J=8 Hz, 1H, H-5), 3.92 (s, 3H, H-14), 3.63+3.38 (q, J=7 Hz, 2H, H-11), 3.20+2.96 (s, 3H, H-13), 1.31+1.17 (t, J=7 Hz, 3H, H-12); $^{13}$C-NMR (125 MHz, acetone-d$_6$) ppm 183.45, 183.37, 155.12, 155.02, 146.51, 140.91, 140.88, 140.11, 139.53, 124.17, 120.44, 120.35, 118.33, 118.25, 116.8, 116.66, 108.71, 44.62, 34.28, 33.99, 13.50, 12.61; MS (CI+) m/z 289.153 ([M+C$_2$H$_5$]$^±$, 42.71), 261.124 (MH$^+$, 100), 233.041 ([MH$^+$—CO], 42.96), 174.055 ($C_{10}H_8NO_2$·$^±$, 86.06), 147.069 ($C_9H_9NO^+$, 23.93), 86.056 ($C_4H_8NO^+$, 62.98); HRMS calcd. for $C_{14}H_{17}N_2O_3^+$ (MH$^+$) 261.1239. found 261.1235; Anal. Calcd. for $C_{14}H_{16}N_2O_3$ (260.2884 g/mol): C, 64.6; H, 6.20; N, 10.76. Found C, 64.271; H, 6.459; N, 10.30.

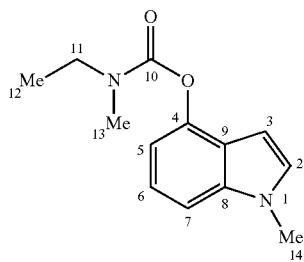 [SMILES: CCN(C)C(=O)Oc1cccc2c1ccn2C]

1-Methyl-1H-indol-4-yl ethylmethylcarbamate, AN-652

Compound AN-652 was prepared from AN-651 according to procedure G. The product was purified by chromatography (hexane:EtOAc 2:1) to give a white solid (yield 83.%), mp 42-45° C.; $^1$H-NMR (300 MHz, acetone-d$_6$) ppm 7.23 (d, J=8 Hz, 1H, H-7), 7.17 (d, J=3 Hz, 1H, H-2), 7.15 (t, J=8 Hz, 1H, H-6), 6.87 (dd, J=8 Hz, 1H, H-5), 6.38 (dd, J=3 Hz, 1H, H-3), 3.78 (s, 3H, H-14), 3.57+3.41 (bq, J=6.5 Hz, 2H, H-11), 3.17+2.99 (s, 3H, H-13), 1.31+1.19 (bt, J=6.5 Hz, 3H, H-12); $^{13}$C-NMR (75 MHz, acetone-d$_6$) ppm 154.63, 145.66, 139.50, 129.82, 123.17, 122.02, 112.29, 107.35, 98.27, 44.58, 34.34, 34.21, 33.06, 13.57, 12.72; MS (CI+) m/z 233.129 (MH$^+$, 79.61), 232.121 (M$^+$, 44.44), 86.069 ($C_4H_8NO^+$, 100); HRMS calcd. for $C_{13}H_{17}N_2O_2^+$ (MH$^+$) 233.129. found 233.1289. Anal. Calcd. for $C_{13}H_{16}N_2O_2$ (232.2783 g/mol): C, 67.22; H, 6.94; N, 12.06. Found C, 67.232; H, 7.238; N, 11.682.

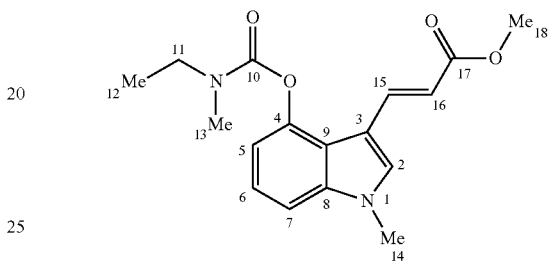

3-((E)-2-(Methoxycarbonyl)vinyl)-1-methyl-1H-indol-4-yl ethylmethylcarbamate, AN-804

Compound AN-804 was prepared from AN-655 according procedure D. The product was purified by chromatography (hexane:EtOAc 2:1) to give a yellow solid (yield 50%), mp 97-100° C. $^1$H-NMR (300 MHz, acetone-d$_6$) ppm 8.03+8.01 (d, J=16 Hz, 1H, H-15), 7.88 (bs, 1H, H-2), 7.31 (d, J=8 Hz, 1H, H-7), 7.21 (t, J=8 Hz, 1H, H-6), 6.90 (bd, J=8 Hz, 1H, H-5), 6.26 (d, J=16 Hz, 1H, H-16), 3.89 (s, 3H, H-14), 3.71 (s, 3H, H-18), 3.71-3.64+3.45-3.38 (m, 2H, H-11), 3.28+3.01 (s, 3H, H-13), 1.36+1.18 (t, J=7 Hz, 3H, H-12); $^{13}$C-NMR (50 MHz, acetone-d$_6$) ppm 168.30, 154.76, 146.33, 140.42, 138.81, 131.32, 123.17, 121.05, 115.53, 113.23, 111.37, 108.39, 51.25, 44.79, 34.32, 33.60, 13.63, 12.71; MS (CI+) m/z 316.142 (M$^+$·, 66.35), 285.120 ([M-OCH$_3$H$_3$]$^+$·, 74.32), 86.057 ($C_4H_8NO^+$, 100); HRMS calcd. for $C_{17}H_{20}N_2O_4^{+·}$ (M$^{+·}$) 316.1423. found 316.1419; Anal. Calcd. for $C_{17}H_{20}N_2O_4$ (316.3517 g/mol): C, 64.54; H, 6.37; N, 8.86. Found C, 64.632; H, 6.531; N, 8.872.

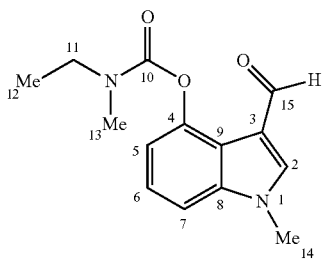

3-Formyl-1-methyl-1H-indol-4-yl ethylmethylcarbamate, AN-655

Compound AN-655 was prepared from AN-652 according to procedure D to give a white solid (yield 78.167%), mp

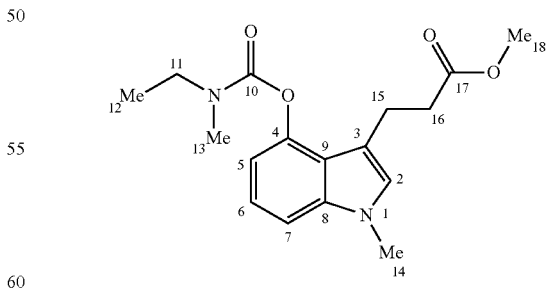

3-(2-(Methoxycarbonyl)ethyl)-1-methyl-1H-indol-4-yl ethyl methyl carbamate, AN-629.[38]

Compound AN-629 was prepared from AN-804 according to procedure F to give a white solid product (yield 96%), mp>270° C., that was used as such without further purification; $^1$H-NMR (300 MHz, acetone-$d_6$) ppm 7.18 (dd, J=8, 1 Hz, 1H, H-7), 7.10 (t, J=8 Hz, 1H, H-6), 6.98 (bs, 1H, H-2), 6.72 (bd, J=7 Hz, 1H, H-5), 3.74 (s, 3H, H-14), 3.63 (s, 3H, H-18), 3.63-3.55+3.43-3.36 (m, 2H, H-11), 3.16+ 2.97 (s, 3H, H-13), 3.04 ("t", J=8 Hz, 2H, H-15), 2.66-2.61 (m, 2H, H-16), 1.28+1.17 (t, J=7 Hz, 3H, H-12); $^{13}$C-NMR (75 MHz, acetone-$d_6$) ppm 173.69, 155.19, 146.21, 146.05, 140.26, 127.99, 122.12, 113.18, 112.97, 107.57, 51.52, 44.63, 44.45, 36.23, 36.15, 34.12, 32.87, 22.46, 13.60, 12.70; MS (CI+) m/z 319.164 (MH$^+$, 71.12), 318.160 (M$^{+\cdot}$, 58.45), 287.132 ([MH-CH$_3$OH]$^+$, 15.07), 245.114 (C$_{14}$H$_{17}$N$_2$O$_2$$^+$, 38.93), 86.053 (C$_4$H$_8$NO$^+$, 100); HRMS calcd. for C$_{17}$H$_{23}$N$_2$O$_4$$^+$ (MH$^+$) 319.1658. found 319.1645.

EtOAc 3:1) to give a white solid (yield 38%), mp 86-89° C.; $^1$H-NMR (300 MHz, acetone-$d_6$) ppm 10.27 (broad, 1H, H-1), 7.25 (bd, J=8 Hz, 1H, H-7), 7.18 (t, J=3 Hz, 1H, H-2), 7.10 (t, J=8 Hz, 1H, H-6), 6.87 (d, J=8 Hz, 1H, H-5), 6.45-6.43 (m, 1H, H-3), 3.55+3.41, (bt, J=7 Hz, 2H, H-11), 3.18+3.01 (s, 3H, H-15), 1.74+1.63 (bquint, J=7 Hz, 2H, H-12), 1.50-1.36 (m, 2H, H-13), 1.01+0.97 (bt, J=7.5 Hz, 3H, H-14); $^{13}$C-NMR (75 MHz, acetone-$d_6$) ppm 155.19, 145.47, 138.95, 125.5, 122.71, 121.96, 112.13, 109.39, 99.07, 49.49, 49.43, 34.92, 30.91, 30.15, 20.85, 14.48; MS (CI+) m/z 247.143 (MH$^+$, 90.44), 246.136 (M$^{+\cdot}$, 28.41), 114.094 (C$_6$H$_{12}$NO$^+$, 100); HRMS calcd. for C$_{14}$H$_{19}$N$_2$O$_2$$^+$ (MH$^+$) 247.1447. found 247.1433; Anal. Calcd. for C$_{14}$H$_{18}$N$_2$O$_2$ (246.3049 g/mol): C, 68.27; H, 7.37; N, 11.37. Found C, 68.562; H, 7.44; N, 11.052.

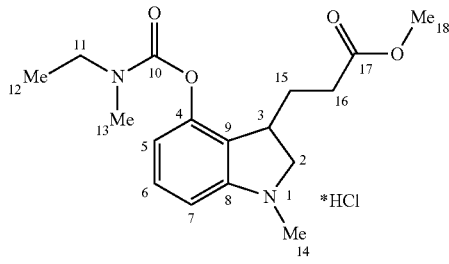 [SMILES: CCN(C)C(=O)Oc1cccc2c1C(CCC(=O)OC)CN2C]

3-(2-(Methoxycarbonyl)ethyl)-1-methylindolin-4-yl ethylmethylcarbamate hydrochloride, AN-698

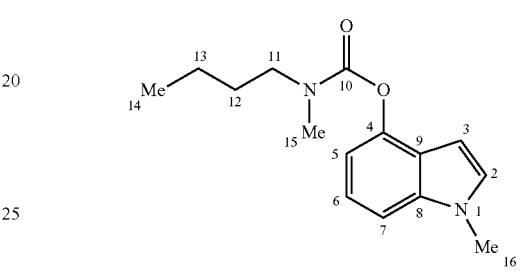

1-Methyl-1H-indol-4-yl butylmethylcarbamate, AN-660

Compound AN-698 was prepared from AN-629 according to procedure E, method I. The crude was a mixture of the methyl ester and the acid. 43% of the crude was dissolved in MeOH and 6 drops of 3N HCl were added. The mixture was stirred over three nights. The solution was evaporated to give an oil (yield 62%); $^1$H-NMR (300 MHz, D$_2$O) ppm 7.57 (t, J=8 Hz, 1H, H-6), 7.47 (d, J=8 Hz, 1H, H-7), 7.28 (d, J=8 Hz, 1H, H-5), 4.08-4.01 (m, 1H, H-2), 3.87-3.77 (m, 2H, H-2+H-3), 3.67 (s, 3H, H-18), 3.58-3.51+3.42-3.35 (m, 2H, H-11), 3.30 (s, 3H, H-14), 3.13+2.99 (s, 3H, H-13), 2.49 (t, J=7.5 Hz, 2H, H-16), 2.22-2.13+1.99-1.86 (m, 2H, H-15), 1.25+1.17 (t, J=7 Hz, 3H, H-12); $^{13}$C-NMR (75 MHz, D$_2$O) ppm 175.78, 154.94, 147.98, 142.23, 131.02, 129.95, 124.65, 124.50, 116.07, 61.30, 52.40, 44.53, 44.41, 42.81, 38.53, 34.081, 30.99, 26.88, 12.41, 11.68; MS (CI+) m/z 321.181 (MH$^+$, 100), 320.175 (M$^{+\cdot}$, 69.90), 86.070 (C$_4$H$_8$NO$^+$, 58.93); HRMS calcd. for C$_{17}$H$_{25}$N$_2$O$_4$$^+$ (MH$^+$) 321.1814. found 321.1813.

Compound AN-660 was prepared from AN-659 according to procedure G. The product was purified by chromatography (hexane:EtOAc 5:1) to give a colourless oil (yield 48%); $^1$H-NMR (300 MHz, acetone-$d_6$) ppm 7.23 (bd, J=8 Hz, 1H, H-7), 7.18 (d, J=3 Hz, 1H, H-2), 7.12 (t, J=8 Hz, 1H, H-6), 6.82 (d, J=8 Hz, 1H, H-5), 6.35 (bd, J=3 Hz, 1H, H-3), 3.82 (s, 3H, H-16), 3.54+3.37 (t, J=7 Hz, 2H, H-11), 3.17+2.98 (s, 3H, H-15), 1.73+1.62 (q, J=7 Hz, 2H, H-12), 1.49-1.34 (m, 2H, H-13), 0.96+0.93 (t, J=8 Hz, 3H, H-14); $^{13}$C-NMR (75 MHz, acetone-$d_6$) ppm 154.89, 145.68, 139.52, 129.80, 123.18, 122.02, 112.24, 107.32, 98.28, 49.54, 49.40, 34.87, 34.69, 33.08, 30.98, 30.21, 20.50, 14.12; MS (CI+) m/z 261.162 (MH$^+$, 100), 260.155 (M$^+$, 46.68), 114.088 (C$_6$H$_{12}$NO$^+$, 61.66); HRMS calcd. for C$_{15}$H$_{21}$N$_2$O$_2$$^+$ (MH$^+$) 261.1603. found 261.1620.

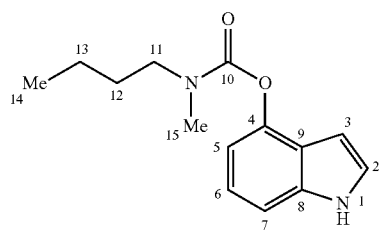

1H-Indol-4-yl-butylmethylcarbamate, AN-659

Compound AN-659 was prepared according to procedure B. The product was purified by chromatography (hexane:

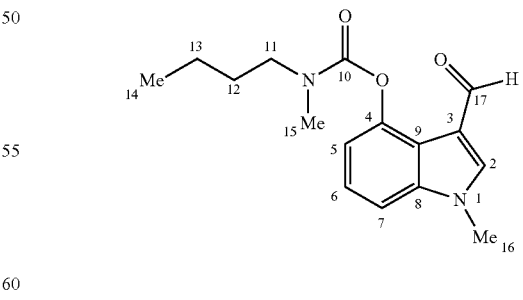

3-Formyl-1-methyl-1H-indol-4-yl butylmethylcarbamate, AN-662

Compound AN-662 was prepared from AN-660 according to procedure D to give a brown oil (yield 81%); $^1$H-NMR (300 MHz, acetone-$d_6$) ppm 9.89+9.86 (s, 1H, H-17), 7.89+7.88 (s, 1H, H-2), 7.29-7.25 (m, 2H, H-6 and H-7), 7.02-6.97 (m, 1H, H-5), 3.745 (s, 3H, H-16), 3.60+3.37 (t, J=7.5 Hz, 2H, H-11), 3.22+3.00 (s, 3H, H-15), 1.73+1.62 (quint, J=7.5 Hz, 2H, H-12), 1.49-1.35 (m, 2H, H-13), 1.01+0.97 (t, J=7 Hz, 3H, H-14); $^{13}$C-NMR (75 MHz, acetone-$d_6$) ppm 183.45, 183.33, 155.47, 155.29, 146.38, 140.74, 140.32, 139.79, 124.09, 120.26, 120.16, 118.10, 116.80, 116.52, 108.66, 49.631, 35.05, 34.91, 33.84, 30.92, 30.15, 20.62, 20.50, 14.20; MS (CI+) m/z 317.184 ([M+$C_2H_5$]$^+$, 33.34), 289.154 (MH$^+$, 59.21), 288.145 (M$^+$, 48.02), 261.158 ([MH$^+$—CO], 15.44), 174.056 ($C_{10}H_8NO_2^+$, 21.32), 114.095 ($C_6H_{12}NO^+$, 100); HRMS calcd. for $C_{16}H_{21}N_2O_3^+$ (MH$^+$) 289.1552. found 289.1540.

1H, H-7), 7.11 (t, J=8 Hz, 1H, H-6), 6.97 (broad, 1H, H-2), 6.72 (b"t", J=6.5 Hz, 1H, H-5), 3.73 (s, 3H, H-16), 3.64 (s, 3H, H-20), 3.54+3.37 (t, J=7.5 Hz, 2H, H-11), 3.17+2.99 (s, 3H, H-15), 3.05 ("t", J=8 Hz, 2H, H-17), 2.64 ("t", J=8 Hz, 2H, H-18), 1.76-1.56 (m, 2H, H-12), 1.50-1.31 (m, 2H, H-13), 1.02+0.93 (m, 3H, H-14); $^{13}$C-NMR (75 MHz, acetone-$d_6$) ppm 173.66, 155.46, 146.08, 140.24, 127.97, 122.11, 121.67, 113.18, 112.91, 107.53, 51.53, 49.56, 36.24, 36.15, 34.85, 34.67, 32.86, 30.98, 30.20, 22.49, 20.52, 14.15; MS (CI+) m/z 347.20 (MH$^+$, 55.11), 246.191 (M$^+$·, 54.01), 273.154 ($C_{16}H_{21}N_2O_2^+$, 20.90), 114.091 ($C_6H_{12}NO^+$, 100); HRMS calcd. for $C_{19}H_{26}N_2O_4^+$· (M$^+$·) 346.1893. found 346.1906.

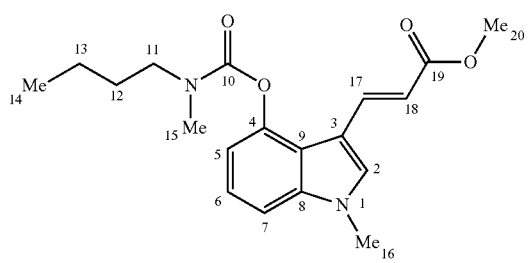 [SMILES: CCCCN(C)C(=O)Oc1cccc2c1c(/C=C/C(=O)OC)cn2C]

3-((E)-2-(Methoxycarbonyl)vinyl)-1-methyl-1H-indol-4-yl butylmethyl carbamate, AN-664

Compound AN-664 was prepared from AN-662 according to procedure D. The product was purified by chromatography (hexane:EtOAc 2:1) to give an oil (yield 67%); $^1$H-NMR (300 MHz, acetone-$d_6$) ppm 8.06+8.02 (d, J=16 Hz, 1H, H-18), 7.76+7.74 (s, 1H, H-2), 7.25-7.16 (m, 2H, H-6 and H-7), 6.92+6.90 (d, J=6 Hz, 1H, H-5), 6.25+6.24 (d, J=16 Hz, 1H, H-17), 3.74 (s, 6H, H-16 and H-20), 3.64+3.40 (t, J=7.5 Hz, 2H, H-11), 3.30+3.04 (s, 3H, H-15), 1.79+1.63 (quint, J=7.5 Hz, 2H, H-12), 1.49-1.30 (m, 2H, H-13), 1.00+0.94 (t, J=7.5 Hz, 3H, H-14); $^{13}$C-NMR (75 MHz, acetone-$d_6$) ppm 168.28, 154.97, 146.13, 140.25, 138.73, 131.39, 131.20, 123.08, 120.88, 115.63, 115.15, 112.98, 111.15, 108.36, 51.27, 49.68, 34.95, 34.70, 33.55, 30.87, 30.20, 20.60, 20.47, 14.16; MS (CI+) m/z 344.174 (M$^+$, 26.53), 114.095 ($C_6H_{12}NO^+$, 100); HRMS calcd. for $C_{19}H_{24}N_2O_4^+$ (M$^+$·) 344.1736. found 344.1736.

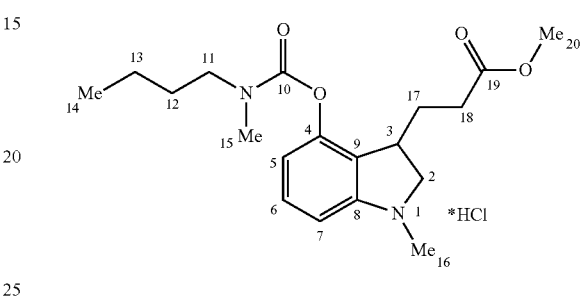

3-(2-(Methoxycarbonyl)ethyl)-1-methylindolin-4-yl butylmethylcarbamate hydrochloride, AN-667

Compound AN-667 was prepared from AN-666 according to procedure E, method I. The crude was dissolved in MeOH and 6 drops of 3N HCl were added. The mixture was stirred over three nights. The solution was evaporated to give an oil (yield 33%); $^1$H-NMR (300 MHz, CD$_3$OD) ppm 7.42 (broad, 1H, H-6), 7.31-7.30 (bm, 1H, H-7), 7.14-7.09 (m, 1H, H-5), 3.82 (bm, 1H, H-2), 3.76-3.70 (bm, 2H, H-2+H-3), 3.67 (s, 3H, H-20), 3.51+3.38 (bm, 2H, H-11), 3.21 (s, 3H, H-16), 3.15+3.01 (s, 3H, H-15), 2.48-2.34 (bt, J=7 Hz, 2H, H-18), 2.20+1.88 (broad, 2H, H-17), 1.70-1.57 (m, 2H, H-12), 1.45-1.33 (m, 2H, H-13), 1.02-0.94 (m, 3H, H-14); $^{13}$C-NMR (75 MHz, CD$_3$OD) ppm 173.34, 154.01, 148.38, 145.10, 144.98, 130.00, 129.90, 129.80, 121.56, 121.16, 112.92, 112.71, 60.99, 60.87, 50.85, 48.93, 40.40, 38.74, 33.93, 33.660, 30.67, 30.60, 29.89, 29.12, 27.34, 27.22, 19.60, 19.50, 12.81; MS (CI+) m/z 349.212 (MIE, 70.32), 348.205 (M$^+$·, 44.07), 114.091 ($C_6H_{12}NO^+$, 100); HRMS calcd. for $C_{19}H_{29}N_2O_4^+$ (MH$^+$) 349.2127. found 349.2124.

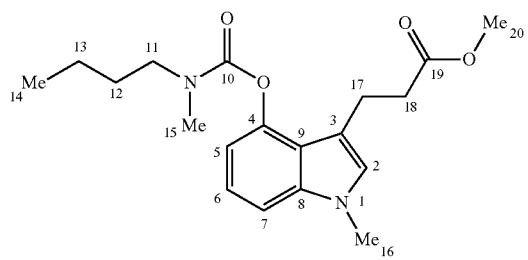 [SMILES: CCCCN(C)C(=O)Oc1cccc2c1c(CCC(=O)OC)cn2C]

3-(2-(Methoxycarbonyl)ethyl)-1-methyl-1H-indol-4-yl butylmethylcarbamate, AN-666

Compound AN-666 was prepared from AN-664 according to procedure F. The product was purified by chromatography (hexane:EtOAc 3:1) to give an oil (yield 59%); $^1$H-NMR (300 MHz, acetone-$d_6$) ppm 7.18 (dd, J=8, 1 Hz,

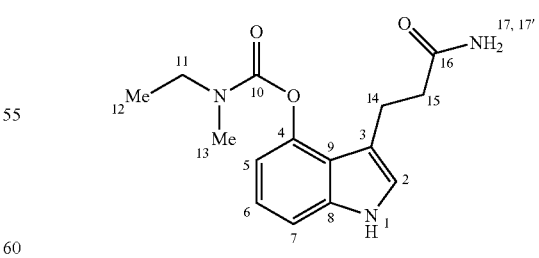

3-(3-Amino-3-oxopropyl)-1H-indol-4-yl ethyl(methyl)carbamate, AN-1147

Compound AN-1147 was prepared from AN-805 by procedure K, was crystallized from EtOAc-hexane, and was isolated as an off-white solid in 60% yield, mp 64-66° C. $^1$H-NMR (300 MHz, CDCl$_3$) ppm δ 8.46 (bs, 1H, H-1), 7.15 (d, J=6.0 Hz, 1H, H-2), 7.07 (t, J=9.0 Hz, 1H, H-7), 6.75 (t, J=9.0 Hz, 1H, H-6), 6.67 (bs, 1H, H-5), 5.56 (bd, J=15.0 Hz, 1H, H-17'), 5.27 (bs, 1H, H-17), 3.41-3.58 (m, 2H, H-11), 3.15+3.01 (s, 3H, H-13), 3.00 (t, J=6.3 Hz, 2H, H-14), 2.42 (t, J=6.3 Hz, 2H, H-15), 1.18-1.31 (m, 3H, H-12); $^{13}$C-NMR (75 MHz, CDCl$_3$) ppm δ 175.84, 155.62, 144.59, 138.76, 122.90, 121.65, 120.19, 112.50, 112.20, 109.27, 44.24+44.13, 36.14+35.99, 34.23+33.94, 21.91, 13.29+12.53; MS (CI$^+$) m/z 318.183 ([M+C$_2$H$_5$]$^+$, 32.84), 290.148 (MH$^+$, 21.29), 289.145 ([M$^+$·, 15.29), 273.123 ([MH$^+$—NH$_3$], 12.26), 231.109 ([M$^+$-C$_2$H$_4$NO], 14.55), 187.080 ([M$^+$·-C$_4$H$_8$NO$_2$], 18.01); HRMS calcd. for C$_{15}$H$_{20}$N$_3$O$_3$ (MIE, DCI$^+$/CH$_4$) 290.1505. found 290.1483, for C$_{17}$H$_{24}$N$_3$O$_3$ ([M+C$_2$H$_5$]$^+$, DCI$^+$/CH$_4$) 318.1818. found 318.1827, for C$_{15}$H$_{174}$N$_2$O$_3$ ([MH$^+$—NH$_3$], DCI$^+$/CH$_4$) 273.1239. found 273.1231.

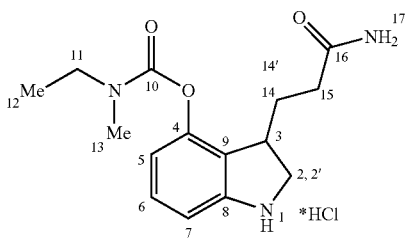

3-(3-Amino-3-oxopropyl)indolin-4-yl ethyl(methyl) carbamate hydrochloride, AN-851

Compound AN-851 was prepared from AN-1147 by procedure E, was stirred at room temperature over night, and was isolated as a colourless oil in 38% yield. $^1$H-NMR (300 MHz, MeOD) ppm δ 7.24-7.60 (m, 3H, H-6+H-5+H-7), 3.94-4.22 (m, 1H, H-2), 3.70-3.78 (m, 2H, H-2'+H-3), 3.40-3.56 (m, 2H, H-11), 3.14+3.00 (s, 3H, H-13), 2.43 ("t", J=7.9 Hz, 2H, H-15), 2.27-2.34 (m, 1H, H-14), 1.85-1.91 (m, 1H, H-14'), 1.22-1.46 (m, 3H, H-12); $^{13}$C-NMR (75 MHz, MeOD) ppm δ 178.65, 154.65, 150.02, 138.26, 132.50, 132.14, 131.70, 131.41, 125.27, 126.02, 117.93, 51.37, 51.16, 45.45, 45.30, 40.59, 34.74, 34.56, 33.07, 32.95, 29.67, 29.39, 13.59, 12.66; MS (CI$^+$) m/z 362.239 ([M+C$_2$H$_{11}$]$^+$, 49.69), 334.217 (M+C$_3$H$_7$]$^+$, 99.97), 320.20 ([M+C$_2$H$_5$]$^+$, 79.22), 292.165 (MH$^+$, 23.11), 275.136 ([MH$^+$—NH$_3$], 23.50), 86.01 (C$_4$H$_8$NO$^+$, 88.33); HRMS calcd. for C$_{17}$H$_{26}$N$_3$O$_3$ ([M+C$_2$H$_5$]$^+$, DCI$^+$/CH$_4$) 320.1974. found 320.2004, for C$_{15}$H$_{22}$N$_3$O$_3$ (MH$^+$, DCI$^+$/CH$_4$) 292.1661. found 292.1655.

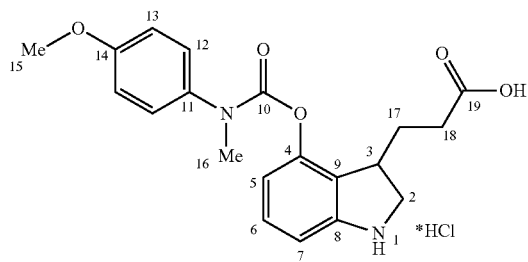 [SMILES: COc1ccc(N(C)C(=O)Oc2cccc3c2C(CCC(=O)O)CN3)cc1]

3-(4-((4-Methoxyphenyl)(methyl)carbamoyl)indolin-3-yl)propanoic acid hydrochloride AN-821

AN-819 was dissolved in 3N HCl and stirred over two nights and then evaporated to give the desired product (yield 93%); $^1$H-NMR (300 MHz, D$_2$O) ppm 7.49-7.25 (m, 5H, H-5+H-6+H-7+H-12), 6.99 (d, J=8.5 Hz, 2H, H-13), 3.95-3.86 (m, 1H, H-2), 3.78 (s, 3H, H-15), 3.63+3.57 (m, 2H, H-2+H-3), 3.43+3.27 (bs, 3H, H-16), 2.20 (m, 2H, H-18), 1.74+1.61 (m, 2H, H-17); $^{13}$C-NMR (50 MHz, D$_2$O) ppm 178.90, 160.31, 151.64, 149.83, 138.81, 137.15, 132.66, 132.38, 129.77, 125.93, 119.27, 116.87, 57.70, 54.31, 41.40, 40.36, 32.93, 29.11.

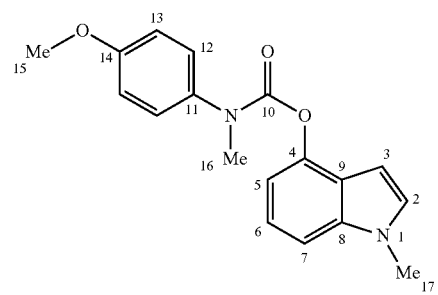

1-Methyl-1H-indol-4-yl 4-methoxyphenylmethylcarbamate, AN-808

Compound AN-808 was prepared from AN-807 according to procedure G. The product was purified by chromatography (hexane:EtOAc 3:1) to give a white solid (yield 84%), mp 84-86° C.; $^1$H-NMR (300 MHz, acetone-d$_6$) ppm 7.43 ("d", J=9 Hz, 2H, H-12), 7.23-7.17 (m, 2H, H-2+H-7), 7.11 (t, J=7.5 Hz, 1H, H-6), 6.98 (d, J=9 Hz 2H, H-13), 6.84 (d, J=7.5 Hz, 1H, H-5), 6.34 (broad, 1H, H-3), 3.80 (s, 6H, H-15+H-17), 3.38 (s, 3H, H-16); $^{13}$C-NMR (50 MHz, acetone-d$_6$) ppm 159.13, 154.42, 145.66, 139.63, 137.55, 129.86, 128.35, 123.07, 122.05, 115.06, 112.13, 107.46, 96.47, 55.76, 38.74, 33.10; MS (CI+) m/z 311.143 (MH$^+$, 100), 310.137 (M$^+$, 36.36), 164.075 (C$_9$H$_{10}$NO$_2^+$, 93.37), 136.086 (C$_8$H$_{10}$NO$^+$, 12.49); HRMS calcd. for C$_{18}$H$_{19}$N$_2$O$_3^+$ (MFE) 311.1396. found 311.1431; Anal. Calcd. for C$_{18}$H$_{18}$N$_2$O$_3$ (310.3471 g/mol): C, 69.66; H, 5.85; N, 9.03. Found C, 69.475; H, 6.040; N, 9.245.

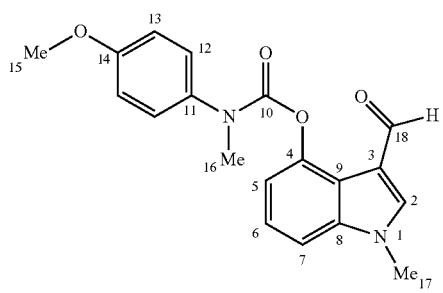

3-Formyl-1-methyl-1H-indol-4-yl 4-methoxyphenylmethylcarbamate, AN-810

Compound AN-810 was prepared from AN-808 according to procedure C to give a white solid (yield 91%), mp 62-64° C.; ¹H-NMR (300 MHz, acetone-d$_6$) ppm 9.79 (s, 1H, H-18), 7.84 (s, 1H, H-2), 7.60-7.50 (broad, 2H, H-12), 7.24 (broad, 1H, H-6 and H-7), 6.97 (broad, 1H, H-5), 6.96 (d, J=8.5 Hz, 2H, H-13), 3.76 (s, 3H, H-15), 3.69 (s, 3H, H-17), 3.60+3.37 (s, 3H, H-16); ¹³C-NMR (75 MHz, acetone-d$_6$) ppm 183.46, 158.93, 154.55, 146.26, 140.83, 137.31, 128.76, 128.02, 124.23, 119.85, 118.19, 116.32, 114.72, 108.82, 55.64, 38.98, 33.82; MS (CI+) m/z 367.167 ([M+C$_2$H$_5$]$^+$, 16.12), 339.133 (MH$^+$, 49.47), 338.125 (M$^{+\cdot}$, 32.13), 311.136 ([MH—CO]$^+$, 14.26), 176.054 (C$_{10}$H$_{10}$NO$_2$$^+$, 34.40), 164.063 (C$_9$H$_{10}$NO$_2$$^+$, 90.07); HRMS calcd. for C$_{19}$H$_{19}$N$_2$O$_4$$^+$ (MH$^+$) 339.1345. found 339.1335.

tography (hexane:EtOAc 2:1) to give a white solid (yield 75%), mp 110-112° C. ¹H-NMR (300 MHz, acetone-d$_6$) ppm 7.48 (d, J=8.5 Hz, 2H, H-12), 7.15 (bm, 2H, H-6 and H-7), 6.99 (d, J=8.5 Hz, 2H, H-13), 6.90 (bm, 2H, H-2+H-5), 3.77 (s, 3H, H-21), 3.71 (s, 3H, H-15), 3.61 (s, 3H, H-17), 3.41 (broad, 3H, H-16), 3.04 (broad, 2H, H-18), 2.60 (broad, 2H, H-19); ¹³C-NMR (75 MHz, acetone-d$_6$) ppm 173.87, 159.05, 154.92, 145.90, 140.06, 137.03, 128.62, 127.89, 122.05, 121.33, 115.17, 114.94, 112.72, 107.62, 55.65, 51.58, 38.81, 35.89, 32.74, 22.30; MS (CI+) m/z 393.175 (MH$^+$, 39.96), 396.168 (M$^{+\cdot}$, 30.87), 323.137 (C$_{19}$H$_{19}$N$_2$O$_3$$^+$, 16.94), 164.051 (C$_9$H$_{10}$NO$_2$$^+$, 100); HRMS calcd. for C$_{22}$H$_{25}$N$_2$O$_5$$^+$ (MH$^+$) 397.1763. found 397.1752.

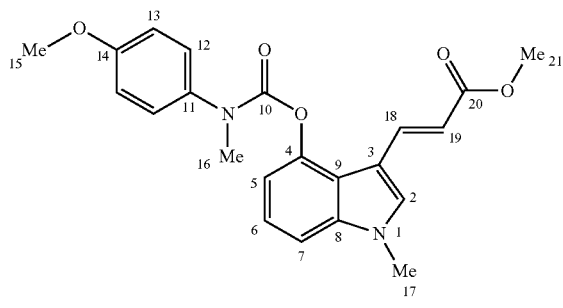 [SMILES: COC(=O)/C=C/c1cn(C)c2cccc(OC(=O)N(C)c3ccc(OC)cc3)c12]

3-((E)-2-(Methoxycarbonyl)vinyl)-1-methyl-1H-indol-4-yl 4-methoxyphenylmethylcarbamate, AN-812

Compound AN-812 was prepared from AN-81 according to procedure D. The product was purified by chromatography (hexane:EtOAc 1:1) to give a bright yellow solid (yield 59%), mp 151-153° C.; ¹H-NMR (300 MHz, acetone-d$_6$) ppm 8.05+8.01 (broad, 1H, H-17), 7.89 (s, 1H, H-2), 7.63+7.46 (s, 2H, H-12), 7.30 (bd, J=7 Hz, 1H, H-7), 7.21 (broad, 1H, H-6), 6.98 (d, J=7.5 Hz, 2H, H-13), 6.87 (broad, 1H, H-5), 6.286 (d, J=16 Hz, 1H, H-18), 3.87 (s, 3H, H-17), 3.80 (s, 3H, H-20), 3.77 (s, 3H, H-15), 3.63+3.35 (s, 3H, H-16); ¹³C-NMR (75 MHz, acetone-d$_6$) ppm 168.05, 154.61, 146.20, 140.48, 138.88, 137.38, 131.36, 128.86, 123.20, 121.07, 115.16, 113.24, 111.34, 108.63, 55.75, 51.33, 39.01, 33.66; MS (CI+) m/z 394.153 (M$^{+\cdot}$, 26.01), 363.163 ([M−MeO]$^{+\cdot}$, 26.16), 164.063 (C$_9$H$_{10}$NO$_2$$^+$, 100); HRMS calcd. for C$_{22}$H$_{22}$N$_2$O$_5$$^{+\cdot}$ (M$^{+\cdot}$) 394.1592. found 394.1532.

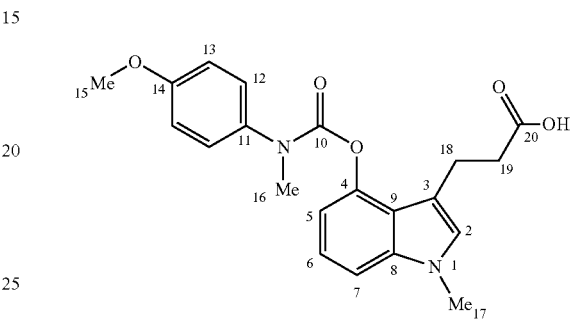

3-(4-((4-Methoxyphenyl)(methyl)carbamoyl)-1-methyl-1H-indol-3-yl)propanoic acid, AN-816

Compound AN-816 was prepared from AN-814 according to procedure H, method I, and obtained as an orange solid (yield 75%), mp 161-163° C. ¹H-NMR (300 MHz, acetone-d$_6$) ppm 7.44 (d, J=8 Hz, 2H, H-12), 7.17 (d, J=7.5 Hz, 1H, H-7), 7.09 (t, J=7.5 Hz, 1H, H-6), 6.96 (bd, J=8 Hz, 3H, H-2+H-13), 6.75 (d, J=7.5 Hz, 1H, H-5), 3.80 (s, 3H, H-15), 3.74 (s, 3H, H-17), 3.34 (broad, 3H, H-16), 2.96 (broad, 2H, H-18), 2.54 (broad, 2H, H-19); ¹³C-NMR (125 MHz, acetone-d$_6$) ppm 174.35, 159.31, 154.97, 146.10, 140.22, 137.10, 128.86, 127.93, 122.04, 121.51, 115.06, 113.14, 112.68, 107.59, 55.68, 38.83, 35.75, 32.85, 22.31; MS (CI+) m/z 383.159 (MH$^+$, 20.20), 382.153 (M$^\pm$, 22.37), 164.057 (C$_9$H$_{10}$NO$_2$$^+$, 99.98); HRMS calcd. for C$_{21}$H$_{22}$N$_2$O$_5$$^{+\cdot}$ (M$^{+\cdot}$) 382.1529. found 382.1527.

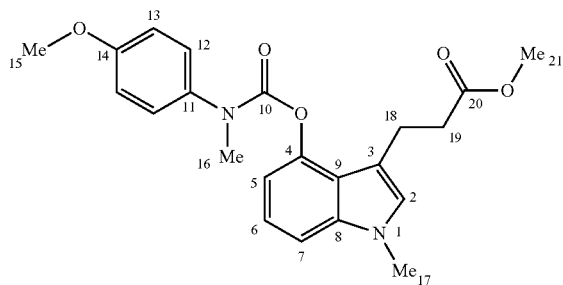

3-(2-(Methoxycarbonyl)ethyl)-1-methyl-1H-indol-4-yl 4-methoxyphenylmethyl carbamate, AN-814

Compound AN-814 was prepared from AN-812 according to procedure F. The product was purified by chroma-

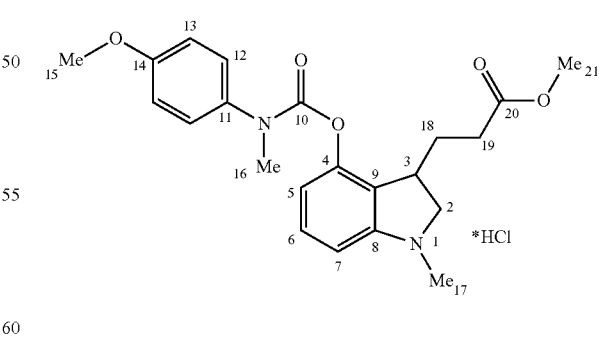

3-(2-(Methoxycarbonyl)ethyl)-1-methylindolin-4-yl 4-methoxyphenylmethyl carbamate hydrochloride, AN-820

Compound AN-820 was prepared from AN-814. AN-814 was dissolved in MeOH and few drops of concentrated HCl were added. The mixture was stirred over night. The solution was evaporated to give an oil (yield 99%). $^1$H-NMR (300 MHz, CD$_3$CN) ppm 7.45-7.27 (m, 5H, H-5+H-6+H-7+H-12), 6.95 (d, J=9 Hz, 2H, H-13), 3.79 (s, 3H, H-21), 3.73+3.45 (broad, 3H, H-2+H-3), 3.65 (s, 3H, H-15), 3.27+3.07 (s, 3H, H-16), 2.24 (broad, 2H, H-19), 1.87+1.71 (broad, 2H, H-18); $^{13}$C-NMR (75 MHz, CD$_3$CN) ppm 173.75, 157.76, 153.54, 149.38, 143.11, 136.34, 131.13, 128.88, 124.83, 116.30, 115.25, 61.26, 56.12, 52.21, 42.57, 39.58, 39.19, 31.94, 28.19.

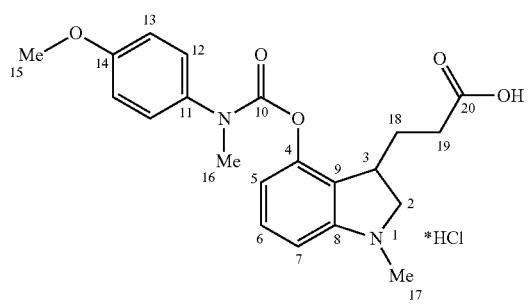 [SMILES: COc1ccc(N(C)C(=O)Oc2cccc3c2C(CCC(=O)O)CN3C)cc1]

3-(4-((4-Methoxyphenyl)(methyl)carbamoyl)-1-methylindolin-3-yl)propanoic acid hydrochloride, AN-822

Compound AN-822 was prepared from AN-816 according to procedure E, method I to give the desired product (yield 65%). $^1$H-NMR (300 MHz, D$_2$O) ppm 7.43-7.31 (m, 2H, H-6+H-7), 7.25 (d, J=9 Hz, 2H, H-12), 7.16 (d, J=8 Hz, 1H, H-5), 6.86 (d, J=9 Hz, 2H, H-13), 3.89+3.82 (m, 1H, H-2), 3.66 (bs, 4H, H-2+H-15), 3.47 (broad, 1H, H-3), 3.31+3.21 (bs, 3H, H-16), 3.16 (bs, 3H, H-17), 2.17-2.12 (m, 2H, H-19), 1.69+1.51 (bm, 2H, H-18); $^{13}$C-NMR (50 MHz, D$_2$O) ppm 178.56, 160.25, 156.16, 149.61, 143.72, 137.08, 132.67, 132.78, 131.67, 129.68, 126.39, 118.20, 116.80, 63.14, 57.65, 45.10, 40.39, 33.03, 28.86 (C-18).

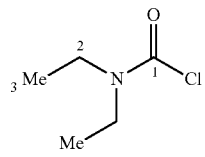

Diethyl Carbamoyl Chloride 2e

Compound 2e was obtained from diethylamine 1e (procedure A) as colourless oil in 80% yield. $^1$H NMR (200 MHz, CDCl$_3$ ppm 3.5-3.4 (m, 4H, H-2), 1.3-1.2 (m, 6H, H-3); $^{13}$C NMR (75 MHz, CDCl$_3$) ppm 146.9, 45.67+44.39, 13.66+12.78; MS (EE): m/z 72 ([M-COCl], 100), 135 (M, 50).

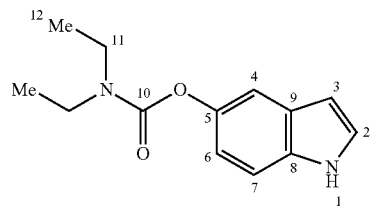

Diethyl-carbamic acid 1H-indol-5-yl ester, AN-782

Compound AN-782 was obtained from 5-hydroxyindole and diethyl carbamoyl chloride 2e (procedure B) and purified by column chromatography (hexane:EtOAc 10:1) to provide AN-782 as a colourless solid in 80% yield. $^1$H NMR (200 MHz, CDCl$_3$ ppm 7.45-7.2 (m, 2H, H-7+H-2), 7.18 (m, 1H, H-4), 6.95 (dd, 1H, J=8.7, 1.9 Hz, H-6), 6.5 (m, 1H, H-3), 3.55-3.38 (m, 4H, H-11), 1.4-1.1 (m, 6H, H-12); $^{13}$C NMR (75 MHz, CDCl$_3$) ppm 155.54, 144.73, 133.46, 127.86, 125.61, 115.98, 112.38, 111.4, 101.19, 42.12, 41.77, 14.13, 13.55; MS (ES$^+$) m/z 233.135 (MH$^+$, 100), 255.118 (MNa$^+$, 50).

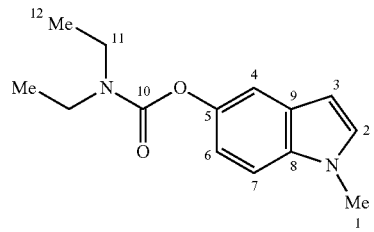

Diethyl-carbamic acid 1-methyl-1H indol-5-yl ester, AN-622

Compound AN-622 was obtained from indole AN-782 (procedure G) as a colourless solid in 90% yield. $^1$H NMR (200 MHz, CDCl$_3$ ppm 7.32 (d, 1H, J=2.18 Hz, H-2), 7.24 (d, 1H, J=8.7 Hz, H-7), 7.06-6.94 (m, 2H, H-6+H-3), 6.42 (dd, 1H, J=3.05, 0.73 Hz, H-4), 3.76 (s, 3H, H-1), 3.5-3.4 (m, 4H, H-11), 1.3-1.15 (m, 6H, H-12); $^{13}$C NMR (75 MHz, CDCl$_3$) ppm 155.24, 144.95, 134.35, 129.68, 128.54, 116.13, 112.98, 109.25, 100.95, 42.07, 41.76, 32.96, 14.21, 13.43; MS (ES$^+$): m/z 247 (MH$^+$, 70), 269 (MNa$^+$, 100).

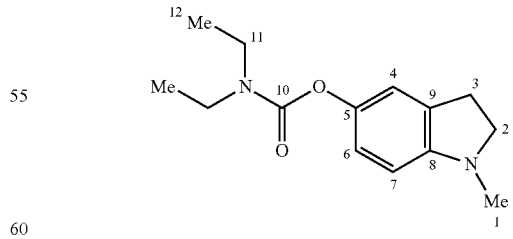

Diethyl-carbamic acid 1-methyl-2,3-dihydro-1H indol-5-yl ester, AN-625

Compound AN-625 was obtained by reduction of AN-622 (procedure E) as a colourless solid in 90% yield. $^1$H NMR (200 MHz, CDCl₃ ppm 6.9-6.8 (m, 2H, H-6+H-7), 6.6-6.4 (m, 1H, H-4), 3.5-3.2 (m, 7H, H-11, H-1, H-2), 3-2.6 (m, 4H, H-11, H-3), 1.3-1.1 (m, 6H, H-12); $^{13}$C NMR (75 MHz, CDCl₃) ppm 155.62, 133.08, 128.1, 121.03, 118.96, 117.32, 116.6, 56.79, 42.24, 41.84, 33.0, 28.39, 14.2, 13.36; MS (ES⁺): m/z 249 (MH⁺, 100).

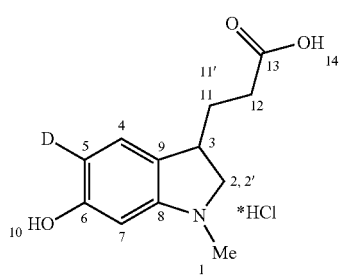 [SMILES: [2H]c1cc2c(cc1O)N(C)CC2CCC(=O)O]

Methyl 3-(5-deuteriu-6-hydroxy-1-methylindolin-3-yl) propanoic acid hydrochloride, AN-849

When compound AN-849 was dissolved in MeOD, the proton at position 5 of the aromatic ring was exchanged with deuterium (C-D). Compound AN-849 prepared from AN-1145 by procedure E, was stirred at room temperature for 2 h, and was isolated as a colourless hygroscopic oil in 63% yield. $^{1}$H-NMR (300 MHz, MeOD) ppm δ 7.33 (bs, 1H, H-4), 6.98 (m, 1H, H-7), 4.08 (t, J=10.8 Hz, 1H, H-2), 3.67 (t, J=10.8 Hz, 1H, H-2'), 3.55 (m, 1H, H-3), 3.25 (s, 3H, H-1), 2.48 (t, J=7.2 Hz, 2H, H-12), 2.15-2.26 (m, 1H, H-11'), 1.80-1.94 (m, 1H, H-11); $^{13}$C-NMR (75 MHz, MeOD) ppm δ 176.35, 160.09, 142.74, 129.32, 127.16, 106.33, 63.71, 43.18, 40.45, 32.35, 32.24, 29.91, 29.80; MS (CI⁺) m/z 221.105 (M⁺·, 71.83), 222.112 (MH⁺, 70.38); HRMS calcd. for C₁₂H₁₆NO₃ (MH⁺, DCI⁺/CH₄) 222.1130. found 222.1123, for C₁₂H₁₅NO₃ (M⁺·, DCI⁺/CH₄) 221.1052. found 221.1046.

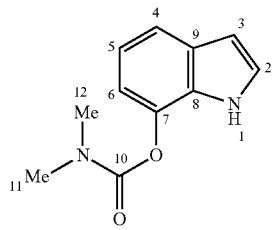

Dimethyl-carbamic acid 1H-indol-7-yl ester

7-Dimethylcarbamoyloxyindole was obtained from 7-hydroxyindole by procedure B and was further purified by column chromatography (hexane-EtOAc 2:1) to provide 19e as a colourless solid in 50% yield. $^{1}$H NMR (200 MHz, CDCl₃ ppm 8.47 (bs, 1H, H-1), 7.48 (dd, 1H, J=8, 2 Hz, H-4), 7.18-7.13 (m, 1H, H-2), 7.06 (t, 1H, J=7.7 Hz, H-5), 6.94 (dd, 1H, J=8, 2 Hz, H-6), 6.56-6.54 (m, 1H, H-3), 3.17 (s, 3H, H-11H-12), 3.07 (s, 3H, H-11H-12); $^{13}$C NMR (75 MHz, CDCl₃) ppm 154.46, 137.13, 130.93, 128.5, 124.7, 119.78, 117.91, 113.72, 103.14, 36.89 (C-11/C-12), 36.74 (C-11/C-12); MS (CI/NH₃) m/z 203 (M–H⁺, 100).

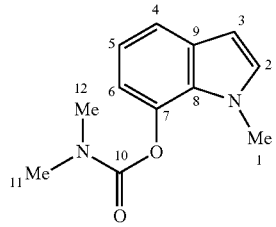

Dimethyl-carbamic acid 1-methyl-1H-indol-7-yl ester AN-621

Compound AN-621 was obtained from 7-dimethylcarbamoyloxyindole according to procedure G as a colourless solid in 85% yield. $^{1}$H NMR (200 MHz, CDCl₃ ppm 7.43 (dd, 1H, J=7.82; 1.04 Hz, H-4), 7.01 (t, 1H, J=7.8 Hz, H-5), 6.93-6.84 (m, 2H, H-6, H-2), 6.45 (d, 1H, J=3.1 Hz, H-3), 3.89 (s, 3H), 3.19 (s, 3H, H-11H-12), 3.07 (s, 3H, H-11H-12); $^{13}$C NMR (75 MHz, CDCl₃) ppm 155.41, 137.41, 132.05, 130.33, 128.85, 119.45, 118.35, 115.26, 101.34, 36.92, 36.53, 35.41; MS (CI/NH₃) m/z 219 (MH⁺, 100).

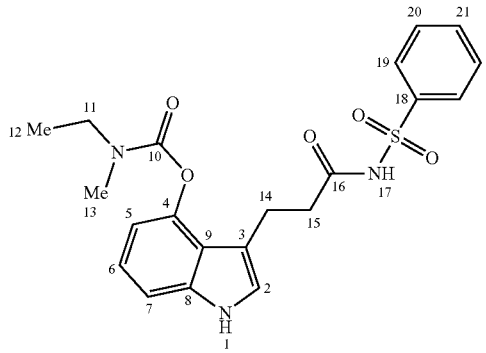 [SMILES: CCN(C)C(=O)Oc1cccc2[nH]cc(CCC(=O)NS(=O)(=O)c3ccccc3)c12]

3-(3-Oxo-3-(phenylsulfonamido)propyl)-1H-indol-4-yl ethyl(methyl)carbamate, AN-898

To a solution of AN-805 (52 mg, 0.17 mmol) in 2 mL DMF, CDI (56 mg, 0.34 mmol) was added and the solution heated at 65° C. for 2 h, then the solution cooled to room temperature. In a separate flask NaH, 60% in oil (21 mg, 0.52 mmol) was added to a solution of benzensulfonamide (81 mg, 0.52 mmol) in DMF. After stirring the foamy white mixture for 2 h the CDI solution was added, and the mixture was stirred at room temperature for 23 h. EtOAc was added followed by extraction with 1 N HCl, the organic phase was separated and washed with water, dried over Na₂SO₄ and evaporated. The product was purified by flash chromatography (EtOAc:hexane 1:7 to 1:5 to 1:1) to give a white solid in 32.5% yield. $^{1}$H-NMR (600 MHz, MeOD+CDCl₃) ppm 7.88 (d, J=9.0 Hz, 2H, H-19), 7.54 (t, J=6.0 Hz, 1H, H-21), 7.44 (t, J=6.0 Hz, 2H, H-20), 7.10 (d, J=9.0 Hz, 1H, H-7), 6.99 (t, J=6.0 Hz, 1H, H-6), 6.40-6.59 (m, 2H, H-5+H-2), 3.39+3.26 (bq, J=9.0 Hz, 2H, H-11), 2.98+2.86 (s, 3H, H-12), 2.89-2.88 (bm, 2H, H-14), 2.29 (t, J=9.0 Hz, 2H, H-15), 1.26+1.06 (t, J=9.0 Hz, 2H, H-11); $^{13}$C-NMR (150 MHz, MeOD+CDCl₃) ppm 171.06, 155.73, 155.49, 144.23, 144.08, 139.10, 138.58, 133.31, 128.53, 127.96, 125.90, 122.99, 122.94, 121.56, 112.11, 111.48, 111.88, 108.97, 43.99, 43.91, 37.45, 37.42, 33.85, 33.60, 21.29, 12.86, 12.08; MALDI (DHB_TA/RP_PepMix) m/z 452.123 (M+Na⁺); HRMS calcd. for $C_{21}H_{23}N_3O_5SNa$ (M+Na⁺) 452.123. found 452.1251.

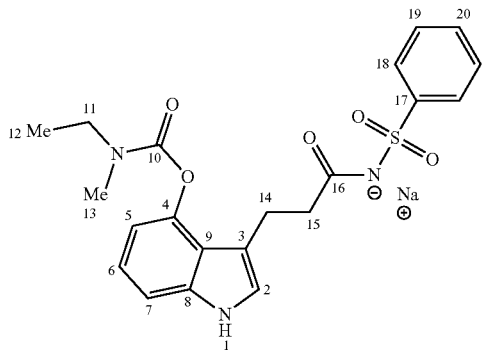 [SMILES: CCN(C)C(=O)Oc1cccc2[nH]cc(CCC(=O)[N-]S(=O)(=O)c3ccccc3)c12 ; [Na+]]

(3-(4-((Ethyl(methyl)carbamoyl)oxy)-1H-indol-3-yl)propanoyl)(phenylsulfonyl) amide sodium salt, AN-899

To a stirred solution of AN-898 (24 mg, 0.056 mmol) in MeOH (0.5 mL), NaOMe (3 mg, 0.056 mmol) was added. To dissolve the solids the mixture was heated, and once a clear solution was obtained, it was further stirred at room temperature for 1-2 h, followed by evaporation of the MeOH to give the Na salt as a white solid in quntitative yield. ¹H-NMR (300 MHz, MeOD) ppm 7.95 (d, J=9.0 Hz, 2H, H-18), 7.63-7.49 (m, 3H, H-20+H-19), 7.18 (d, J=9.0 Hz, 1H, H-7), 7.02 (t, J=9.0 Hz, 1H, H-6), 6.84 (s, 1H, H-2), 6.64-6.61 (m, 1H, H-5), 3.50-3.26 (m, 2H, H-11), 3.06+2.89 (bs, 3H, H-13), 2.91 (bt, J=7.2 Hz, 2H, H-14), 2.52 (bt, J=7.2 Hz, 2H, H-15), 1.22+1.10 (t, J=7.2 Hz, 3H, H-12); ¹³C-NMR (75 MHz, MeOD) ppm 178.26, 156.99, 145.89, 143.57, 140.46, 133.23, 129.47, 128.64, 123.81, 122.28, 121.49, 114.05, 112.93, 112.75, 110.11, 45.17, 45.01, 40.46, 40.31, 34.38, 23.10, 13.54, 12.71; MALDI (DHB_DHB/RN_PepMix) m/z 428.129 (M-Na⁺); HRMS calcd. for $C_{21}H_{22}N_3O_5$(M-Na⁺) 428.129. found 428.1275.

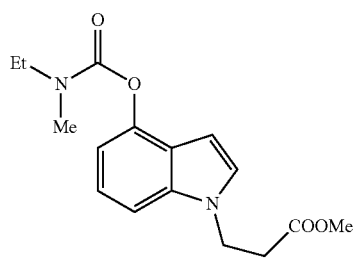 [SMILES: CCN(C)C(=O)Oc1cccc2c1ccn2CCC(=O)OC]

Methyl 3-(4-((Ethyl(methyl)carbamoyl)oxy)-1H-indol-1-yl)propanoate, AN-1245

Compound AN-1245, was prepared by procedure N. The reaction product was dissolved in dichloromethane, and filtered through a plug of silica gel, eluted with EtOAc-hexane (1:2). Evaporation of the filtrate gave the product as a yellow oil in 94% yield. ¹H-NMR (300 MHz, CDCl₃) ppm δ 7.26-7.16 (m, 2H, H-6+H-7), 7.10 (d, J=3.3 Hz, 1H, H-2), 6.97-6.88 (m, 1H, H-5), 6.43 (d, J=3.3 Hz, 1H, H-3), 4.41 (t, J=6.6 Hz, 2H, H-14), 3.65 (s, 3H, H-17), 3.62-3.39 (m, 2H, H-11), 3.16+3.04 (bs, 3H, H-13), 2.79 (t, J=6.6 Hz, 2H, H-15), 1.40-1.17 (m, 3H, H-12); ¹³C-NMR (75 MHz, CDCl₃) ppm δ 171.47, 154.15, 144.62, 137.49, 127.90, 122.25, 121.86, 111.82, 106.43, 98.32, 51.77, 44.07, 41.92, 34.58, 34.23, 33.83, 13.18, 12.44; MS (CI⁺) m/z 304.141 (M·⁺, 38.10), 305.146 (MH⁺, 100.00), 307.167 (M⁺C₂H₅⁺, 14.55); HRMS calcd. for $C_{16}H_{21}N_2O_4$ (MH⁺, CI/CH₄) 305.1501. found 305.1460.

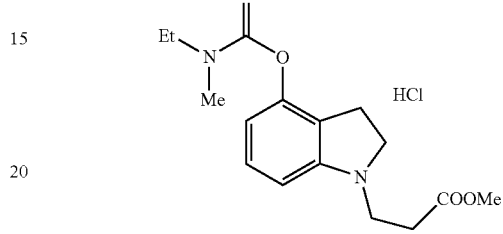

Methyl 3-(4-((Ethyl(methyl)carbamoyl)oxy)indolin-1-yl)propanoate, AN-1244

Compound AN-1244 prepared from AN-1245 by procedure E Method I, was isolated by chromatography eluted with EtOAc-hexane (1:8), as a colourless oil in 66.5% yield. ¹H-NMR (300 MHz, CDCl₃) ppm δ 7.032 (t, J=7.9 Hz, 1H, H-6), 6.41 (bd, J=7.9 Hz, 1H, H-5), 6.33 (d, J=7.9 Hz, 1H, H-7), 3.67 (s, 3H, H-17), 3.49-3.32 (m, 6H, H-11+H-2+H-14), 3.03+2.97 (bs, 3H, H-13), 2.89 (t, J=7.9 Hz, 2H, H-3), 2.58 (t, J=7.9 Hz, 2H, H-15), 1.28-1.13 (m, 3H, H-12); ¹³C-NMR (75 MHz, CDCl₃) ppm δ 172.62, 153.95, 153.59, 148.13, 128.54, 121.49, 111.48, 104.09, 52.95, 51.76, 44.99, 44.10, 34.30, 33.86, 32.29, 25.87, 13.18, 12.51; MS (CI⁺) m/z 306.161 (M·⁺, 100.00), 307.167 (MH⁺, 89.41); HRMS calcd. for $C_{16}H_{22}N_2O_4$ (M·⁺, CI/CH₄) 306.1580. found 306.1613, for $C_{16}H_{23}N_2O_4$ (MH⁺, CI/CH₄) 307.1658. found 307.1666.

Methyl 3-(4-((Ethyl(methyl)carbamoyl)oxy)indolin-1-yl)propanoate Hydrochloride AN-1243

The hydrochloride salt was isolated as a yellow viscous oil. ¹H-NMR (200 MHz, CD₃OD) ppm δ 7.55-7.37 (m, 2H, H-5+H-6), 7.23 (bd, J=7.8 Hz, 1H, H-7), 3.98 (t, J=7.5 Hz, 2H, H-2), 3.83 (t, J=6.9 Hz, 2H, H-14), 3.74 (s, 3H, H-17), 3.53+3.42 (q, J=7.2 Hz, 2H, H-11), 3.24 (t, J=7.5 Hz, 2H, H-3), 3.00+3.13 (bs, 3H, H-13), 2.95 (t, J=6.9 Hz, 2H, H-15), 1.34-1.13 (m, 3H, H-12); ¹³C-NMR (50 MHz, CD₃OD) ppm δ 172.23, 154.73, 149.90, 143.98, 131.08, 129.25, 123.94, 116.06, 55.46, 52.79, 45.33, 34.72, 34.44, 30.46, 26.78, 13.44, 12.60; MS (CI⁺) m/z 306.165 (M·⁺, 88.18), 307.169 (MH⁺, 99.99); HRMS calcd. for $C_{16}H_{23}N_2O_4$ (MH⁺, CI/CH₄) 307.1658. found 307.1689.

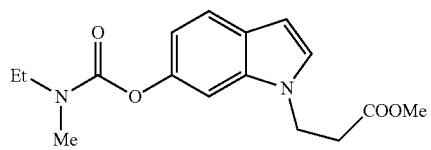 [SMILES: CCN(C)C(=O)Oc1ccc2ccn(CCC(=O)OC)c2c1]

Methyl 3-(6-((Ethyl(methyl)carbamoyl)oxy)-1H-indol-1-yl)propanoate, AN-1246

Compound AN-1246 prepared by procedure N. The reaction product was dissolved in dichloromethane, and filtered through a plug of silica gel, eluted with EtOAc-hexane (1:5). Evaporation of the filtrate gave the product as a white solid, mp 94-96° C., in 85% yield. $^1$H-NMR (300 MHz, CDCl$_3$) ppm δ 7.55 (d, J=8.4 Hz, 1H, H-4), 7.16-7.09 (m, 2H, H-2+H-5), 6.88 (bd, J=8.1 Hz, 1H, H-7), 6.45 (d, J=3.5 Hz, 1H, H-3), 4.39 (t, J=6.9 Hz, 2H, H-14), 3.65 (s, 3H, H-17), 3.57-3.40 (m, 2H, H-11), 3.11+3.02 (bs, 3H, H-13), 2.81 (t, J=6.9 Hz, 2H, H-15), 1.34-1.18 (m, 3H, H-12); $^{13}$C-NMR (75 MHz, CDCl$_3$) ppm δ 171.69, 147.36, 135.81, 128.41, 126.35, 121.29, 114.47, 102.50, 101.82, 52.00, 44.16, 41.97, 34.79, 34.20, 33.93, 13.39, 12.70; MS (CI$^+$) m/z 304.145 (M$^{.+}$, 100.00), 305.150 (MH$^+$, 67.59), 86.056 ((C$_4$H$_8$NO)$^+$, 95.87); HRMS calcd. for C$_{16}$H$_{20}$N$_2$O$_4$ (M$^+$, CI/CH$_4$) 304.1423. found 304.1450, for C$_{16}$H$_{21}$N$_2$O$_4$ (MH$^+$, CI/CH$_4$) 305.1501. found 305.1505.

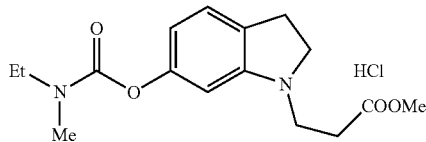 [SMILES: CCN(C)C(=O)Oc1ccc2c(c1)N(CCC(=O)OC)CC2 ; Cl]

Methyl 3-(6-((Ethyl(methyl)carbamoyl)oxy)indolin-1-yl)propanoate AN-1247A

Compound AN-1247A prepared by procedure E Method I, was isolated by chromatography eluted with EtOAc-hexane (1:9), as a white solid, in 31% yield. $^1$H-NMR (300 MHz, CDCl$_3$) ppm δ 6.97 (d, J=7.9 Hz, 1H, H-4), 6.30 (bd, J=7.9 Hz, 1H, H-5), 6.24 (s, 1H, H-7), 3.68 (s, 3H, H-17), 3.50-3.36 (m, 6H, H-2+H-11+H-14), 3.04+2.98 (bs, 3H, H-13), 2.92 (t, J=8.4 Hz, 2H, H-3), 2.59 (t, J=7.9 Hz, 2H, H-15), 1.27-1.14 (m, 3H, H-12).

Methyl 3-(6-((Ethyl(methyl)carbamoyl)oxy)indolin-1-yl)propanoate hydrochloride, AN-1247B The hydrochloride salt AN-1247B was crystallized from MeOH-ether as a white solid, mp 131-134° C., in quantitative yield. $^1$H-NMR (300 MHz, CD$_3$OD) ppm δ 7.47 (d, J=8.4 Hz, 1H, H-4), 7.37 (s, 1H, H-7), 7.19 (bd, J=8.4 Hz, 1H, H-5), 3.99 (t, J=7.5 Hz, 2H, H-2), 3.81 (t, J=7.0 Hz, 2H, H-14), 3.74 (s, 3H, H-17), 3.57-3.38 (m, 2H, H-11), 3.30 (t, J=7.5 Hz, 2H, H-3) 3.11+2.99 (bs, 3H, H-13), 2.93 (t, J=7 Hz, 2H, H-15), 1.31-1.15 (m, 3H, H-12); $^3$C-NMR (75 MHz, CD$_3$OD) ppm δ 172.37, 155.781, 152.88, 143.11, 133.00, 127.59, 124.07, 113.23, 56.19, 52.792, 52.663, 45.32, 45.22, 34.64, 34.33, 30.44, 28.59, 13.42, 12.60; MS (CI$^+$) m/z 306.167 (M$^{.+}$, 38.43), 307.167 (MH$^+$, 67.12), 233.149 (M-C$_3$H$_5$O$_2$, 39.42); HRMS calcd. for C$_{16}$H$_{23}$N$_2$O$_4$ (MH$^+$, CI/CH$_4$) 307.1658. found 307.1669.

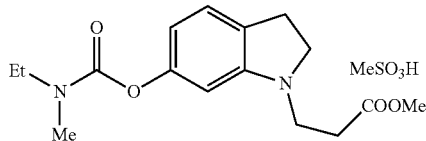 [SMILES: "MeSO3H" ; CCN(C)C(=O)Oc1ccc2c(c1)N(CCC(=O)OC)CC2]

Methyl 3-(6-((Ethyl(methyl)carbamoyl)oxy)indolin-1-yl)propanoate methanesulfonate, AN-1247C Compound AN-1247C prepared from AN-1247A (89 mg, 0.29 mmol) that was treated with a solution of methanesulfonic acid (0.018 mL, 0.29 mmol) in dry CH$_2$Cl$_2$ (2 mL, 0.29 mmol). It was isolated as a white crystalline solid from MeOH-ether in quantitative yield. $^1$H-NMR (300 MHz, CD$_3$OD) ppm δ 7.47 (d, J=8.4 Hz, 1H, H-4), 7.37 (s, 1H, H-7), 7.19 (bd, J=8.4 Hz, 1H, H-5), 3.99 (t, J=7.5 Hz, 2H, H-2), 3.81 (t, J=7.0 Hz, 2H, H-14), 3.74 (s, 3H, H-17), 3.57-3.38 (m, 2H, H-11), 3.30 (t, J=7.5 Hz, 2H, H-3) 3.11+2.99 (bs, 3H, H-13), 2.93 (t, J=7 Hz, 2H, H-15), 1.31-1.15 (m, 3H, H-12); $^{13}$C-NMR (150 MHz, CD$_3$OD) ppm δ 172.94, 156.02, 152.90, 145.95, 131.85, 127.04, 55.90, 52.66, 51.21, 51.15, 45.29, 45.19, 39.45, 34.60, 34.29, 31.08, 28.65, 13.40, 12.59.

Example 2

Procedure A

Reduction of Nitro Compounds

To a solution of a nitro substituted compound (24 mmol) in MeOH or EtOH (400 mL) was slowly added 10% PdC (0.4 g). The mixture was stirred at room temperature for 24 h under a H$_2$ atmosphere. The catalyst was removed by filtration through celite and the filtrate was concentrated to give the product.

Procedure B

Synthesis of a Benzimidazole

A solution of an o-diaminobenzene (0.59 mmol) in formic acid (7 mL) was refluxed for 5-6 h and was then evaporated to dryness. The residue was partitioned between EtOAc (15 mL) and concentrated 15% NaOH, where the pH of the aqueous phase was approximately 8. The layers were separated and theaqueous layer was further extracted with EtOAc. The combined organic extract was driedover MgSO$_4$ and evaporated under reduced pressure to give the benzimidazole.

Procedure C

Aza-Michael Reaction

To a magnetically stirred solution of a benzimidazole (1.34 mmol) and methyl acrylate (2.7 mmol) in CH$_3$CN (3 mL) was added DBU (0.67 mmol) at room temperature. After 4 h, the mixture was evaporated and the residue was partitioned between EtOAc (20 mL) and sat. aq. NaHCO$_3$ (5 mL). The aqueous layer was extracted with additional EtOAc (5×20 mL), and the organic layers were combined, washed with brine, dried over MgSO$_4$, filtered and evaporated to give the N-alkylated product.

Procedure D

Protection with TBSCl

To a solution of a phenol (6.53 mmol) in DMF (8 mL), under N$_2$ at rt was added imidazole (8.36 mmol). The mixture was stirred at rt for 10 min TBSCl (8.36 mmol) was then added and the obtained mixture was stirred at 2 h. The mixture was then diluted with CH$_2$Cl$_2$ and extracted with water (2×30 mL). The organic layer was washed with brine, dried over MgSO$_4$, filtered and evaporated under reduced pressure to give the TBS-protected phenol.

Procedure E

Synthesis of Carbamates

A carbamoyl chloride (0.82 mmol) was added to a solution of 5-substituted-benzimidazole; or to 4-, 6- or 7-hydroxyindole (0.41 mmol) in dry CH$_2$Cl$_2$ (2 mL) containing DBU (0.45 mmol) and 4-DMAP (10% mol). The mixture was stirred at rt for 2-72 h and was then quenched by addition of water. The organic phase was separated and the aqueous phase was extracted with CH$_2$Cl$_2$. The combined organic layer was washed with 5% NaHCO$_3$ or 2N NaOH, brine, dried over MgSO$_4$ and evaporated to give the crude carbamates, which were purified by chromatography.

Procedure F

One-Pot Synthesis of a Benzimidazole

To a stirred mixture of an o-nitroaniline (3 mmol), iron powder (30 mmol) and NH$_4$Cl (30 mmol), were added 2-PrOH (5 mL) and formic acid (5 mL), and the vial was sealed with a Teflon-lined cap. The mixture was stirred at 80° C. for 2 h, and was then diluted with 2-PrOH (10 mL) and filtered. The filtrate was concentrated to dryness, and the residue was partitioned between EtOAc (20 mL) and sat. aq. NaHCO$_3$ (5 mL). The aqueous layer was extracted with additional EtOAc (5×20 mL), and the combined organic layer was washed with brine, dried over MgSO$_4$, filtered and evaporated to give the benzimidazole.

Procedure J

Amine Alkylation

A solution of a benzimidazole (1.1 mmol), of ethylbromoacetate (1.54 mmol) and K$_2$CO$_3$ (2 mmol) in 4 mL of DMF was stirred at room temperature for 72 h. The solvent was then evaporated and the residue was dissolved in a mixture of 2 mL of water and 30 mL of MeCN. The obtained solution was dried over anhydrous Na$_2$SO$_4$ and the solvent was evaporated to give the N-alkylated product.

Procedure K

Synthesis of indolyl-3-oxoacetyl chlorides

To a solution of an indole (8.96 mmol) in anhydrous diethyl ether (12 mL) with stirring in an ice bath was added oxalyl chloride (13.09 mmol). After stirring for 15 min, n-hexane (24 mL) was added, and the reaction flask was placed in a freezer and stored overnight. The resulting yellow crystals were separated from the solution by filtration.

Procedure L

Synthesis of indolyl-3-oxoacetamides

The indolyl-oxoacetyl chloride (4.15 mmol) was dissolved in (15 mL) DCM, to which was added 4 mL of a 2 M dimethylamine THF solution. The mixture was stirred for 4 h at room temperature, the solvent was then evaporated and the residue was dissolved in EtOAc and washed with saturated aqueous NaHCO$_3$, brine, dried over anhydrous Na$_2$SO$_4$, filtered and evaporated to give the indolyl-oxoacetamide.

Procedure M

Synthesis of 3-(2-(dimethylamino)ethyl)-1H-indoles

To a suspension of LiAlH$_4$ (14.4 mmol) in anhydrous THF (45 mL) was dropwise added a solution of an indolyl-oxoacetamide (4.11 mmol) in anhydrous THF (15 mL), and then the mixture was refluxed for 2 h. After cooling to room temperature, water and a solution of 15% NaOH was added dropwise to destroy the excess hydride, the mixture was filtered through celite, and the filtrate was evaporated to give the 3-(2-(dimethylamino)ethyl)-1H-indols.

Procedure N

Protection of Amine with Boc

A mixture of an indole (5 mmol), tert-Boc$_2$O (5 mmol), and 4-DMAP (0.5 mmol) in dry CH$_2$Cl$_2$ (15 mL) was stirred at room temperature for 24 h. The mixture was diluted with CH$_2$Cl$_2$ and extracted water. The organic layer was washed with brine and dried over Na$_2$SO$_4$, filtered and evaporated to give the N-Boc protected product.

Procedure O

Deprotection of the O-Benzyl Group and Reduction of the Indole

To a solution of an indolic derivative protected with benzyl group (1 eq) in EtOH, was added 10% or 5% PdC (10% ww) or (1 eq). The mixture was stirred under H$_2$ at a 1 atm pressure for 2 h-2 d at room temperature. The mixture was then filtered through celite and concentrated to give the deprotected indole or indoline.

Procedure P

Removal of N-Tert-Boc Group and Preparation of Hydrochloride Salt

HCl gas was slowly bubbled through a cold (0-3° C.) solution of an N-Boc protected compound (0.1 mmol) in dry ether (5 mL) during 3 h. The reaction was monitored by TLC till the disappearance of the starting material. The mixture was evaporated to give the hydrochloride salt.

Procedure Q

Synthesis of 3-(2-(dimethylamino)methyl)-1H-indoles

An indole (4.48 mmol), AcOH (1 mL), 2 M dimethylamine (5.37 mmol), and 37% formaldehyde (5 mmol), were mixed together at 5° C. and stirred at room temperature for 24 h. The solvent was then evaporated and the residue was dissolved in DCM and acidified with 4N HCl, the aqueous phase was separated and extracted with 24% NaOH. The organic layer was washed with brine, dried over Na$_2$SO$_4$, filtered and evaporated to give the indolyl-3-methyl(dimethylamine).

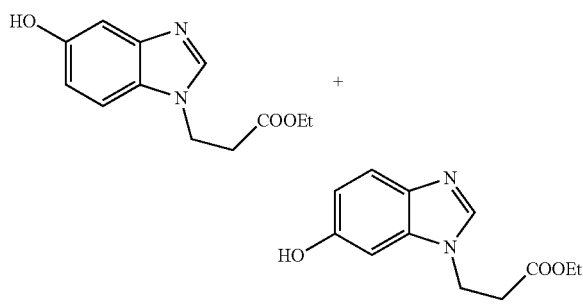 [SMILES: CCOC(=O)CCn1cnc2cc(O)ccc21 ; CCOC(=O)CCn1cnc2ccc(O)cc21]

Ethyl 3-(5-hydroxy-1H-benzo[d]imidazol-1-yl)propanoate and Ethyl 3-(6-hydroxy-1H-benzo[d]imidazol-1-yl)propanoate, AN-1269 (1-325)

The mixture of isomers AN-1269 prepared by procedure J, was isolated as a red solid in quantitative yield. $^1$H-NMR (300 MHz, Acetone-d$_6$) ppm δ 8.02+7.95 (s, 1H, H-2, H-2'), 7.44+7.39 (d, J=8.40 Hz, 1H, H-7, H-7'), 7.15+7.03 (d, J=1.8 Hz, 1H, H-4, H-4'), 6.90+6.84 (dd, J=8.40, 1.8 Hz, 1H, H-6, H-5' or H-6', H-5), 4.53+4.47 (t, J=6.6 Hz, 2H, H-10, H-10'), 4.06 (q, J=7.20 Hz, 2H, H-13, H-13'), 2.92 (m, 2H, H-11, H-11'), 1.14 (t, J=7.20, 3H, H-14, H-14').

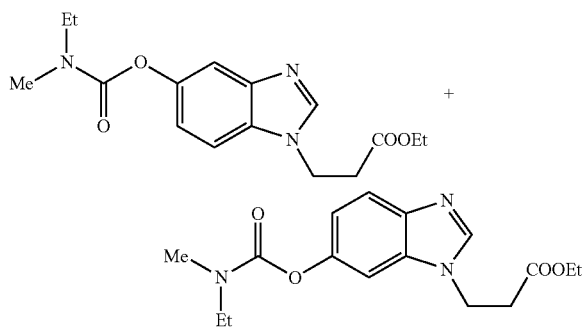

Ethyl 3-(5-(ethyl(methyl)carbamoyloxy)-1H-benzo[d]imidazol-1-yl)propanoate and Ethyl 3-(6-(ethyl(methyl)carbamoyloxy)-1H-benzo[d]imidazol-1-yl)propanoate, AN-1268 (1-330)

The mixture of isomers AN-1268, prepared by procedure E, was isolated as a yellow oil in 30% yield. $^1$H-NMR (300 MHz, Acetone-d$_6$) ppm δ 8.11+8.09 (s, 1H, H-2, H-2'), 7.61+7.55 (d, J=8.72 Hz, 1H, H-7, H-7'), 7.40 (m, 1H, H-4, H-4'), 7.05+6.99 (dd, J=8.72, 2.4 Hz, 1H, H-6, H-5'), 4.57 (dt, J=6.69 Hz, 2H, H-10, H-10'), 4.06 (m2H, H-13, H-13'), 3.52+3.38 (m, 2H, H-17, H-17'), 3.10 (m, 3H, H-16, H-16'), 2.94 (m, 2H, H-11, H-11'), 1.19 (m, 6H, H-14, H-14', H-18, H-18'). $^{13}$C-NMR (75 MHz, Acetone-d$_6$) ppm δ 171.51 (C-12, C-12'), 148.69+148.08 (C-9, C-8' or C-9', C-8), 145.71+145.29 (C-2, C-2'), 120.45+118.19 (C-6, C-5'), 117.38+113.50 (C-7, C-7'), 110.57+104.42 (C-4, C-4'), 61.18 (C-13, C-13'), 44.53 (C-10, C-10'), 41.19+41.10 (C-17, C-17'), 34.99 (C-11, C-11'), 34.34+34.06 (C-16, C-16'), 14.36 (C-14, C-14'), 13.51+12.70 (C-18, C-18').

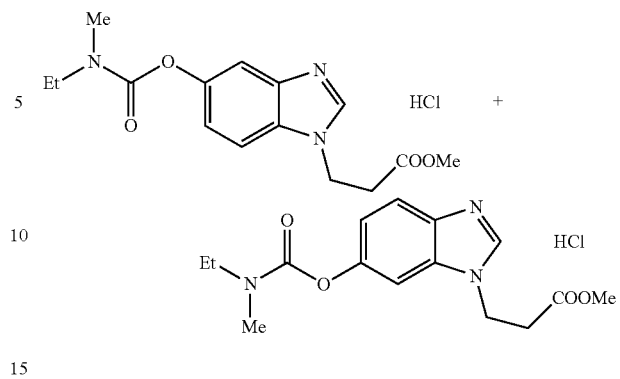

Methyl 3-(6-((ethyl(methyl)carbamoyl)oxy)-1H-benzo[d]imidazol-1-yl)propanoate and Methyl 3-(5-((ethyl(methyl)carbamoyl)oxy)-1H-benzo[d]imidazol-1-yl)propanoate hydrochloride, AN-1257 (SF-I-336)

The mixture of isomers AN-1257, prepared by procedure P, was isolated as an orange oil in quantitative yield. $^1$H-NMR (300 MHz, Acetone-d$_6$) ppm δ 9.61 (s, 1H, H-2, H-2'), 7.90+7.82 (d, J=8.98 Hz, 1H, H-7, H-7'), 7.72+7.60 (m, 1H, H-4, H-4'), 7.27+7.22 (m, 1H, H-6, H-5'), 4.80 (dt, J=7 Hz, 2H, H-10, H-10'), 3.98+3.88 (m2H, H-13, H-13'), 3.41+3.23 (m, 2H, H-17, H-17'), 3.08 (m, 2H, H-11, H-11'), 2.99+2.84 (s, 3H, H-16, H-16'), 1.15+0.99 (m, 6H, H-14, H-14', H-18, H-18'). $^{13}$C-NMR (75 MHz, Acetone-d$_6$) ppm δ 171.20 (C-12, C-12'), 150.93 (C-15, C-15'), 142.91 (C-2, C-2'), 122.20+121.96 (C-6, C-5'), 116.61+114.06 (C-7, C-7'), 109.36+107.06 (C-4, C-4'), 61.43 (C-13, C-13'), 44.69 (C-10, C-10'), 43.44+43.36 (C-17, C-17'), 34.46 (C-16, C-16'), 34.10+34.04 (C-11, C-11'), 14.36 (C-14, C-14'), 13.50+12.64 (C-18, C-18').

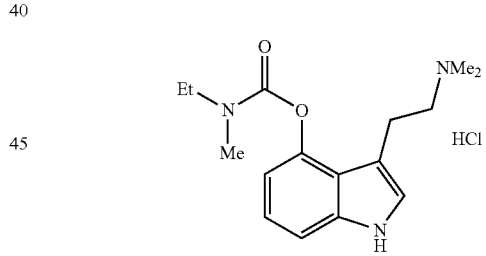

3-(2-(Dimethylamino)ethyl)-1H-indol-4-yl ethyl (methyl)carbamate hydrochloride, AN-1252 (SF-II-67)

Compound AN-1252 was isolated as a off-white amorphous solid in 13% yield. $^1$H-NMR (300 MHz, MeOD) ppm δ 7.28 (d, J=8.1 Hz, 1H, H-7), 7.24 (s, 1H, H-2), 7.11 (t, J=8.1 Hz, 1H, H-6), 6.69 (m, 1H, H-5), 3.62+3.46 (m, 2H, H-15), 3.46+3.20 (m, 4H, H-10, H-11), 3.03+3.22 (s, 3H, H-14), 2.87 (s, 6H, H-12), 1.22-1.33 (m, 3H, H-16); $^{13}$C-NMR (50 MHz, MeOD) ppm δ 157.17 (C-13), 145.84 (C-8), 140.64 (C-4), 125.36 (C-6), 123.10 (C-2), 121.18 (C-9), 113.34+133.13 (C-5), 110.53 (C-7), 108.33 (C-3), 59.64 (C-11), 47.71 (C-15), 45.36 (C-12), 34.63 (C-14), 22.90 (C-10), 13.69+12.77 (C-16).

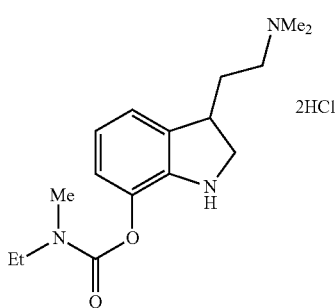 [SMILES: CCN(C)C(=O)Oc1cccc2c1NCC2CCN(C)C ; "2HCl"]

3-(2-(Dimethylamino)ethyl)indolin-7-yl ethyl(methyl)carbamate dihydrochloride, AN-1253 (SF-II-102a)

Compound AN-1253 was isolated as a brown foam in 11% yield. $^1$H-NMR (400 MHz, MeOD) ppm δ 7.55 (t, J=7.8 Hz, 1H, H-5), 7.44 (d, J=7.8 Hz, 1H, H-4), 7.30 (m, 1H, H-6), 4.06 (dd, J=11.6, 8.00 Hz, 1H, H-2), 3.78 (m, 1H, H-3), 3.68 (m, 1H, H-2'), 3.57+3.44 (q, J=7.2 Hz, 2H, H-15), 3.35 (m, 2H, H-11), 3.15+3.02 (s, 3H, H-14), 2.93 (s, 6H, H-12), 2.39+2.12 (m, 2H, H-10), 1.28+1.21 (t, J=3.2 Hz, 3H, H-16); $^{13}$C-NMR (100 MHz, MeOD) ppm δ 154.20+154.14 (C-13), 144.25 (C-8), 141.16+141.11 (C-7), 132.60 (C-4), 128.90 (C-9), 123.74 (C-5), 123.35+123.39 (C-6), 56.23 (C-11), 52.26 (C-2), 45.57+45.39 (C-15), 43.66+43.54 (C-3), 40.86 (C-12), 34.79+34.54 (C-14), 29.77+29.74 (C-10), 13.47+12.57 (C-16).

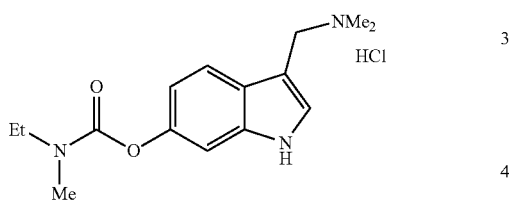

3-((Dimethylamino)methyl)-1H-indol-6-yl ethyl(methyl)carbamate hydrochloride, AN-1254 (SF-II-124)

Compound AN-1254 was isolated as a brown foam in 52% yield.

Example 3

Procedure V: Knoevenagel condensation. A solution of dioxane (3 mL), cyanoacetic acid or tetrazoleacetic acid (1.5 mmol), and Et$_3$N (3.8 mmol) was stirred for 10 min at room temperature. 1H-formylindole (1.0 mmol) and piperidine (2.2 mmol) were added, and the mixture was stirred at reflux temperature 2-24 h. In cases where the reaction progress was slow (as monitored by TLC in ethyl acetate hexane 2:1), a piperidine aliquot was added. When the reaction finished, the mixture cooled to room temperature, diluted with EtOAc and washed with 1M KHSO$_4$ and brine, dried over Na$_2$SO$_4$ and concentrated to give the product.

Procedure VI: Reduction of α,β-unsaturated cyano compounds. A stirred suspension of an α,β-unsaturated cyano compound (1.0 mmol) in absolute EtOH (5 mL), and CHCl$_3$ (0.25 mL) containing PtO$_2$ (10 wt %) was placed, at room temperature, under H$_2$ at atmospheric pressure. After 24 h, the mixture was filtered through celite and washed with MeOH. The solvent was removed under reduce pressure and the residue was dissolved in EtOAc and washed with 1M KHSO$_4$. The acidic phase was separated and NaOH (solid) was added until pH~14. The mixture was then extracted with EtOAc, and brine, dried over Na$_2$SO$_4$ and concentrated to give the product which crystallized from CHCl$_3$: MeOH.

Procedure VII: Reduction of indoles. Et$_3$SiH (3 mmol) was added to a solution of 1H-indole (1 mmol) in TFA (8 mL) and the mixture was stirred at 70° C. for 4 h. After evaporation of the solvent, the residual oil was made basic (pH 10-14) by addition of 8% aqueous NaOH and extracted with EtOAc. The organic phase was washed with brine, dried over Na$_2$SO$_4$ and evaporated under reduced pressure to give oil, which was purified by flash chromatography. In cases of tetrazole derivatives the solvent was evaporated and the products were isolated by flash chromatography.

Procedure VIII: Preparation of amine hydrochloride salts. HCl gas was slowly bubbled through a solution of an amino derivative of an indole or indoline compound in absolute EtOH. The solvent was evaporated to give the hydrochloride salt.

Procedure IX: Preparation of tetrazole potassium salts. To a solution of a tetrazole (1 mmol) in EtOH, Me$_3$SiO$^-$K$^+$ (1 mmol) was added, and the obtained solution was stirred at room temperature for 1 h. The solvent was evaporated and the product was crystallized from ether or hexane.

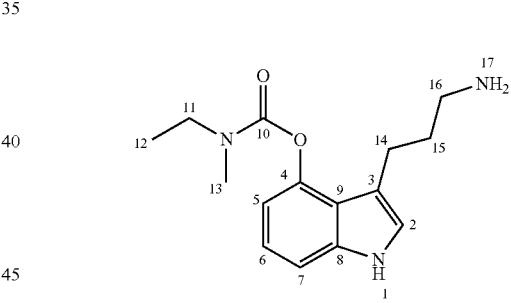

3-(3-Aminopropyl)-1H-indol-4-yl ethyl(methyl)carbamate, AN-919 (EN-I-255)

AN-919 prepared by procedure VI, was purified by chromatography, eluted with EtOAc:MeOH (10:1→5:1→1:1), as a yellow solid in 77.5% yield, mp 68-72° C. $^1$H-NMR (600 MHz, CDCl$_3$) ppm δ 9.76+9.75 (s, 1H, H-1), 7.76 (bs, 2H, H-17), 7.19+7.18 (d, J=7.8 Hz, 1H, H-7), 6.99+6.98 (t, J=7.8 Hz, 1H, H-6), 6.65+6.61 (d, J=7.8 Hz, 1H, H-5), 6.54+6.49 (s, 1H, H-2), 3.41+3.33 (q, J=6.6 Hz, 2H, H-11), 2.99+2.93 (s, 3H, H-13), 2.54 (m, 2H, H-14), 2.40 (m, 2H, H-16), 1.79 (m, 2H, H-15), 1.17+1.11 (t, J=7.2 Hz, 3H, H-12). $^{13}$C-NMR (150 MHz, CDCl$_3$) ppm δ 155.99+155.78 (C-10), 144.4+144.41 (C-4), 138.80 (C-8), 123.52+123.47 (C-6), 121.55 (C-3), 120.20+120.12 (C-9), 112.20+112.00 (C-2), 111.49+111.44 (C-5), 109.69 (C-7), 44.39+44.19 (C-11), 39.17+39.11 (C-16), 34.43+33.97 (C-13), 27.25 (C-15), 22.68+22.60 (C-14), 13.34+12.67 (C-12).

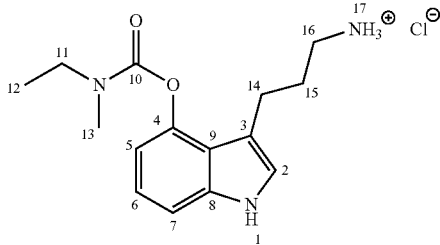

3-(4-((Ethyl(methyl)carbamoyl)oxy)-1H-indol-3-yl)propan-1-aminium chloride, AN-910 (EN-I-257)

AN-910 was prepared by procedure VIII to give a yellow solid in quantitative yield. $^1$H-NMR (300 MHz, MeOD) ppm δ 7.90 (s, 3H, H-17), 7.24+7.23 (d, J=8.4 Hz, 1H, H-7), 7.08 (s, 1H, H-2), 7.07 (t, J=7.8 Hz, 1H, H-6), 6.67+6.66 (d, J=7.2 Hz, 1H, H-5), 3.63+3.45 (q, J=7.1 Hz, 2H, H-11), 3.23+3.05 (s, 3H, H-13), 2.92-2.83 (m, 4H, H-14, H-16), 2.0 (quin, J=7.4 Hz, 2H, H-15), 1.33+1.22 (t, J=6.8 Hz, 3H, H-12).

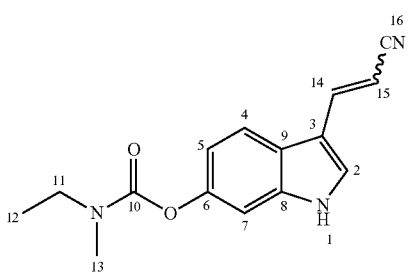

3-(2-Cyanovinyl)-1H-indol-6-yl ethyl(methyl)carbamate, AN-920 (EN-I-258)

AN-920 was prepared by procedure V as a cis/trans mixture where the trans-isomer was the major product, and was purified by column chromatography eluted with EtOAc: Hexane (1:5). Even after chromatography the cis/trans mixture remained since the compound isomerized even in the solution used for determining its NMR spectrum. The product was obtained as an orange solid in 87% yield, mp 175-177° C. (E)-3-(2-cyanovinyl)-1H-indol-6-yl ethyl(methyl)carbamate $^1$H-NMR (300 MHz, CDCl$_3$) ppm δ 9.63 (s, 1H, H-1), 7.48 (d, J=7.48 Hz, 1H, H-4), 7.32 (d, J=16.5 Hz, 1H, H-14), 7.20 (d, J=1.2 Hz, 1H, H-7), 6.92+6.91 (s, 1H, H-2), 6.88 (bd, J=8.7 Hz, 1H, H-5), 5.57 (d, J=16.5 Hz, 1H, H-15), 3.58-3.47 (m, 2H, H-11), 3.14+3.06 (s, 3H, H-13), 1.31+1.23 (t, J=7.2 Hz, 3H, H-12). $^{13}$C-NMR (75 MHz, CDCl$_3$) ppm δ 155.67 (C-10), 147.70 (C-6), 143.84 (C-14), 137.38 (C-8), 130.18 (C-2), 122.19 (C-9), 120.09 (C-4, C-3), 115.81+115.72 (C-5), 112.28 (C-16), 106.37 (C-7), 89.53 (C-15), 44.37 (C-11), 34.35+34.05 (C-13), 13.35+12.67 (C-12). (Z)-3-(2-cyanovinyl)-1H-indol-6-yl ethyl(methyl)carbamate $^1$H-NMR (300 MHz, CDCl$_3$) ppm δ 9.76 (s, 1H, H-1), 7.72+7.71 (s, 1H, H-2), 7.39 (d, J=8.4 Hz, 1H, H-4), 7.19 (d, J=11.7 Hz, 1H, H-14), 6.97 (s, 1H, H-7), 6.83 (d, J=8.7 Hz, 1H, H-5), 5.07 (d, J=11.7 Hz, 1H, H-15), 3.59-3.44 (m, 2H, H-11), 3.14+3.07 (s, 3H, H-13), 1.24-1.34 (m, 3H, H-12). $^{13}$C-NMR (75 MHz, CDCl$_3$) ppm δ 155.67 (C-10), 147.51 (C-6), 140.47 (C-14), 135.56 (C-8), 127.98 (C-2), 124.30 (C-9), 119.92 (C-3), 118.23 (C-4), 115.23+ 115.13 (C-5), 110.90 (C-16), 106.17 (C-7), 87.14 (C-15), 44.38 (C-11), 34.56+34.05 (C-13), 13.36+12.70 (C-12).

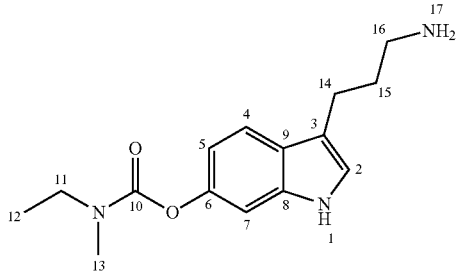 [SMILES: CCN(C)C(=O)Oc1ccc2c(CCCN)c[nH]c2c1]

3-(3-Aminopropyl)-1H-indol-6-yl ethyl(methyl) carbamate AN-925 (EN-I-263)

AN-925 prepared by procedure VI, was purified by chromatography, eluted with EtOAc:EtOH:NH$_3$ (20:1:1), and isolated as a viscous yellow solid in 33.7% yield. $^1$H-NMR (600 MHz, CDCl$_3$) ppm δ 8.32 (s, 1H, H-1), 7.49 (d, J=8.4 Hz, 1H, H-4), 7.09 (bs, 1H, H-7), 6.85 (m, 2H, H-5, H-2), 3.50+3.42 (bq, J=6.6 Hz, 2H, H-11), 3.09+3.00 (s, 3H, H-13), 2.74-2.71 (m, 4H, H-16, H-14), 1.82 (quin, J=6.6 Hz, 2H, H-15), 1.25+1.19 (m, 3H, H-12). $^{13}$C-NMR (150 MHz, CDCl$_3$) ppm δ 155.66+155.48 (C-10), 147.35 (C-6), 136.44 (C-8), 125.32 (C-9), 121.82 (C-2), 119.07 (C-4), 115.97 (C-3), 113.76 (C-5), 104.54 (C-7), 44.19 (C-11), 41.94 (C-16), 34.41+33.95 (C-13), 33.70 (C-15), 22.55 (C-14), 13.37+12.66 (C-12).

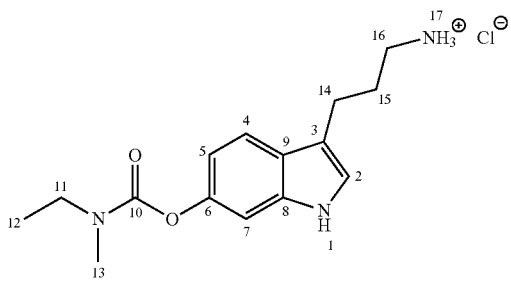 [SMILES: [Cl-] ; CCN(C)C(=O)Oc1ccc2c(CCC[NH3+])c[nH]c2c1]

3-(6-((Ethyl(methyl)carbamoyl)oxy)-1H-indol-3-yl)propan-1-aminium chloride, AN-911 (EN-I-266)

AN-911 prepared by procedure VIII was isolated in quantitative yield. $^1$H-NMR (600 MHz, MeOD) ppm δ 7.51 (d, J=8.4 Hz, 1H, H-4), 7.10 (s, 1H, H-2), 7.08 (d, J=1.2 Hz, 1H, H-7), 6.77 (dd, J=8.4, 1.2 Hz, 1H, H-5), 3.53+3.40 (m, 2H, H-11), 3.12+2.99 (s, 3H, H-13), 2.93 (t, J=7.5 Hz, 2H, H-16), 2.85 (t, J=7.5 Hz, 2H, H-14), 2.04 (quin, J=7.8 Hz, 2H, H-15), 1.20-1.29 (m, 3H, H-12). $^{13}$C-NMR (150 MHz, MeOD) ppm δ 157.26 (C-10), 148.30 (C-6), 138.07 (C-8), 126.30 (C-9), 123.95 (C-2), 119.43 (C-4), 114.56 (C-3), 114.47+114.41 (C-5), 105.54 (C-7), 45.12 (C-11), 40.52 (C-16), 34.55+34.28 (C-13), 29.29 (C-15), 23.00 (C-14), 13.45+12.69 (C-12).

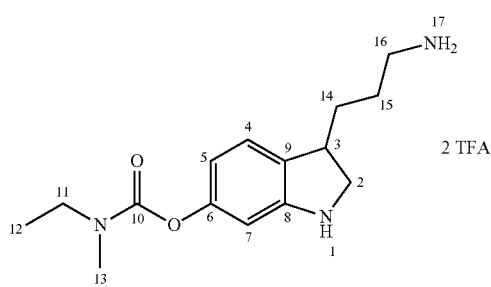 [SMILES: CCN(C)C(=O)Oc1ccc2c(c1)NCC2CCCN]

3-(3-Aminopropyl)indolin-6-yl ethyl(methyl)carbamate ditrifluoroacetate, AN-921 (EN-I-268)

AN-921 prepared by procedure VII, was isolated by chromatography, eluted with CH$_2$Cl$_2$:EtOH (40:1→30:1→10:1), as a yellow solid in 75% yield. $^1$H-NMR (400 MHz, MeOD) ppm δ 7.04 (d, J=8.8 Hz, 1H, H-4), 6.37-6.34 (m, 2H, H-5, H-7), 3.66 (t, J=7.8 Hz, 1H, H-2), 3.46+3.37 (bq, J=7.0 Hz, 2H, H-11), 3.28-3.22 (m, 1H, H-3), 3.21 (t, J=6.8 Hz, 1H, H-2), 3.05+2.96 (s, 3H, H-13), 2.95-2.92 (m, 2H, H-16), 1.89-1.81 (m, 1H, H-14), 1.79-1.68 (m, 2H, H-15), 1.64-1.52 (m, 1H, H-14), 1.23+1.16 (t, J=6.8 Hz 3H, H-12). $^{13}$C-NMR (150 MHz, MeOD) ppm δ 156.71 (C-10), 154.16 (C-8), 152.85 (C-6), 131.00 (C-9), 124.89 (C-4), 112.42+112.33 (C-5), 104.92+104.84 (C-7), 54.33 (C-2), 45.07 (C-11), 42.20 (C-3), 40.15 (C-16), 34.49+34.21 (C-13), 32.12 (C-15), 26.18 (C-14), 13.36+12.61 (C-12).

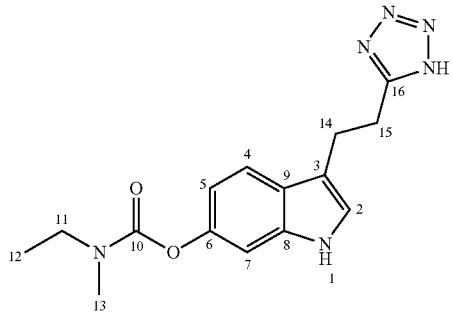

3-(2-(1H-tetrazol-5-yl)ethyl)-1H-indol-6-yl ethyl (methyl)carbamate, AN-923 (EN-I-309)

AN-923 prepared by procedure II was isolated as an orange solid in 32% yield, mp 164-167° C. $^1$H-NMR (300 MHz, MeOD) ppm δ 7.40 (d, J=8.4 Hz, 1H, H-4), 7.06 (s, 1H, H-7), 6.62 (s, 1H, H-2), 6.75 (d, J=8.4 Hz, 1H, H-5), 3.47+3.60 (q, J=6.6 Hz, 2H, H-11), 3.28-3.12 (m, 4H, H-14, H-15), 3.08+2.95 (s, 3H, H-13), 1.24+1.17 (t, J=6.6 Hz, 3H, H-12). $^{13}$C-NMR (75 MHz, CDCl$_3$) ppm δ 157.74 (C-16), 157.23 (C-10), 148.22 (C-6), 137.86 (C-8), 126.08 (C-9), 124.04 (C-2), 119.25 (C-4), 114.51 (C-5), 114.02 (C-3), 105.53 (C-7), 45.08 (C-11), 34.54+34.26 (C-13), 25.50 (C-15), 24.56 (C-14), 13.45+12.70 (C-12).

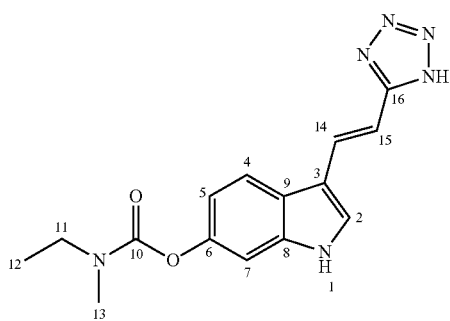 [SMILES: CCN(C)C(=O)Oc1ccc2c(/C=C/c3nnn[nH]3)c[nH]c2c1]

(E)-3-(2-(1H-tetrazol-5-yl)vinyl)-1H-indol-6-yl ethyl(methyl)carbamate, AN-922 (EN-I-304)

AN-922 prepared by procedure V was isolated as an orange solid in 51% yield, mp above 200° C. $^1$H-NMR (700 MHz, MeOD) ppm δ 7.90 (d, J=8.4 Hz, 1H, H-4), 7.86 (d, J=16.8 Hz, 1H, H-14), 7.68 (s, 1H, H-2), 7.20 (s, 1H, H-7), 7.03 (d, J=16.8 Hz, 1H, H-15), 6.96 (bd, J=8.4 Hz, 1H, H-5), 3.55+3.41 (q, J=7.0 Hz, 2H, H-11), 3.13+3.00 (s, 3H, H-13), 1.29+1.20 (t, J=7.0 Hz, 3H, H-12). $^{13}$C-NMR (176 MHz, CDCl$_3$) ppm δ 157.0+156.95 (C-10), 156.50 (C-16), 149.06 (C-6), 139.08 (C-8), 134.61 (C-14), 130.88 (C-2), 124.19 (C-9), 120.90 (C-4), 116.61+116.53 (C-5), 114.08 (C-3), 106.45+106.39 (C-7), 104.13 (C-15), 45.18 (C-11), 34.58+34.31 (C-13), 13.46+12.67 (C-12).

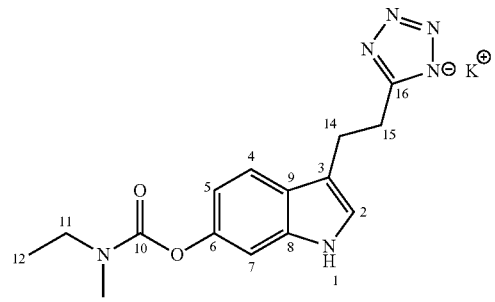

Potassium 5-(2-(6-((ethyl(methyl)carbamoyl)oxy)-1H-indol-3-yl)ethyl)tetrazol-1-ide, AN-915 (EN-I-314)

AN-915 prepared by procedure IX was isolated in quantitative yield. $^1$H-NMR (400 MHz, MeOD) ppm δ 7.51 (d, J=8.4 Hz, 1H, H-4), 7.06 (d, J=2.0 Hz, 1H, H-7), 7.02 (s, 1H, H-2), 6.75 (d, J=8.8, 2 Hz, 1H, H-5), 3.52-3.45+3.40-3.30 (m, 2H, H-11), 3.25-3.13 (m, 4H, H-14, H-15), 3.07+2.95 (s, 3H, H-13), 1.27-1.13 (m, 3H, H-12). $^{13}$C-NMR (100 MHz, CDCl$_3$) ppm δ 163.33 (C-16), 157.30 (C-10), 148.08 (C-6), 137.85 (C-8), 126.58 (C-9), 123.69 (C-2), 119.54 (C-4), 116.04 (C-3), 114.16 (C-3), 105.35 (C-7), 45.07 (C-11), 34.54+34.25 (C-13), 27.45 (C-15), 26.00 (C-14), 13.46+12.71 (C-12).

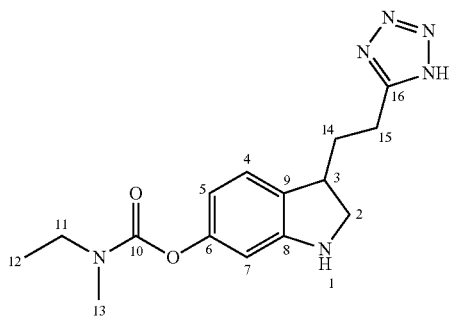 [SMILES: CCN(C)C(=O)Oc1ccc2c(c1)NCC2CCc1nnn[nH]1]

3-(2-(1H-tetrazol-5-yl)ethyl)indolin-6-yl ethyl(methyl)carbamate, AN-924 (EN-I-313)

AN-924 prepared by procedure VII, was isolated by chromatography, eluted with CHCl$_3$:EtOH (40:1→30:1→10:1), as a yellow solid in 66% yield. $^1$H-NMR (300 MHz, MeOD) ppm δ 7.16 (d, J=7.8 Hz, 1H, H-4), 6.62 (bs, 2H, H-5, H-7), 3.75 (t, 1H, J=11.5 Hz, H-2), 3.47 (q, J=6.9 Hz, 1H, H-11), 3.40-3.28 (m, 3H, H-11, H-3, H-2), 3.05+2.94 (s, 3H, H-13), 3.05-2.98 (m, 2H, H-15), 2.28-2.20+2.03-1.91 (m, 2H, H-14), 1.26+1.12 (m, 3H, H-12). $^{13}$C-NMR (75 MHz, CDCl$_3$) ppm δ 157.52 (C-16), 156.35+156.30 (C-10), 152.96 (C-8), 149.46+149.24 (C-6), 132.10 (C-9), 125.58 (C-4), 116.08+115.85 (C-5), 107.81+107.63 (C-7), 53.66 (C-2), 45.08 (C-11), 41.81 (C-3), 34.54+34.24 (C-13), 32.88 (C-15). 21.76 (C-14). 13.40+12.62 (C-12).

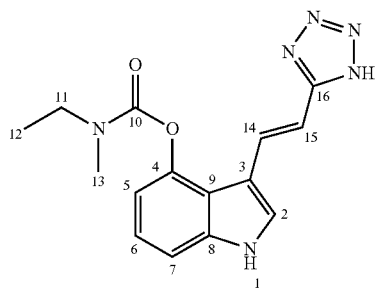 [SMILES: CCN(C)C(=O)Oc1cccc2[nH]cc(/C=C/c3nnn[nH]3)c12]

(E)-3-(2-(1H-tetrazol-5-yl)vinyl)-1H-indol-4-yl ethyl(methyl)carbamate, AN-926 (EN-I-291)

AN-926 prepared by procedure V was isolated as an orange solid in 66% yield, mp above 195° C. $^1$H-NMR (600 MHz, MeOD) ppm δ 7.97+7.98 (d, J=16.2 Hz, 1H, H-14), 7.75+7.73 (s, 1H, H-2), 7.31 (d, J=8.4 Hz, 1H, H-7), 7.16 (t, J=7.8 Hz, 1H, H-6), 6.87+6.86 (d, J=16.2 Hz, 1H, H-15), 6.82 (t, J=7.8 Hz, 1H, H-5), 3.68+3.35 (q, J=7.2 Hz, 2H, H-11), 3.29+2.99 (s, 3H, H-13), 1.32+1.04 (t, J=7.2 Hz, 3H, H-12). $^{13}$C-NMR (150 MHz, CDCl$_3$) ppm δ 156.66+156.56 (C-10), 156.47 (C-16), 146.16+146.01 (C-4), 140.57 (C-8), 134.29+134.18 (C-14), 127.12+126.84 (C-2), 123.64 (C-6), 120.57 (C-9), 115.05+114.73 (C-5), 113.45 (C-3), 110.85+110.75 (C-7), 105.16+105.66 (C-15), 45.33 (C-11), 34.64+34.56 (C-13), 13.58+12.51 (C-12).

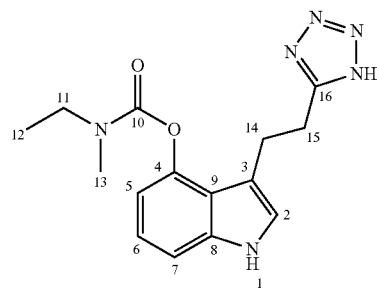 [SMILES: CCN(C)C(=O)Oc1cccc2[nH]cc(CCc3nnn[nH]3)c12]

3-(2-(1H-tetrazol-5-yl)ethyl)-1H-indol-4-yl ethyl (methyl)carbamate, AN-927 (EN-I-301)

AN-927 prepared by procedure II was isolated as a white solid in 76% yield, mp 185-188° C. $^1$H-NMR (200 MHz, MeOD) ppm δ 7.19 (d, J=8.2 Hz, 1H, H-7), 7.03 (t, J=7.8 Hz, 1H, H-6), 6.87 (s, 1H, H-2), 6.67+6.66 (d, J=7.4 Hz, 1H, H-5), 3.51+3.34 (q, J=7.0 Hz, 2H, H-11), 3.21 (s, 4H, H-15, H14), 2.94+2.67 (s, 3H, H-13), 1.20+1.08 (t, J=7.0 Hz, 3H, H-12). $^{13}$C-NMR (50 MHz, CDCl$_3$) ppm δ 158.80 (C-16), 156.98 (C-10), 145.90+145.70 (C-4), 140.48 (C-8), 124.09 (C-2), 122.50 (C-6), 121.30 (C-9), 113.09 (C-5), 112.91 (C-3), 110.27 (C-7), 45.16+45.00 (C-11), 34.40 (C-13), 26.62+26.45 (C-15), 25.75 (C-14), 13.51+12.62 (C-12).

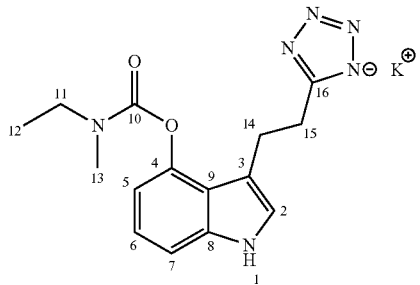 [SMILES: CCN(C)C(=O)Oc1cccc2[nH]cc(CCc3nnn[n-]3)c12 ; [K+]]

Potassium 5-(2-(4-((ethyl(methyl)carbamoyl)oxy)-1H-indol-3-yl)ethyl)tetrazol-1-ide, AN-928 (EN-I-308)

AN-928 prepared by procedure IX was isolated as a white solid in quantitative yield. $^1$H-NMR (200 MHz, MeOD) ppm δ 7.19 (d, J=8.4 Hz, 1H, H-7), 7.03 (t, J=7.8 Hz, 1H, H-6), 6.97+6.96 (s, 1H, H-2), 6.64+6.63 (d, J=7.8 Hz, 1H, H-5), 3.49+3.32 (q, J=7.2 Hz, 2H, H-11), 3.22-3.19+3.18-3.15 (m, 4H, H-15, H14), 3.07+2.92 (s, 3H, H-13), 1.16+1.06 (t, J=7.2 Hz, 3H, H-12). $^{13}$C-NMR (150 MHz, CDCl$_3$) ppm δ 163.22 (C-16), 157.13+157.05 (C-10), 146.08+145.90 (C-4), 140.49 (C-8), 123.71 (C-2), 122.25 (C-6), 121.66 (C-9), 114.90 (C-3), 112.91+112.74 (C-5), 110.11+110.05 (C-7), 45.13+44.95 (C-11), 34.37+34.32 (C-13), 28.03+27.85 (C-15), 26.65+26.58 (C-14), 13.42+12.55 (C-12).

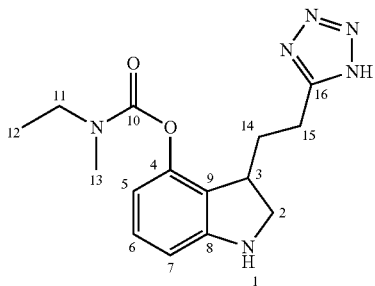 [SMILES: CCN(C)C(=O)Oc1cccc2c1C(CCc1nnn[nH]1)CN2]

3-(2-(1H-tetrazol-5-yl)ethyl)indolin-4-yl ethyl(methyl)carbamate, AN-929 (EN-I-301)

AN-929 prepared by procedure VII, was isolated by chromatography, eluted with CH$_2$Cl$_2$:EtOH (50:1→30:1→20:1) in 39% yield. $^1$H-NMR (400 MHz, MeOD) ppm δ 6.95 (t, J=7.6 Hz, 1H, H-6), 6.37+6.35 (d, J=7.6 Hz, 1H, H-5), 6.33 (d, J=7.6 Hz, 1H, H-7), 3.65 (t, J=9.2 Hz, 1H, H-2), 3.6-3.53 (m, 1H, H-3), 3.50-3.35 (m, 2H, H-11), 3.33-3.30 (m, 1H, H-2), 3.04+2.97 (s, 3H, H-13), 2.95-2.80 (m, 2H, H-15), 2.10-2.01+1.95-1.86 (m, 2H, H-14), 1.18+1.13 (t, J=7.2 Hz, 3H, H-12). $^{13}$C-NMR (100 MHz, CDCl$_3$) ppm δ 156.28 (C-16), 155.71+155.52 (C-10), 153.62 (C-8), 148.40 (C-4), 129.64 (C-6), 122.55 (C-9), 112.67+112.54 (C-5), 107.08 (C-7), 51.82+51.76 (C-2), 44.45 (C-11), 38.90 (C-3), 34.56+34.12 (C-13), 31.46 (C-14), 19.46+19.37 (C-15), 13.27+12.53 (C-12).

3-(2-(1H-tetrazol-5-yl)ethyl)-4-((ethyl(methyl)carbamoyl)oxy)indolin-1-ium chloride, AN-930 (EN-I-305)

AN-930 prepared by procedure VIII was isolated in quantitative yield. $^1$H-NMR (300 MHz, MeOD) ppm δ 7.51 (t, J=7.8 Hz, 1H, H-6), 7.42 (d, J=7.8 Hz, 1H, H-7), 7.27 (d, J=7.8 Hz, 1H, H-5), 4.03 (dd, J=12.6, 1H, 9.3 Hz, H-2), 3.78-3.87 (m, 2H, H-3, H-2), 3.46+3.36 (quin, J=6.7, 2H, H-11), 3.11-3.07 (m, 2H, H-15), 3.06+2.95 (s, 3H, H-13), 2.38-2.23+2.19-2.09 (m, 2H, H-14), 1.20+1.13 (t, J=7.2 Hz, 3H, H-12). $^{13}$C-NMR (75 MHz, CDCl$_3$) ppm δ 157.25 (C-16), 154.75 (C-10), 150.04 (C-8), 138.34 (C-4), 132.17 (C-9), 131.56 (C-6), 125.53+125.37 (C-5), 118.02 (C-7), 51.37+51.27 (C-2), 44.46+45.28 (C-11), 41.06 (C-3), 34.72+34.50 (C-13), 31.46 (C-14), 21.76 (C-14), 13.52+12.61 (C-12).

Table of Additional Compounds of the Invention

| ID | Name | Formula / Analysis | Structure |
|---|---|---|---|
| AN-1251 | Methyl 3-(7-hydroxyindolin-3-yl)propanoate hydrochloride | C$_{12}$H$_{16}$ClNO$_3$<br>257.71<br>C, 55.93; H, 6.26; Cl, 13.76; N, 5.43; O, 18.62 | COOMe-substituted 6-hydroxyindoline · HCl |
| AN-1252 | 3-(2-(Dimethylamino)ethyl)-1H-indol-4-yl ethyl(methyl)carbamate hydrochloride | C$_{16}$H$_{24}$ClN$_3$O$_2$<br>325.83<br>C, 58.98; H, 7.42; Cl, 10.88; N, 12.90; O, 9.82 | Et,Me-carbamate indol-4-yl, NMe$_2$ · HCl |
| AN-1253 | 3-(2-(Dimethylamino)ethyl)indolin-7-yl ethyl(methyl)carbamate dihydrochloride | C$_{16}$H$_{27}$Cl$_2$N$_3$O$_2$<br>364.31<br>C, 52.75; H, 7.47; Cl, 19.46; N, 11.53; O, 8.78 | Indolin-7-yl Et,Me-carbamate, NMe$_2$ · 2HCl |

-continued

Table of Additional Compounds of the Invention

| | | | |
|---|---|---|---|
| AN-1254 | 3-((Dimethylamino)methyl)-1H-indol-6-yl ethyl(methyl)carbamate hydrochloride | C₁₅H₂₂ClN₃O₂ 311.81 C, 57.78; H, 7.11; Cl, 11.37; N, 13.48; O, 10.26 | 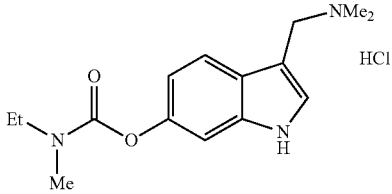 [SMILES: CCN(C)C(=O)Oc1ccc2c(CN(C)C)c[nH]c2c1 ; Cl] |
| AN-1255 | 3-(2-(Dimethylamino)ethyl)-6-((ethyl(methyl)carbamoyl)oxy)-1H-indole-1-carboxylic acid | C₁₇H₂₄ClN₃O₄ 369.84 C, 55.21; H, 6.54; Cl, 9.59; N, 11.36; O, 17.30 | 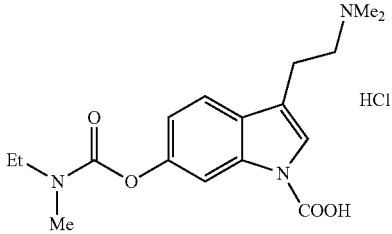 [SMILES: CCN(C)C(=O)Oc1ccc2c(CCN(C)C)cn(C(=O)O)c2c1 ; Cl] |
| AN-1256 SF-II-130b | 3-(2-(Dimethylamino)ethyl)-1H-indol-6-yl ethyl(methyl)carbamate hydrochloride | C₁₆H₂₄ClN₃O₂ 325.83 C, 58.98; H, 7.42; Cl, 10.88; N, 12.90; O, 9.82 | 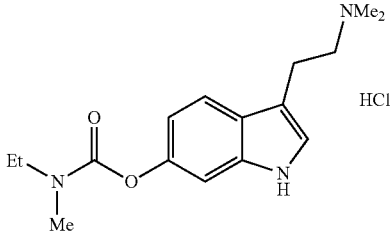 [SMILES: CCN(C)C(=O)Oc1ccc2c(CCN(C)C)c[nH]c2c1 ; Cl] |
| AN-1257 SF-I-336 | Ethyl 3-(5-((ethyl(methyl)carbamoyl)oxy)-1H-benzo[d]imidazol-1-yl)propanoate hydrochloride Ethyl 3-(6-((ethyl(methyl)carbamoyl)oxy)-1H-benzo[d]imidazol-1-yl)propanoate hydrochloride | C₁₆H₂₂ClN₃O₄ 355.82 C, 54.01; H, 6.23; Cl, 9.96; N, 11.81; O, 17.99 | 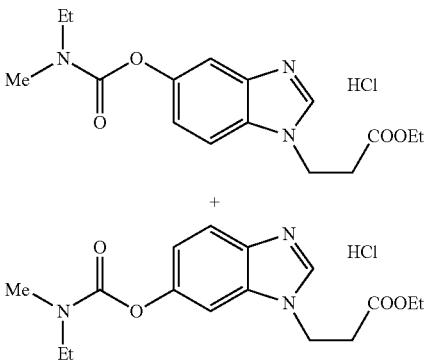 [SMILES: CCOC(=O)CCn1cnc2cc(OC(=O)N(C)CC)ccc21 ; Cl ; CCOC(=O)CCn1cnc2ccc(OC(=O)N(C)CC)cc21 ; Cl] |
| AN-1258 SF-II-144 | 3-((Dimethylamino)methyl)-1H-indol-4-yl ethyl(methyl)carbamate hydrochloride | C₁₅H₂₂ClN₃O₂ 311.81 C, 57.78; H, 7.11; Cl, 11.37; N, 13.48; O, 10.26 | 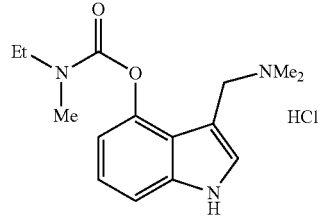 [SMILES: CCN(C)C(=O)Oc1cccc2[nH]cc(CN(C)C)c12 ; Cl] |
| AN-1259 | 3-(2-(Dimethylamino)ethyl)-1H-indol-7-yl ethyl(methyl)carbamate hydrochloride | C₁₆H₂₄ClN₃O₂ 325.83 C, 58.98; H, 7.42; Cl, 10.88; N, 12.90; O, 9.82 | 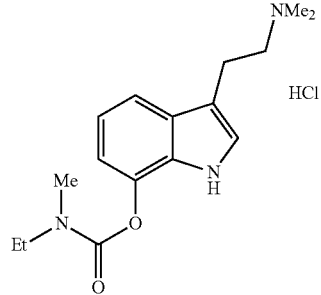 [SMILES: CCN(C)C(=O)Oc1cccc2c(CCN(C)C)c[nH]c12 ; Cl] |

Table of Additional Compounds of the Invention

| | | | |
|---|---|---|---|
| AN-1260 | 3-(2-(Dimethylamino)ethyl)indolin-6-yl ethyl(methyl)carbamate dihydrochloride | $C_{16}H_{27}Cl_2N_3O_2$<br>364.31<br>C, 52.75; H, 7.47; Cl, 19.46; N, 11.53; O, 8.7 | 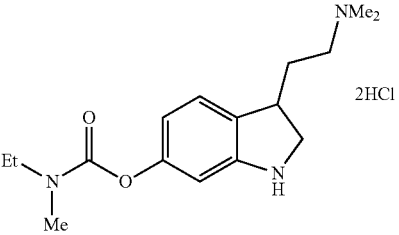 [SMILES: CCN(C)C(=O)Oc1ccc2c(c1)NCC2CCN(C)C ; "2HCl"] |
| AN-1261 | 3-(2-(Dimethylamino)ethyl)indolin-4-yl ethyl(methyl)carbamate dihydrochloride | $C_{16}H_{27}Cl_2N_3O_2$<br>364.31<br>C, 52.75; H, 7.47; Cl, 19.46; N, 11.53; O, 8.7 | 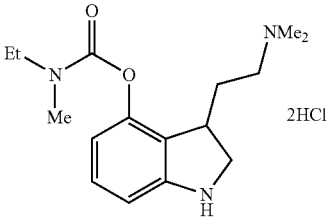 [SMILES: CCN(C)C(=O)Oc1cccc2c1C(CCN(C)C)CN2 ; "2HCl"] |
| AN-1262 | 3-((Dimethylamino)methyl)indolin-4-yl ethyl(methyl)carbamate hydrochloride | $C_{15}H_{25}Cl_2N_3O_2$<br>350.28 | 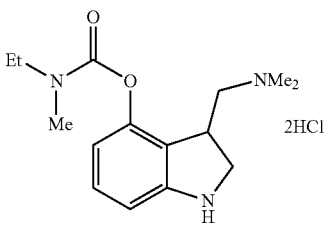 [SMILES: CCN(C)C(=O)Oc1cccc2c1C(CN(C)C)CN2 ; "2HCl"] |
| AN-1263 | 3-((Dimethylamino)methyl)indolin-6-yl ethyl(methyl)carbamate dihydrochloride | $C_{15}H_{25}Cl_2N_3O_2$<br>350.28<br>C, 51.43; H, 7.19; Cl, 20.24; N, 12.00; O, 9.14 | 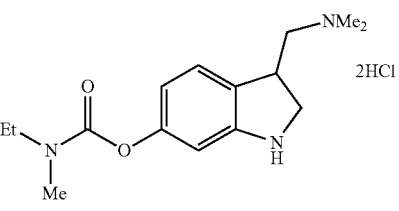 [SMILES: CCN(C)C(=O)Oc1ccc2c(c1)NCC2CN(C)C ; "2HCl"] |
| AN-1264 | 3-((Dimethylamino)methyl)indolin-7-yl ethyl(methyl)carbamate dihydrochloride | $C_{15}H_{25}Cl_2N_3O_2$<br>350.28<br>C, 51.43; H, 7.19; Cl, 20.24; N, 12.00; O, 9.14 | 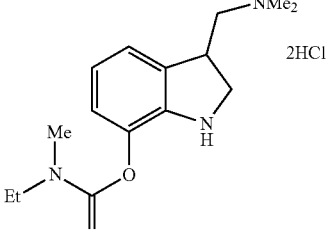 |
| AN-1265 | 3-((Dimethylamino)methyl)-1H-indol-7-yl ethyl(methyl)carbamate hydrochloride | $C_{15}H_{22}ClN_3O_2$<br>311.81<br>C, 57.78; H, 7.11; Cl, 11.37; N, 13.48; O, 10. | 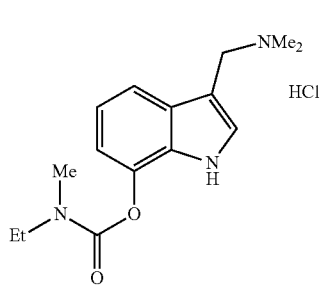 [SMILES: CCN(C)C(=O)Oc1cccc2c(CN(C)C)c[nH]c12 ; Cl] |

-continued

Table of Additional Compounds of the Invention

| | | | |
|---|---|---|---|
| AN-1267 | Methyl 3-(6-((ethyl(methyl)carbamoyl)oxy)-1H-benzo[d]imidazol-1-yl)propanoate and Methyl 3-(5-((ethyl(methyl)carbamoyl)oxy)-1H-benzo[d]imidazol-1-yl)propanoate | $C_{15}H_{19}N_3O_4$ 305.14 C, 59.01; H, 6.27; N, 13.76; O, 20.96 | (structures) |
| AN-1268 | Ethyl 3-(5-((ethyl(methyl)carbamoyl)oxy)-1H-benzo[d]imidazol-1-yl)propanoate and Ethyl 3-(6-((ethyl(methyl)carbamoyl)oxy)-1H-benzo[d]imidazol-1-yl)propanoate | $C_{16}H_{21}N_3O_4$ 319.36 C, 60.18; H, 6.63; N, 13.16; O, 20.04 | (structures) |
| AN-1269 | Ethyl 3-(5-hydroxy-1H-benzo[d]imidazol-1-yl)propanoate and Ethyl 3-(6-hydroxy-1H-benzo[d]imidazol-1-yl)propanoate | $C_{12}H_{14}N_2O_3$ 234.25 C, 61.53; H, 6.02; N, 11.96; O, 20.49 | (structures) |

Biological Experimental Data

Methods

A. Measurement of Radical Scavenging

A mixture comprising glucose oxidase (GO), luminol, sodium selenite [IV] (SEL+5) and cobalt [II] ($Co^{+2}$) all in Hank's Balance Salt Solution (HBSS) was used (Ginsburg et al, 2004). The production of $H_2O_2$ produces a burst of luminescence within 30-60 sec, which lasts for 7-10 min. The luminescence involves oxidation of SEL+5 to it SEL+6 and also the generation of oxidants, which are catalyzed by $Co^{+2}$. This method mimics infection and inflammation conditions in which there is an accumulation of several oxidant species. This method provides a source of several radicals. Reduction in luminescence by the compounds is due to their ability to sequester radicals and was measured after addition of several concentrations of each compound. The concentration of each compound that reduced the luminescence by 50% was calculated.

B. Measurement of Acetylcholinesterase (AChE) and Butylcholinesterase (BuChE) Inhibition In Vitro AChE-inhibitory activity of compounds of the invention was determined by the method of Ellmann et al. (1961) using human or bovine erythrocytes (Sigma, Israel) as the enzyme source for AChE and human or equine serum as a source of BuChE. The enzyme was incubated at 37° C. with 6-10 concentrations of the compounds tested and samples were collected at 15, 30, 60 and 120 min Aliquots were transferred to an Elisa multiscan microplate reader (Labsystems) at 15-60 sec time intervals for the determination of residual AChE activity, with Ascent PC software. The rate of development of a yellow colour (OD/min) was measured at 412λ at 37° C. in 0.2 mL wells containing AChE 0.023 units per mL, 5,5'-dithiobis-2-nitrobenzoic acid (DTNB) 0.00025M, acetylthiocholine iodide (AcTh) 0.075M, and BSA (0.025%) in phosphate buffer pH 7. The % inhibition of AChE by each concentration was calculated by comparison with the activity of the enzyme in the absence of drug. The concentration of each drug that inhibited the enzyme at the time of peak activity (usually 120 min for both enzymes) by 50% ($IC_{50}$) was calculated. BuChE-inhibitory activity was determined as described above using BuChE (Sigma Israel) with butylthiocholine iodide (BuTh) 0.075M as a substrate.

C. Measurement of Protective Activity Against Oxidative Stress in Cell Cultures a) Cardiomyocytes Compounds of the invention were tested for their potential to protect against cell death induced by oxidative stress in a cell line derived from rat cardiac myoblasts (H9c2) (Hescheler et al., 1991). Cells were cultured in Dulbecco's Modified Eagle's Medium (DMEM), 4500 mg/L D-glucose with 10% foetal calf serum (FCS), 10000 U/mL penicillin, 100 mg/mL streptomycin and 25 μg/mL Amphotericin B at 37° C. with 95% air and 5% $CO_2$. One day prior to the measurement, cells were seeded in 96 well-plates at a density of 5,000 cells/well and incubated with 100 μM $H_2O_2$ for 1 h. This concentration was found to induce 30-50% cell mortality. Cells were incubated with different compounds of the invention in several concentrations ranging from 0.0001-100 μM, for 1, 4 or 7 h prior to addition of $H_2O_2$. Cell viability was measured by means of Alamar Blue (AbD Serotec, BUF012A). In order to compare the protective effect of the compounds this degree of cell death was normalized to 100% in each experiment. The effect of the drugs is expressed as percent reduction of this value.

b) Chick Telencephalon Neurones

Chick embryos aged 8-9 days were transferred to a plastic dish, and decapitated. Both hemispheres were removed, collected and cleaned from any loose tissue. Hemispheres were mechanically dissociated and 2 ml of the resulting cell suspension, containing 9×105 cells/ml medium, were added to each well. For assessment of neuroprotection against the effect of reduced neurotrophic support (low serum) the cells were grown in Eagle's Minimum Essential Medium (EMEM) with 1 g glucose/l, 2% FCS, 0.01% gentamycin and 2 mM L-glutamine. Different concentrations of the compounds of the invention ranging from 1 nM-10 μM were applied when neurons were plated out on day one in vitro (DIV1). At DIV8, viability of neurons was analysed by the MTT (3-(4,5-dimethylthiazol-2-yl)-2,5, diphenyl tetrazolium bromide) assay. For assessment of protection against oxidative stress induced by $H_2O_2$ cell cultures were maintained at 37° C., 95% humidity and 5% $CO_2$ in DMEM with 4.5 g glucose/l, 5% Nu Serum, 0.01% gentamycin and 2 mM L-glutamine. At DIV8, $H_2O_2$ 200 μM was applied for 24 h together with different concentrations of drug ranging from 1 nM-10 μM. At DIV9, viability of neurons was analysed by the MTT assay. MTT measures the activity of mitochondrial dehydrogenase in viable cells and is based on the reduction of yellow MTT to dark blue formazan crystals by mitochondrial dehydrogenases (succinate dehydrogenase). For determination of cell viability, MTT solution was added to each well in a final concentration of 0.5 mg/ml. After 2 hours, the MTT containing medium was aspired. Cells were lysed with 3% SDS and formazan crystals were dissolved in isopropanol/HCl. To determine optical density, a plate-reader (Anthos HT II) was used at a wavelength of 570 nm. Cell viability was expressed in optical density (OD) units.

D. Measurement of Anti-Inflammatory Activity in Cell Culture

Primary microglial cells were obtained from brains of 1-3 day-old mice as described by Reichert et al., (2003). The enzymatically dissociated cells were plated on poly-L-lysine-coated flasks for one week and re-plated for 2 h on bacteriological plates and non-adherent cells were removed by washing. For macrophages, a mouse cell line RAW 264.7 cells were used. Both types of cells were seeded at density of 1×10⁵ per well in 48-well culture plates and grown overnight in DMEM containing 1 g/L glucose, 10% fetal calf serum (FCS), 10% Colony Stimulating Factor (CSF), 50 μg/mL, 0.01% gentamicin and 1% L-Glutamine. On the day of experiment, serial dilutions of the compounds were prepared in serum free DMEM medium. The wells were washed with PBS (pH 7.4) and diluted compounds were added at final concentrations of 1 pM-1 μM per well. The plates with compounds of the invention were incubated for 30 min at 37° C. prior to stimulation with lipopolysaccharide (LPS 5 μg/mL) from *Escherichia coli* (Sigma-Aldrich).

Supernatants were harvested after 6 and 20 h for detection of TNF-α and IL-6 respectively, and after 24 h for detection of nitric oxide (NO). NO production was detected by a colourimetric method using Griess reagent £0.2% naphthylenediamine dihydrochloride, and 2% sulphanilamide in 5% phosphoric acid), which measures the concentration of nitrite, a stable metabolite produced from NO. Cytokine production was quantified by means of an ELISA kit according to the manufacturer's instructions (Bio Legend, San Diego, Calif.). TNF-α protein was detected by means of the sandwich ELISA method. The cells were incubated for 6 h in 48-well plates. 50 μL of medium was applied to each well, which was coated with capture anti-mouse TNF-α antibody (BioLegend, San Diego, Calif., USA) in 96-wells plate. The plate was incubated overnight at 4° C. After 3 washes with PBS/Tween20 solution the cells were blocked with 10% BSA in PBS solution for 1 h followed by 3 additional washes. Anti-mouse TNF-α antibody was applied for detection for 1 h at room temperature. A chemiluminescence reaction was performed by adding a pNPP One Component Microwell Substrate reagent (SouthernBiotech, Birmingham, Ala., USA) and colour intensity was evaluated on a plate reader at 410 nm.

The BV2 mouse microglial cells were created by infecting primary mouse microglia with v-raf/v-myc oncogen-carrying retrovirus and donated by Dr. Sigal Fleisher—Berkovich (Ben-Gurion University of the Negev). The cells were cultured in RPMI 1640 containing 0.4 mM L-Glutamine, 10% FCS, 100 units/ml penicillin, 100 μg/ml streptomycin and maintained in a humidified incubator at 37° C. with 5% $CO_2$. For measurement of the effect of compounds on the release of NO the cells were seeded in a density of 80,000 cells/ml and confluence of about 60%, and incubated with test compounds (in the absence of FCS) for 80 mM All the medium was removed and fresh medium containing FCS and LPS (10 μg/ml) added and the cells maintained at 37° C. for 24 h. The release of NO into the medium was determined by measurement of nitrite levels using Griess reagent reaction. For measurement of protein levels of cytokines cells were seeded in a density of 80,000 and incubated with test compounds (in the absence of FCS) and then with LPS as described above. The medium was centrifuged and supernatants collected after 6 h for TNF-α (Biolegend) and after 20 h for IL-6 (Biolegend).

For detection of cytokine mRNA, microglial and RAW 264.7 cells were collected from 48-well plate 3 h after activation with LPS (5 g/mL). Cells were centrifuged at 4° C., 13,000 rpm for 3 mM and supernatant was discarded. Total RNA from RAW 264.7 cells was isolated using Total RNA Extraction kit (Geneaid Biotech, Taiwan) and reversed transcribed by High Capacity cDNA Transcription kit (Applied Biosystems). The resulting cDNA was subjected to 40 cycles of TaqMan® Gene Expression Assay (Applied Biosystems). Primers for TNF-α, IL-6 were used for gene expression test. The results were normalized according to hypoxanthine phosphor ribosyltransferase (HPRT) gene.

E. Acetylcholinesterase (AChE) and Butylcholinesterase (BuChE) Inhibition Ex Vivo Compounds of the invention or saline were administrated by intraperitoneal (ip) injection or gavage to groups of 6-7 male ICR or Balb C mice (5-6 weeks of age). The mice were sacrificed 15, 30, 60 or 120 min after drug administration and the brain (minus cerebellum), spleen, and muscle were rapidly removed, weighed and put on ice. Blood was also collected in heparinised tubes, centrifuged at 14000 rpm at room temperature for 4 mM to provide plasma. Phosphate buffer pH 7 was added to each tissue to produce concentrations of 1 mg/mL for brain and spleen and 8 mg/mL for muscle. The tissues were homogenised in cold phosphate buffer pH 7 containing 0.1% Triton and centrifuged at 14000 rpm. Aliquots of plasma and the supernatant of all tissues were incubated with AcTh or BuTh and DTNB in phosphate buffer pH 7 and the rate of development of the yellow colour was measured as described above. Enzyme activity was measured for each time and drug concentration and percent inhibition of the AChE or BuChE activity was calculated by comparison with that of control mice injected with saline. Results are represented as p moles acetylthiocholine or butythiocholine hydrolysed/min/gm tissue.

F. Temperature Measurements in Rats

An indirect estimate of AChE inhibition in the hypothalamus can be obtained by measuring the fall in body temperature, to which in rats, it is closely correlated. Monitoring body temperature at different times after drug administration enables one to assess in vivo both the extent of drug effect and its duration in the same group of rats. Test compounds or saline were administrated by ip injection or by gavage to female Wistar rats aged 3-4 months. Body temperature was measured rectally by means of a thermocouple probe, before and every 30 min after drug administration until this returned to pre-injection values. The change in body temperature induced by the drug was computed for each dose at each time point in comparison with the temperature prior to drug injection.

G. Evaluation of Anti-Inflammatory Activity in Mice

Male Balb/c mice (aged 5-6 weeks) were injected ip with the test compounds or saline followed 5-30 min later by LPS (10 mg/kg). For evaluation of cytokine mRNA the mice were sacrificed at the desired time after drug administration (2 h for measurements on the spleen and 4 h for those on the brain, the brain (minus cerebellum) and spleen were rapidly removed, frozen in liquid nitrogen and stored until use at −80° C. RNA extraction were performed using columns (Geneaid, RT050) and was reverse transcribed into cDNA using high capacity cDNA reverse transcription kit (Applied Biosystems, 4374966). For qRT-PCR we used TaqMan Fast Universal PCR Master Mix (Applied Biosystems, 4352042) and TaqMan Gene Expression Assays reagents (Applied Biosystems, 4331182). HPRT was used as house-keeping gene and all results are normalized thereto.

For measurement of cyclooxenase (COX) mRNA male Balb/c mice (aged 5-6 weeks) were injected i.p. with LPS (10 mg/kg) 10 min after ip injection of AN827 or saline. The mice were sacrificed after 4 h and the brain rapidly removed, snap frozen in liquid nitrogen and stored at (−80° C.) until use. mRNA extraction was performed using columns (Geneaid) and reverse transcribed into cDNA using high capacity cDNA reverse transcription kit (Applied Biosystems). For quantitative reverse transcriptase polymerase chain reaction (qRT-PCR) we used TaqMan Fast Universal PCR Master Mix (Applied Biosystems) and TaqMan Gene Expression Assays on demand (Applied Biosystems). Hypoxanthine phosphor ribosyltransferase (HPRT) was used as a housekeeping gene and all results are normalized to it.

For measurement of cytokine protein levels, mice were treated with saline or LPS as described above and sacrificed 4 h or 8 h after drug administration, the spleen and rapidly brain removed. The brain was separated into fore, mid and hind sections (minus cerebellum) and frozen in liquid nitrogen and stored at −80° C. until use. Tissues were weighed and diluted in PBS containing 0.8% NaCl, 0.144% $NaHPO_4$, 0.024% $KH_2PO_4$ and protease inhibitor cocktail (Sigma Israel, P8340) and homogenised in an Ultra-TURRAX® homogeniser at a speed of 24,000 rpm, centrifuged at 14000 g for 15 min at 4° C. The supernatant was rapidly frozen in liquid nitrogen and stored until use at −80° C. Cytokines were detected by using Elisa kits (Biolegend) and protein determination performed with Bradford reagent (Bio-RAD, 500-0006).

H. Measurement of Effect of Compounds of the Invention in a Model of Crohn's Disease in Rats Inflammation in the colon was induced in male rats of the Sabra strain (250-300 g) by intra-colonic administration of 1 mL of dinitrobenzensulfonic acid (DNBS) (35 mg/mL in ethanol 25% v/v) under isoflurane anaesthesia. The novel drugs (827B or 680D) or saline was given rectally 1 h prior to DNBS at a dose of 1 mg/kg (2.5 µmoles/kg), and then twice daily at the same dose 12, 24, 36, 48, 60 and 72 h later. A group of control rats received saline rectally instead of DNBS and were pre-treated with saline instead of drug. The rats were anaesthetized by ip injection of a mixture of xylazine 3 mg, ketamine 85 mg, 1 mL/kg. The colon was exposed through a longitudinal abdominal incision. The area of ulceration was estimated. Segments of 10 cm of the colon were removed, cut open and rinsed with ice-cold saline. After cleaning with cold saline (0.9%) the wet weight of the colon was measured. Pieces of colon were analysed for activity of myeloperoxidase (MPO), a marker of neutrophil granulocyte infiltration into the inflamed colon tissue. One unit of MPO activity was defined as the amount of enzyme present that produced a change in absorbance of 1 U/min at 25° C. Results were quantified as U/g protein.

Measurement of Effect of Compounds of the Invention in a Model of Ulcerative Colitis in Mice Acute colitis was induced in male BALB/c OlaHsd mice aged 8-9 weeks by administration of 5% Dextran Sulfate Sodium Salt (DSS) solution (M.Wt.=36,000-50, MP Biomedicals, LLC, Solon, Ohio, USA) in water for 8 days. The DSS solution was freshly prepared daily. Mice were divided into three groups. Group 1 drank water and were injected subcutaneously (s.c) with saline 1 ml/kg once daily for 8 days; Group 2 drank 5% DSS and were injected s.c with saline, 1 ml/kg once daily for 8 days; Group 3 drank 5% DSS and were injected s.c with 5 mg/kg once daily with compound 680E (toluene sulphonate salt) for 8 days. Body weight, stool consistency and the presence of blood in the stools was recorded daily for each mouse. These data were used to calculate a disease activity index (DAI) as described [Kullmann F, et al. Clinical and histopathological features of dextran sulfate sodium induced acute and chronic colitis associated with dysplasia in rats. Int J Colorectal Dis 2001; 16: 238-246] on days 7 and 8. The score ranged between 0-4 for all three parameters and was composed as follows: Weight loss: none=0, 1-5%=1, 5-10%=2, 10-20%=3, >20%=4. Percent of weight loss on days 7 and 8 relative to the first day was calculated for all the groups. Stool evaluation: normal pellets=0, loose stools which do not stick to the anus=2, diarrhoea=4. Bleeding: none=0, hemoccult=2, gross bleeding=4. The maximum DAI score was 4 based on combination of scores of weight loss (refer to the first day of the experiment), stool consistency and bleeding divided by 3. After sacrifice the length of the colon segment from the cecum to the rectum was measured.

Results

A. Radical Scavenging Properties of Compounds of the Invention

Several of the compounds showed radical scavenging activity with $IC_{50}$s (concentration required to reduce radical by 50%) ranging from 0.07-24.1 µM. (see Table 1 below).

TABLE 1

Radical scavenging properties of indoline carbamates and their hyroxyl derivatives

| Compound | Glucose oxidase IC$_{50}$ (μM) | Sin1 IC$_{50}$ (μM) |
|---|---|---|
| 856 | 0.77 ± 0.03 | NT |
| 854 | 1.38 ± 0.10 | 0.57 ± 0.01 |
| 1243 | 0.30 ± 0.01 | 8.49 ± 0.003 |
| 890 | 0.07 ± 0.01 | 2.13 ± 0.18 |
| 850 | 1.59 ± 0.39 | NT |
| 699 | 1.64 ± 0.06 | NT |
| 827 | 1.46 ± 0.05 | 4.55 ± 0.48 |
| 698 | 3.13 ± 0.36 | NT |
| 851 | 2.39 ± 0.40 | NT |
| 667 | 6.84 ± 0.05 | NT |
| 821 | 4.33 ± 0.06 | NT |
| 822 | 10.2 ± 4.1 | NT |
| 819 | 19.0 ± 0.6 | 3.18 ± 0.20 |
| 820 | 15.3 ± 0.01 | NT |
| 885 | 1.15 ± 0.01 | NT |
| 1247 | 0.22 ± 0.04 | 2.18 ± 0.17 |
| 681 | 1.14 ± 0.09 | NT |
| 680 | 1.45 ± 0.05 | 2.36 ± 0.05 |
| 677 | 24.1 ± 0.18 | NT |
| 691 | 6.27 ± 0.05 | NT |
| 685 | 3.41 ± 0.02 | NT |
| 687 | 2.24 ± 0.03 | NT |
| 834 | 1.44 ± 0.04 | NT |
| 832 | 0.67 ± 0.05 | 3.54 ± 0.21 |
| 833 | 0.45 ± 0.03 | NT |
| 848 | 2.34 ± 0.02 | 3.07 ± 0.66 |
| 849 | 0.84 ± 0.05 | NT |
| 682 | 1.34 ± 0.01 | 2.33 ± 0.08 |

Values represent mean ± SD from three independent experiments.
NT = not tested

B. In Vitro AChE and BuChE Inhibition of Compounds of the Invention

AChE and BuChE inhibitory activity expressed as IC$_{50}$ (concentration that inhibited the enzyme activity by 50%) for the tested compounds of the invention is summarized in Table 2. For compounds with the same carbamate and other substituents e.g. AN-618 and AN-856; AN-622 and AN-625; AN-683 and AN-685, the acid or ester derivatives of the indolines were more potent AChE inhibitors than their respective indole analogues. Compounds with a carbamate moiety consisting of N,N-dimethyl; N-methyl-N-ethyl; N-methyl-N-butyl; or N-methyl-N-(4-methoxyphenyl) in position 4 or 7 of the indole or indoline ring were more potent AChE inhibitors than their analogues with the carbamate in positions 5 or 6.

TABLE 2

Cholinesterase inhibition by carbamate derivatives of indoles and indolines

| AN-Compound | IC$_{50}$ (μM) AChE 120' | IC$_{50}$ (μM) BChE 120' |
|---|---|---|
| 618 | 600.0 | NT |
| 604 | 160.0 | NT |
| 619 | 3.5 | NT |
| 628 | ~17 | 9.4 |
| 629 | 180.0 | NT |
| 626 | 200.0 | NT |
| 620 | 4.0 | NT |
| 602 | >600 | NT |
| 617 | 600.0 | NT |
| 634 | >>100 | NT |
| 669 | 660.0 | NT |
| 622 | >500 | NT |
| 625 | 50.0 | NT |
| 635 | >>100 | NT |
| 633 | ~90 | NT |
| 668 | 930.0 | NT |
| 627 | 1.1 | NT |
| 689 | 135.3 | NT |
| 676 | 33.0 | NT |
| 683 | >800 | NT |
| 684 | 110.4 | NT |
| 621 | 0.30 | NT |
| 624 | 0.91 | NT |
| 623 | 20.0 | NT |
| 632 | ~60 | NT |
| 630 | ~15 | NT |

TABLE 3

Cholinesterase inhibition by carbamate derivatives of indoline propionic esters, acids and amines

| Compound | IC$_{50}$ (μM) AChE 120 min | IC$_{50}$ (μM) BuChE 120 min |
|---|---|---|
| 856 | 1.20 | 1.3 |
| 854 | 7.20 | 0.70 |
| 1243 | 5.60 | 0.70 |
| 890 | 0.40 | 0.20 |
| 850 | 19.0 | 0.30 |
| 699 | 124 | 9.70 |
| 827 | 7.40 | 0.30 |
| 698 | 58.7 | 6.80 |
| 871 | 40.2 | 0.56 |
| 851 | 62.0 | 8.50 |
| 667 | 68.1 | 197 |
| 821 | 37.8 | 417 |
| 857 | 0.066 | 3.6 |
| 822 | 125 | >600 |
| 819 | 1.20 | 4.60 |
| 820 | 246 | >600 |
| 885 | 418 | 58.7 |
| 1247 | 473 | 6.80 |
| 681 | 175 | 10.0 |
| 680 | 55.2 | 3.90 |
| 677 | 62.3 | 404 |
| 691 | 122 | 66.8 |
| 685 | 38.2 | 54.0 |
| 687 | 17.4 | 372 |
| 852 | 61.6 | 0.08 |
| 910 | 0.32 | 0.23 |
| 1252 | 0.24 | 0.11 |
| 1257 | 16.2 | 0.11 |
| 911 | 24.0 | 0.10 |

The most potent AChE inhibitors were AN-857, IC$_{50}$ of 66 nM; AN1252, IC$_{50}$ of 240 nM; AN910, IC$_{50}$ of 320 nM and AN-621, IC$_{50}$ of 330 nM. The IC$_{50}$s of the remaining compounds with the carbamate moiety in the 4, 6 or 7 position ranged from of 0.4->500 μM. AN-857 was also the most selective AChE inhibitor, being 55 times more effective against AChE than against BuChE. The most potent BuChE inhibitors were AN-852 with an IC$_{50}$ of 80 nM; AN911, AN1252 and AN1257 with IC$_{50}$, of 100-110 nM. AN-852 was the most selective BuChE inhibitor being 770 times more effective against BuChE than against AChE. The IC$_{50}$s of the remaining compounds with the carbamate moiety in the 4, 6 or 7 position ranged from of 1->250 μM.

C. Protection Activity of Compounds of the Invention Against Oxidative Stress in Cell Cultures a) Cardiomyocytes Some of the compounds listed in Table 4 reduced apoptosis induced by $H_2O_2$ in cardiomyocytes by more than 50% at concentrations ranging from 100 pM-1 µM (AN-699, AN-827, AN-832, AN-850, AN-667, AN-854, AN-821, AN-681, AN-680 and AN-677). It is noteworthy that the concentrations at which many compounds protected cells from apoptosis due to oxidative stress were much lower than those that scavenged Off and other radicals (as compared with the results provided in Table 1).

TABLE 4

| AN-Compound | Cardiomyocte cell line Conc' >50% protection $H_2O_2$ Alamar blue |
|---|---|
| 855A | 1 µM |
| 834 | 0.1-10 nM |
| 832A | 0.1 nM-10 nM |
| 833 | no effec ≤ 100 µM |
| 854A | 0.1 nM-100 nM |
| 850A | 100 nM |
| 699 | 1 nM-1 µM |
| 827A | 0.1 nM-100 nM |
| 698 | 1 nM-1 µM |
| 871 | no effect ≤ 100 µM |
| 886 | no effect ≤ 100 µM |
| 667 | 1 nM-1 µM |
| 857A | 10-100 µM |
| 819 | 0.001-1 nM |
| 682A | 1 nM-100 µM |
| 848A | no effect ≤ 100 µM |
| 681A | 1-100 nM |
| 680A | 0.1 nM-100 nM |
| 677 | 1-10 nM |
| 691 | 100 µM |
| 685 | 0.001-0.1 nM |
| 687 | 0.1-10 µM | b) Chick Telencephalon Neurones

Table 5 lists compounds of the invention measured for their protective activity against cell death under oxidative stress in chick neurones, at concentrations ranging from 1 nM-10 µM (Table 4). AN-827C, AN-855C and AN-832D also afforded protection against cell death induced by $H_2O_2$ exposure.

TABLE 5

| AN-Compound | Primary culture chick neurones Neuronal cultures | |
|---|---|---|
| | $H_2O_2$ MTTassay | Serum deprivation |
| 855C | 1-10 µM | 1-50 nM |
| 832D | 1-100 nM | 2.5-10 µM |
| 854C | no effect ≤10 µM | 2.5-10 µM |
| 827C | 1 nM | 5-10 µM |

D. Anti-Inflammatory Activity of Compounds of the Invention in Cell Culture a) Mouse Microglia The most potent inhibitors of the release of NO from LPS-stimulated mouse microglial cells were AN-832, AN-834, AN-680C, AN-681, AN-827B, AN-848, all of which reduced NO release by more than 30% in concentrations ranging from 10 nM-10 µM. Several of them also reduced the release of TNF-α and IL-6 protein in this concentration range (Table 6).

b) Microglia Cell Line (BV2)

Several of the compounds that were active against LPS induced release of NO from primary microglial cells also inhibited NO release following LPS in the BV2 glial cell line at concentrations starting at 100 pM (Table 7).

c) Mouse Macrophage Cell Line (RAW 264.7 Cells)

Figure 2:
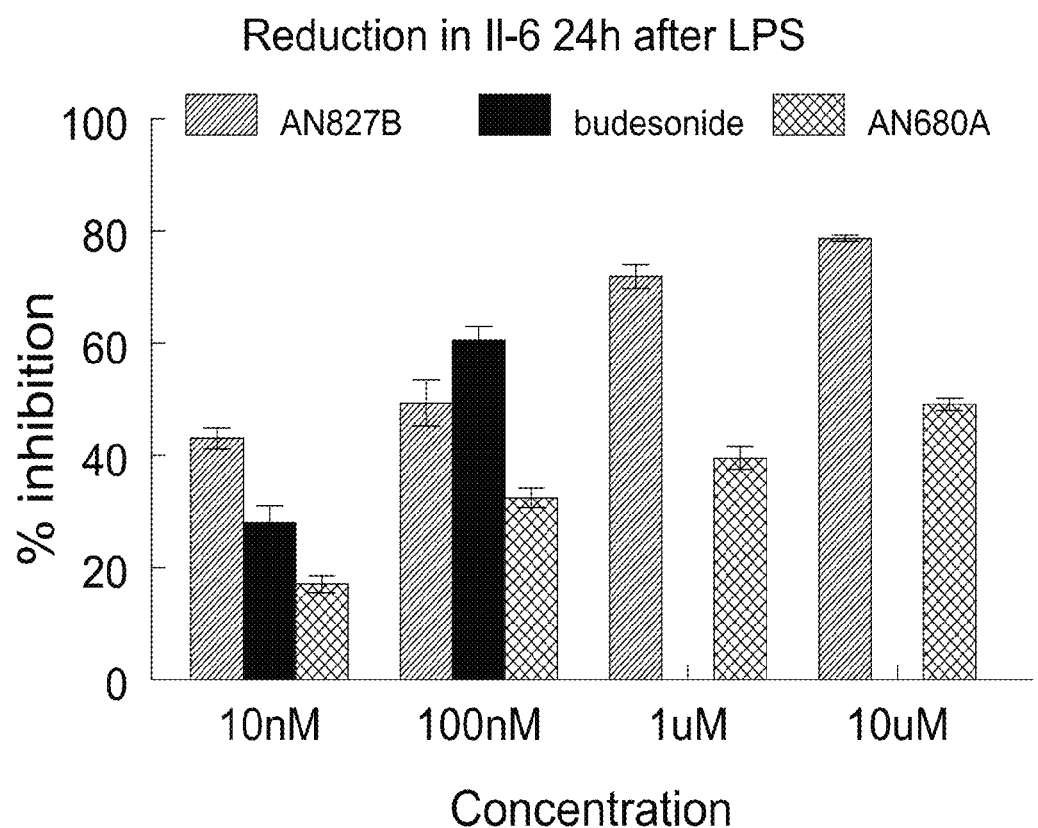
FIG. 2 shows the reduction of 11-6 protein induced from RAW cells by LPS by compounds AN-827C (mesylate salt), AN-680C (citrate salt) as compared with budesonide.
Figure 3:
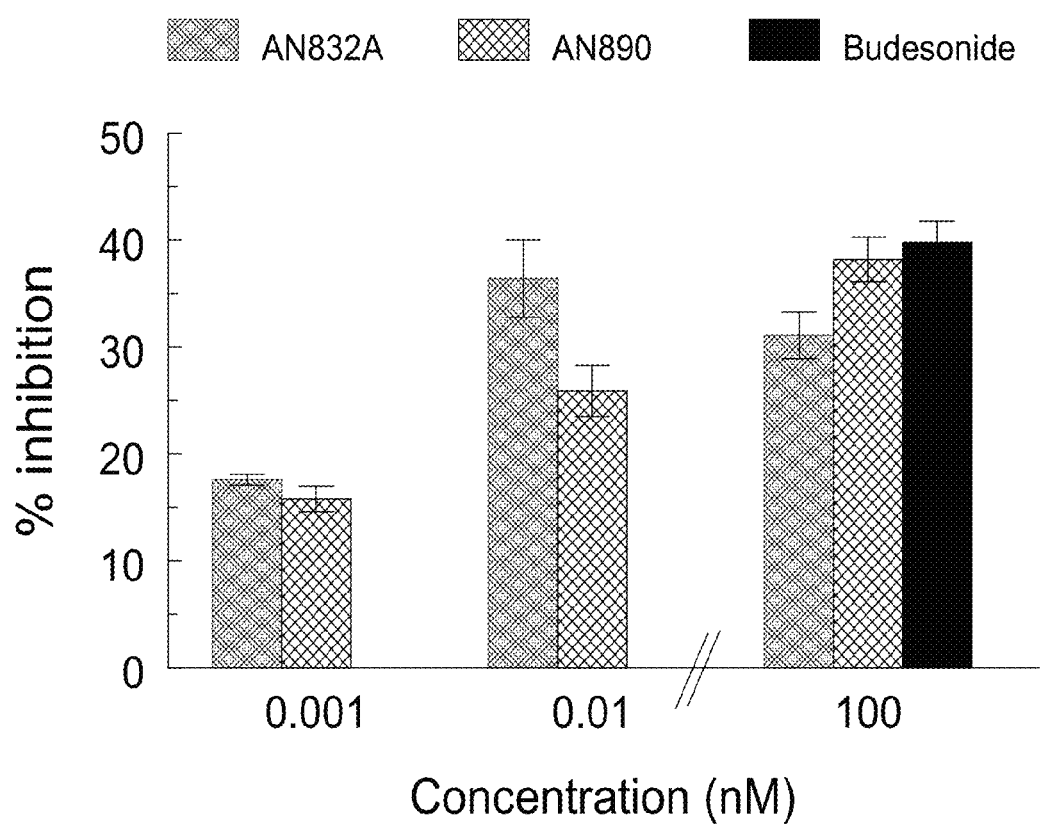
FIG. 3 shows the inhibition of the level of TNF-α induced in RAW cells by LPS by AN-832 and AN-890.

Compounds of the invention were shown to inhibit the release of NO from LPS-stimulated RAW 264.7 cells by more than 30% at concentrations ranging from 1 pM-10 µM. These include AN-832, AN-827B, AN-867, AN850B, AN-819, AN-680D, AN-878, AN-681, AN-685, AN-890 and AN-894 (Table 7). They were more potent than the steroid, budesonide which caused significant inhibition at concentrations of 10 and 100 nM (FIG. 1). Some of these compounds also inhibited the release of IL-6 and TNF-α protein in a concentration range of 100 pM-100 nM (Table 8)(See also FIGS. 2 and 3).

TABLE 7

Nitric oxide (NO) reduction of indolines in BV2 microglia and macrophages cell cultures

| | Reduction in NO levels by at >20%* | | | |
|---|---|---|---|---|
| | BV2 Microglia | | RAW Macrophages | |
| Compound | range (nM) | % peak reduction | range (nM) | % peak reduction |
| 854 | None | — | $10^{-3}$-100 | 45.2 ± 1.4 |
| 890 | None | — | $10^{-3}$-100 | 54.6 ± 2.3 |
| 832 | None | — | $10^{-3}$-100 | 46.1 ± 3.0 |
| 850 | $10^{-2}$-100 | 37.6 ± 5.0 | NT | NT |
| 827B | $10^{-1}$-100 | 43.9 ± 3.8 | $10^{-2}$-100 | 46.4 ± 4.1 |
| 681 | None | — | $10^{-1}$-100 | 50.1 ± 4.1 |
| 680D | $10^{-3}$-100 | 37.1 ± 5.3 | $10^{-3}$-100 | 47.8 ± 1.8 |
| 911 | NT | | $10^{-2}$-100 | 66.6 ± 1.9 |
| 910 | NT | | $10^{-2}$-1 | 29.3 ± 1.2 |
| 1252 | NT | | $10^{-2}$-1000 | 36.4 ± 1.8 |
| 1257 | NT | | $10^{-2}$-1000 | 34.5 ± 1.2 |

None—No reduction up till 100 nM.
NT—Not tested.

TABLE 8

TNF-α reduction by indolines in microglia and macrophages cell cultures

| | Reduction in TNF-α levels* | | | |
|---|---|---|---|---|
| | BV2 Microglia | | RAW Macrophages | |
| Compound | range (nM) | % peak reduction | range (nM) | % peak reduction |
| 855 | $10^{-1}$-100 | 38.2 ± 3.2 | NT | NT |
| 854 | 100 | 8.4 ± 1.7 | $10^{-3}$-100 | 41.1 ± 3.8 |
| 1243 | 100 | 18.6 ± 1.0 | $10^{-1}$-10 | 20.3 ± 5.4 |
| 890 | None | — | $10^{-3}$-100 | 36.6 ± 4.1 |
| 832 | $10^{-1}$-100 | 38.2 ± 3.2 | $10^{-3}$-100 | 39.2 ± 2.6 |
| 850 | $10^{-3}$-100 | 30.5 ± 0.6 | None | — |
| 827 | $10^{-1}$-100 | 38.5 ± 3.2 | $10^{-1}$-100 | 30 ± 3 |
| 682 | $10^{-2}$-100 | 17.6 ± 1.3 | $10^{-1}$-100 | 55.0 ± 1.3 |
| 1248 | $10^{-3}$-10 | 22.1 ± 3.3 | $10^{-1}$-10 | 51.2 ± 3.5 |
| 681 | None | — | 0.1-100 | 29.2 ± 5.6 |
| 680 | None | — | $10^{-3}$-100 | 34.5 ± 1.6 |

None—No reduction up till 100 nM.
NT—Not tested.

E. Acetylcholinesterase (AChE) Inhibition Ex Vivo

Compounds AN-890, AN-827, AN-850, AN-854, AN-860, AN-861 and AN-819, AN-878, inhibited ChE in plasma, muscle, and spleen after ip and or oral administration in mice. The most potent compound was AN-890, which at 1 mg/kg inhibited ChE in plasma and spleen equally well after ip and oral administration 30 to 120 min after ip injection but had little or no effect in skeletal muscle.

F. Fall in Body Temperature in Rats

Figure 4:
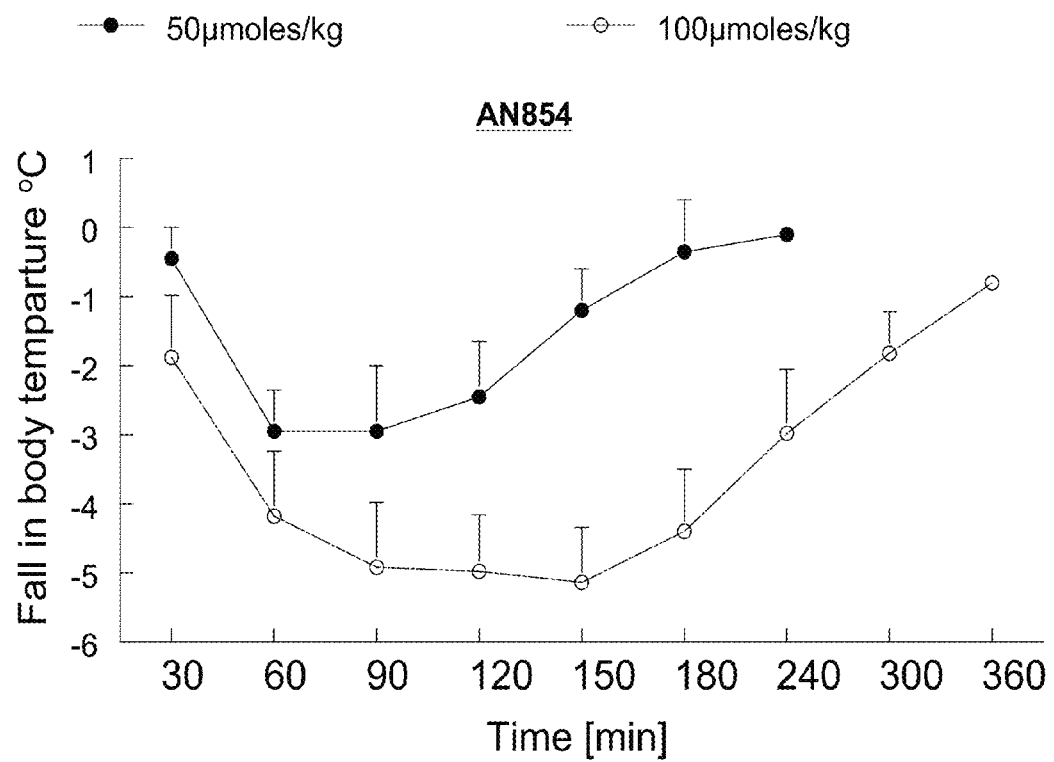
FIG. 4 shows the fall in body temperature in rats induced by ip injection of two doses of AN-854.

AN 854, AN827B and AN680B lowered body temperature by more than 2° C. in female rats, (equivalent to more than 74% inhibition in ChE in the hypothalamus Wang et al., 2001). This was seen at a dose of AN-854 (50 μmoles/kg) (which only inhibited ChE in the mouse brain by 30% (FIG. 4), with AN-872C and AN-680D at 200 μmoles/kg and 100 μmoles/kg, respectively which caused no significant inhibition in mouse brain. This disparity was probably due to removal of the inhibitor from the enzyme during the brain homogenisation and extraction procedure.

G. Anti-Inflammatory Activity in Mice

Figure 5:
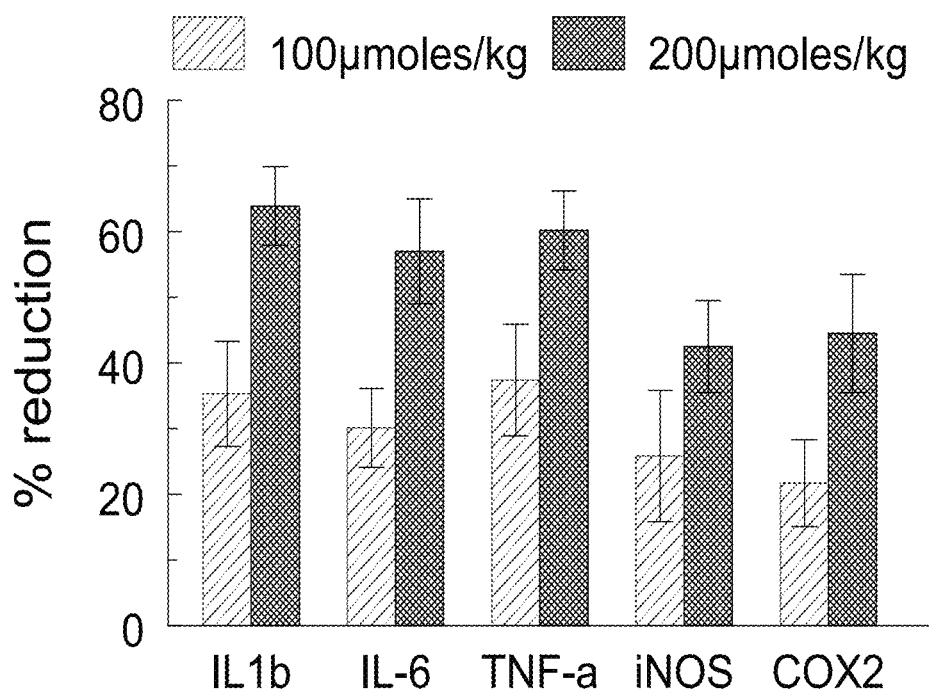
FIG. 5 shows the dose related reduction by AN-827B (the mesylate salt) in cytokine signaling 4 h after its ip injection together with LPS 10 mg/kg in mice. Data represent a dose-related reduction produced by drug pre-treatment (%) in cytokine and inducible nitric oxide synthase (iNOS) and cyclo-oxygenase (COX2) mRNA as measured by RT-PCR in the brain of mice compared to those in mice given LPS and saline.
Figures 6A, 6B:
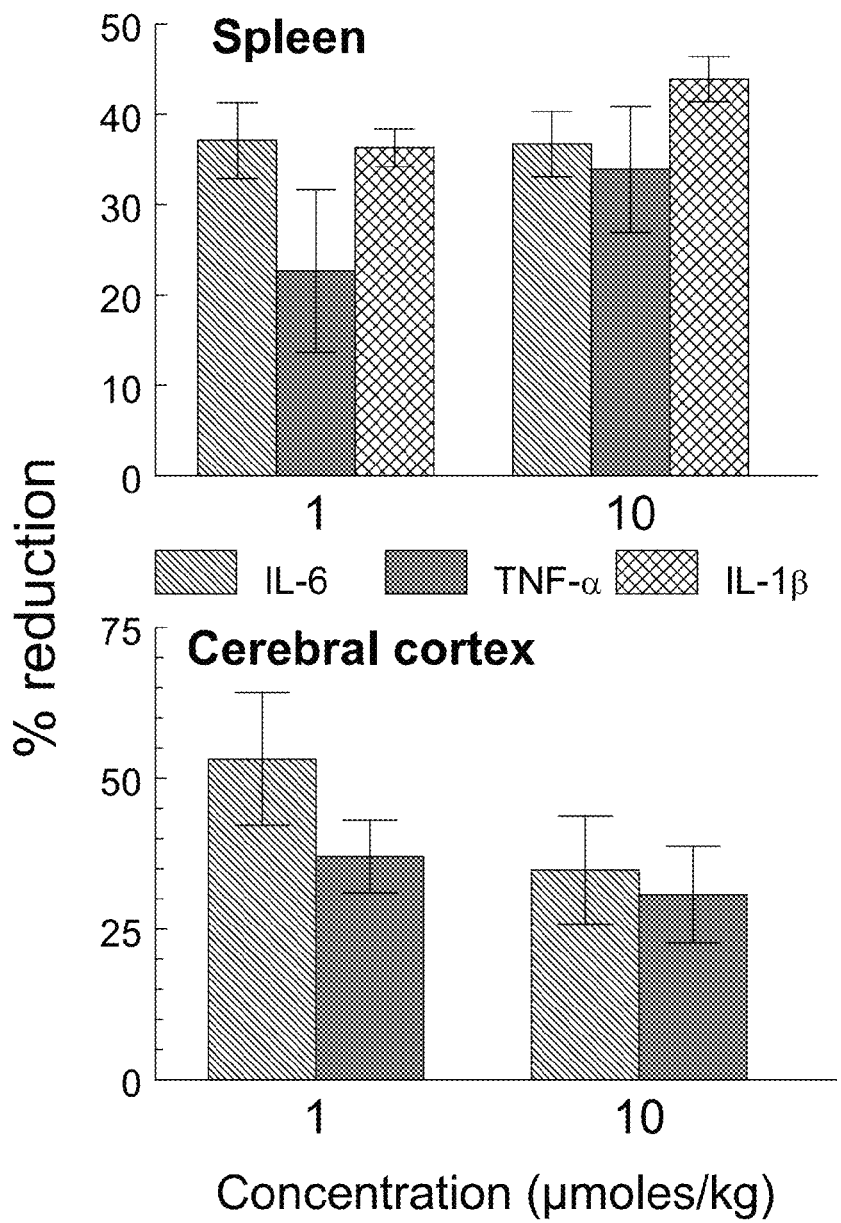
FIGS. 6A-6B show the reduction by compound AN-680D in cytokine levels in spleen (FIG. 6A) and cerebral cortex (FIG. 6B) of brain of mice 8 h after their elevation by ip injection of LPS 10 mg/kg LPS. Data are expressed as reduction (%) in cytokine levels induced by drug pre-treatment compared to levels in mice given LPS and saline.

Several compounds reduced the levels of IL-1β, IL-6, TNF-α and inducible nitric oxide synthase (iNOS) mRNA, the enzyme responsible for the synthesis of NO, that had been elevated in the brain of mice 4 h after ip injection of the compounds together with LPS. FIG. 5 shows the effect of two doses of AN-680D in the brain of mice. Some of the compounds also reduced the levels of IL-6 and TNF-α protein in different brain areas, 8 h after injection with LPS, and in the spleen 4 h after injection with LPS. FIG. 6 shows the reduction by two doses of AN-680D of cytokine levels in the spleen and cerebral cortex.

H. Anti-Inflammatory Effect in a Rat Model of Colitis

Figures 7A, 7B, 7C:
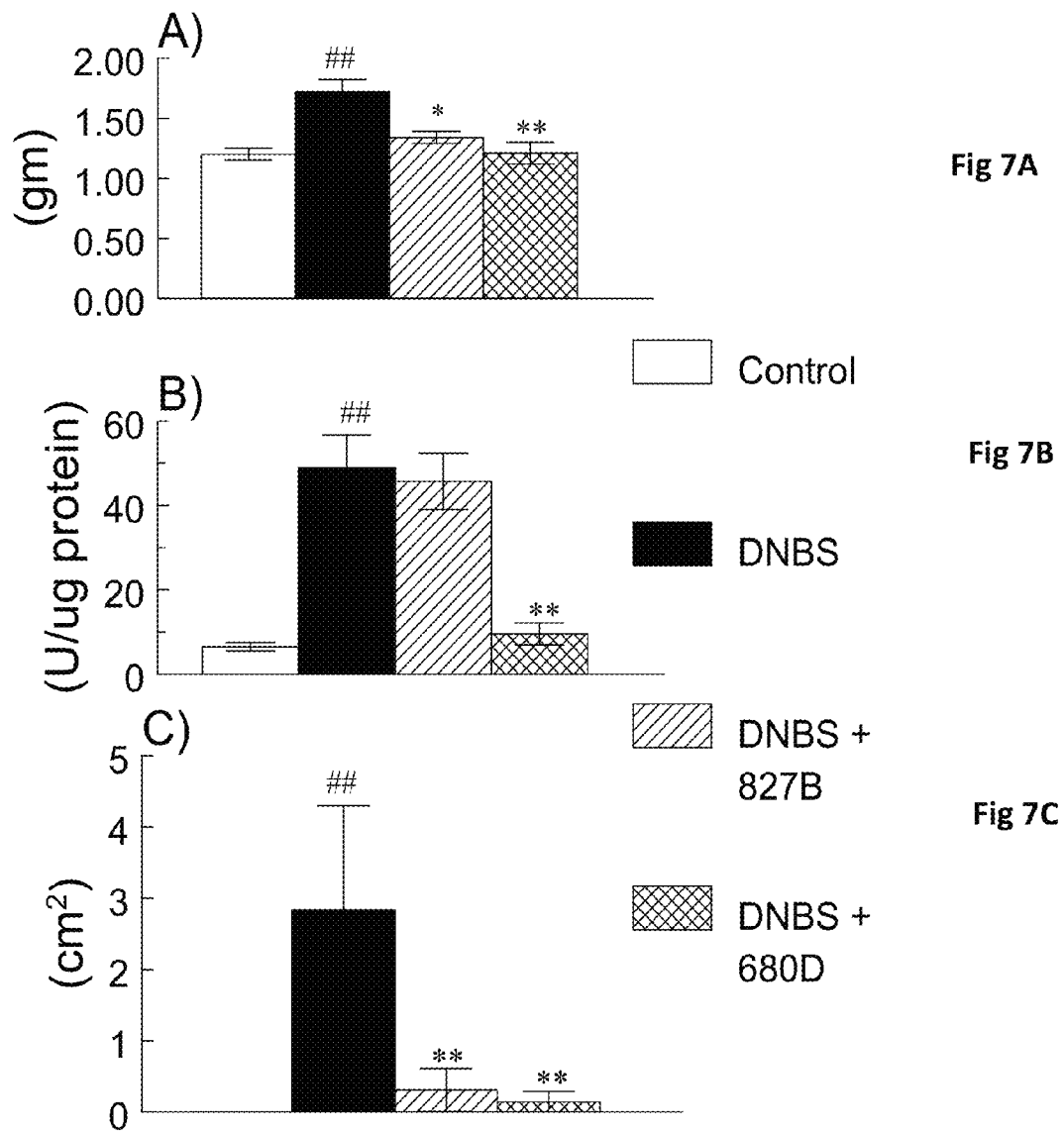
FIGS. 7A-7C show the effect of AN-827B (2.5 μmoles/kg) of the mesylate salt and 680D (2.5 μmoles/kg of the mesylate salt) administered rectally twice daily on colon weight (FIG. 7A), MPO (a quantitative marker of neutrophil granulocyte infiltration, (FIG. 7B) and on area of ulcers (FIG. 7C) induced in rat colon by DTNB administration. Data represent mean±SEM from 10 rats per group. Significantly different from DTNB alone * p<0.05; ** p<0.01.

Rectal administration of AN-680D 1 mg/kg (2.5 μmoles/kg) prior to and after DNBS reduced the area of colonic ulceration by 95%, colon weight by 30% and MPO activity by 80% (FIG. 7A-C). Rectal administration of AN-827B (1 mg/kg, 2.5 μmoles kg) prior to, and after DNBS reduced the area of colonic ulceration by 90% and colon weight by 22%. AN-827B (25 μmoles/kg) reduced MPO activity by 70%.

I. Anti-Inflammatory Effect in a Mouse Model of Colitis

Subcutaneous administration of AN-680E at a dose of 5 mg/kg (10.5 μmoles/kg) in mice drinking 5% DSS solution reduced colon shrinkage on day 8 by 17%, weight loss by 80%, and DAI by 50% (FIG. 8A-D).

The invention claimed is:

1. A compound of general formula (I), or a stereoisomer or salt thereof:

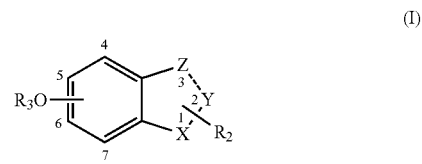

wherein

----- is a single or double bond;

X is $NR_1$, Y is CH and Z is $CR_2$;

$R_1$ is selected from H, straight or branched $C_1$-$C_5$ alkyl, straight or branched $C_2$-$C_6$ alkenyl; straight or branched $C_2$-$C_6$ alkynyl; wherein said alkyl, alkenyl and alkynyl are each optionally substituted by at least one group selected from —C(=O)O($C_1$-$C_5$alkyl), $NR_7R_8$ and amino;

$R_2$ is selected from H, —COH, straight or branched $C_1$-$C_{10}$ alkyl, straight or branched $C_2$-$C_{10}$ alkenyl; wherein said alkyl and alkenyl are each substituted by at least one substituent selected from $NO_2$, amino, amido, tetrazolyl, pentazolyl, —CONHSO$_2$H, —CONHSO$_2$phenyl and —COR$_4$; provided that when $R_1$ is H, $R_2$ is different than H;

$R_4$ is selected from —OH, —NH$_2$, —O($C_1$-$C_{10}$alkyl), wherein said alkyl is optionally interrupted by at least one heteroatom selected from O or S; said alkyl is optionally substituted by at least one group selected from amino, morpholino, —O($C_1$-$C_5$alkyl), and —OCO($C_1$-$C_5$alkyl);

$R_3$ is —CONR$_5$R$_6$, wherein said —OR$_3$ is substituted at positions 4, 6 or 7;

$R_5$, $R_6$, $R_7$ and $R_8$ are each independently and differently selected from straight or branched $C_1$-$C_{10}$ alkyl and aryl; each optionally substituted by at least one substituent selected from —OH, $C_1$-$C_5$ alkoxy.

2. A compound according to claim 1, wherein —OR$_3$ is substituted at position 4.

TABLE 6

| | LPS-stimulated microglial cells Primary culture of microglial cells | | | | | |
|---|---|---|---|---|---|---|
| AN- | >30% reduction | >30% reduction cytokine release | | | | >30% increase |
| Compound | NO release | TNF-α | IL-1β | IL-6 | iNOS | IL10 |
| 855A | no effect | no effect | no effect | 100 nM | | 1 nM + 10-100 μM |
| | ≤100 μM | ≤100 μM | ≤100 μM | | | |
| 834A | 0.1 μM | | | | | |
| 832A | 0.01 μM-10 μM | 100 nM-100 μM | 10 nM | 10-100 nM | | no effect |
| 856A | 10 μM | | | | | |
| 854A | 1 μM | no effect | 10 nM | 100 μM | 1-100 μM | no effect |
| | | ≤100 μM | | | | |
| 850A | 0.1 mM | | | | | |
| 827A | 100 μM | no effect | 100 μM | 100 μM | 100 μM | 1 + 100 nM and 10-100 μM |
| | | ≤100 μM | | | | |
| 682A | 10 nM and 1-10 μM | no effect | 100 nM | 100 nM | | 1 nM + 10 μM |
| | | ≤100 μM | | | | |
| 680A | 1-10 mM | no effect | no effect | no effect | No effect | 1 nM – 1 μM |
| | | ≤100 μM | ≤100 μM | ≤100 μM | | |
| 685A | | no effect | no effect | no effect | 1-100 μM | 10 μM |
| | | ≤100 μM | ≤100 μM | ≤100 μM | | |

3. A compound according to claim 1, wherein —OR$_3$ is substituted at position 6.

4. A compound according to claim 1, wherein —OR$_3$ is substituted at position 7.

5. A compound according to claim 1, being a pharmaceutically acceptable salt thereof.

6. A composition comprising at least one compound of claim 1.

7. A method for the treatment of a disease, disorder, condition or symptom in a subject associated with the inhibition of at least one of oxidative stress and inflammation, said method comprises administering to said subject a compound according to claim 1.

8. A method according to claim 7, wherein said disease, disorder, condition or symptom is selected from at least one of ulcerative colitis, Crohn's disease, rheumatoid arthritis, diabetes, cardiac failure, chronic liver disease, chronic lung disease, meningitis, infective brain disease, complex regional pain syndrome (CRPS) and any combinations thereof.

9. The method of claim 7, wherein the disease, disorder, condition or symptom is ulcerative colitis.

* * * * *